United States Patent
Weber

(10) Patent No.: US 10,603,101 B2
(45) Date of Patent: Mar. 31, 2020

(54) APPARATUS, SYSTEMS AND METHODS FOR MINIMALLY INVASIVE DISSECTION OF TISSUES

(71) Applicant: Paul Joseph Weber, Nendaz (CH)

(72) Inventor: Paul Joseph Weber, Nendaz (CH)

( * ) Notice: Subject to any disclaimer, the term of this patent is extended or adjusted under 35 U.S.C. 154(b) by 425 days.

(21) Appl. No.: 15/464,199

(22) Filed: Mar. 20, 2017

(65) Prior Publication Data

US 2017/0273733 A1    Sep. 28, 2017

Related U.S. Application Data

(60) Provisional application No. 62/409,575, filed on Oct. 18, 2016, provisional application No. 62/313,707, filed on Mar. 26, 2016.

(51) Int. Cl.
*A61B 18/14* (2006.01)
*A61B 18/00* (2006.01)
*A61B 90/98* (2016.01)

(52) U.S. Cl.
CPC .......... *A61B 18/1402* (2013.01); *A61B 90/98* (2016.02); *A61B 2018/00005* (2013.01); *A61B 2018/00571* (2013.01); *A61B 2018/00589* (2013.01); *A61B 2018/1417* (2013.01); *A61B 2018/1467* (2013.01)

(58) Field of Classification Search
CPC .......... A61B 2018/00005; A61B 2018/00571; A61B 2018/00589; A61B 2018/1417; A61B 2018/1467
See application file for complete search history.

(56) References Cited

U.S. PATENT DOCUMENTS

| | | | |
|---|---|---|---|
| 4,473,077 A | 9/1984 | Noiles | |
| 5,104,394 A | 4/1992 | Knoepfler | |
| 5,170,925 A | 12/1992 | Madden | |
| 5,222,961 A | 6/1993 | Nakao | |
| 5,282,807 A | 2/1994 | Knoepfler | |
| 5,308,358 A | 5/1994 | Bond et al. | |
| 5,314,424 A | 5/1994 | Nicholas | |
| 5,368,606 A | 11/1994 | Marlow et al. | |
| 5,391,166 A | 2/1995 | Eggers | |
| 5,630,539 A | 5/1997 | Plyley | |
| 5,810,805 A | 9/1998 | Sutcu | |
| 5,980,520 A * | 11/1999 | Vancaillie | A61B 18/149 606/46 |
| 6,203,540 B1 | 3/2001 | Weber | |

(Continued)

OTHER PUBLICATIONS

International Search PCT/NZ17/50029, dated Oct. 19, 2017, 2 pgs.
Written Opinion PCT/NZ17/50029, dated Oct. 19, 2017, 3 pgs.

*Primary Examiner* — Michael F Peffley
*Assistant Examiner* — Bo Ouyang
(74) *Attorney, Agent, or Firm* — Matthew D. Thayne; Thayne and Davis LLC

(57) ABSTRACT

Electrosurgical lysing devices and related systems and methods. In some embodiments, the lysing device may comprise a lysing tip comprising a plurality of beads and at least one lysing member, such as a lysing rod, defining at least one lysing segment extending between each pair of adjacent beads. The at least one lysing member may extend through a tunnel extending at least partially through each of the plurality of beads so as to define the at least one lysing segment between each pair of adjacent beads.

24 Claims, 75 Drawing Sheets

(56) References Cited

U.S. PATENT DOCUMENTS

| | | |
|---|---|---|
| 6,391,023 B1 | 5/2002 | Weber |
| 6,432,101 B1 | 8/2002 | Weber |
| 6,440,121 B1 | 8/2002 | Weber |
| 6,494,881 B1 * | 12/2002 | Bales .................. A61B 18/149 606/41 |
| 6,602,252 B2 | 8/2003 | Mollenauer |
| 6,623,481 B1 | 9/2003 | Garbagnati |
| 6,974,450 B2 | 12/2005 | Weber |
| 6,978,921 B2 | 12/2005 | Shelton |
| 7,300,397 B2 | 11/2007 | Adler et al. |
| 7,390,317 B2 | 6/2008 | Taylor et al. |
| 7,438,702 B2 | 10/2008 | Hart et al. |
| 7,494,460 B2 | 2/2009 | Haarstad et al. |
| 7,494,488 B2 | 2/2009 | Weber |
| 7,559,887 B2 | 7/2009 | Dannan |
| 7,563,250 B2 | 7/2009 | Wenchell |
| 7,690,547 B2 | 4/2010 | Racenet |
| 7,828,775 B2 | 11/2010 | Okoniewski |
| 7,828,808 B2 | 11/2010 | Hinman et al. |
| 7,833,275 B2 | 11/2010 | Mears et al. |
| 7,845,534 B2 | 12/2010 | Viola |
| 7,857,754 B2 | 12/2010 | Spivey et al. |
| 8,029,475 B2 | 10/2011 | Franer et al. |
| 8,033,995 B2 | 10/2011 | Cropper et al. |
| 8,056,788 B2 | 11/2011 | Mastri |
| 8,070,676 B2 | 12/2011 | Ewers et al. |
| 8,075,477 B2 | 12/2011 | Nakamura et al. |
| 8,075,530 B2 | 12/2011 | Taylor et al. |
| 8,147,457 B2 | 4/2012 | Michael et al. |
| 8,152,773 B2 | 4/2012 | Albrecht et al. |
| 8,152,774 B2 | 4/2012 | Pasqualucci |
| 8,172,806 B2 | 5/2012 | Smith |
| 8,192,405 B2 | 6/2012 | Racenet et al. |
| 8,225,798 B2 | 7/2012 | Baldwin et al. |
| 8,240,538 B1 | 8/2012 | Manoux |
| 8,409,172 B2 | 4/2013 | Moll et al. |
| 8,423,182 B2 | 4/2013 | Robinson et al. |
| 8,424,739 B2 | 4/2013 | Racenet |
| 8,425,406 B2 | 4/2013 | Smith et al. |
| 8,430,851 B2 | 4/2013 | McGinley et al. |
| 8,444,631 B2 | 5/2013 | Yeung et al. |
| 8,458,896 B2 | 6/2013 | Chandrasekaran et al. |
| 8,475,359 B2 | 7/2013 | Asada et al. |
| 8,506,555 B2 | 8/2013 | Ruiz Morales |
| 8,523,043 B2 | 9/2013 | Ulrich |
| 8,535,312 B2 | 9/2013 | Horner |
| 9,028,491 B2 | 4/2015 | Ellman |
| 9,039,736 B2 | 5/2015 | Scirica |
| 9,138,207 B2 | 9/2015 | Igov |
| 9,155,536 B1 | 10/2015 | Hausen |
| 9,333,029 B2 | 5/2016 | Baldwin et al. |
| 2002/0128648 A1 * | 9/2002 | Weber ................ A61B 18/1402 606/45 |
| 2003/0216725 A1 | 11/2003 | Woloszko et al. |
| 2004/0243157 A1 | 12/2004 | Connor et al. |
| 2006/0079934 A1 * | 4/2006 | Ogawa ................... A61B 17/29 606/205 |
| 2007/0043352 A1 | 2/2007 | Garrison et al. |
| 2009/0118730 A1 | 5/2009 | Mollenauer |
| 2009/0236398 A1 | 9/2009 | Cole |
| 2011/0112524 A1 * | 5/2011 | Stern .................. A61M 25/0147 606/33 |
| 2011/0251610 A1 | 10/2011 | Ellman |
| 2013/0338652 A1 | 12/2013 | Weber |
| 2015/0320437 A1 | 11/2015 | Worrell |
| 2015/0320438 A1 | 11/2015 | Weisenburgh |
| 2015/0359585 A1 | 12/2015 | Weber |
| 2017/0100190 A1 * | 4/2017 | Gupta .................. A61B 18/149 |

\* cited by examiner

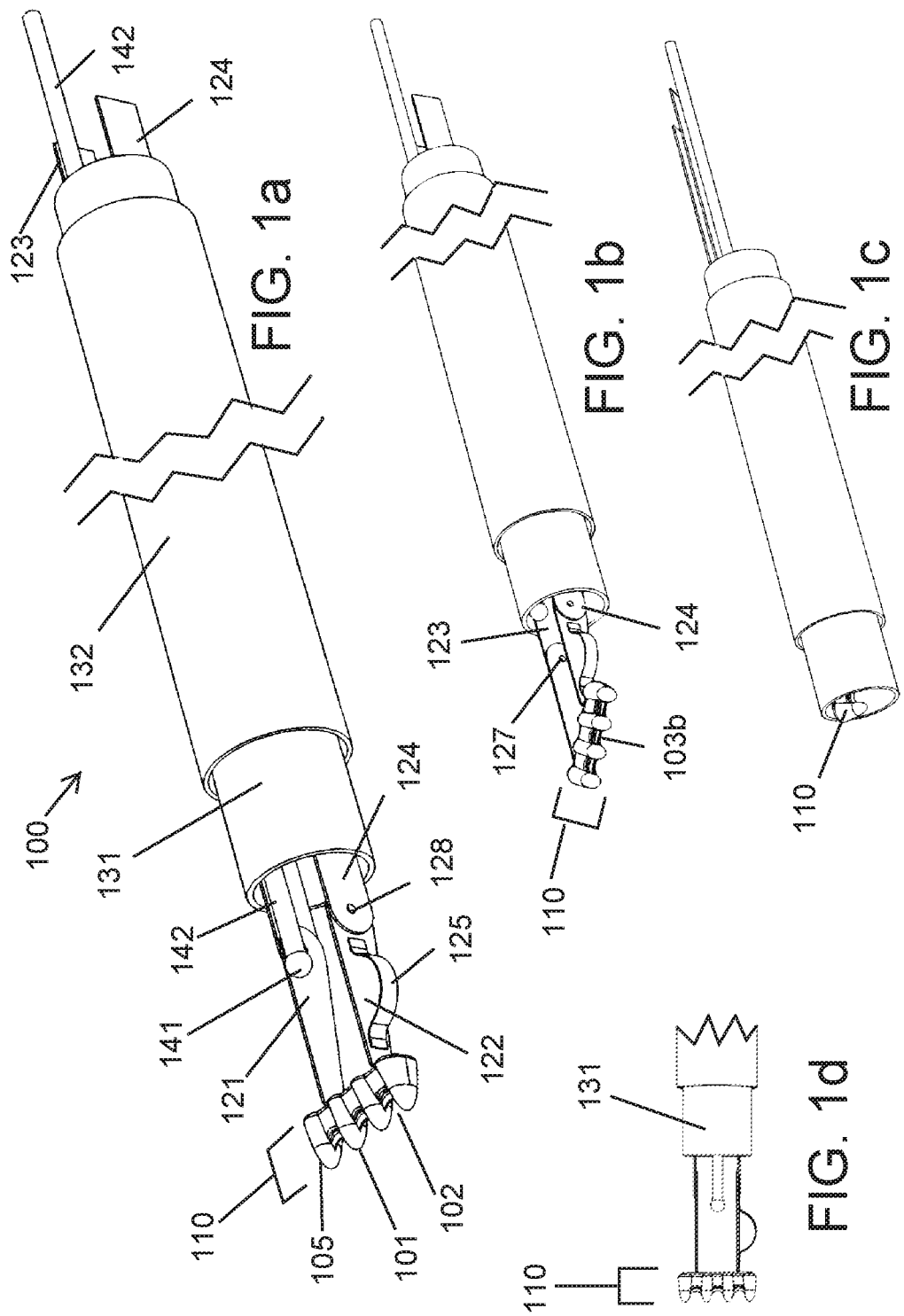

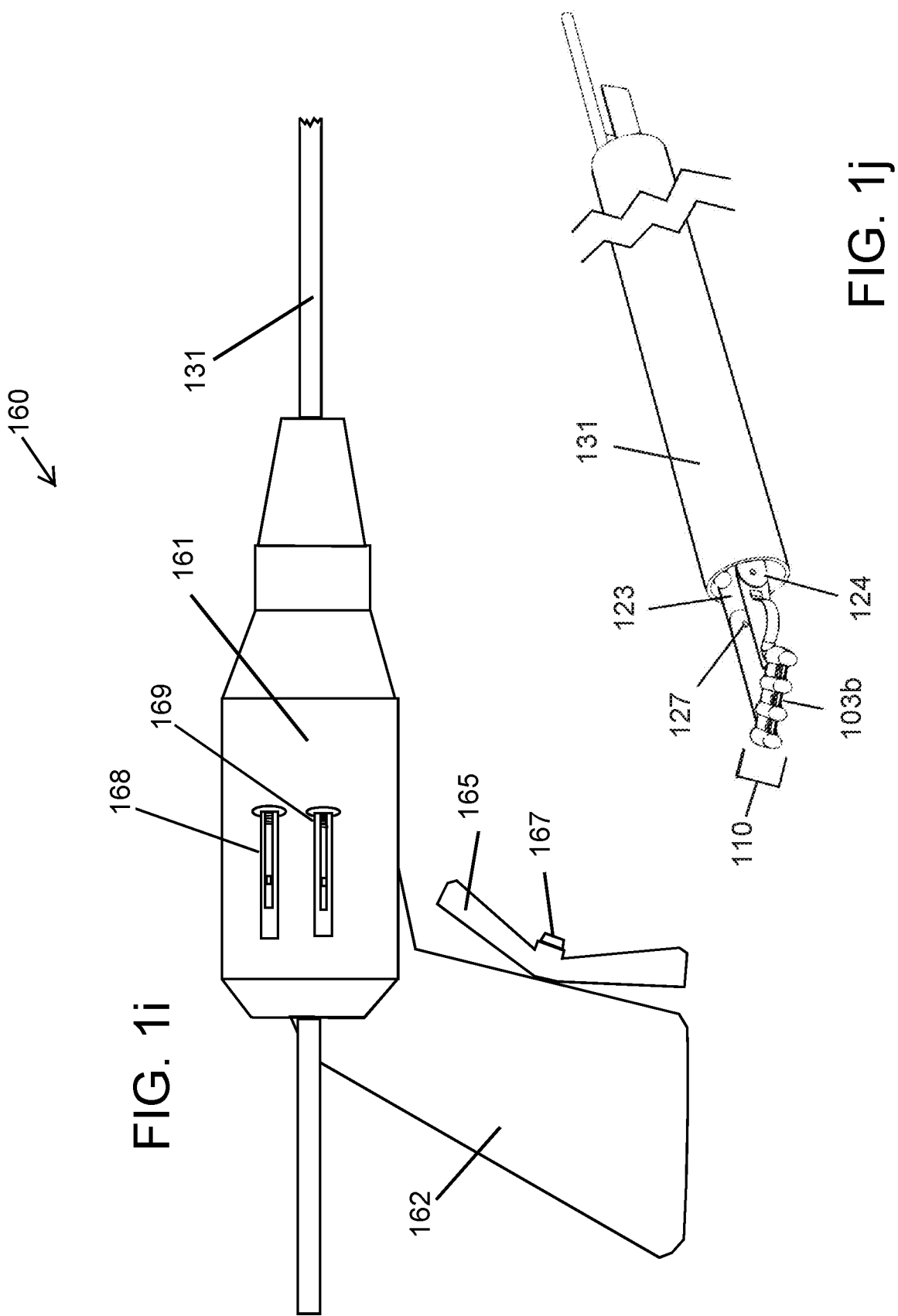

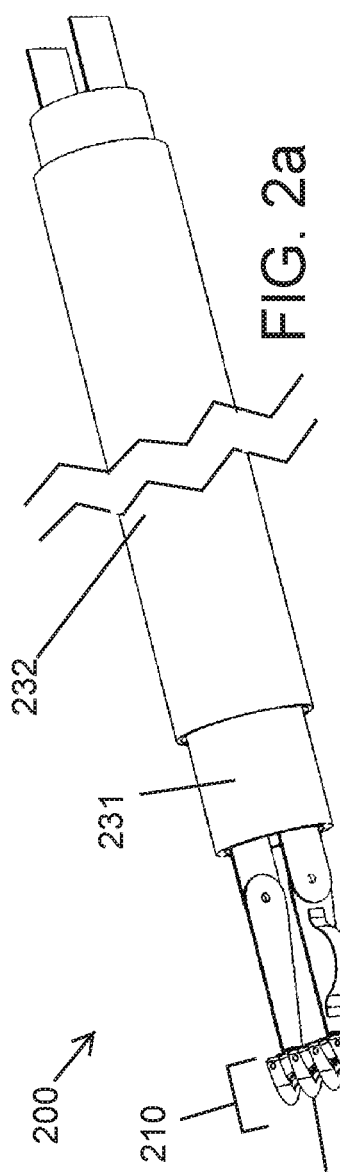
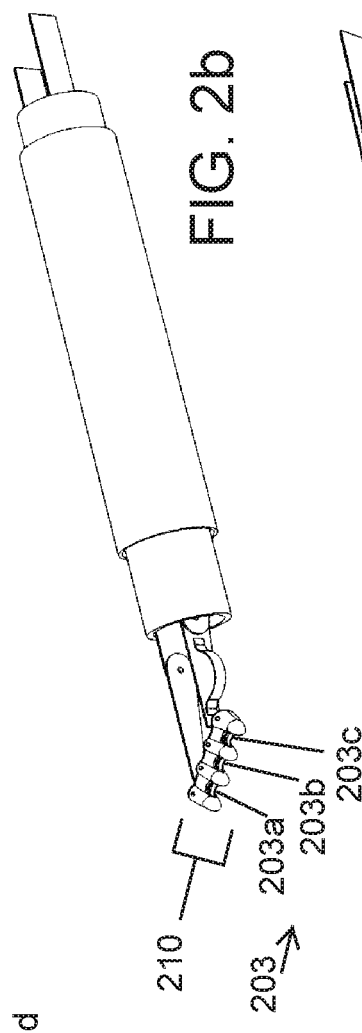
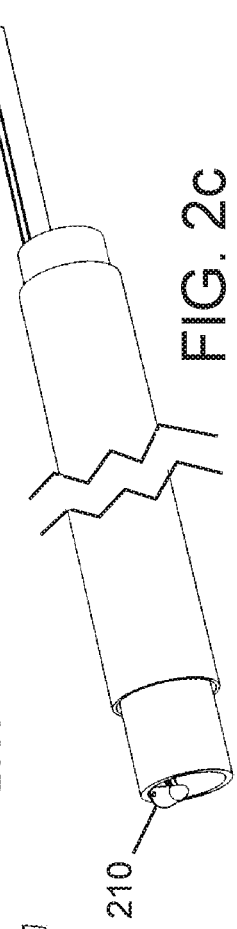
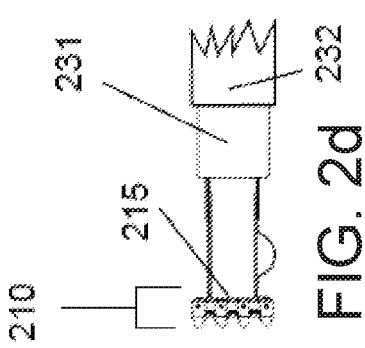
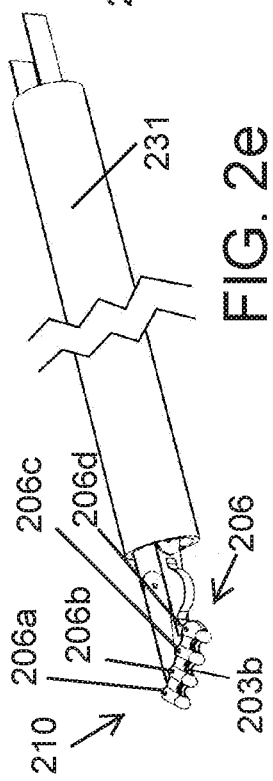

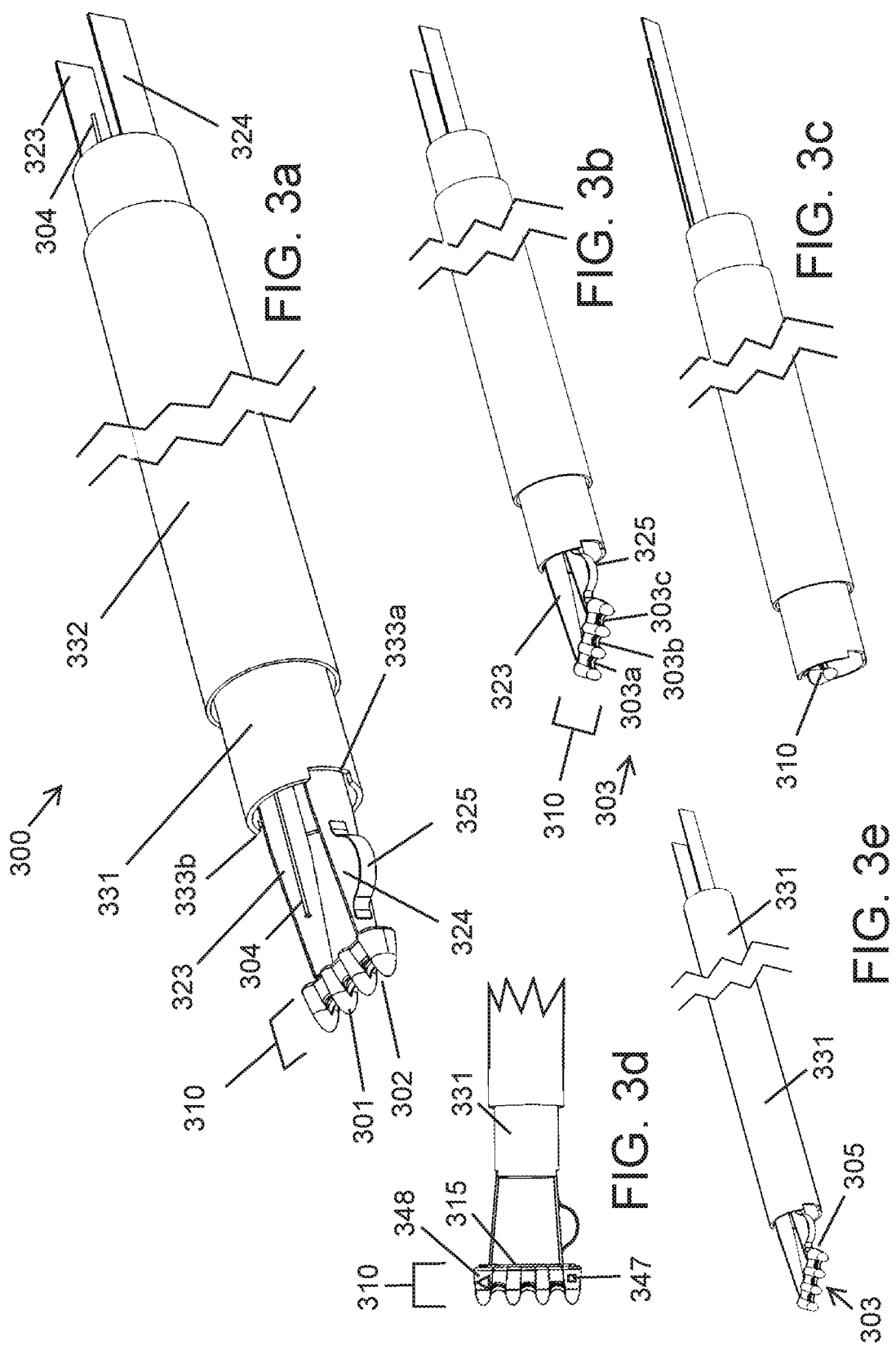

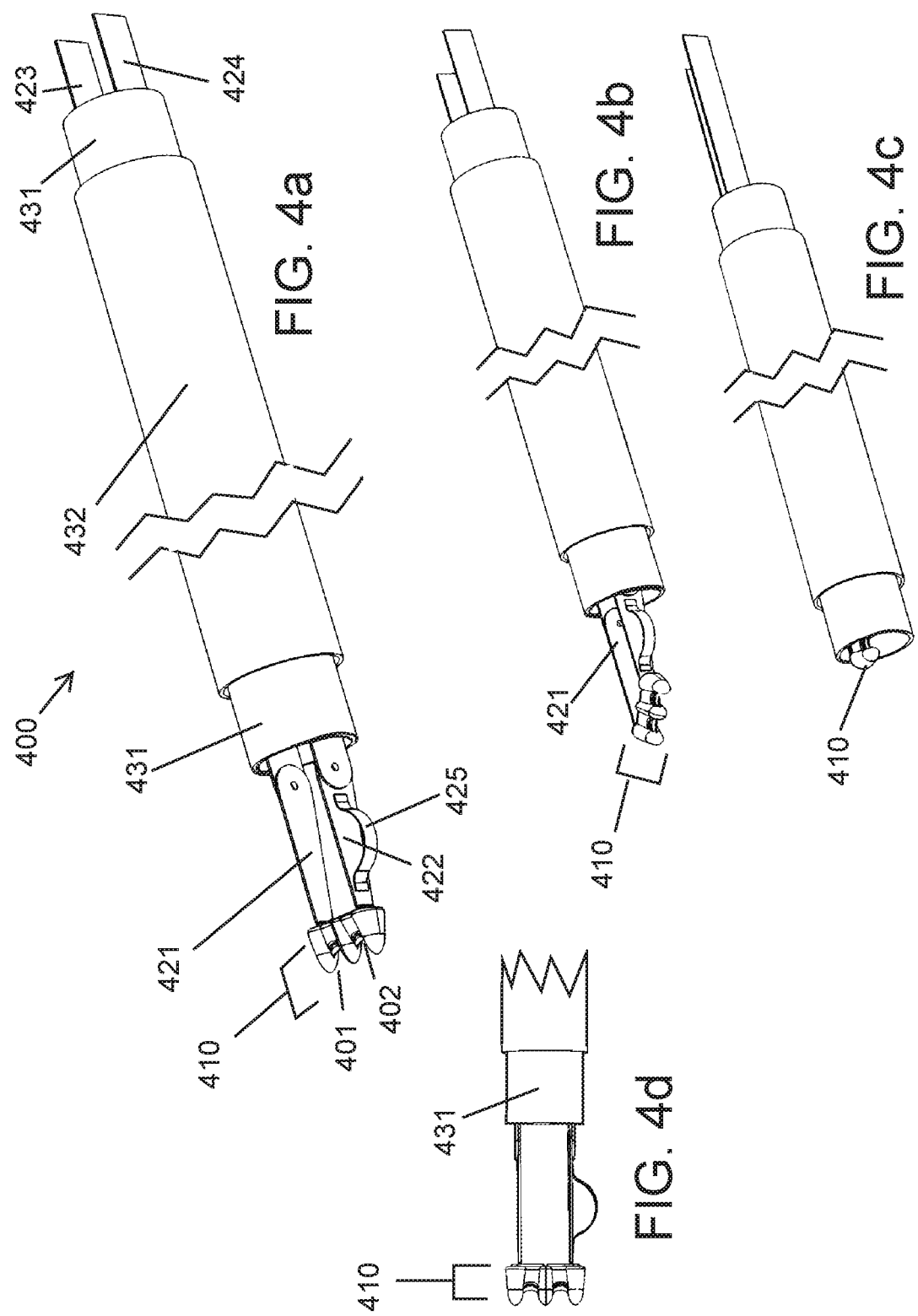

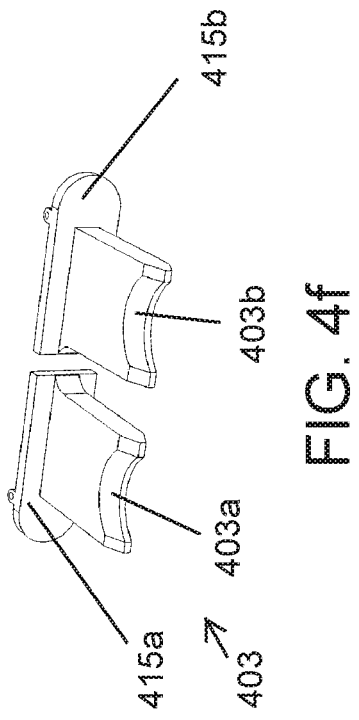
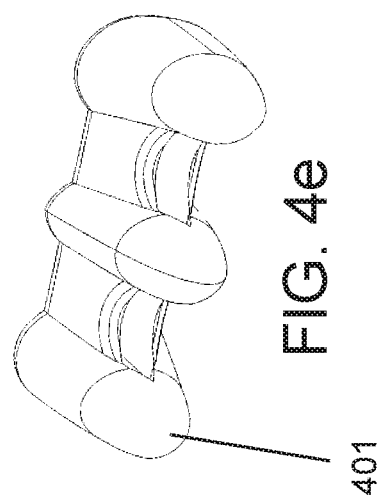
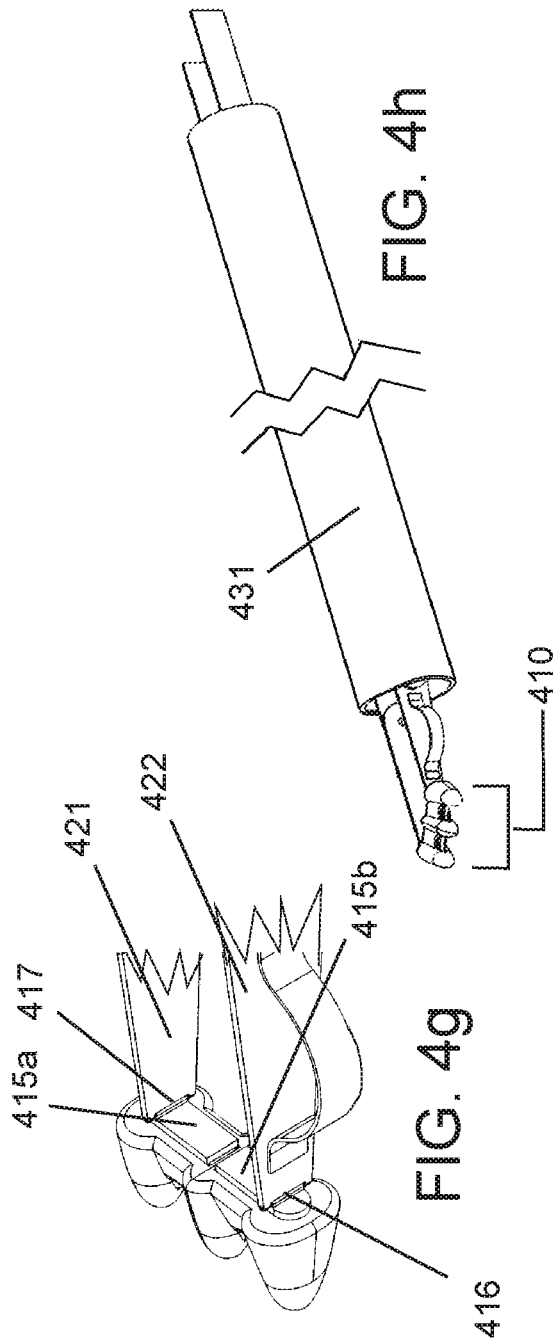

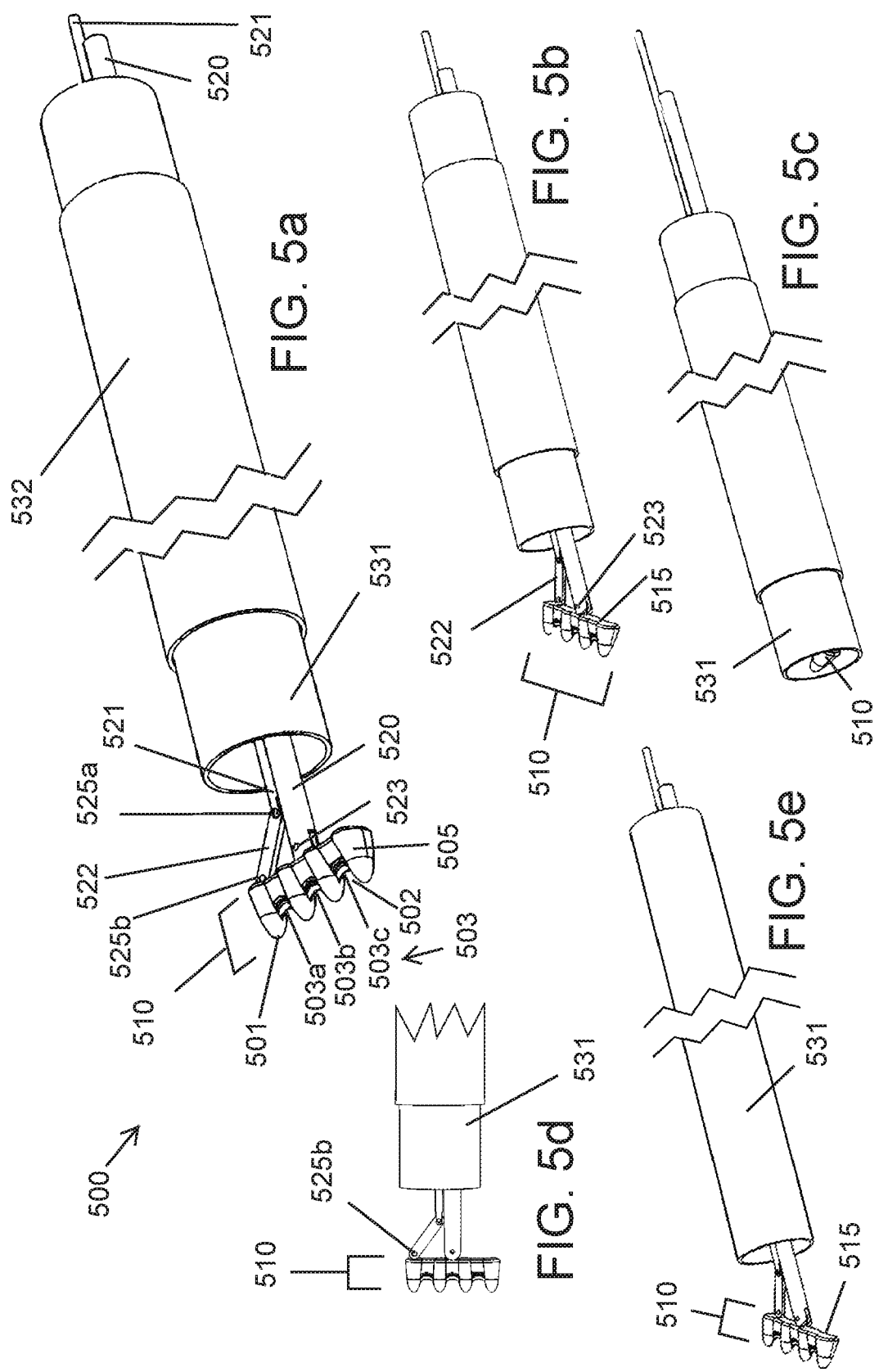

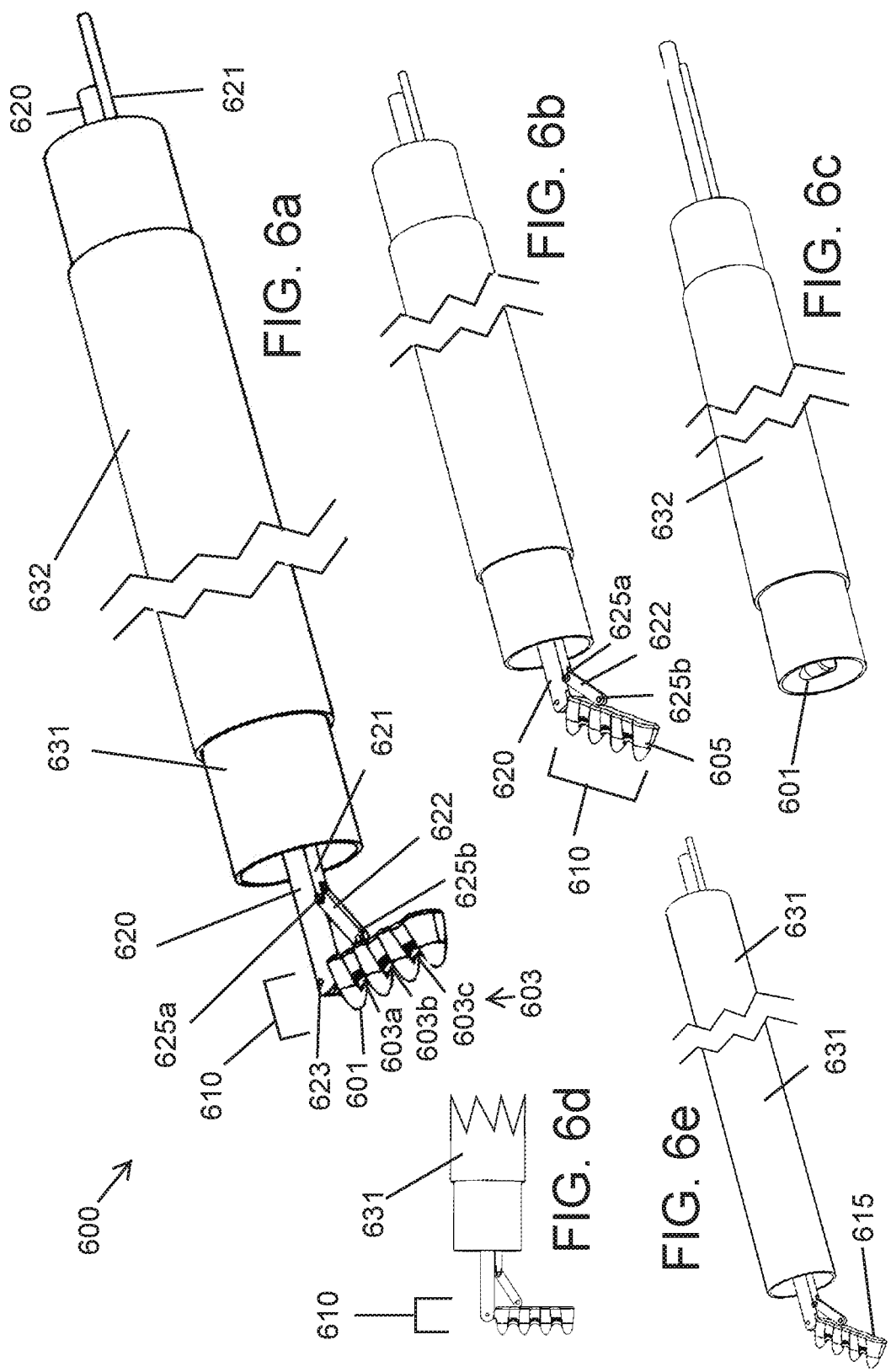

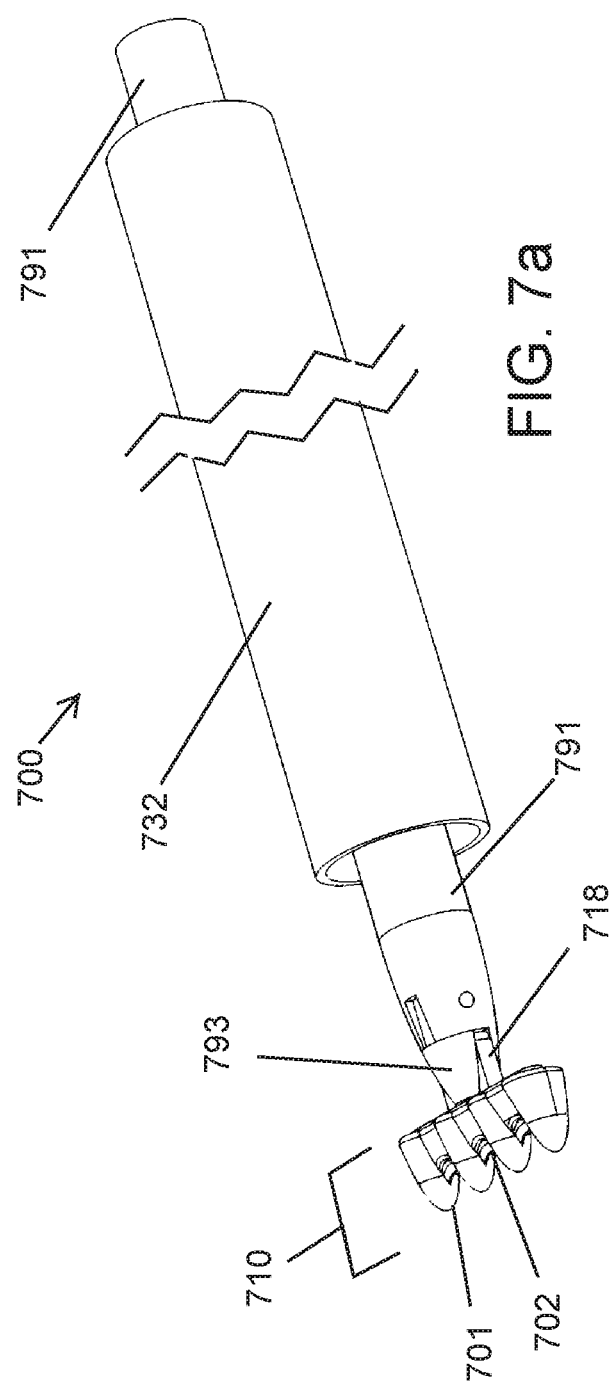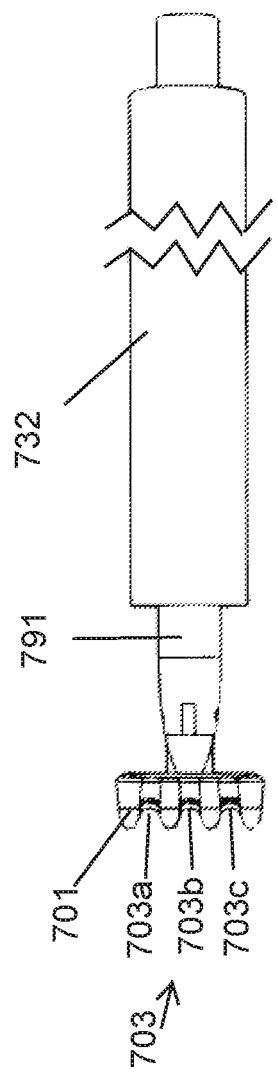

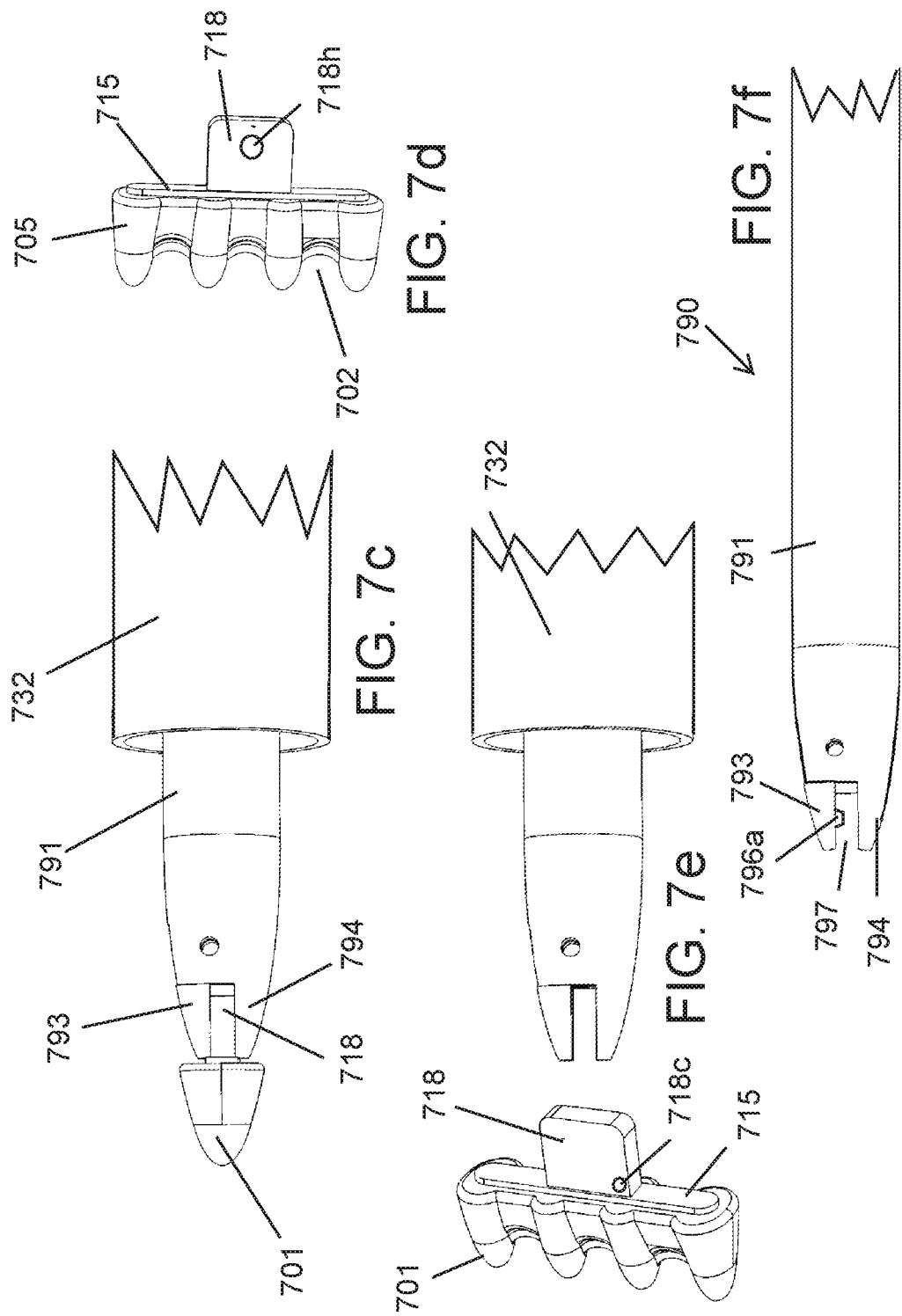

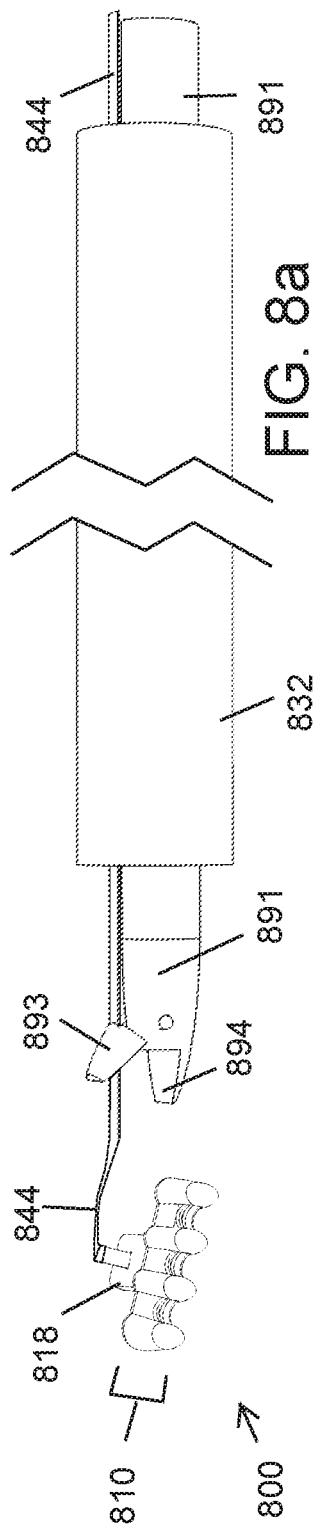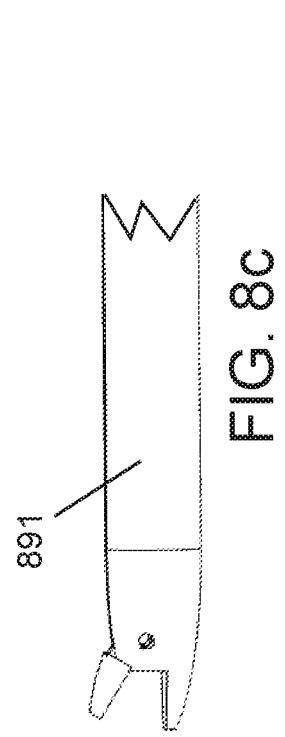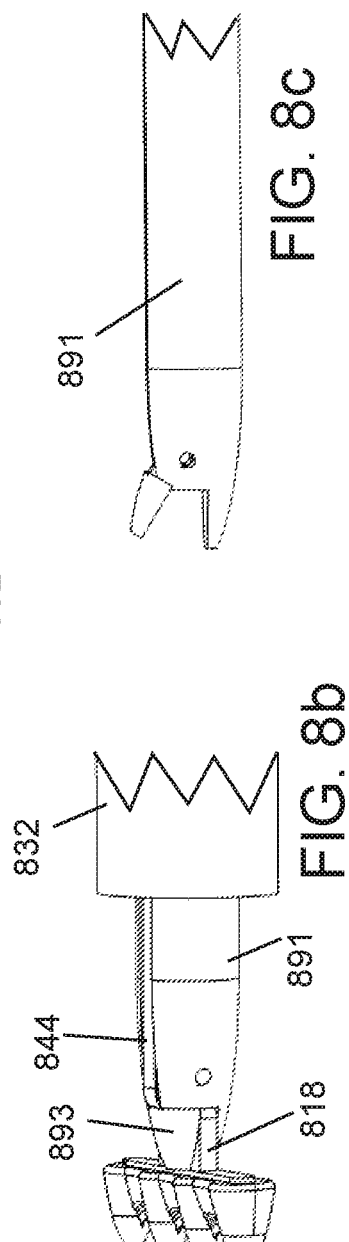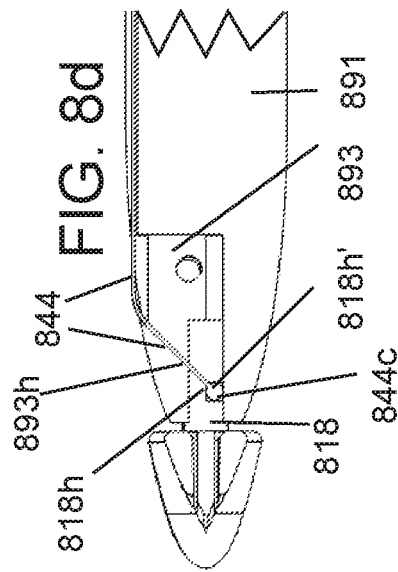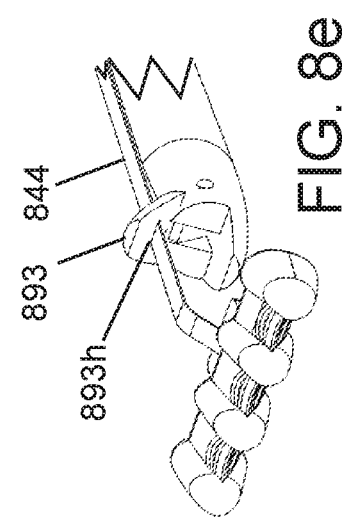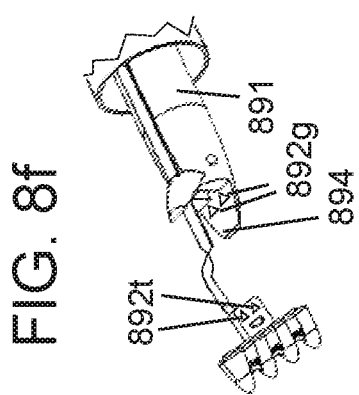

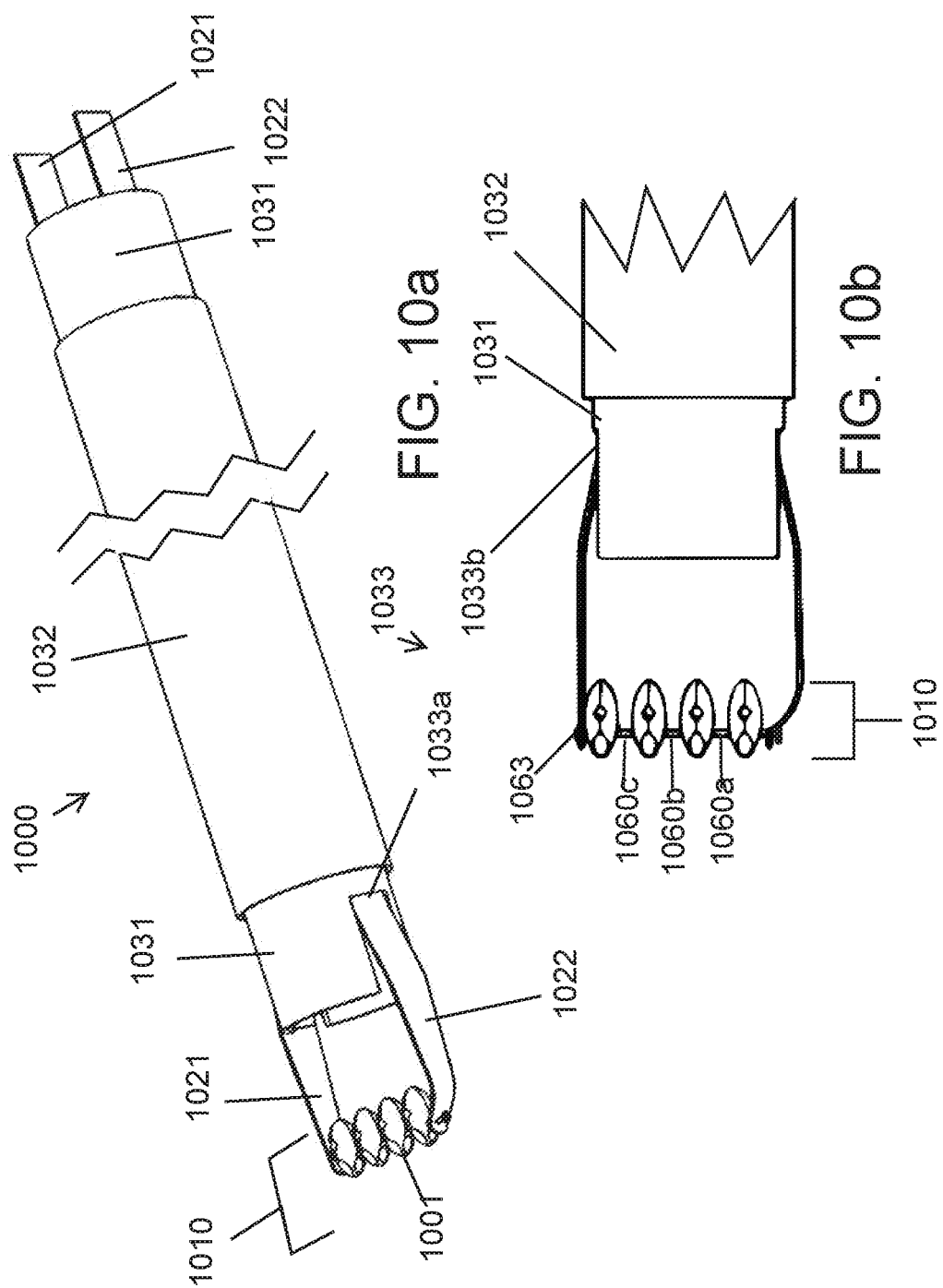

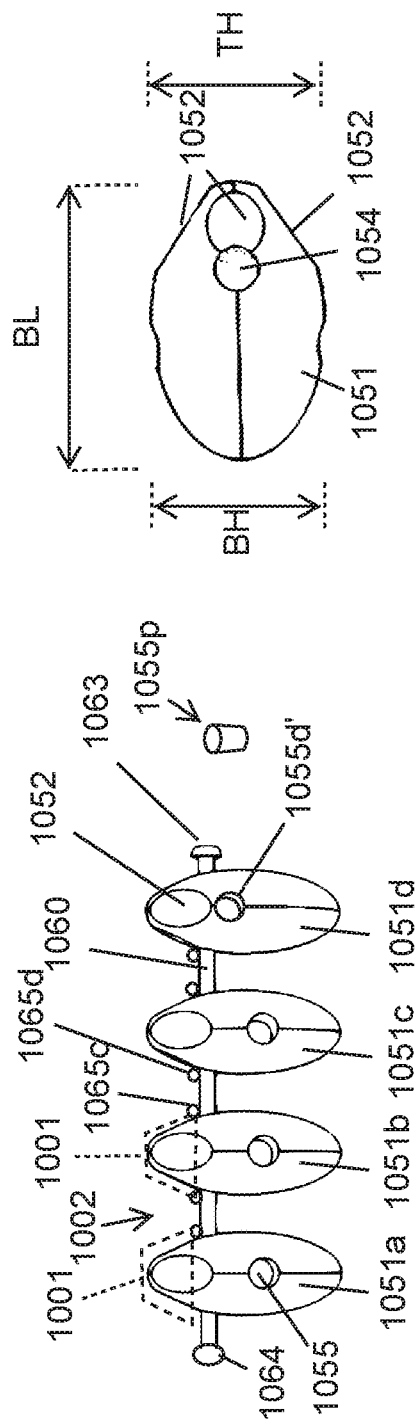
FIG. 10c
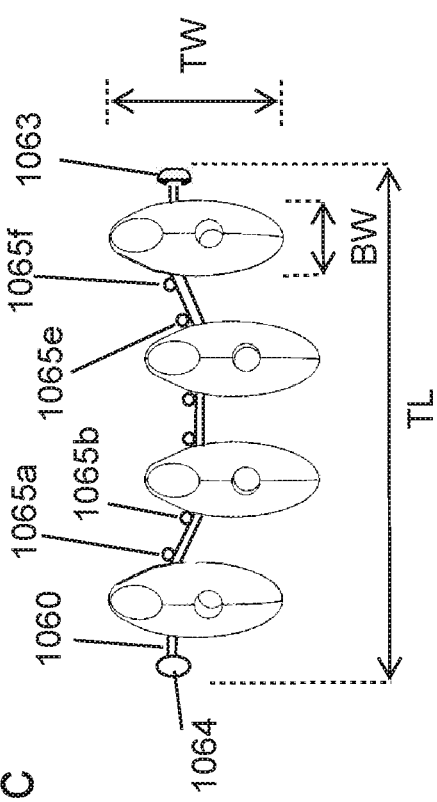
FIG. 10d
FIG. 10e

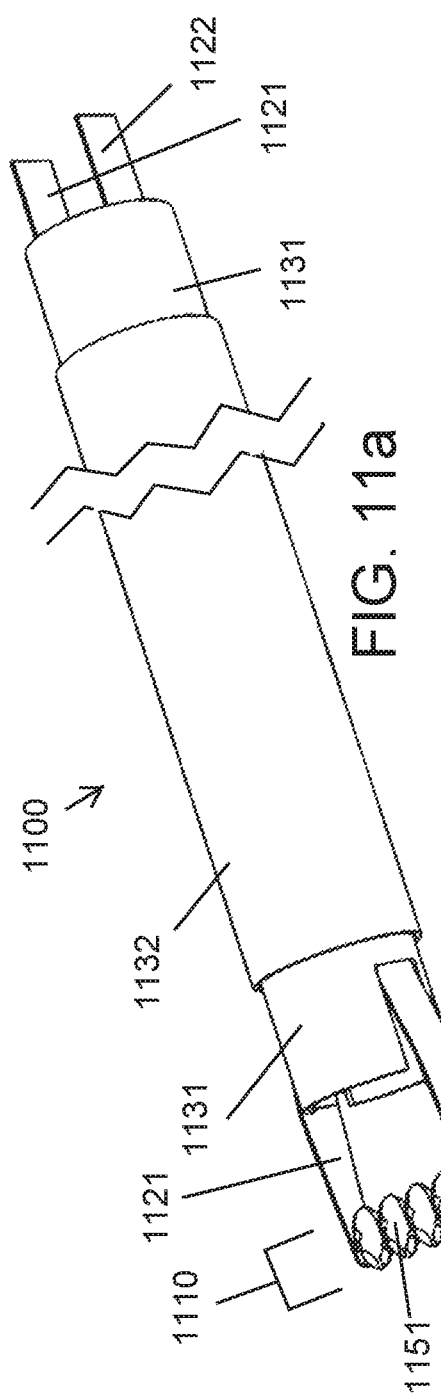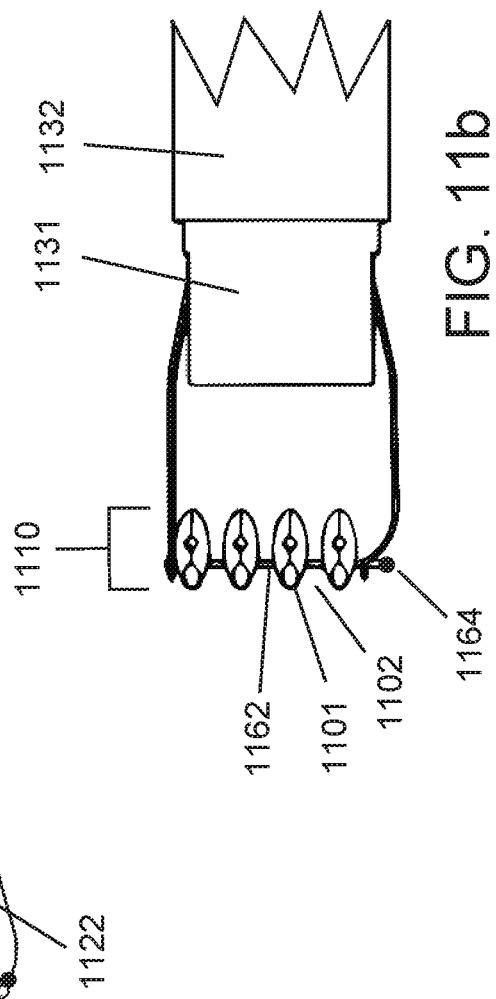

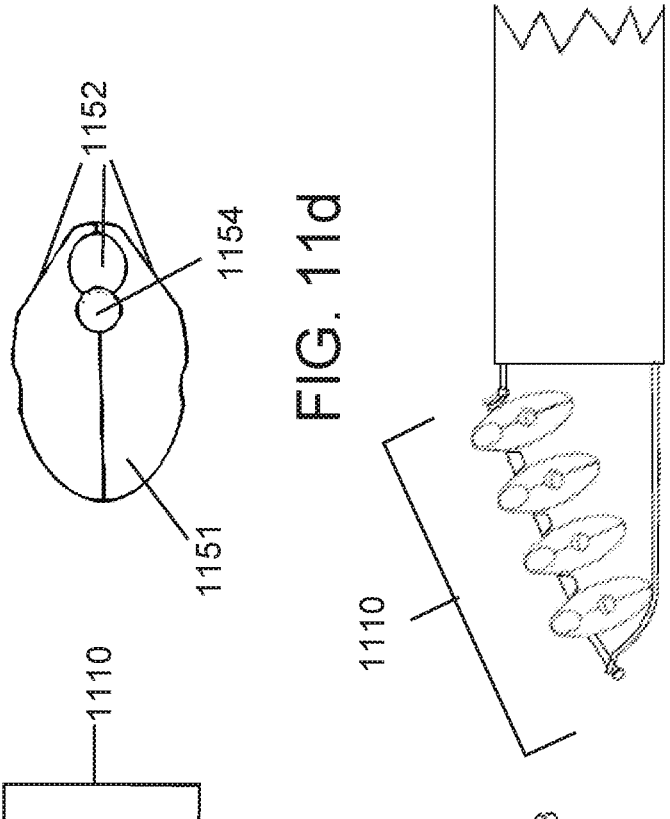
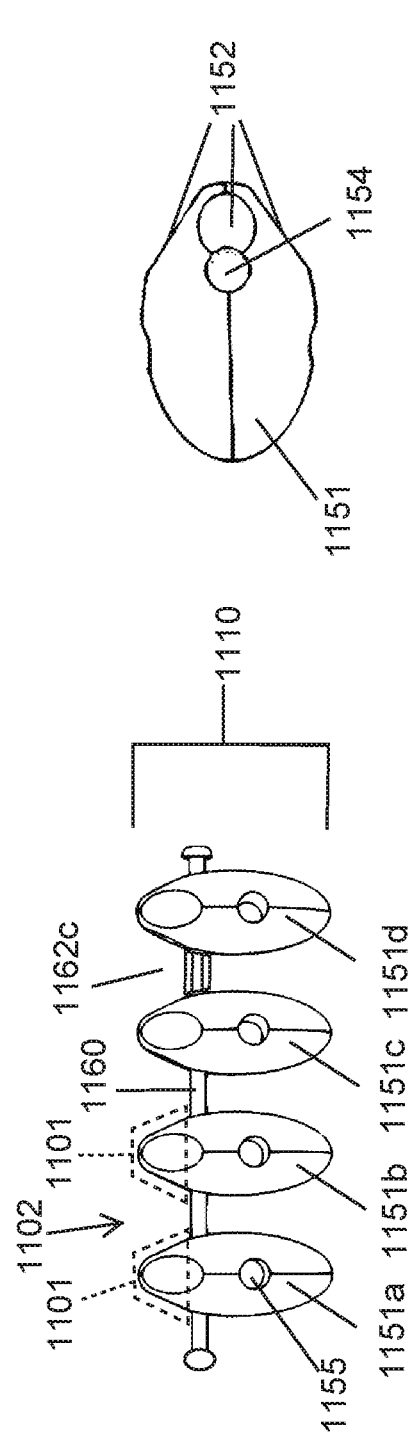
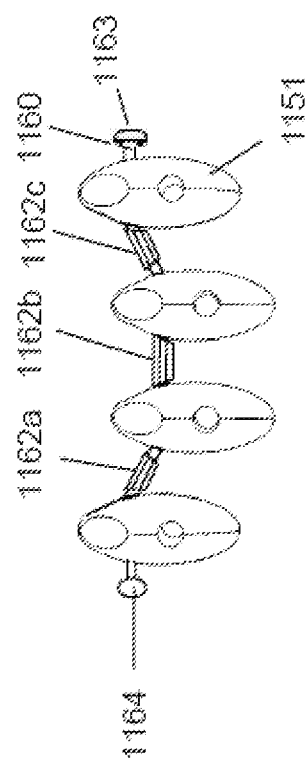

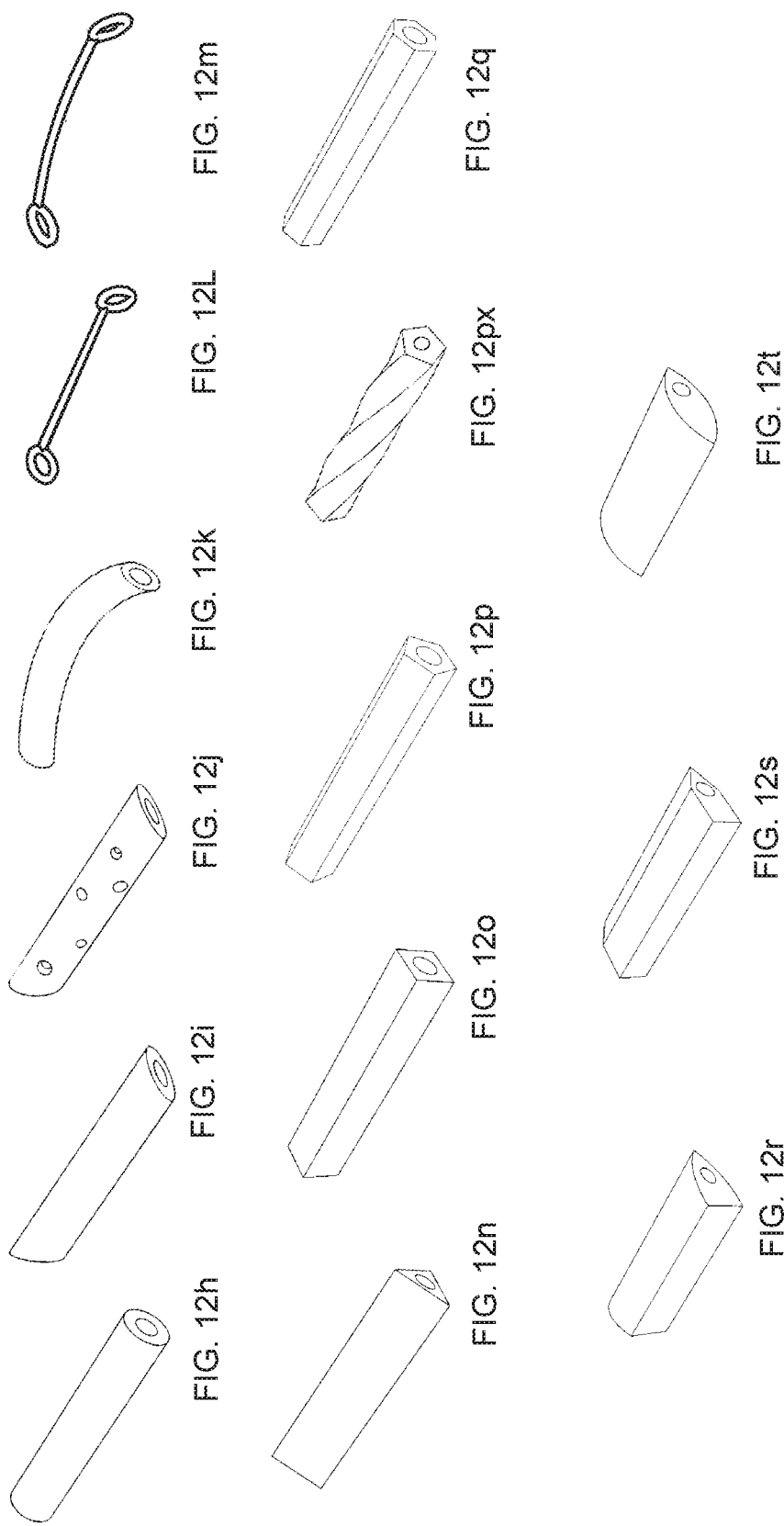

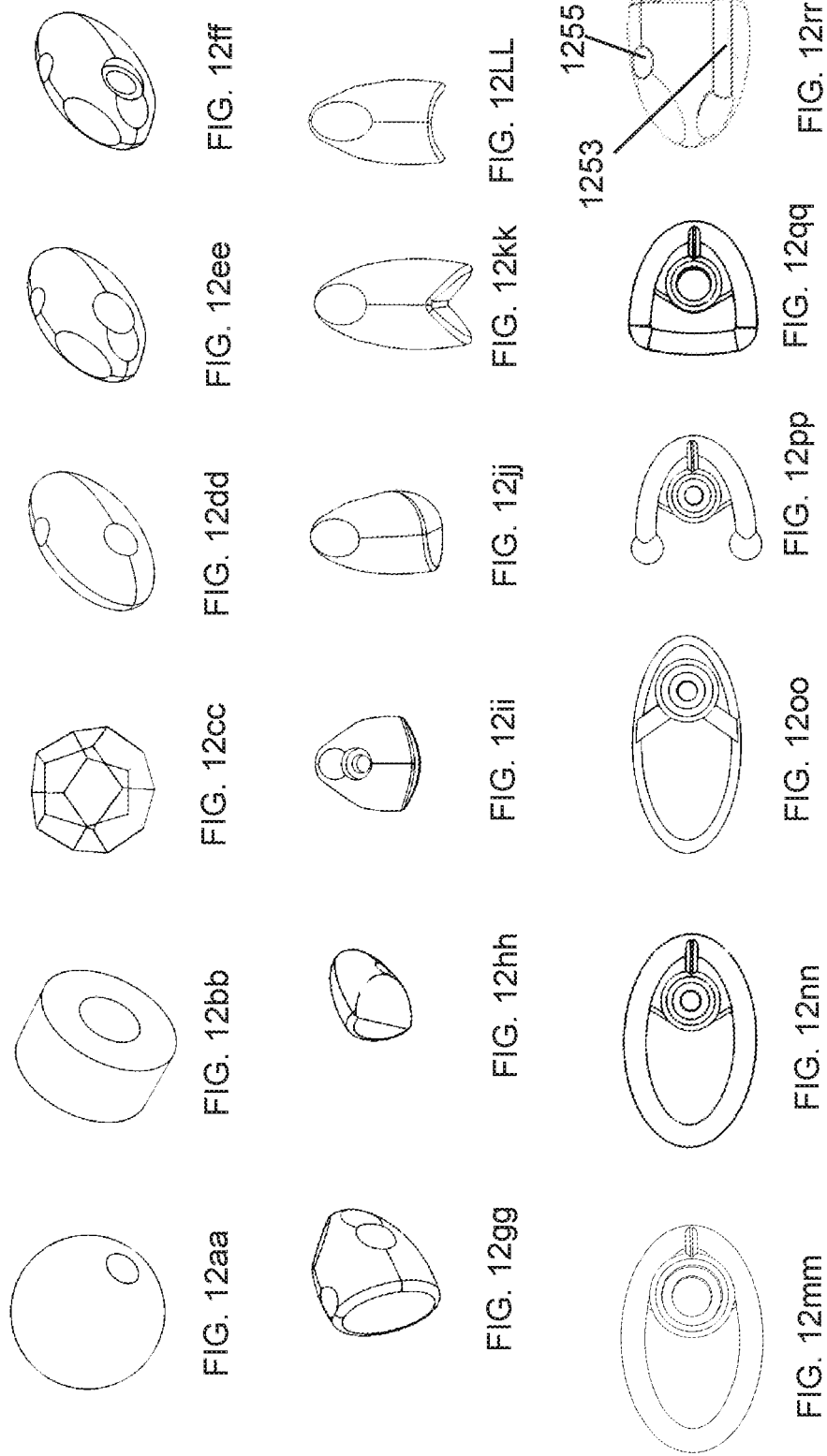

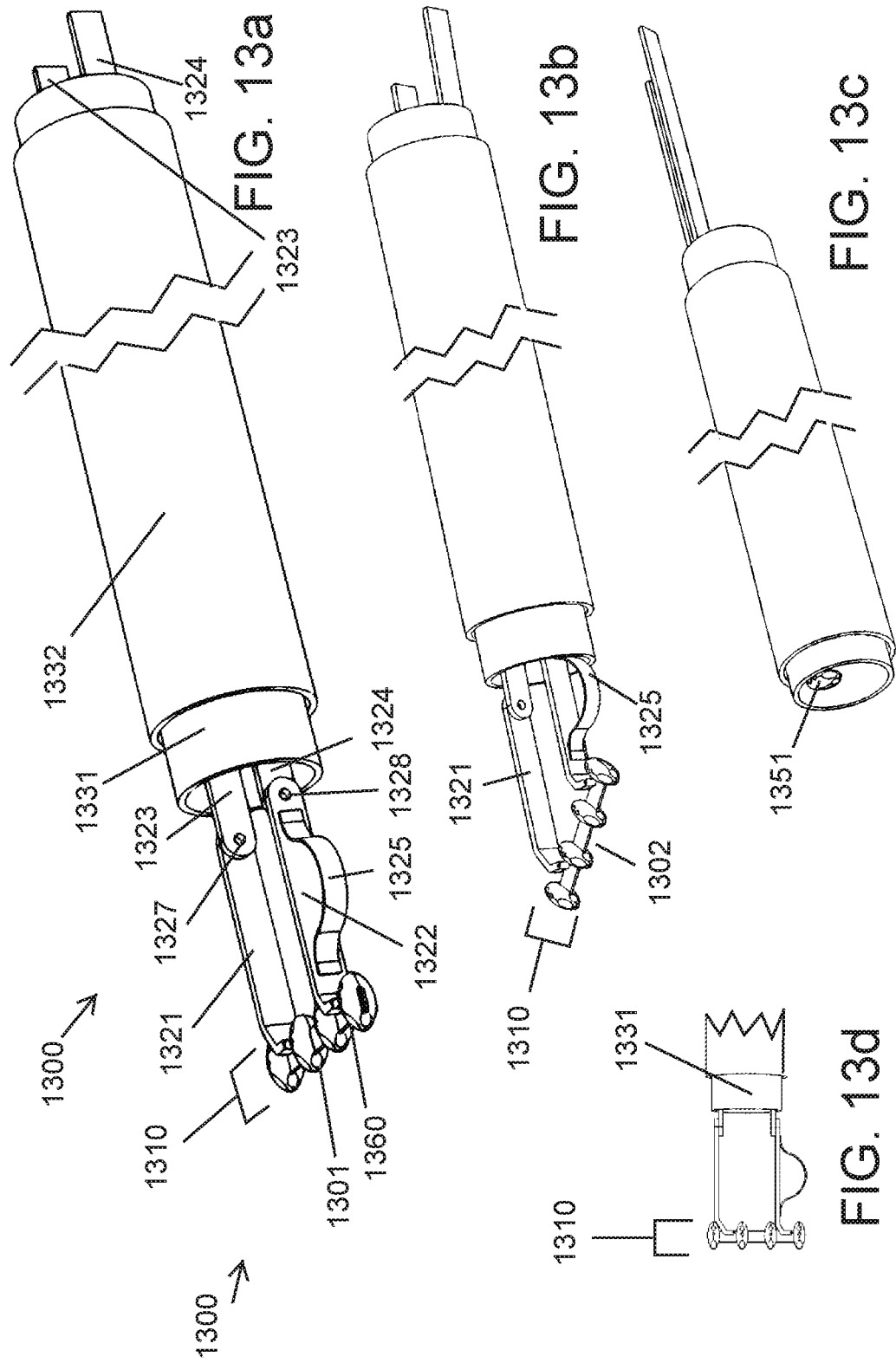

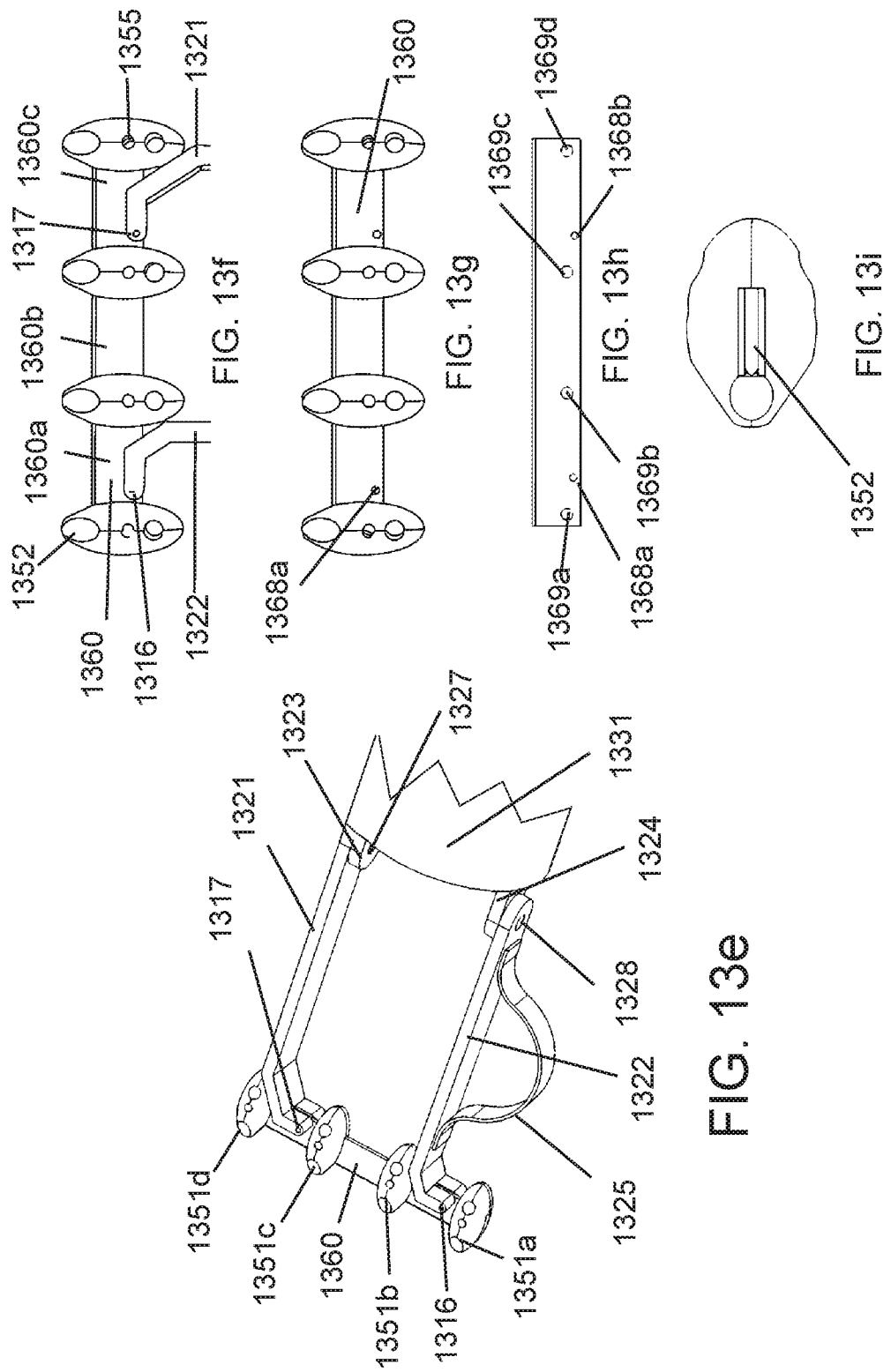

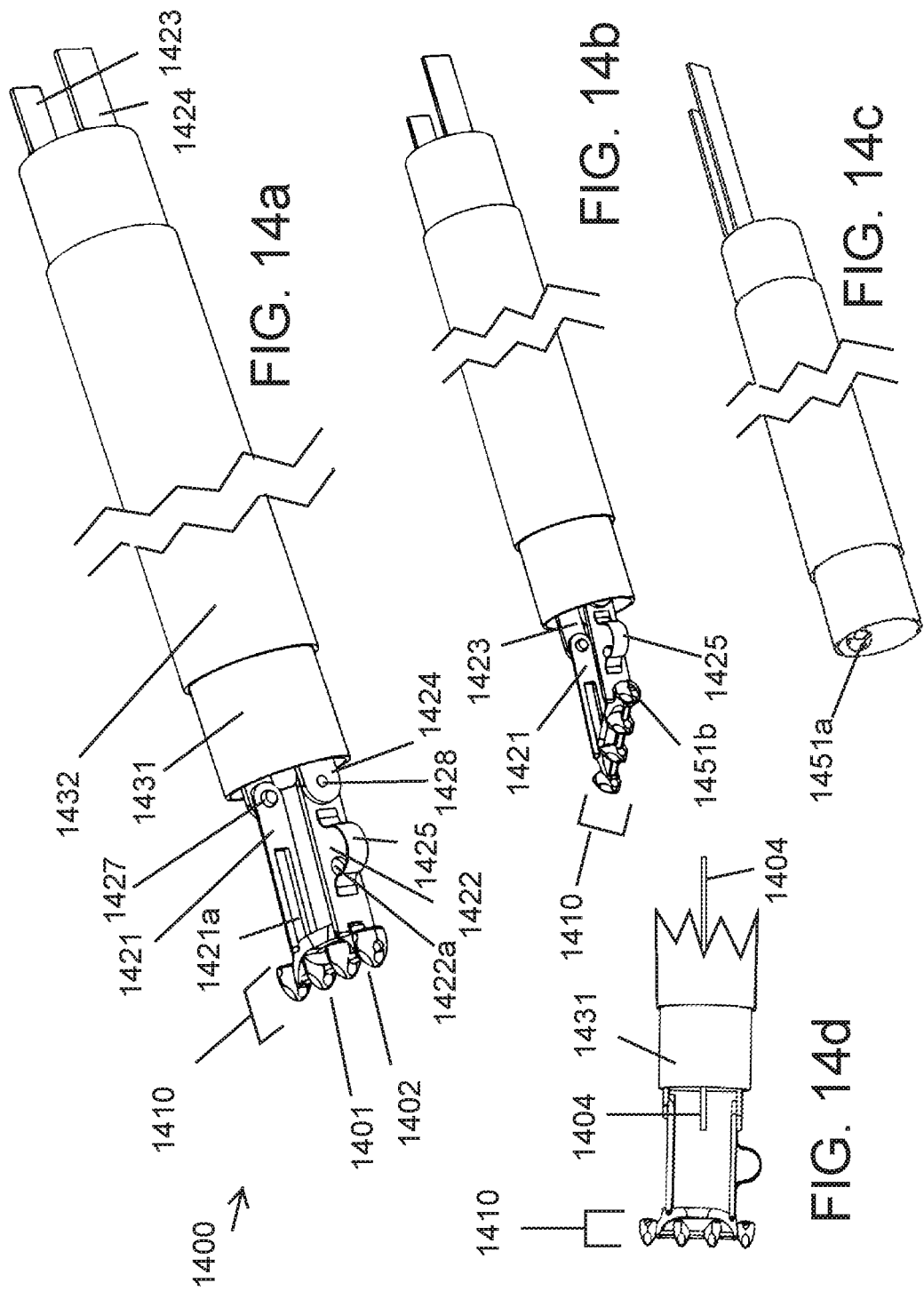

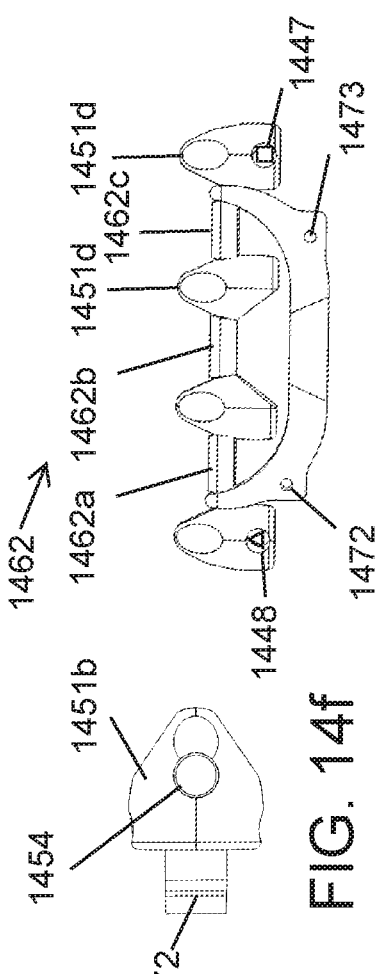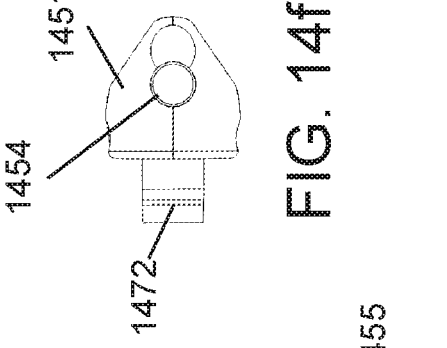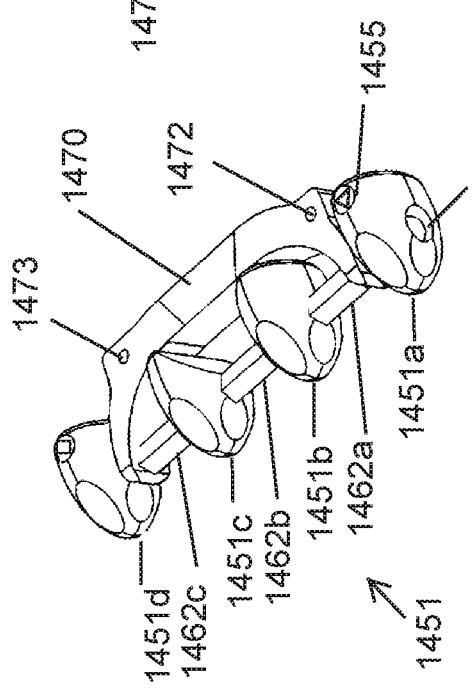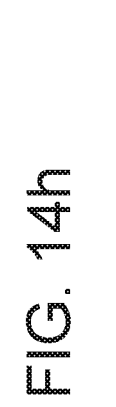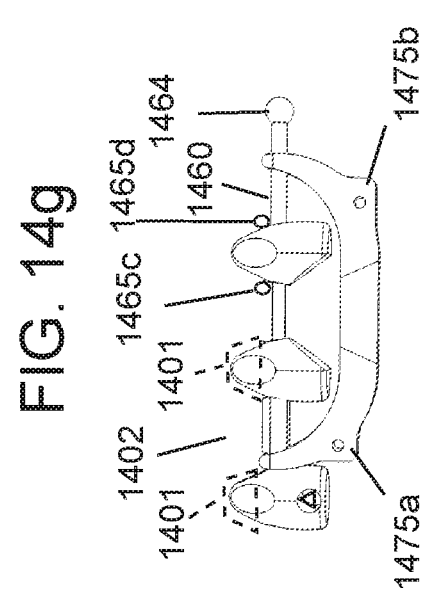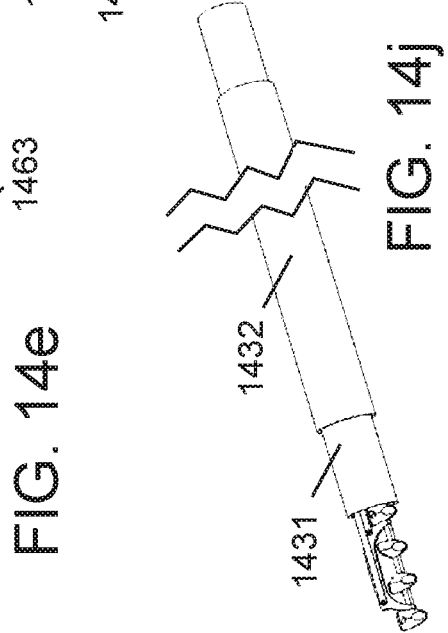

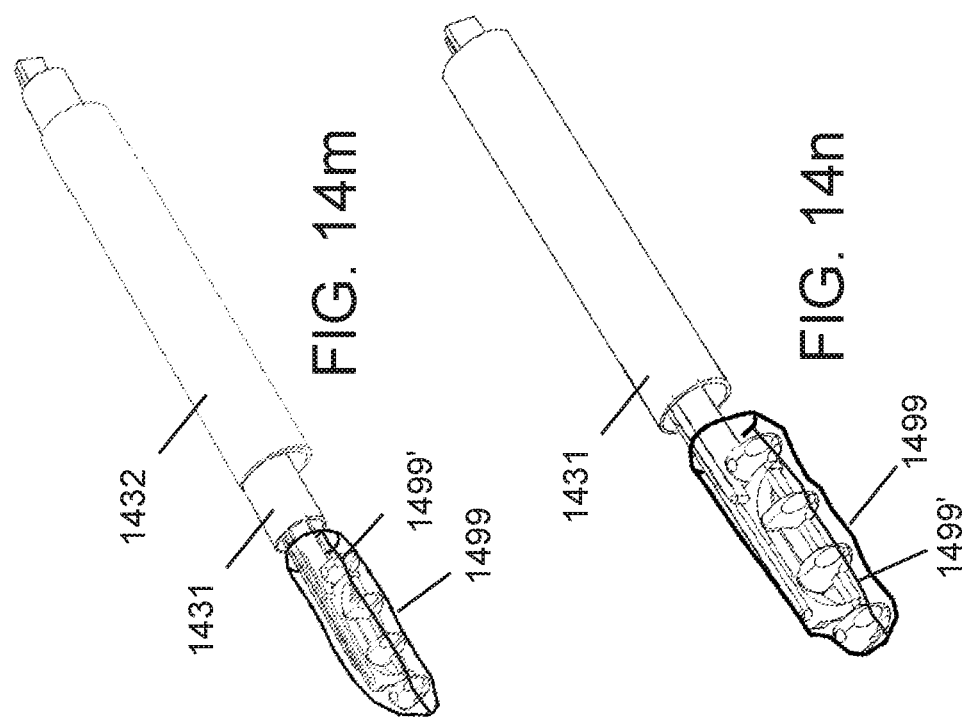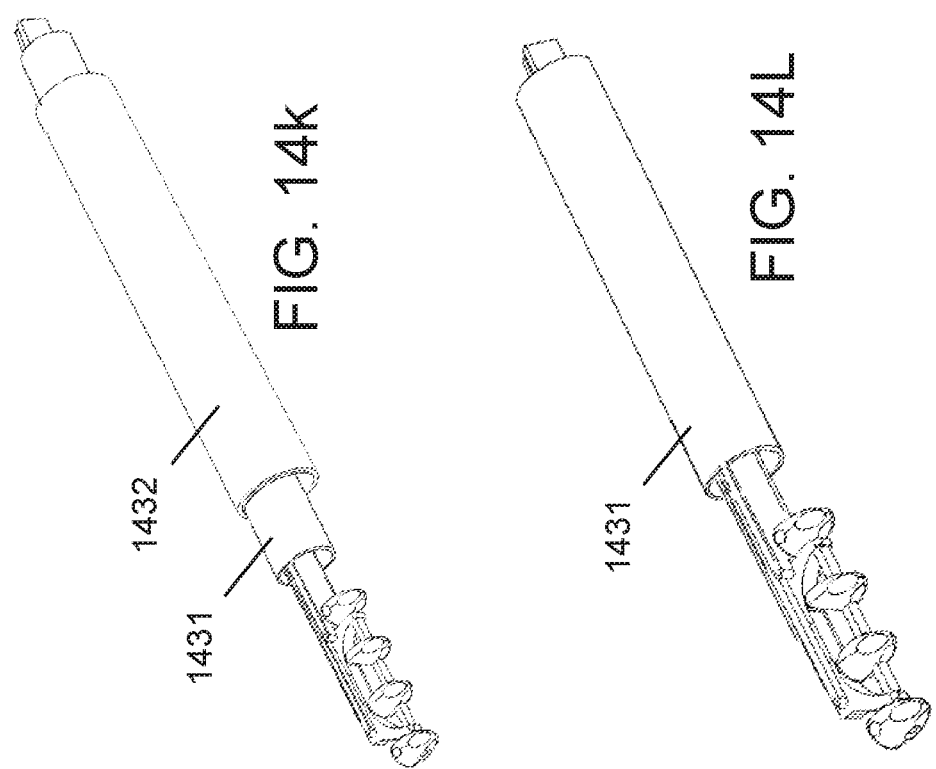

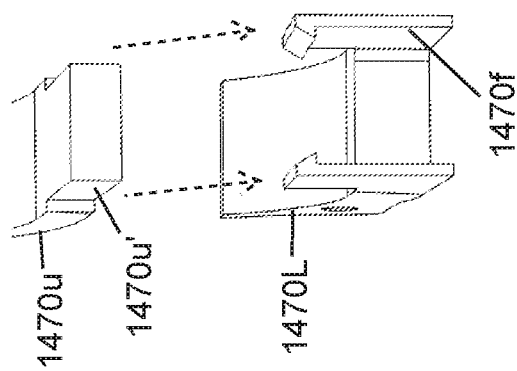
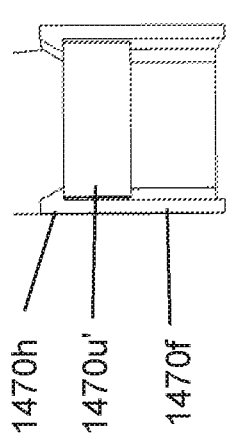
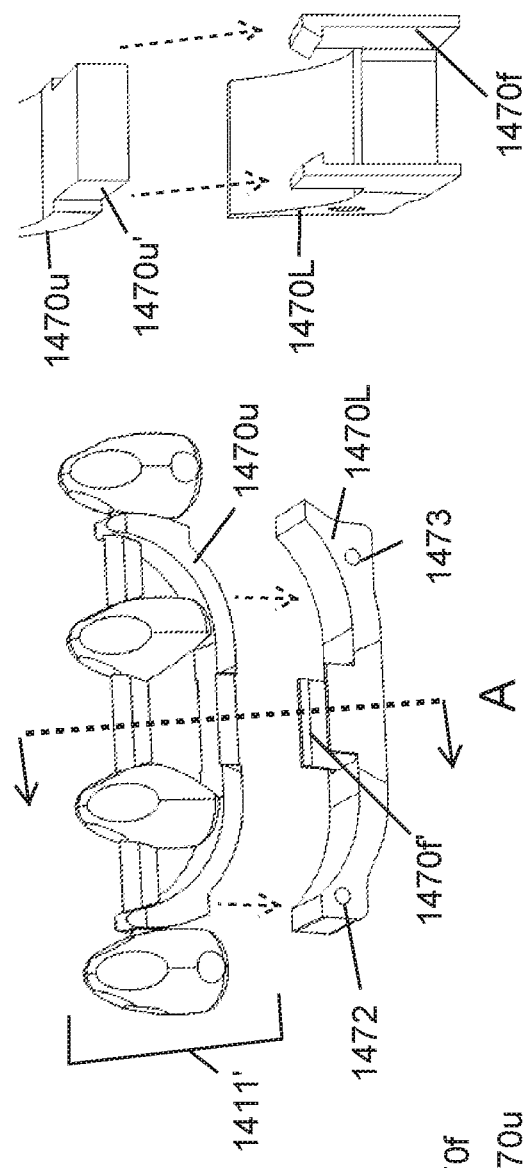
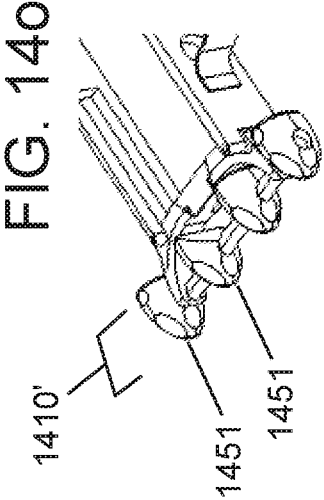
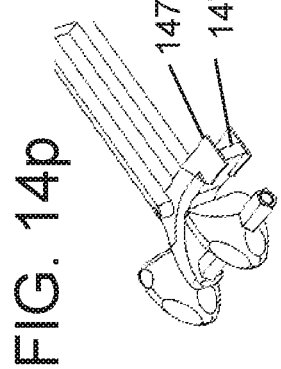
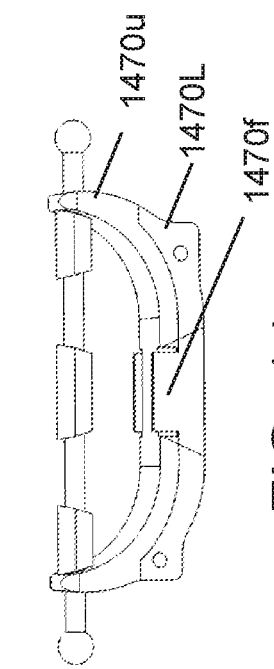

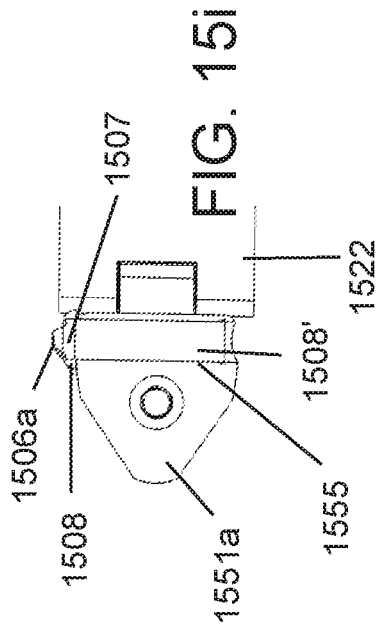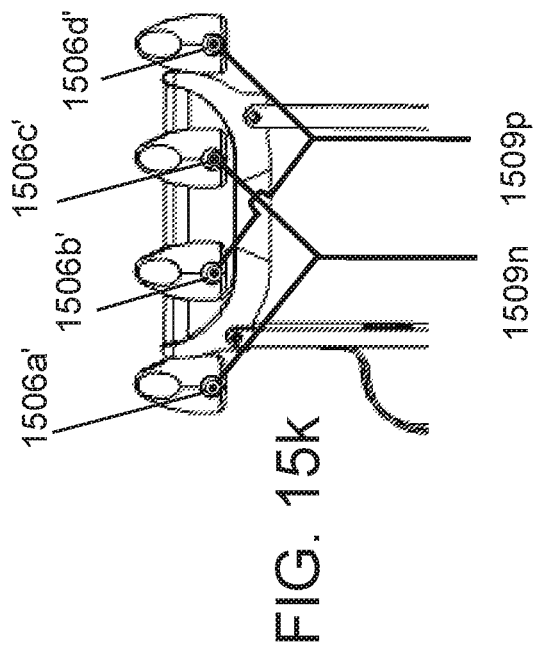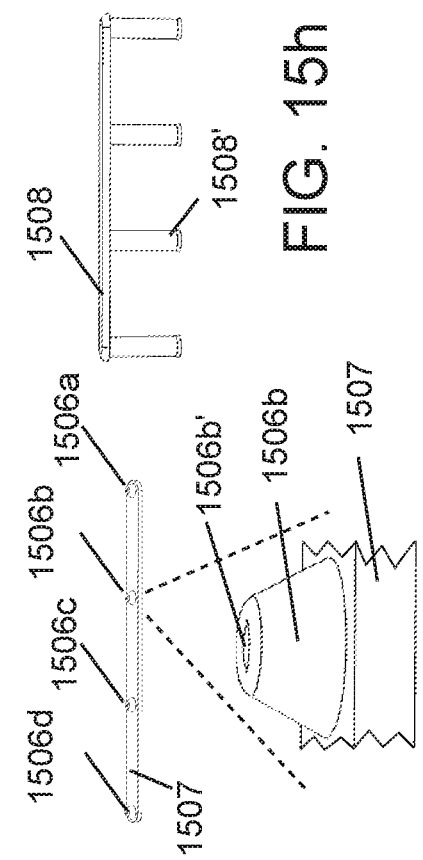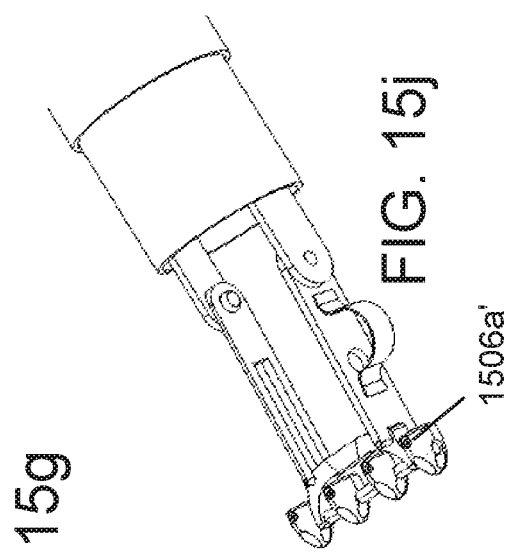

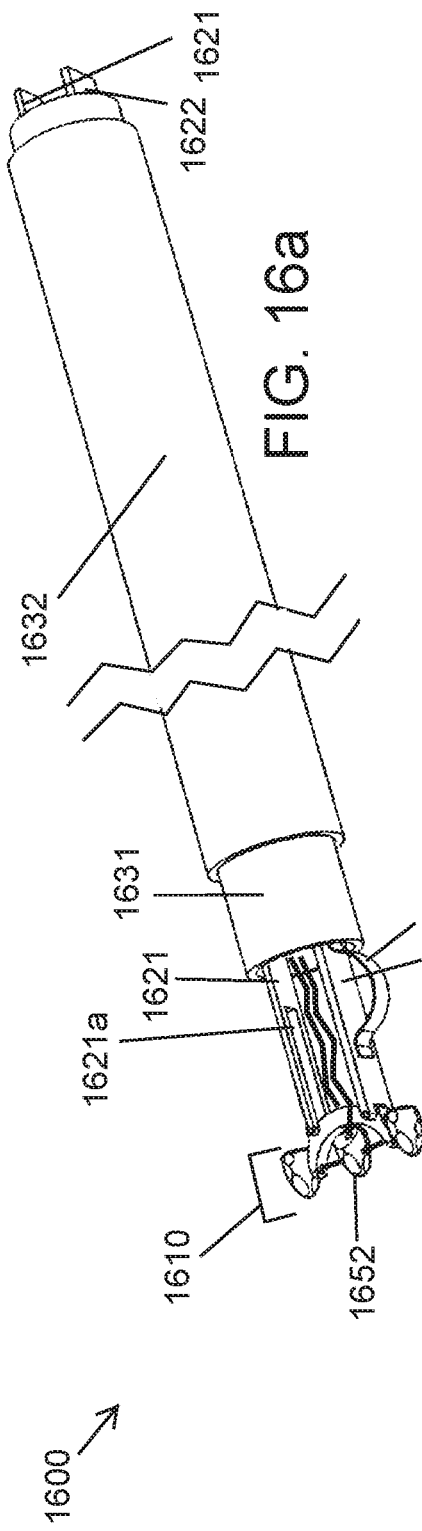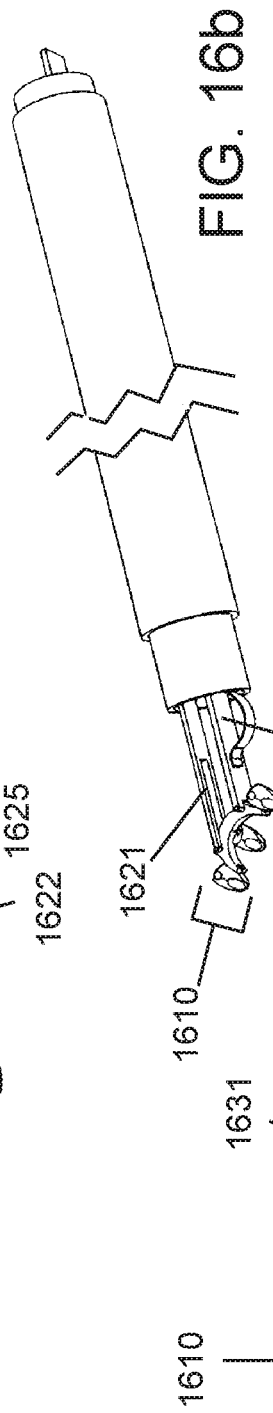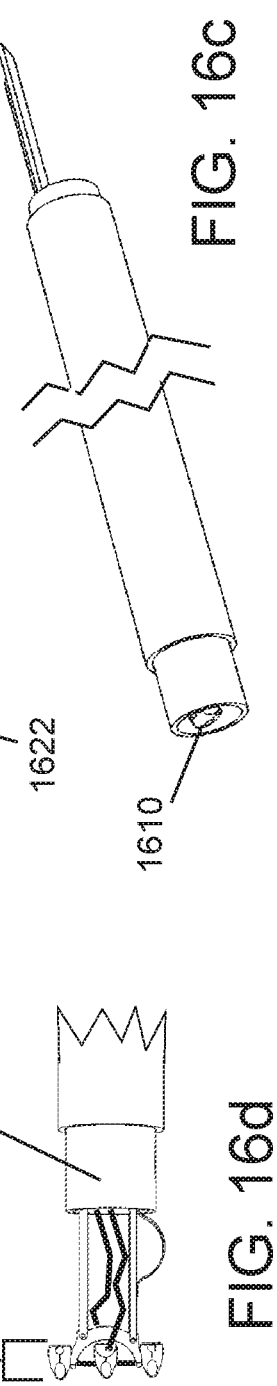

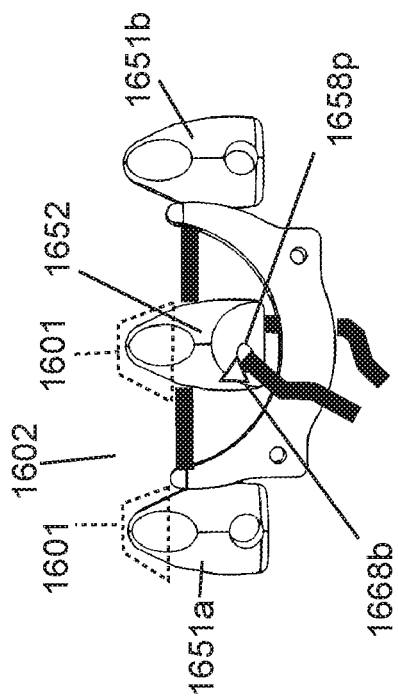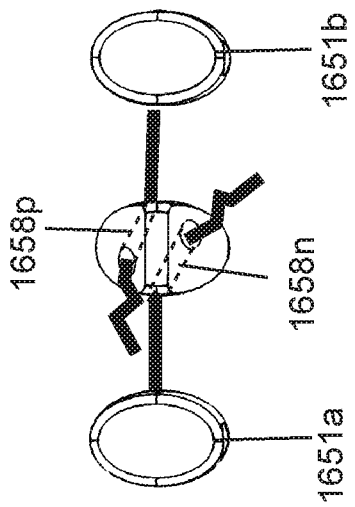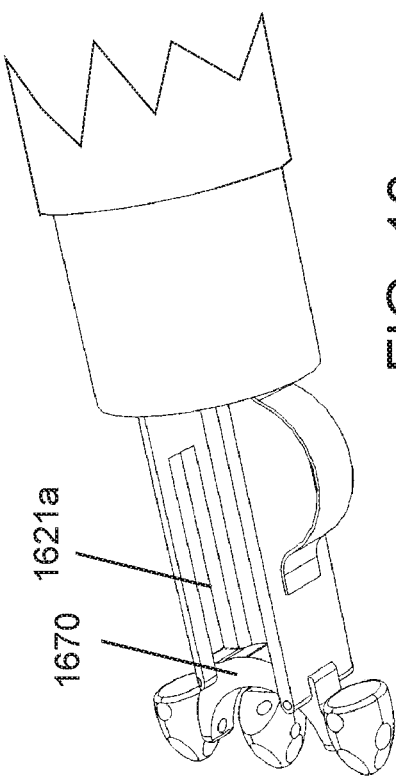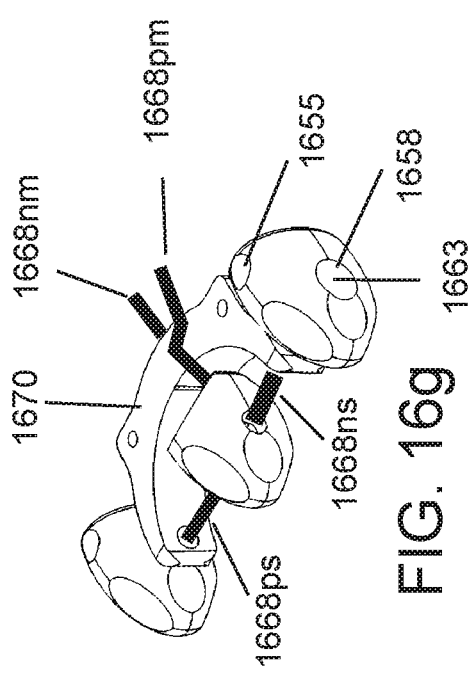

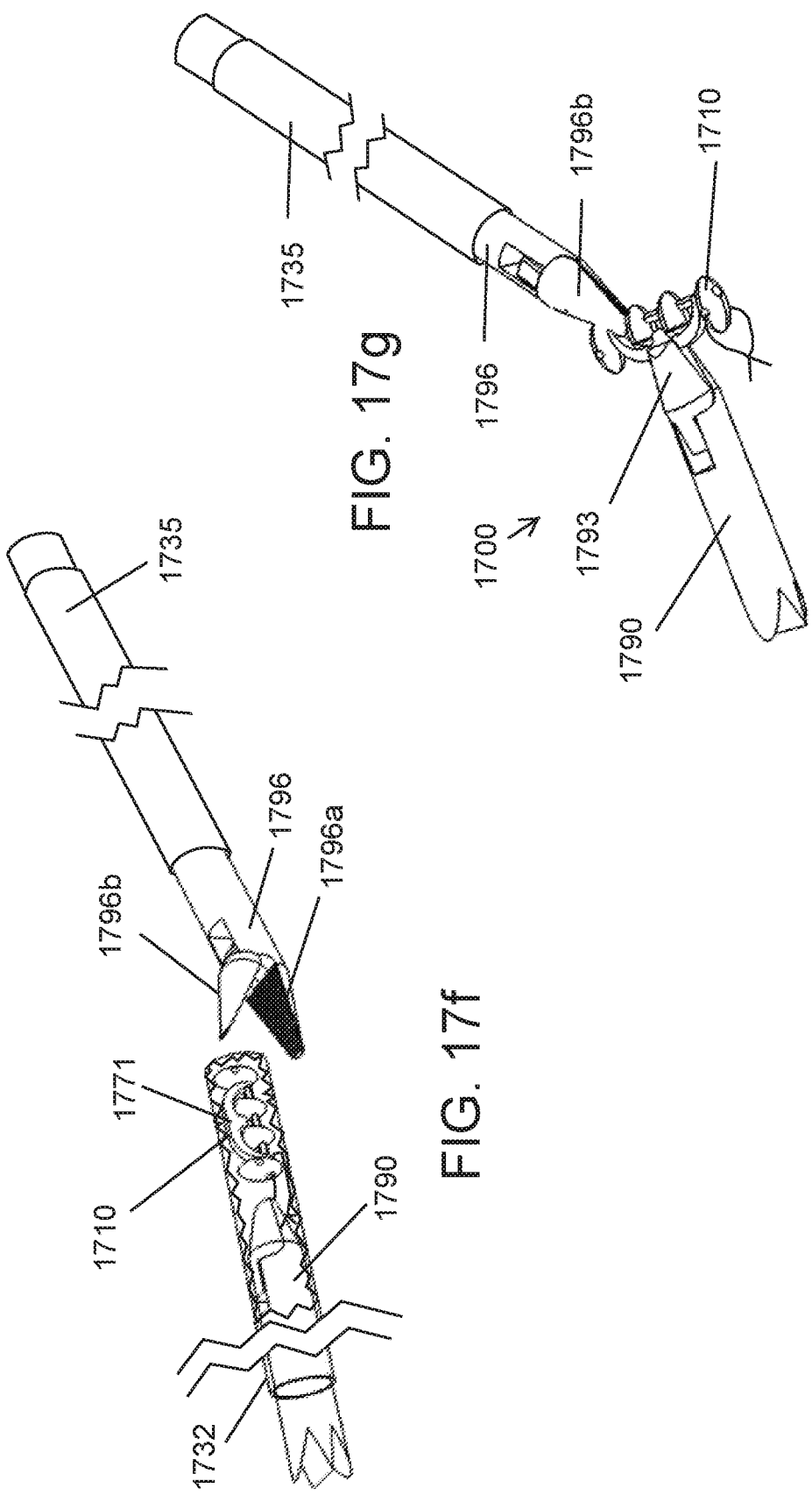

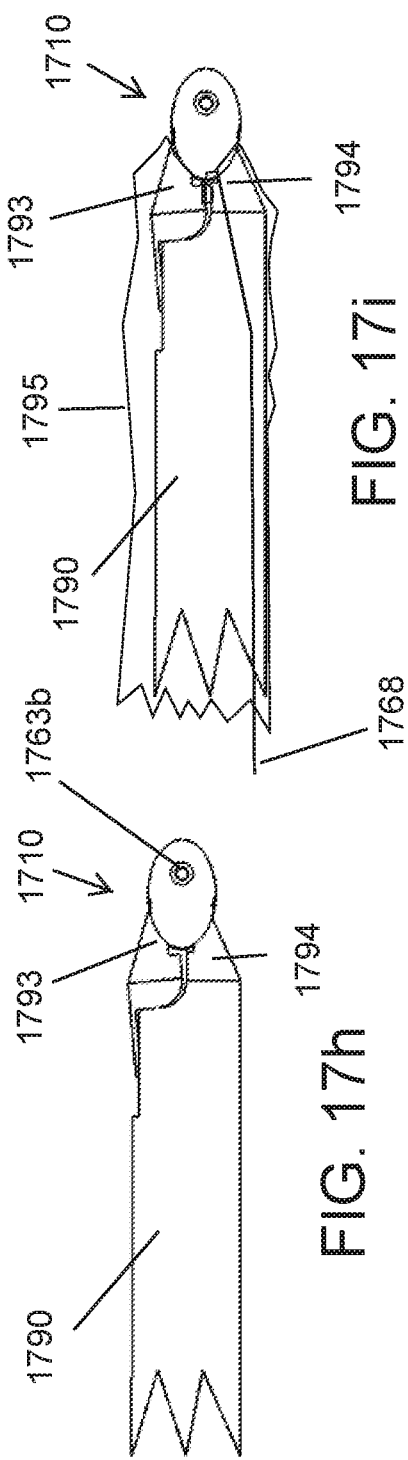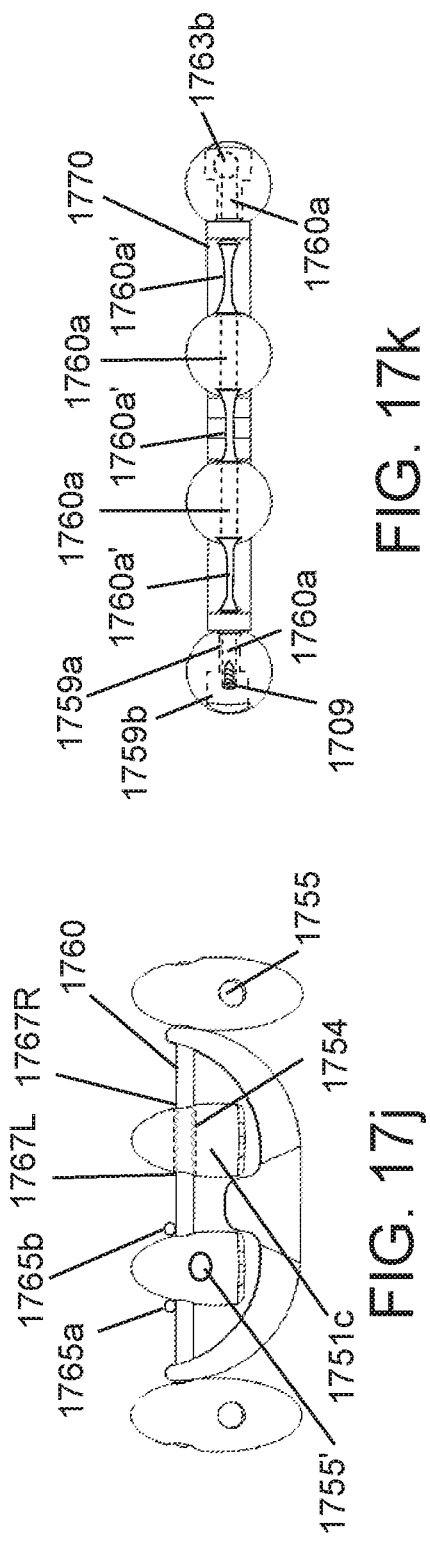

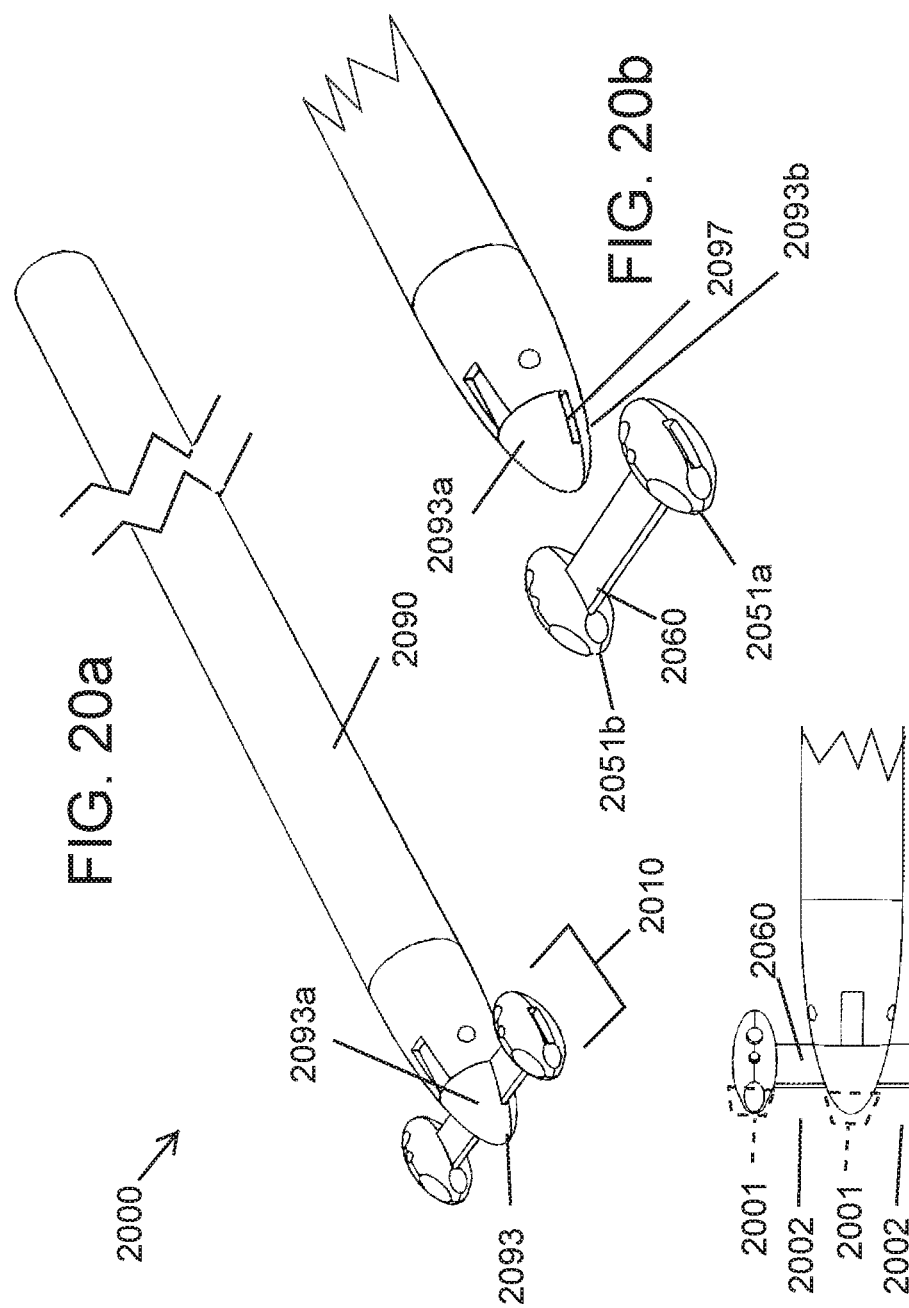

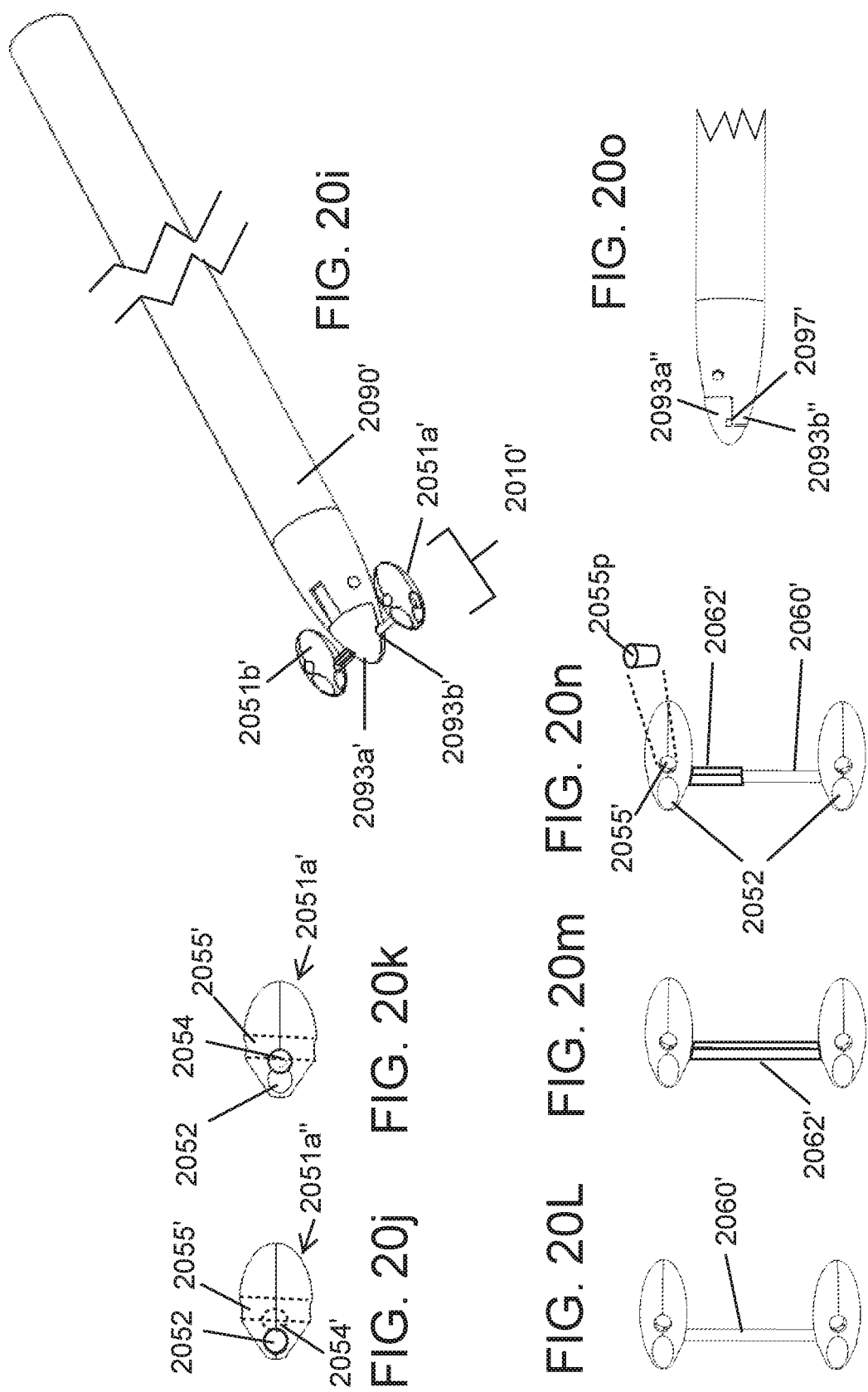

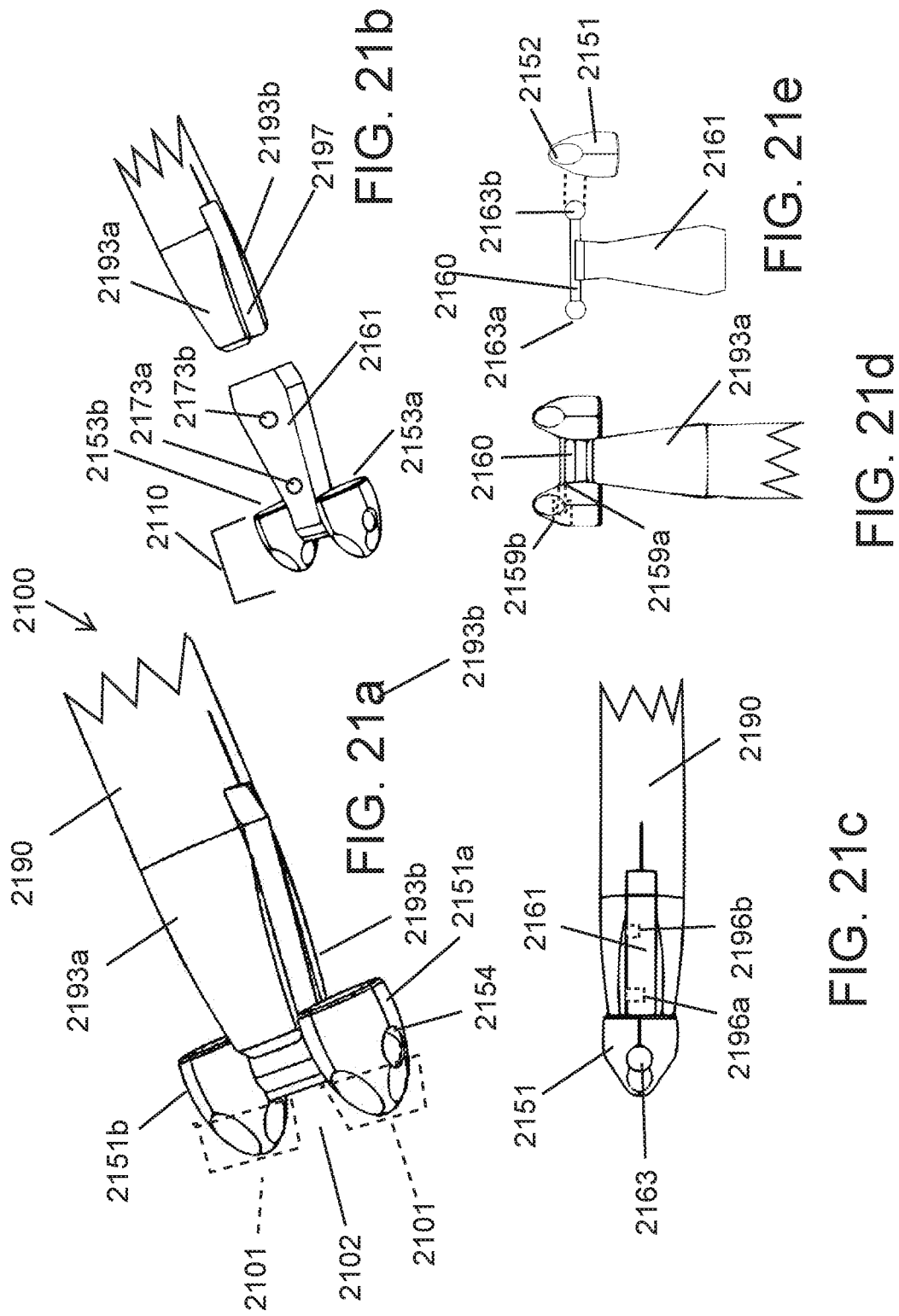

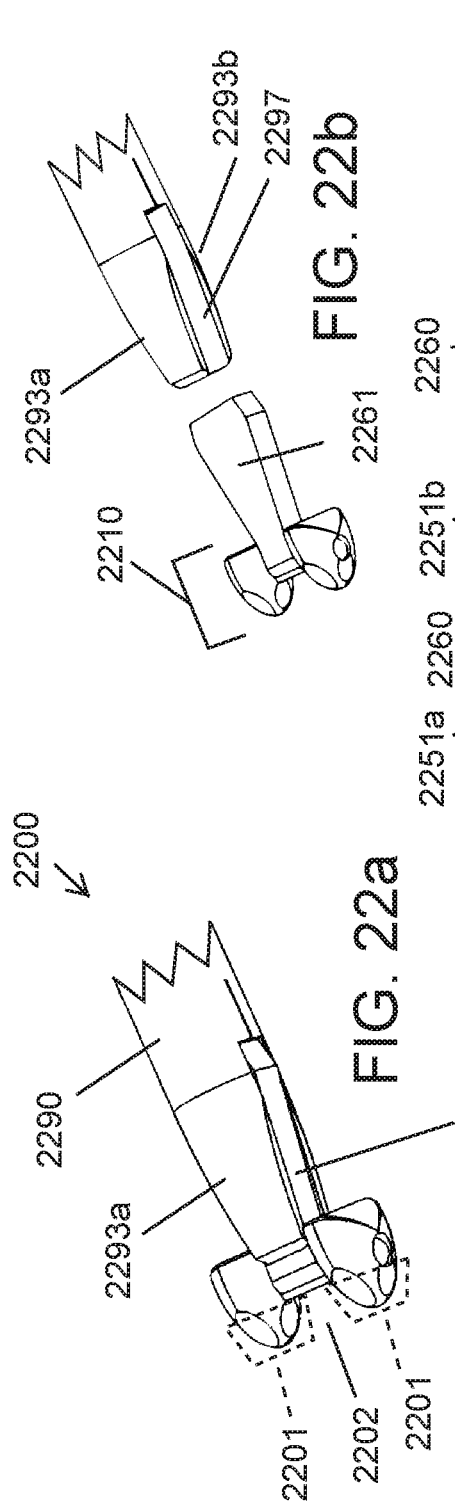

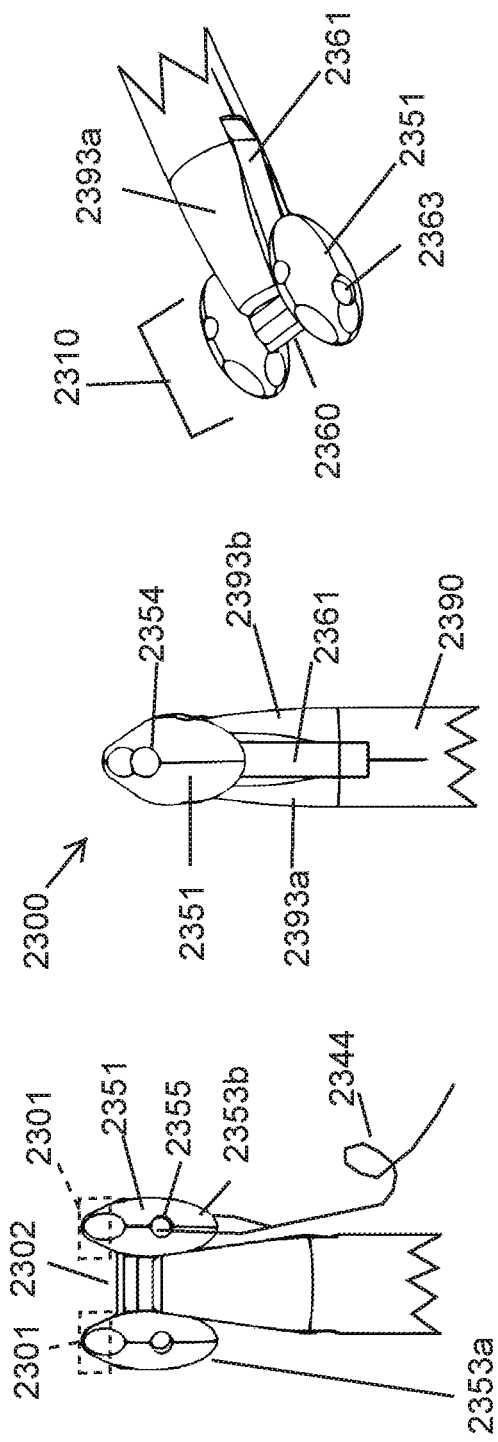
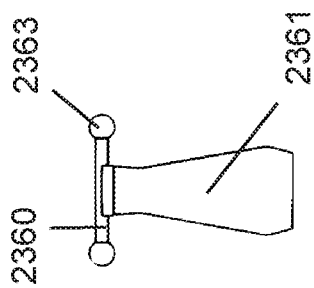
FIG. 23c
FIG. 23b
FIG. 23d
FIG. 23a

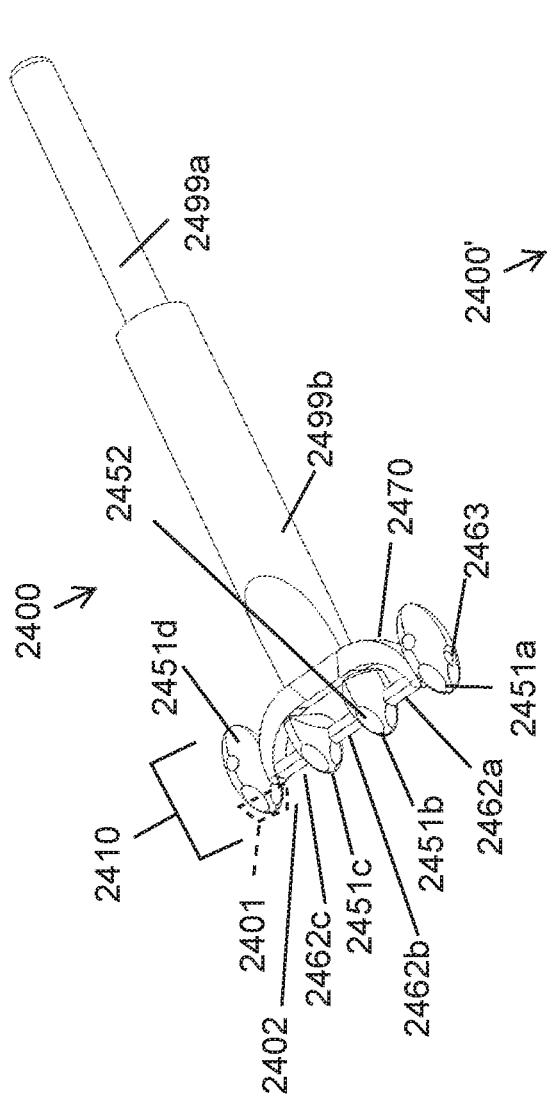
FIG. 24a
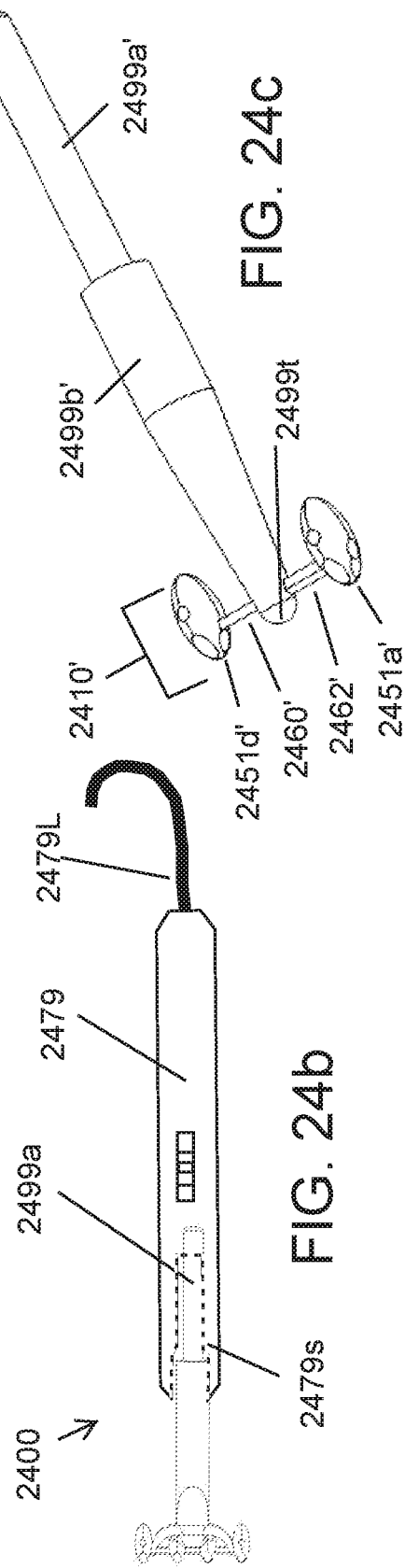
FIG. 24b
FIG. 24c

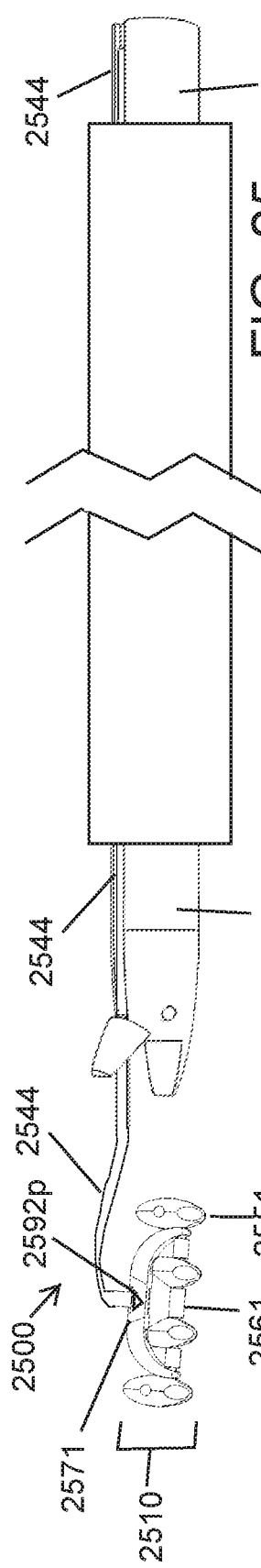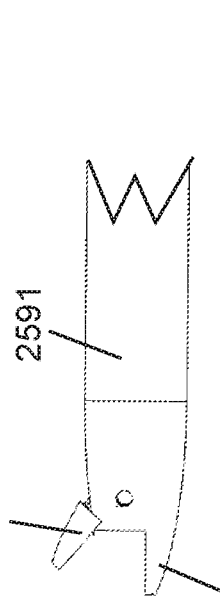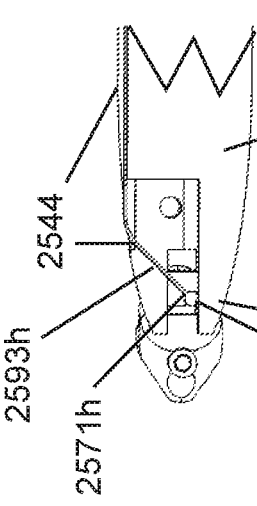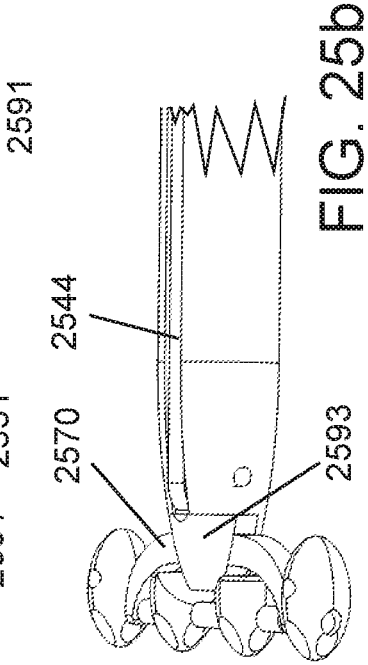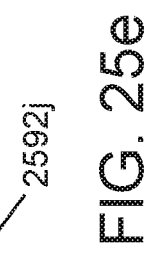
FIG. 25a
FIG. 25b
FIG. 25c
FIG. 25d
FIG. 25e

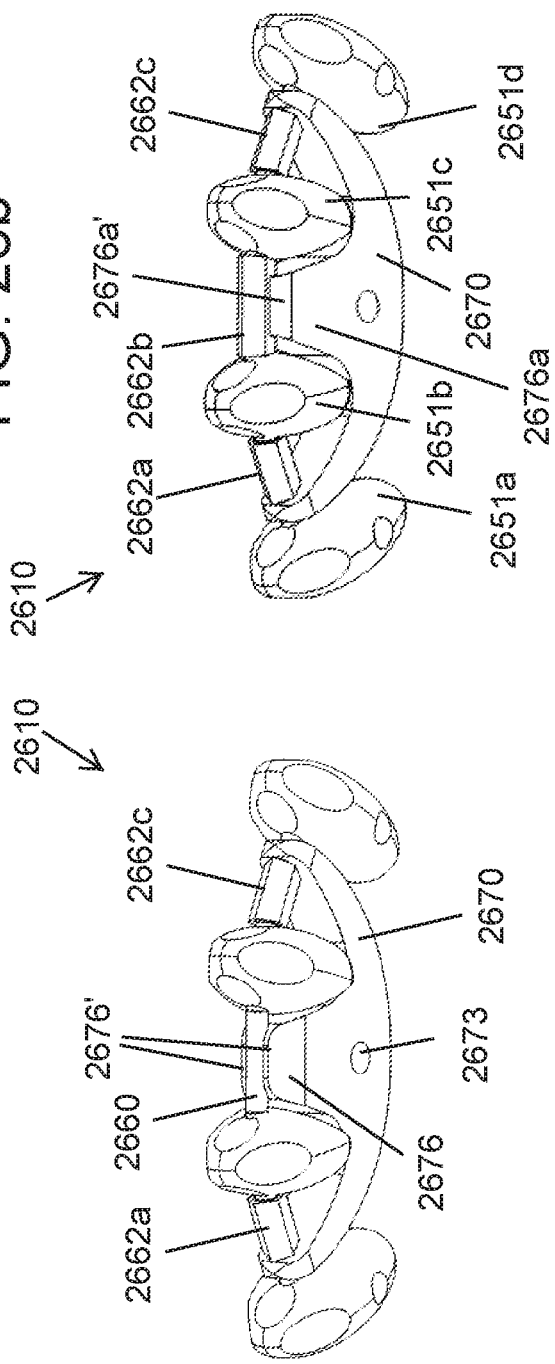

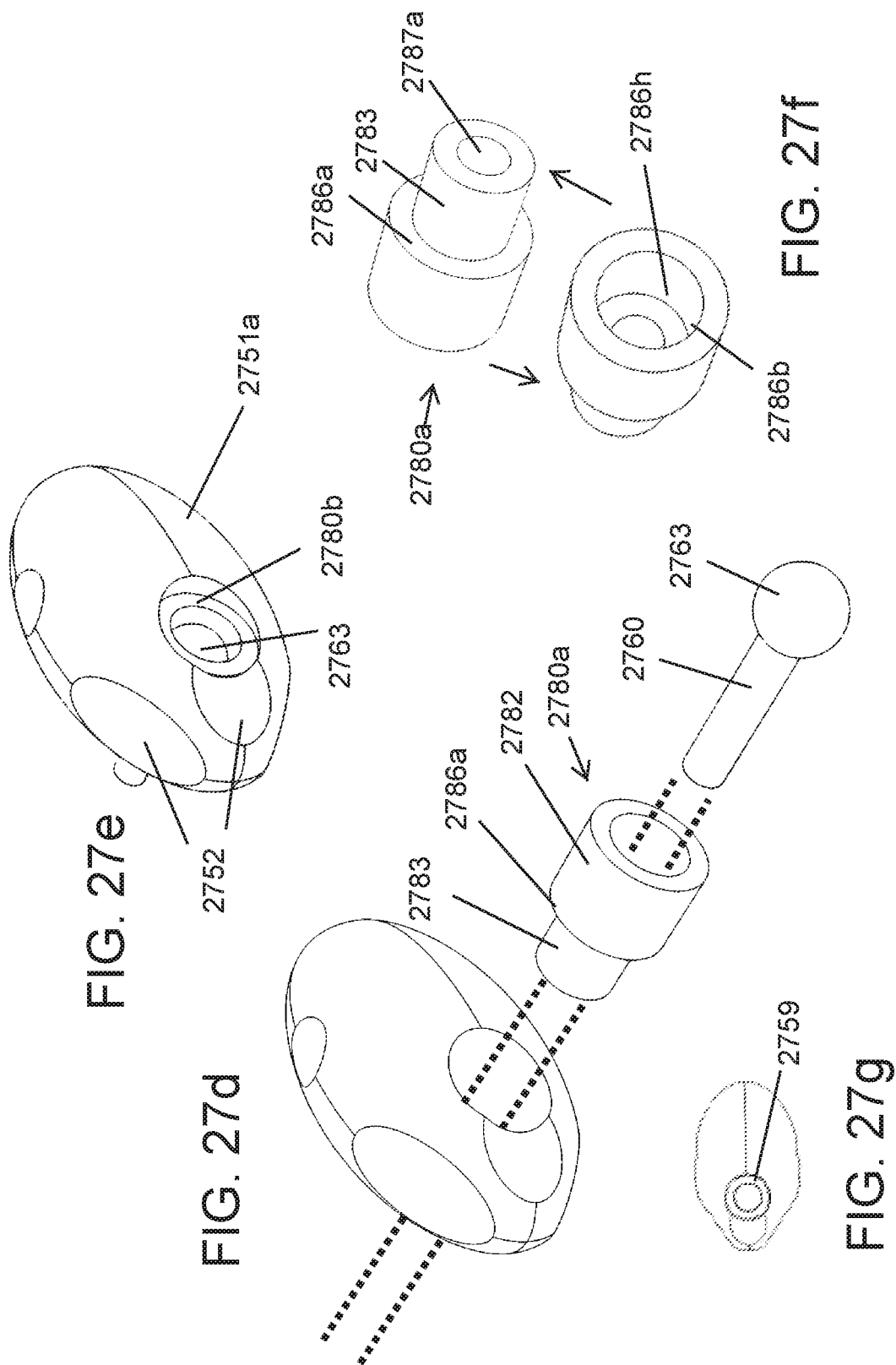

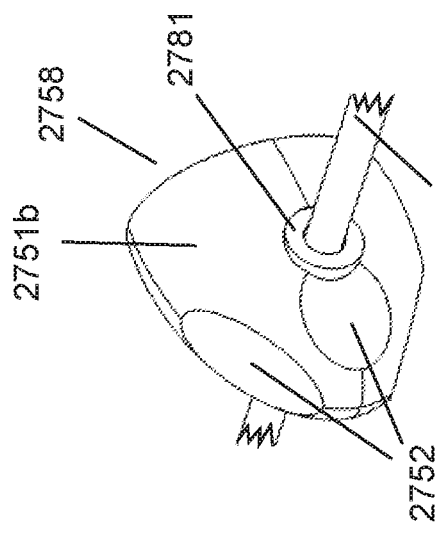
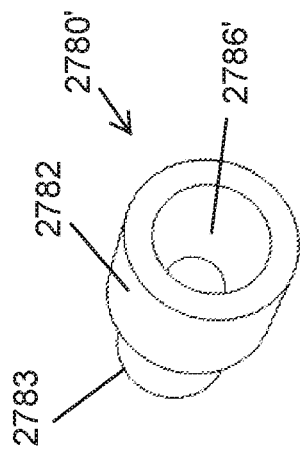
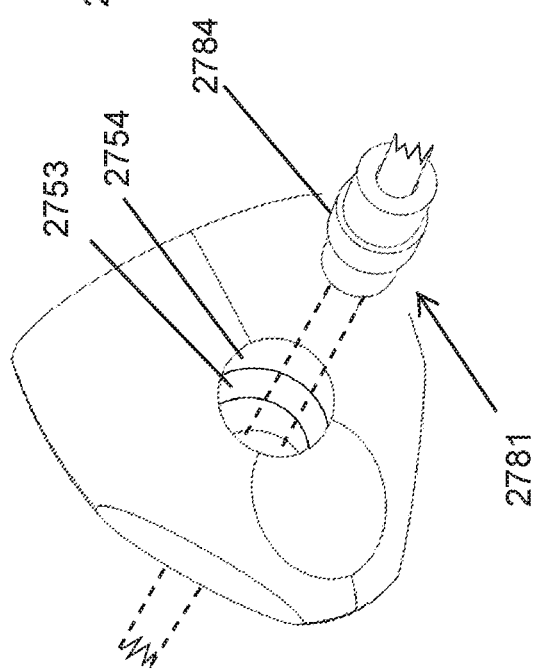
FIG. 27h
FIG. 27j
FIG. 27i

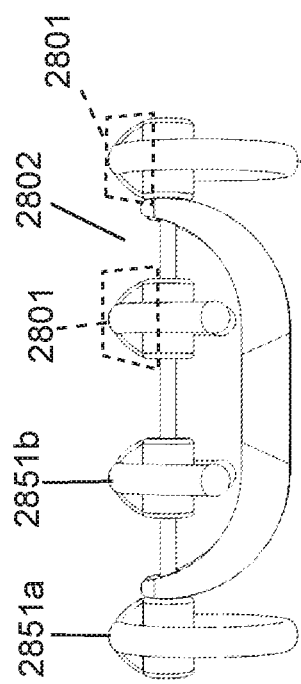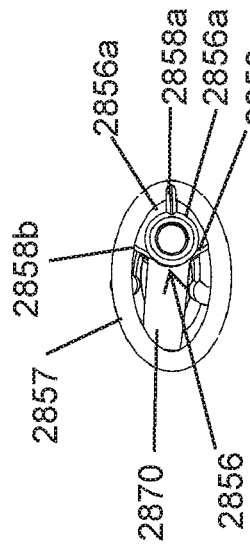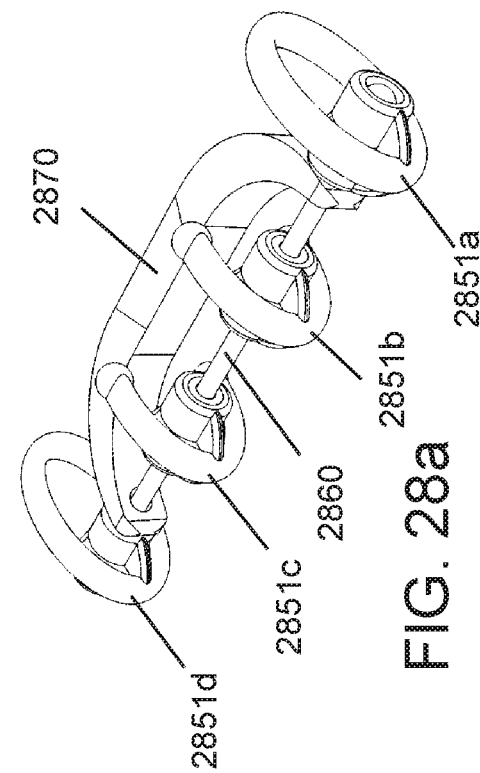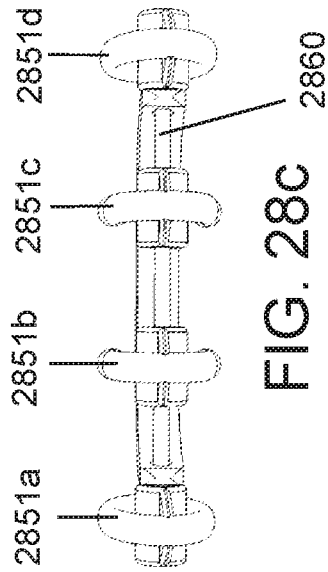

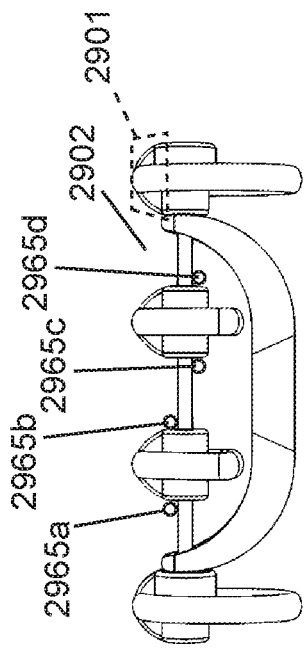
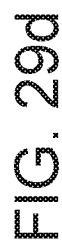
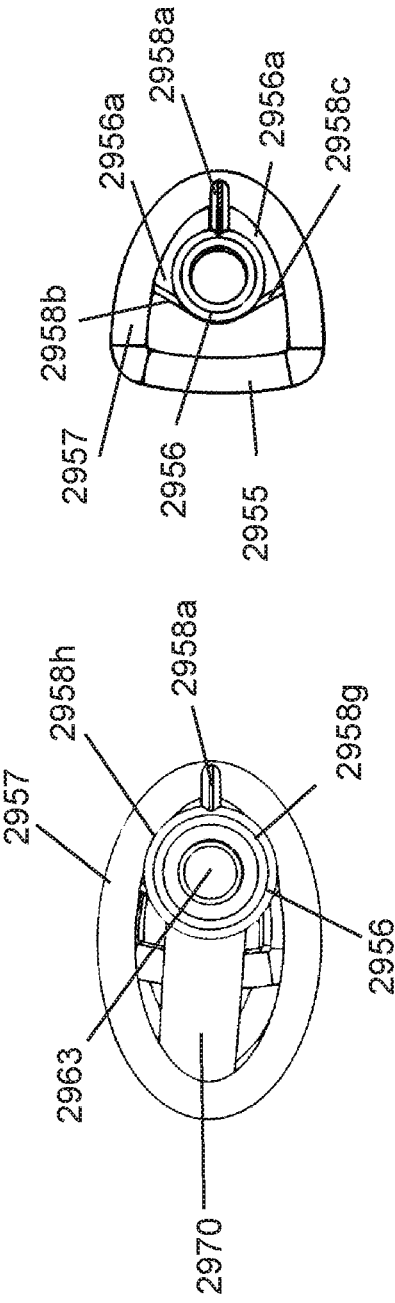
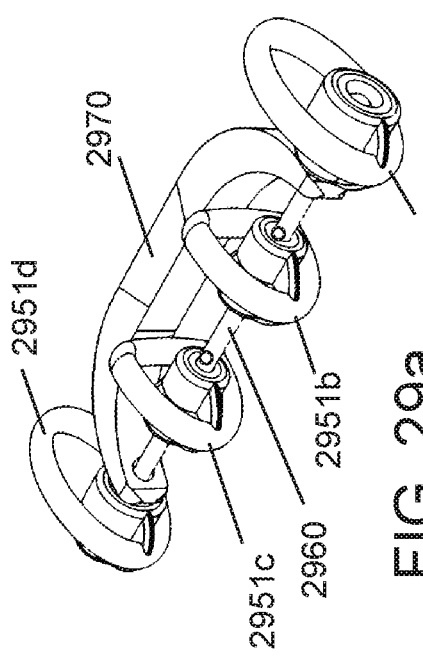

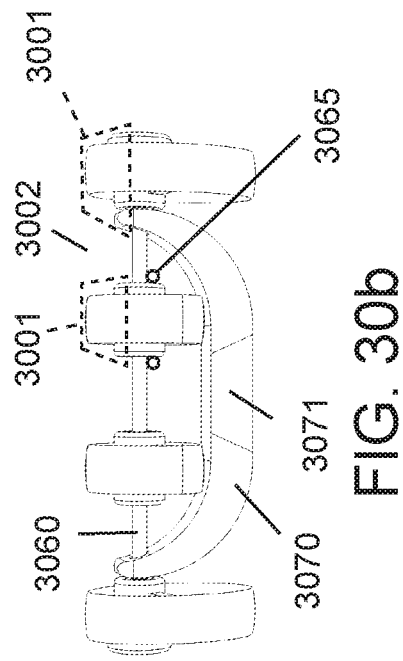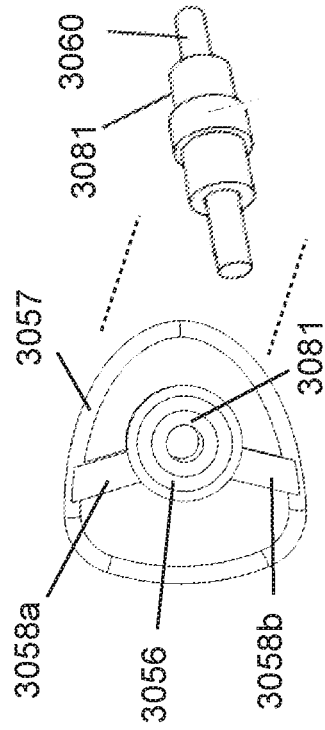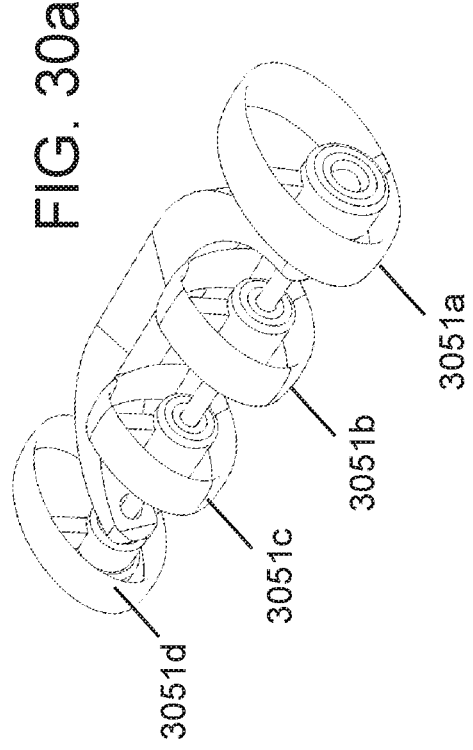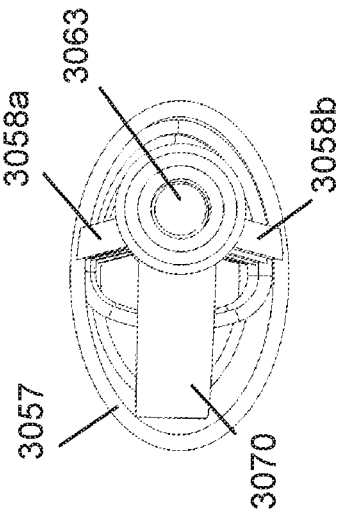
FIG. 30a
FIG. 30b
FIG. 30c
FIG. 30d

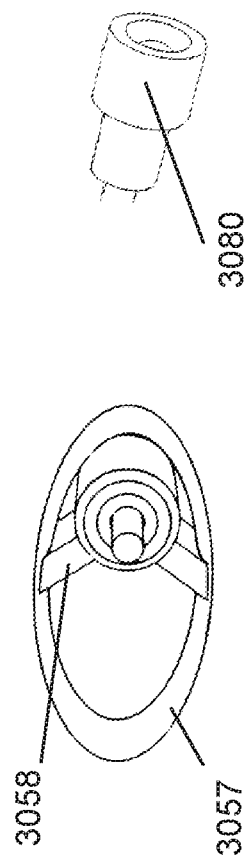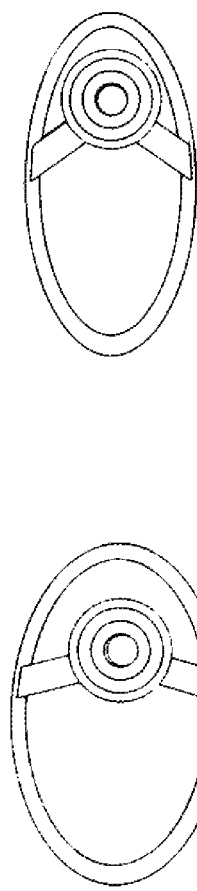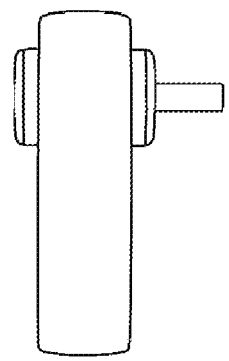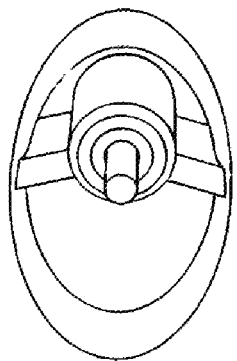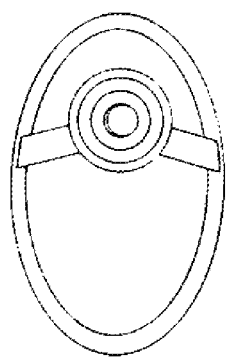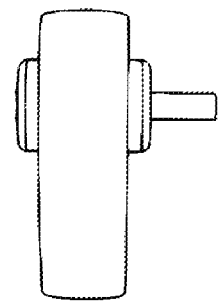

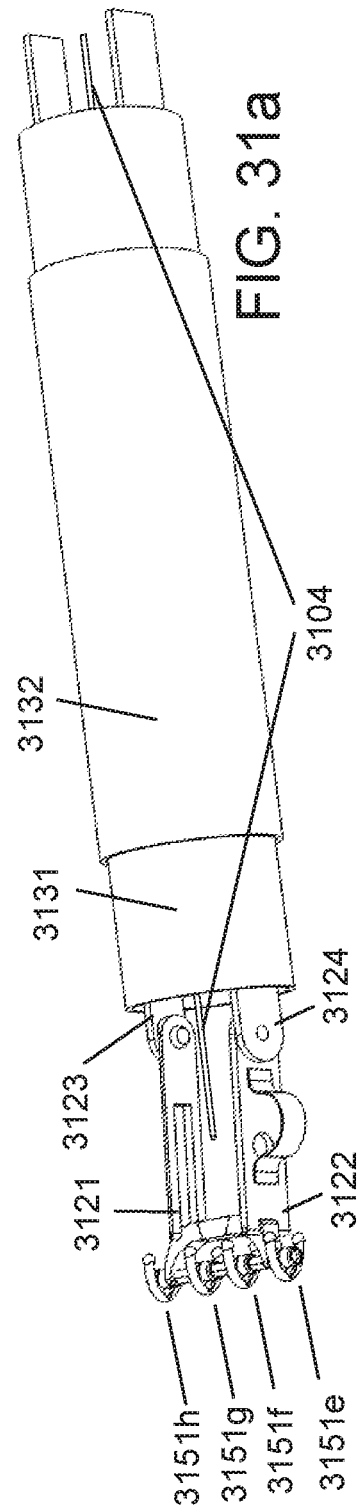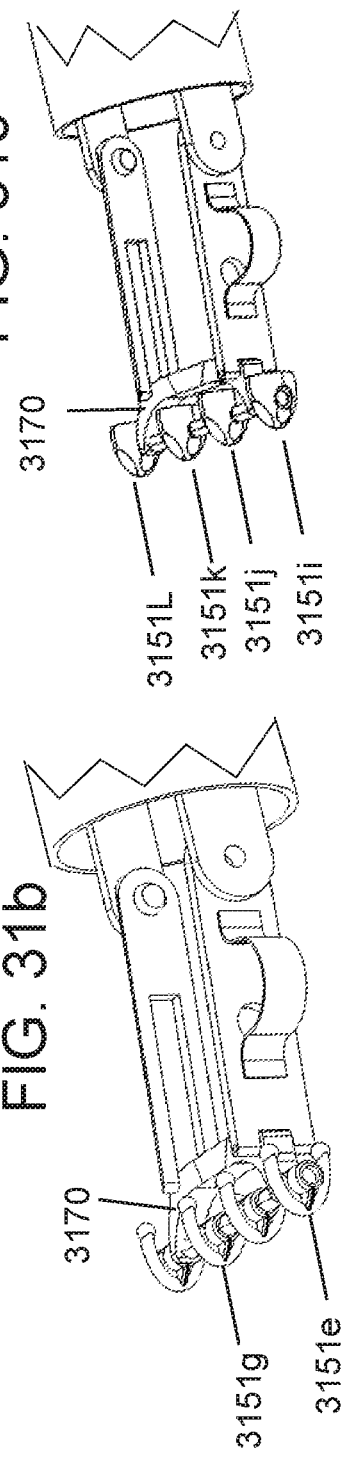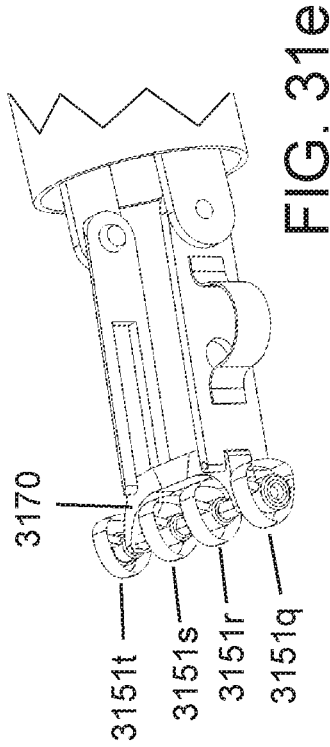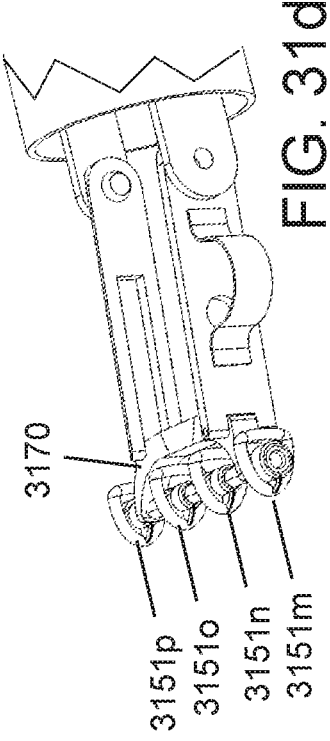

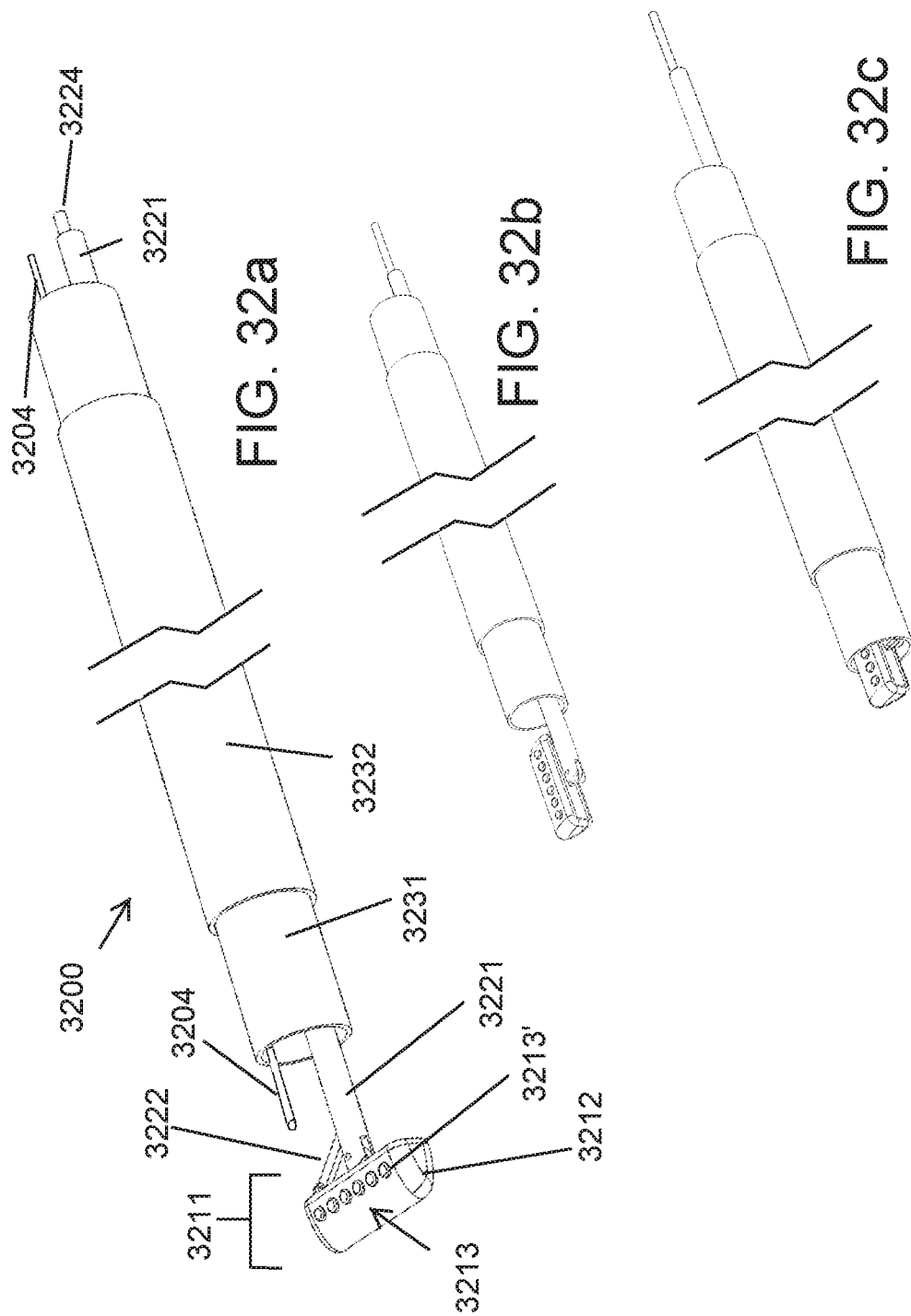

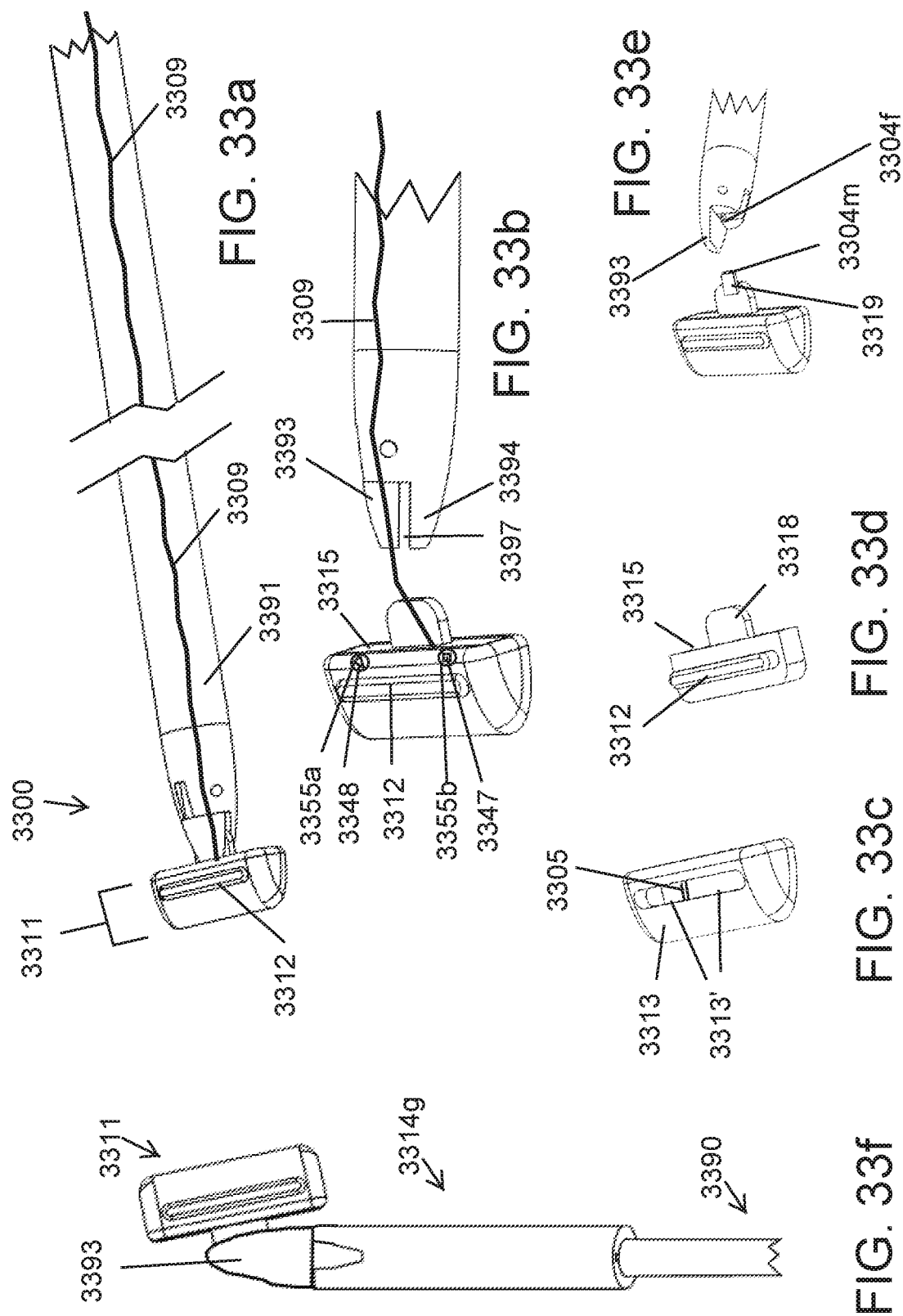

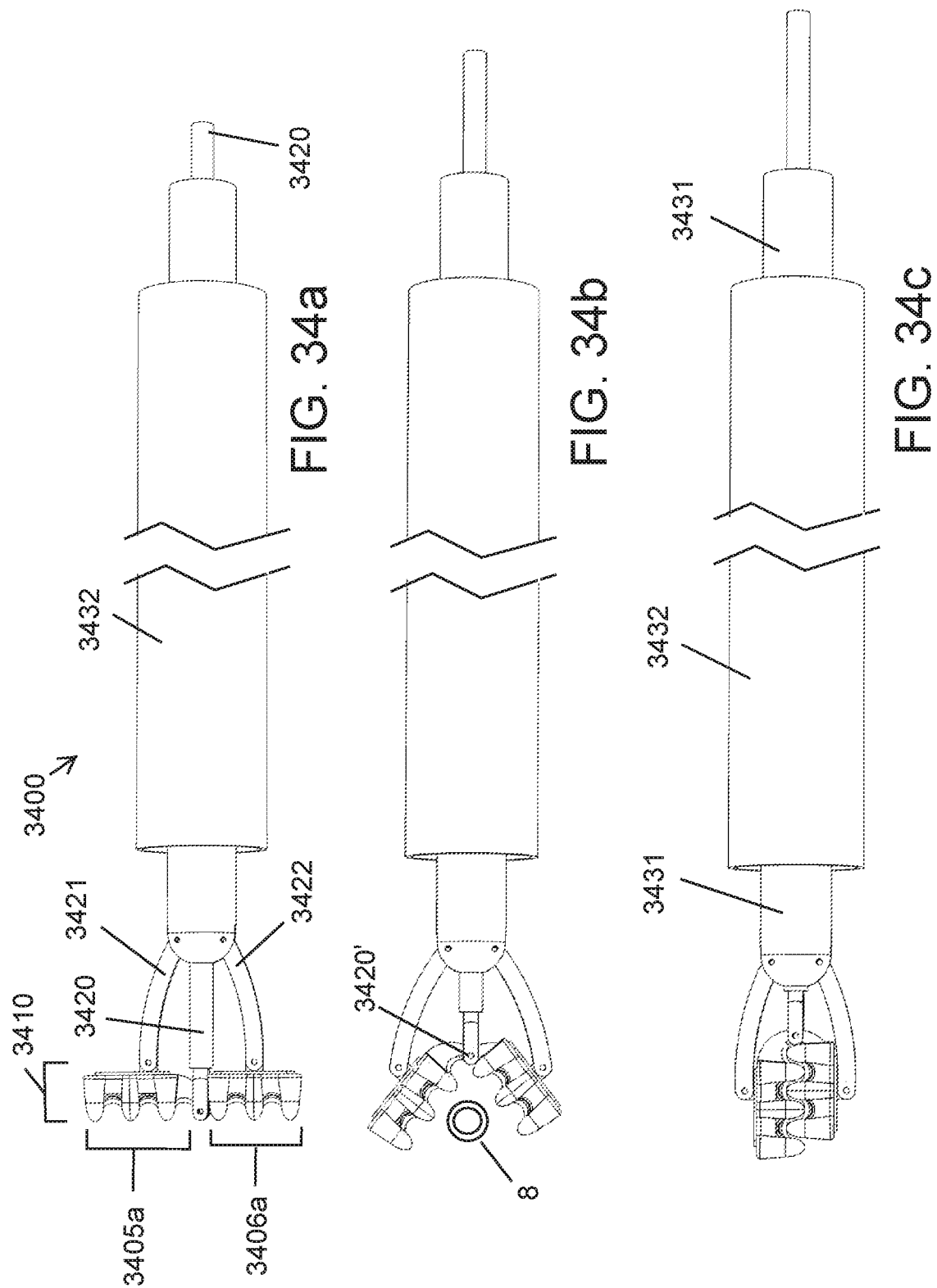

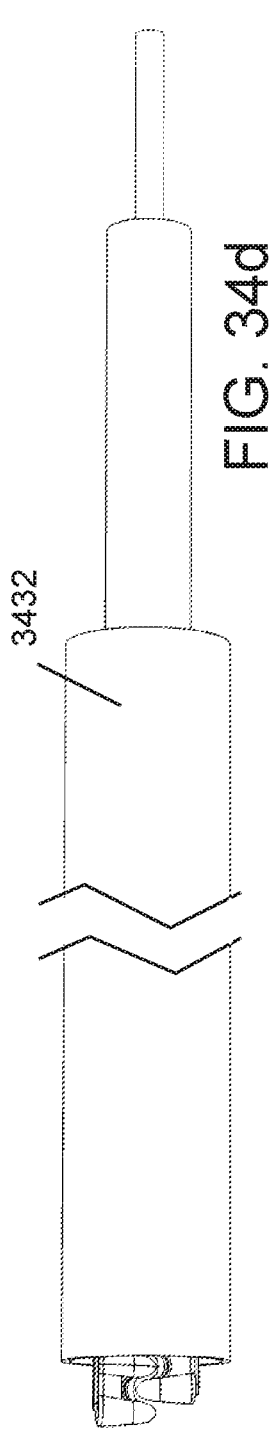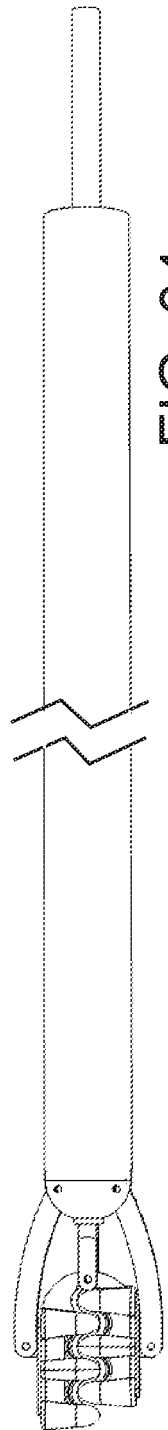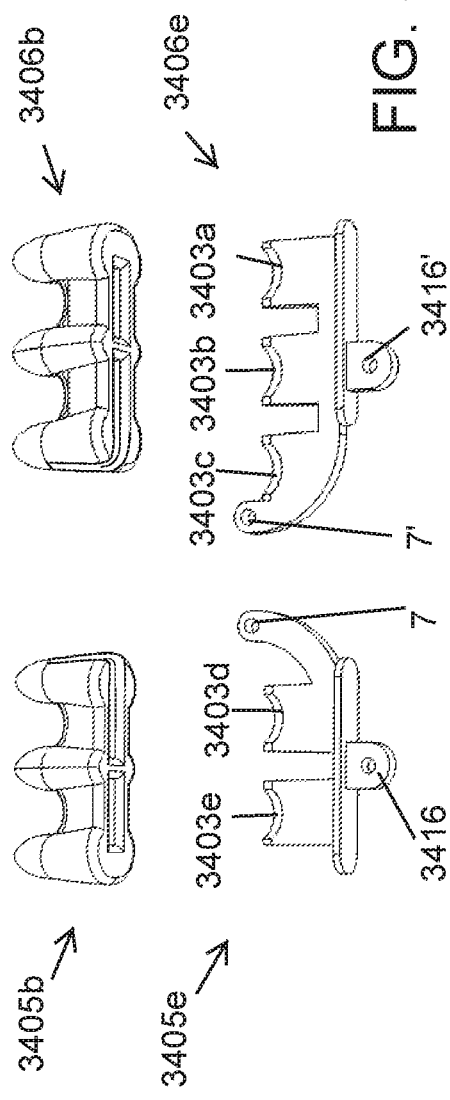

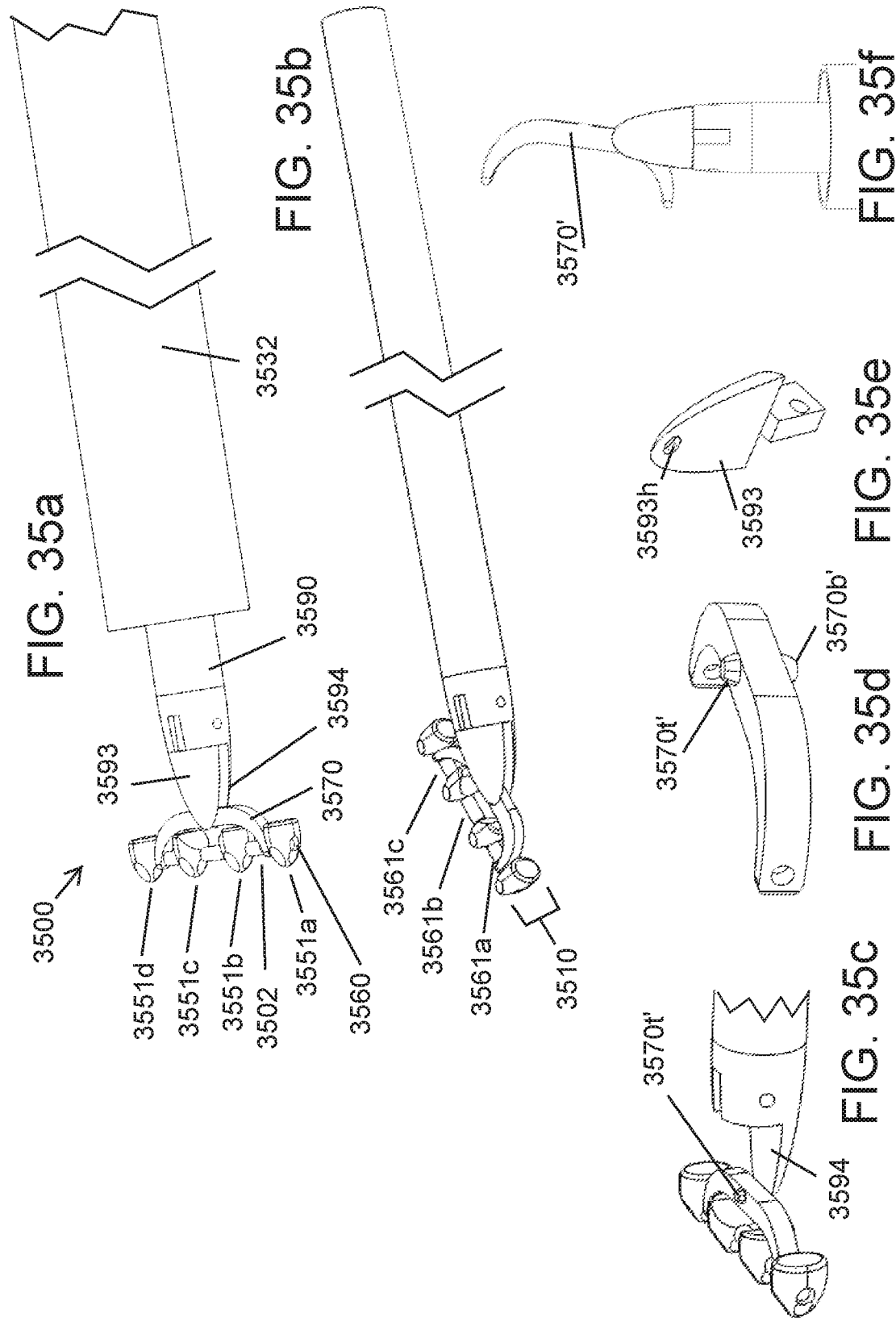

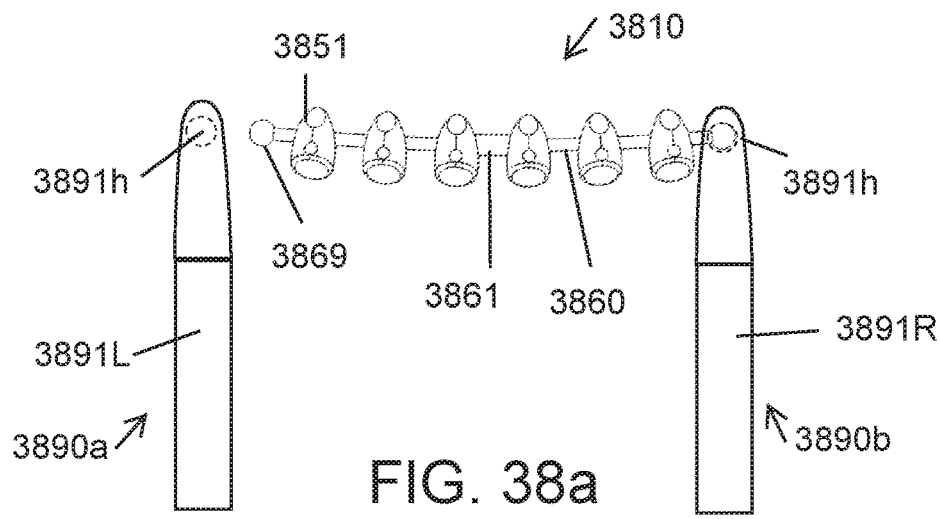
FIG. 38a
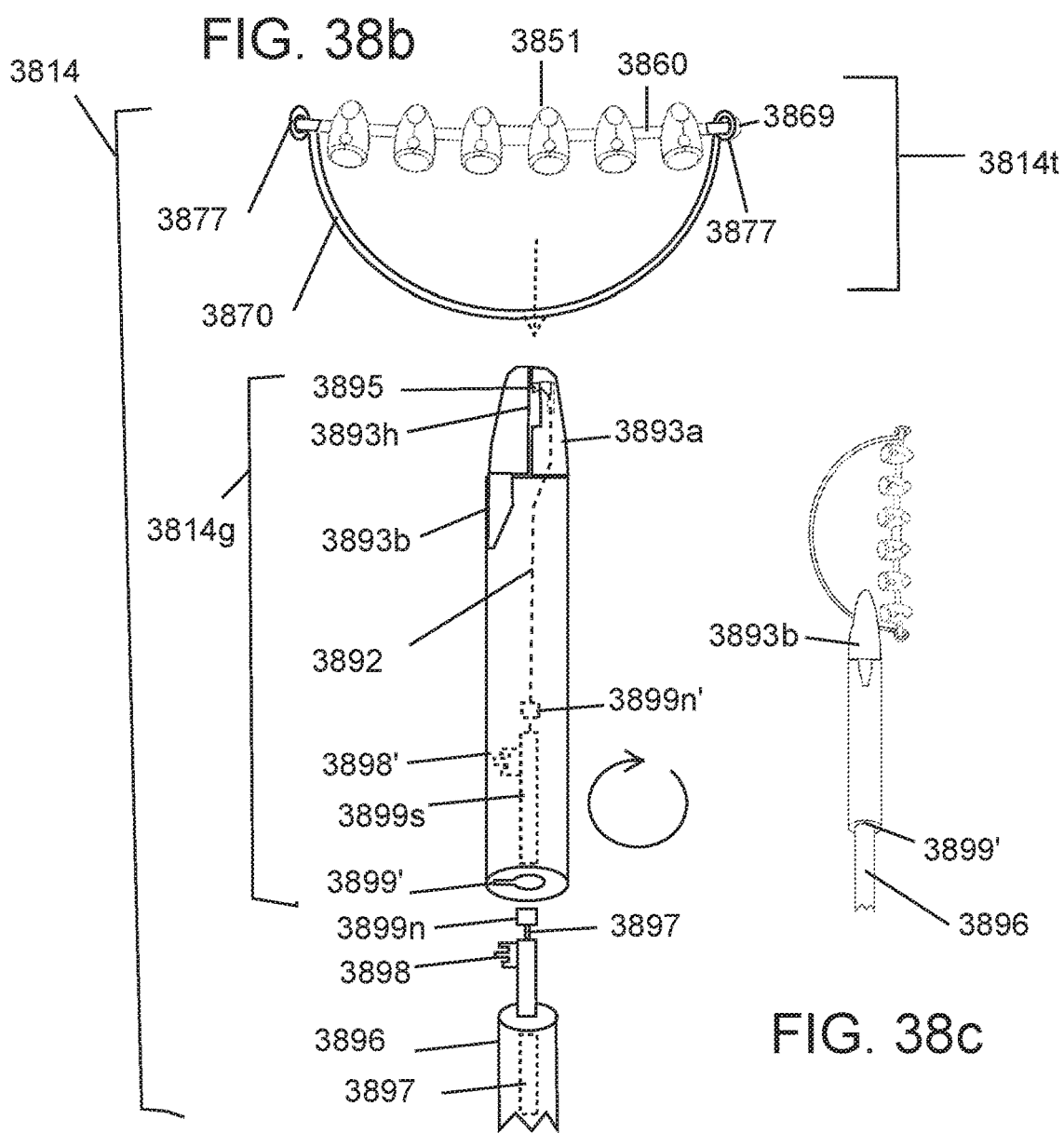
FIG. 38b
FIG. 38c

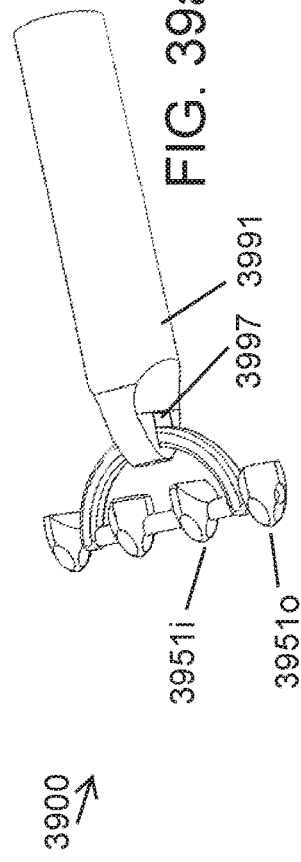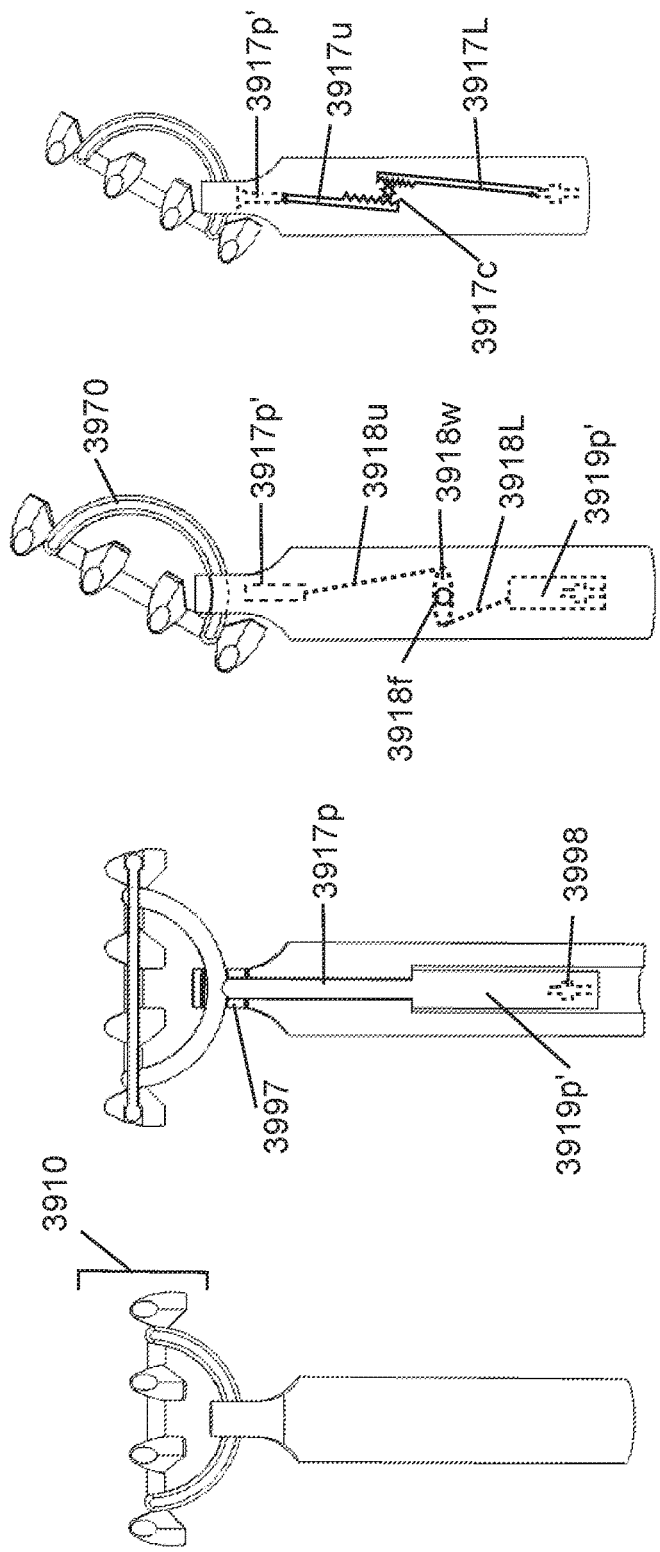
FIG. 39a
FIG. 39b
FIG. 39c
FIG. 39d
FIG. 39e

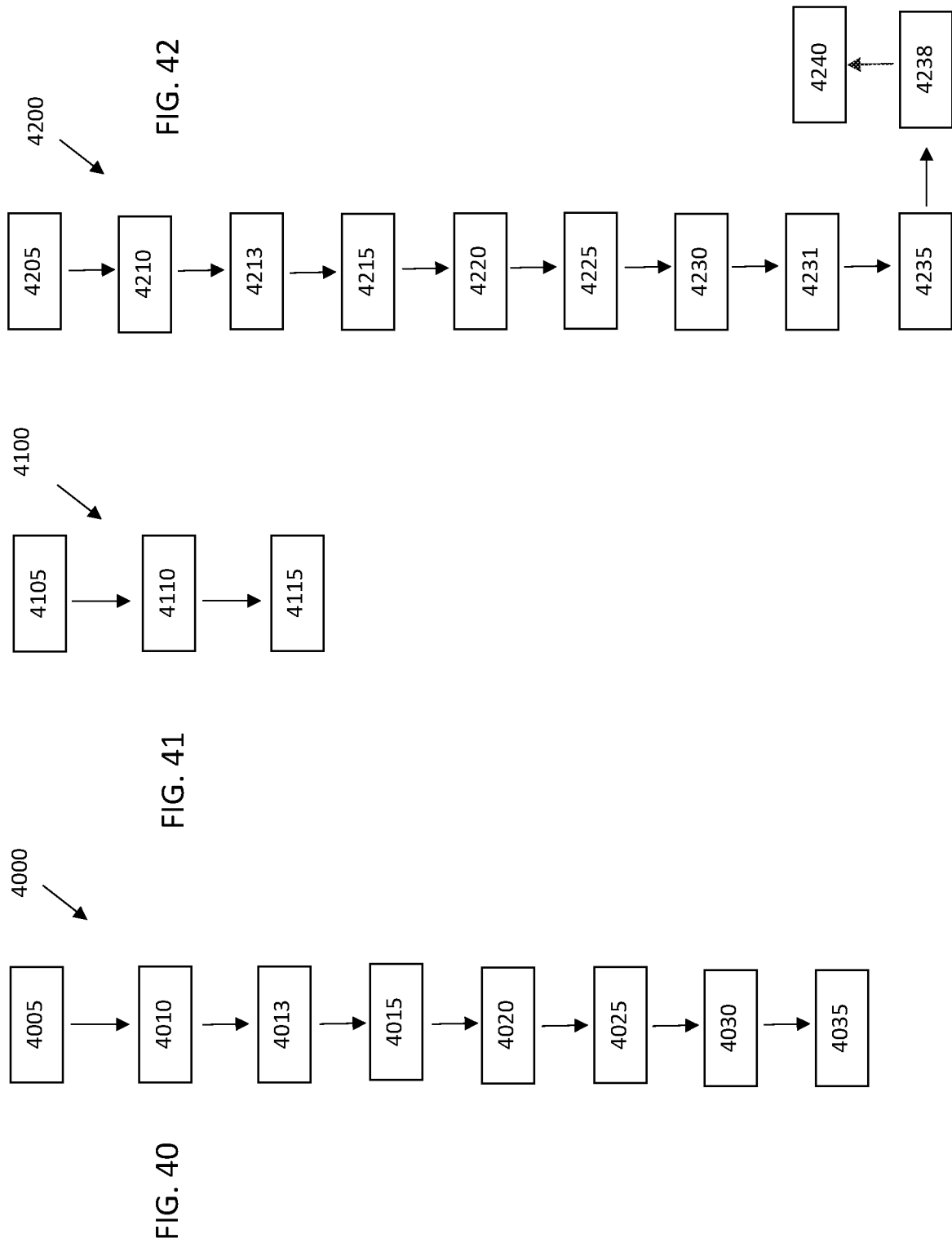

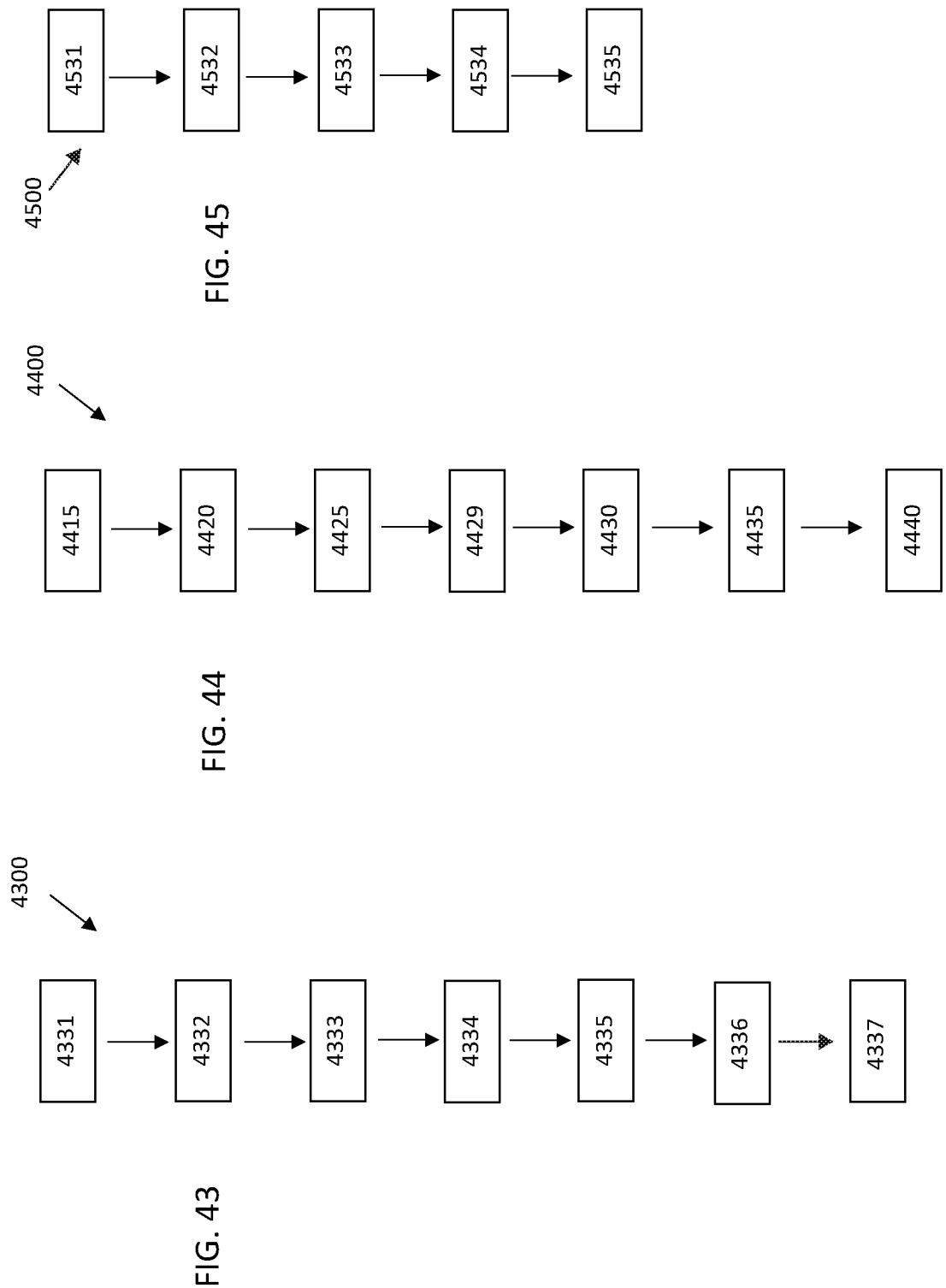

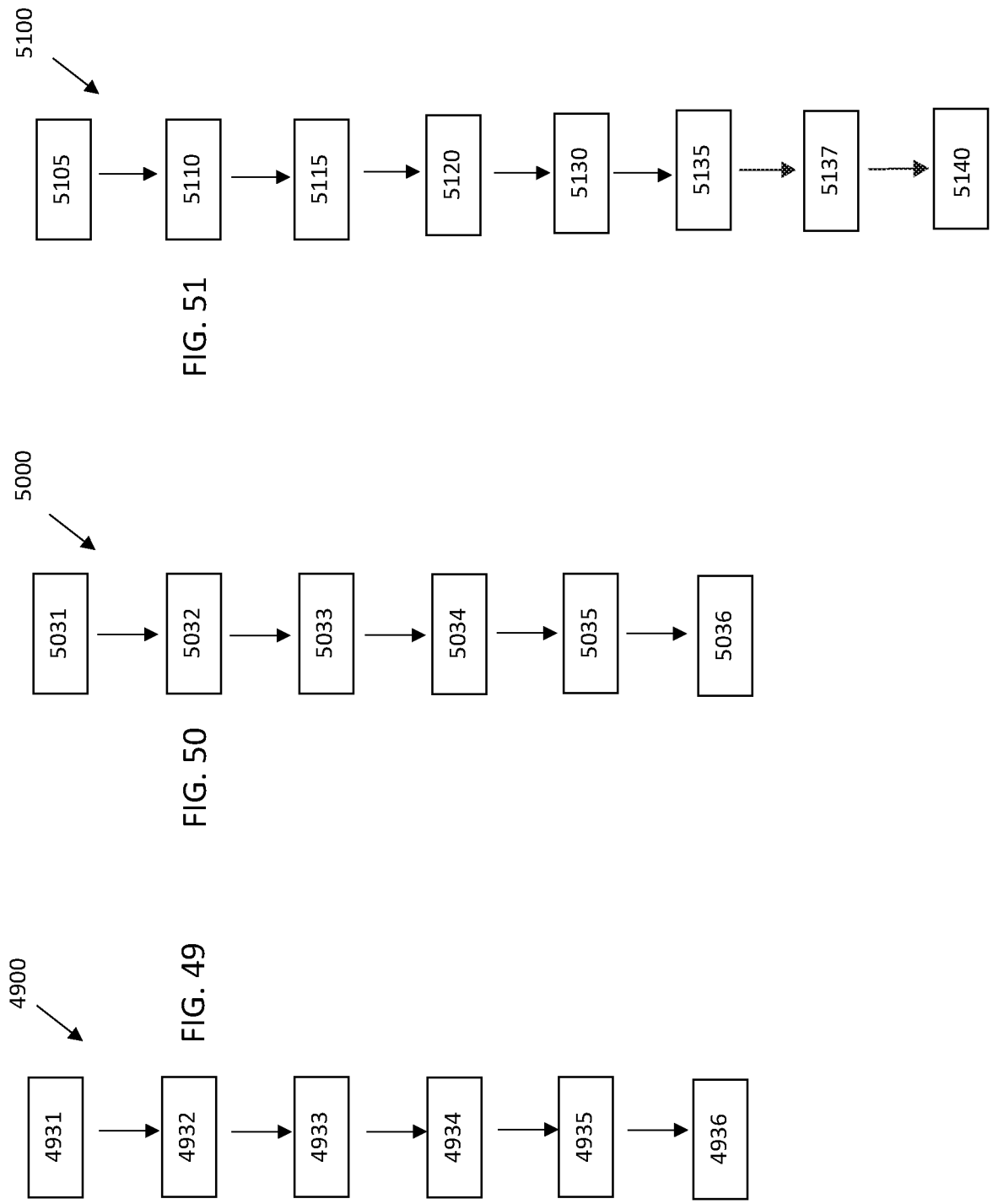

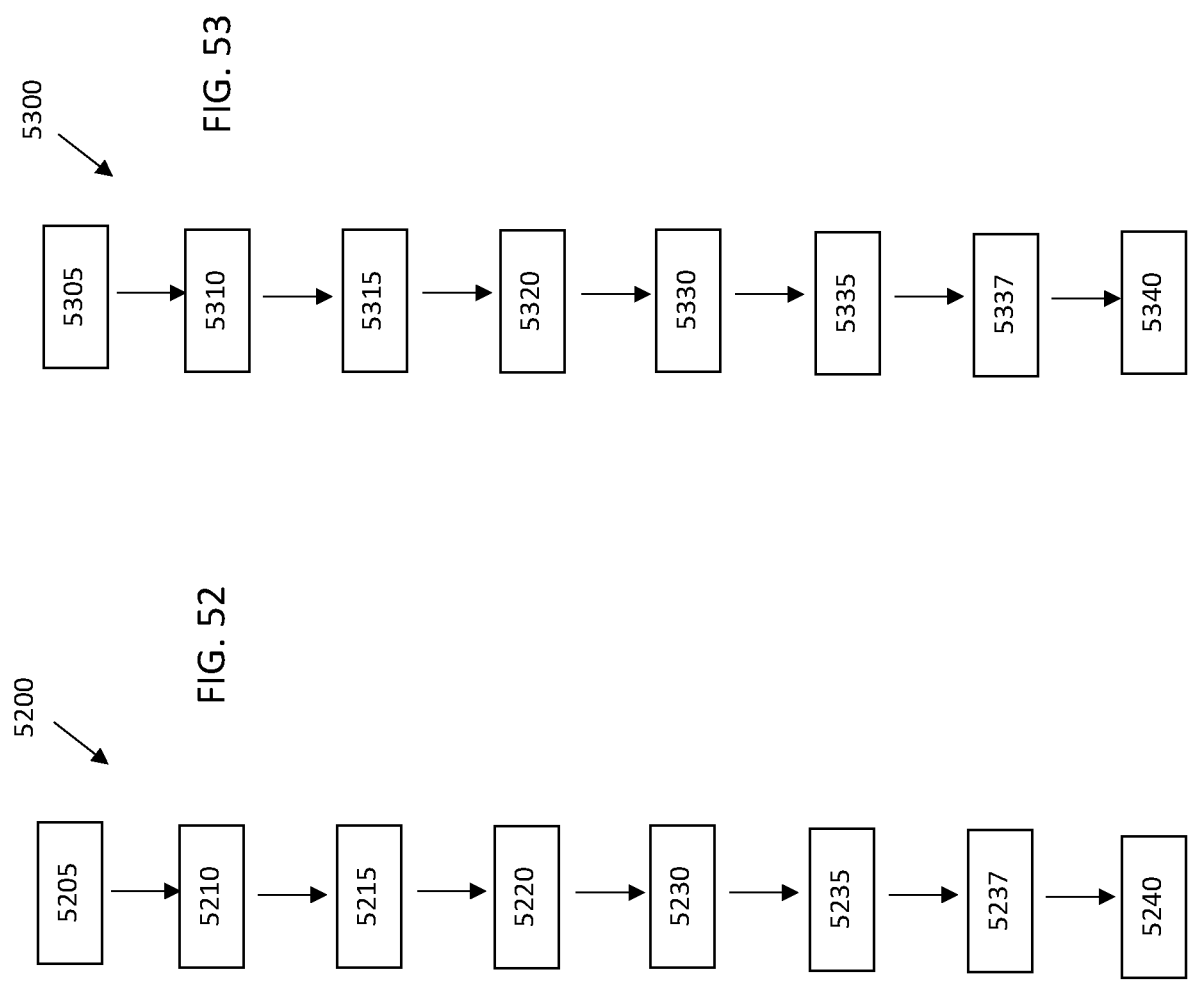

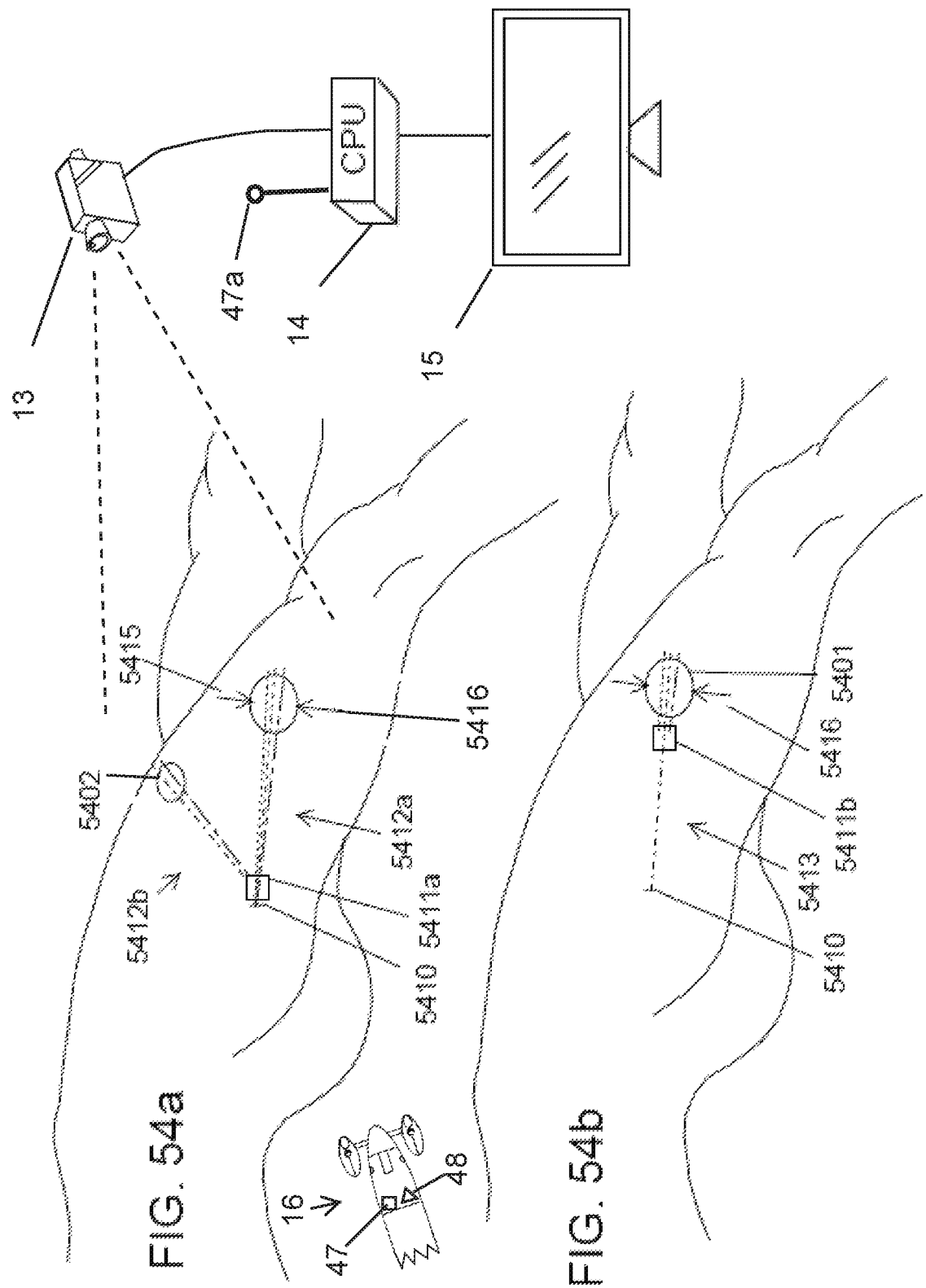

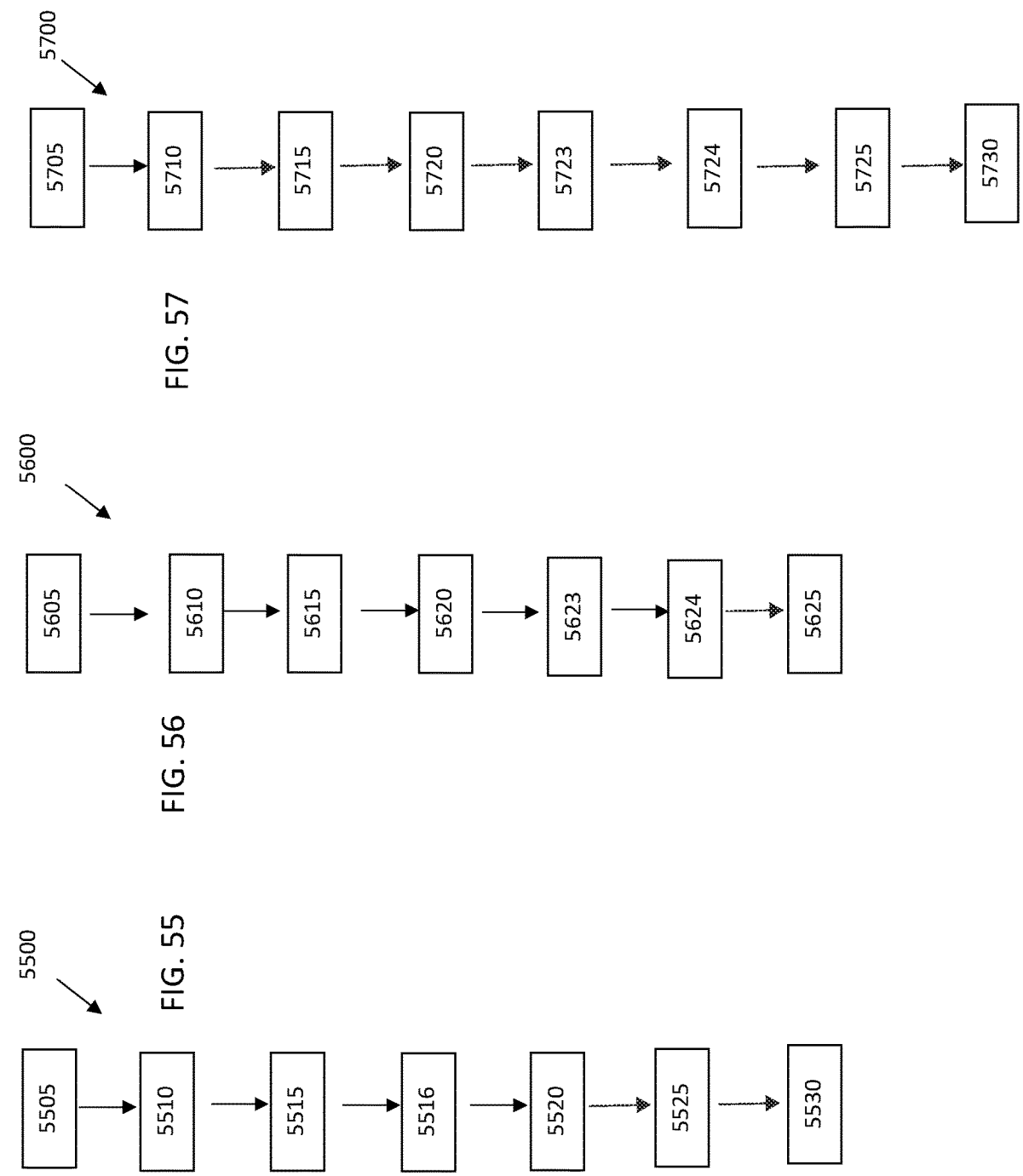

APPARATUS, SYSTEMS AND METHODS FOR MINIMALLY INVASIVE DISSECTION OF TISSUES

RELATED APPLICATIONS

This application claims the benefit under 35 U.S.C. § 119(e) of U.S. Provisional Patent Application No. 62/313,707 filed on Mar. 26, 2016 and titled "Apparatus & Systems For Minimally Invasive Dissection of Tissues via Cannula" and further claims the benefit under 35 U.S.C. § 119(e) of U.S. Provisional Patent Application No. 62/409,575 filed on Oct. 18, 2016 and titled "Apparatus, Systems, and Methods for Minimally Invasive Dissection of Tissues." Each of the aforementioned applications is incorporated herein by reference in its entirety.

SUMMARY

Examples of certain preferred embodiments and implementations of the invention are disclosed below in connection with the following numbered paragraphs.

1. An electrosurgical device configured for deployment through a cannula, comprising:
   a lysing tip configured for delivery of electrosurgical energy, wherein the lysing tip comprises:
      an energy delivery side configured to receive and deliver electrosurgical energy for one or both of tissue dissection and modification; and
      an orientational-deployment side opposite from the energy delivery side, wherein the orientational-deployment side is configured to allow for the lysing tip to be repositioned between a delivery configuration in which the lysing tip can be positioned within a lumen of the cannula with the energy delivery side facing an interior surface of the lumen and a treatment configuration in which the lysing tip is positioned outside of the cannula such that the energy delivery side extends at least substantially perpendicular to an axis of the cannula; and
   a deployment assembly coupled with the orientational-deployment side of the lysing tip, wherein the deployment assembly is configured to allow for selective repositioning between the delivery configuration and the treatment configuration.

2. The electrosurgical device of example 1, wherein the lysing tip is configured is configured such that the energy delivery side extends at least substantially parallel to the axis of the cannula in the delivery configuration.

3. The electrosurgical device of example 1, wherein the lysing tip is configured such that the energy delivery side extends at an acute angle relative to the axis of the cannula in the delivery configuration.

4. The electrosurgical device of example 1, wherein the deployment assembly comprises a first actuation rod and a second actuation rod coupled with the lysing tip.

5. The electrosurgical device of example 4, further comprising a retraction guide configured to facilitate repositioning of the lysing tip between the treatment configuration and the delivery configuration.

6. The electrosurgical device of example 5, wherein the retraction guide is configured to provide a restorative force to the lysing tip by contacting the cannula when the lysing tip is repositioned from the treatment configuration to the delivery configuration.

7. The electrosurgical device of example 6, wherein the retraction guide comprises a spring positioned on at least one of the first actuation rod and the second actuation rod.

8. The electrosurgical device of example 4, further comprising at least one canal configured to supply fluids to a surgical site adjacent to the lysing tip during a surgical procedure.

9. The electrosurgical device of example 8, wherein the at least one canal is configured to be selectively extended towards the lysing tip and withdrawn from the lysing tip.

10. The electrosurgical device of example 4, wherein the first actuation rod comprises a first hinge, and wherein the second actuation rod comprises a second hinge.

11. The electrosurgical device of example 10, wherein the first hinge and the second hinge are configured to allow the lysing tip to be selectively rotated at least one of above and below a cross-sectional profile of an opening at a distal end of the cannula in the treatment configuration.

12. The electrosurgical device of example 1, further comprising at least one energy window formed on at least one of an upper surface and a lower surface of the lysing tip.

13. The electrosurgical device of example 12, wherein the at least one energy window comprises a plurality of energy windows.

14. The electrosurgical device of example 13, wherein at least a subset of the plurality of energy windows are at least one of physically and energetically isolated from one another.

15. The electrosurgical device of example 14, wherein the at least a subset of the plurality of energy windows is configured to deliver a modality of energy that differs from at least a second subset of the plurality of energy windows.

16. The electrosurgical device of example 1, wherein the lysing tip comprises an antenna configured to provide location data regarding the lysing tip.

17. The electrosurgical device of example 16, wherein the antenna comprises an RFID tag.

18. The electrosurgical device of example 1, wherein the lysing tip comprises a bipolar lysing tip configured to deliver bipolar electrosurgical energy, and wherein the lysing tip comprises a first set of lysing elements and a second set of lysing elements, wherein the first set of lysing elements is electrically isolated from the second set of lysing elements.

19. The electrosurgical device of example 18, wherein the lysing tip comprises a first linking member electrically coupled to the first set of lysing elements and a second linking member electrically coupled to the second set of lysing elements, and wherein the first linking member is electrically isolated from the second linking member.

20. An electrosurgical system, comprising:
   an electrosurgical device comprising a lysing tip having a first end and a second end opposite from the first end, wherein the lysing tip comprises:
      a plurality of protrusions; and
      at least one lysing segment positioned between at least two adjacent protrusions in the plurality of protrusions;
   a cannula configured for delivery of the electrosurgical device; and
   a deployment assembly coupled with the electrosurgical device, wherein the electrosurgical device and the deployment assembly are configured such that the at least one lysing segment is positioned to face an interior wall of the cannula during delivery of the electrosurgical device, and such that the at least one lysing segment can be rotated after extending through a distal end of the cannula to allow at least one of the first end and the second end to protrude beyond a cross-sectional profile of an opening at the distal end.

21. The electrosurgical system of example 20, wherein the electrosurgical device and the deployment assembly are configured such that the at least one lysing segment can be rotated after extending through a distal end of the cannula to allow both the first end and the second end of the lysing tip to protrude beyond a cross-sectional profile of the opening at the distal end.

22. The electrosurgical system of example 20, further comprising a second cannula comprising a cross-sectional area greater than a cross-sectional area of the cannula, wherein the second cannula is configured to be positioned outside the cannula during delivery of the electrosurgical device.

23. The electrosurgical system of example 22, wherein the electrosurgical device is configured such that the plurality of protrusions is unable to be fully received within the second cannula.

24. The electrosurgical system of example 20, further comprising a spot coagulator configured to extend through the cannula and deliver electrosurgical energy therethrough.

25. The electrosurgical system of example 24, wherein the spot coagulator is configured to be selectively movable relative to the lysing tip.

26. The electrosurgical system of example 20, further comprising means for fixing a rotational orientation of the lysing tip relative to the cannula.

27. The electrosurgical system of example 26, wherein the means for fixing a rotational orientation of the lysing tip relative to the cannula is positioned on the cannula.

28. The electrosurgical system of example 26, wherein the means for fixing a rotational orientation of the lysing tip relative to the cannula comprises at least one slot formed in a distal end of the cannula.

29. The electrosurgical system of example 28, wherein the at least one slot is configured to receive at least a portion of the lysing tip therein in a treatment configuration in which the lysing tip is positioned outside of the cannula such that the energy delivery side extends at least substantially perpendicular to the axis of the cannula.

30. The electrosurgical system of example 20, wherein the at least one lysing segment is made up of a cermet material.

31. The electrosurgical system of example 20, wherein the deployment assembly comprises:
a first actuation rod; and
an intermediate hinge member coupled with the first actuation rod and coupled with the lysing tip, wherein the intermediate hinge member is configured such that actuation of the first actuation rod results in pivoting of the lysing rod between a delivery configuration in which the lysing tip can be positioned within a lumen of the cannula with the at least one lysing segment facing an interior surface of the lumen and a treatment configuration in which the lysing tip is positioned with at least one of the first end and the second end protruding beyond a cross-sectional profile of the opening of the cannula at the distal end.

32. The electrosurgical system of example 31, wherein the intermediate hinge member is coupled with the lysing tip in between two opposing ends of the lysing tip.

33. The electrosurgical system of example 32, wherein the lysing tip further comprising a linking member positioned along a proximal side of the lysing tip, and wherein the intermediate hinge member is coupled with the linking member.

34. The electrosurgical system of example 32, wherein the deployment assembly further comprises a second actuation rod.

35. The electrosurgical system of example 34, wherein the second actuation rod is pivotably coupled to the lysing tip.

36. The electrosurgical system of example 35, wherein the second actuation rod is pivotably coupled to the lysing tip at one end of the two opposing ends of the lysing tip.

37. The electrosurgical system of example 31, wherein the intermediate hinge member is coupled with the lysing tip at one end of two opposing ends of the lysing tip.

38. The electrosurgical system of example 37, wherein the deployment assembly further comprises a second actuation rod.

39. The electrosurgical system of example 38, wherein the second actuation rod is configured to advance and withdraw the lysing tip within the cannula.

40. The electrosurgical system of example 39, wherein the second actuation rod is coupled with the lysing tip along a central portion of the lysing tip between the two opposing ends.

41. A surgical system, comprising:
a surgical lysing tip comprising:
a treatment side; and
an orientational-deployment side opposite from the treatment side, wherein the surgical lysing tip comprises a lysing tip axis extending at least substantially along the treatment side and along the orientational-deployment side;
a cannula configured for delivery of the surgical lysing tip, wherein the cannula comprises a cannula axis; and
a deployment assembly coupled with the orientational-deployment side of the surgical lysing tip and configured to pivot the surgical lysing tip following delivery of the surgical lysing tip through a distal opening of the cannula, wherein the deployment assembly is configured to allow the surgical lysing tip to be delivered through the cannula along the cannula axis such that the lysing tip axis is at least substantially aligned with the cannula axis during delivery, and wherein the deployment assembly is configured to allow the surgical lysing tip to be selectively pivoted after the surgical lysing tip has passed through the distal opening such that the lysing tip axis is positioned at an angle with respect to the cannula axis and such that at least one of two opposing ends of the surgical lysing tip defining the lysing tip axis protrudes beyond a cross-sectional profile of the distal opening of the cannula.

42. The surgical system of example 41, wherein the surgical system is configured to allow the surgical lysing tip to be selectively pivoted after the surgical lysing tip has passed through the distal opening such that the lysing tip axis is positioned at an angle with respect to the cannula axis and such that both of the two opposing ends of the surgical lysing tip defining the lysing tip axis protrude beyond the cross-sectional profile of the distal opening of the cannula.

43. An electrosurgical device, comprising:
a lysing tip comprising:
a plurality of beads;
at least one lysing member defining at least one lysing segment extending between each pair of adjacent beads; and
a tunnel extending at least partially through each of the plurality of beads, wherein the at least one lysing member is positioned to extend at least partially through the tunnel to define the at least one lysing segment between each pair of adjacent beads.

44. The electrosurgical device of example 43, wherein each of the plurality of beads is non-symmetrical relative to an axis defined by the at least one lysing member.

45. The electrosurgical device of example 43, wherein the lysing tip comprises a plurality of lysing segments.

46. The electrosurgical device of example 44, wherein each of the plurality of lysing segments is formed by a single lysing member.

47. The electrosurgical device of example 44, wherein at least one lysing segment of the plurality of lysing segments extends at an angle relative to at least one other lysing segment of the plurality of lysing segments.

48. The electrosurgical device of example 47, wherein the plurality of lysing segments extend in an arced shape along a treatment side of the lysing tip.

49. The electrosurgical device of example 48, wherein at least a first lysing segment of the plurality of lysing segments extends in a first direction, wherein at least a second lysing segment of the plurality of lysing segments extends in a second direction angled towards a first side of the lysing tip relative to the first direction, and wherein at least a third lysing segment of the plurality of lysing segments extends in a third direction angled towards a second side of the lysing tip opposite from the first side relative to the first direction.

50. The electrosurgical device of example 43, wherein each of at least a subset of the plurality of beads comprises a plurality of facets formed thereon.

51. The electrosurgical device of example 50, wherein each of the at least a subset of the plurality of beads comprises facets formed on leading surfaces of the beads, and wherein the facets are configured to facilitate movement of the lysing tip between tissue layers during a surgical procedure.

52. The electrosurgical device of example 51, wherein each of the at least a subset of the plurality of beads comprises a first facet formed on an upper leading surface and a second fact formed on a lower leading surface, and wherein the upper leading surface is angled towards the lower leading surface so as to form a wedge shape.

53. The electrosurgical device of example 43, wherein each of at least a subset of the plurality of beads comprises a substantially flattened trailing end.

54. The electrosurgical device of example 53, wherein the at least a subset of the plurality of beads comprises a substantially frusto-ellipsoidal shape.

55. The electrosurgical device of example 43, wherein each of at least a subset of the plurality of beads comprises a substantially ellipsoidal shape.

56. The electrosurgical device of example 55, wherein each of the plurality of beads comprises a substantially ellipsoidal shape.

57. The electrosurgical device of example 43, further comprising a first actuation rod coupled adjacent to a first end of the lysing tip and a second actuation rod coupled adjacent to a second end of the lysing tip opposite from the first end.

58. The electrosurgical device of example 57, wherein the first actuation rod and the second actuation rod are configured to pivot the lysing tip between a delivery configuration and a treatment configuration.

59. The electrosurgical device of example 58, wherein the lysing tip is configured to be delivered through a cannula with the first actuation rod and the second actuation rod extending through the cannula, wherein the electrosurgical device is configured such that the lysing tip cannot be fully received in the cannula in the treatment configuration.

60. The electrosurgical device of example 59, wherein the electrosurgical device is configured so as to extend the lysing tip at an angle relative to an axis of the cannula in the delivery configuration, and wherein the electrosurgical device is configured such that the lysing tip can be fully received in the cannula in the delivery configuration.

61. The electrosurgical device of example 60, wherein at least one of the first actuation rod and the second actuation rod comprises a first bend at or near a distal end of the at least one of the first actuation rod and the second actuation rod.

62. The electrosurgical device of example 61, wherein the first bend defines a widened area for receipt of a portion of the lysing tip during repositioning of the lysing tip between the treatment configuration and the delivery configuration.

63. The electrosurgical device of example 62, wherein the at least one of the first actuation rod and the second actuation rod comprises a second bend positioned distally of the first bend, and wherein the second bend extends in a direction opposite of the first bend.

64. The electrosurgical device of example 58, wherein the first actuation rod comprises a first opening for receiving a first end of the lysing member therethrough, and wherein the second actuation rod comprises a second opening for receiving a second end of the lysing member opposite from the first end therethrough.

65. The electrosurgical device of example 64, wherein the first opening is elongated to allow the lysing member to pivot within the first opening as the lysing tip is repositioned between the treatment configuration and the delivery configuration.

66. The electrosurgical device of example 65, wherein the first opening is elongated at least substantially in a direction of an axis of the first actuation rod.

67. The electrosurgical device of example 43, wherein at least a subset of the plurality of beads is configured to rotate about the at least one lysing member.

68. The electrosurgical device of example 67, wherein the at least a subset of the plurality of beads is configured to rotate in an upward direction relative to the lysing tip within a range of between about 2 degrees and about 110 degrees, and wherein the at least a subset of the plurality of beads is configured to rotate in a downward direction relative to the lysing tip within a range of between about 2 degrees and about 110 degrees.

69. The electrosurgical device of example 67, wherein each of the plurality of beads is configured to be independently rotatable about the at least one lysing member with respect to the other beads of the plurality of beads.

70. The electrosurgical device of example 64, wherein the first opening comprises internal beveling adjacent to the first opening, and wherein the internal beveling is configured to facilitate pivoting of the lysing tip between the treatment configuration and the delivery configuration.

71. The electrosurgical device of example 43, further comprising:
    a first coupling tip at a first end of the at least one lysing member; and
    a second coupling tip at a second end of the at least one lysing member opposite from the first end, wherein the first coupling tip and the second coupling tip are configured to secure the at least one lysing member to two outermost beads of the plurality of beads.

72. The electrosurgical device of example 71, wherein the first coupling tip differs from the second coupling tip.

73. The electrosurgical device of example 71, wherein the first coupling tip comprises a weld defining a cross-sectional dimension greater in at least one direction that a cross-sectional dimension of the at least one lysing member.

74. The electrosurgical device of example 43, further comprising a plurality of spacers coupled with the at least one lysing member, wherein each of the plurality of spacers is positioned between two adjacent beads of the plurality of beads.

75. The electrosurgical device of example 74, wherein the at least one lysing member comprises a single lysing rod.

76. The electrosurgical device of example 75, wherein the single lysing rod comprises a circular shape in cross section.

77. The electrosurgical device of example 75, wherein each of the plurality of spacers comprises an opening configured to receive a portion of the single lysing rod therethrough.

78. The electrosurgical device of example 77, wherein the single lysing rod has a cross-sectional shape that differs from a cross-sectional shape of an exterior surface of each of the plurality of spacers.

79. The electrosurgical device of example 74, wherein each of the plurality of spacers comprises a leading edge for delivery of electrosurgical energy from the at least one lysing member.

80. The electrosurgical device of example 79, wherein each of the plurality of spacers comprises only a single edge.

81. The electrosurgical device of example 80, wherein, other than the single edge, each of the plurality of spacers comprises an at least substantially smooth exterior surface such that at least substantially all of the electrosurgical energy from the at least one lysing member is delivered through the single edge.

82. The electrosurgical device of example 74, wherein each of the plurality of spacers comprises a conductive material such that electrosurgical energy from the at least one lysing member can be delivered through the spacers.

83. The electrosurgical device of example 74, wherein each of the plurality of spacers comprises an insulating material, and wherein each of the plurality of spacers comprises one or more openings configured to allow for delivery of electrosurgical energy through the one or more openings.

84. The electrosurgical device of example 74, wherein the at least one lysing member comprises a lysing rod having a circular cross-sectional shape, and wherein each of the plurality of spacers is crimped onto the lysing rod in between two adjacent beads of the plurality of beads.

85. The electrosurgical device of example 74, wherein the spacers are configured to at least substantially prevent rotation of the plurality of beads with respect to the at least one lysing member.

86. The electrosurgical device of example 74, wherein the spacers are configured to selectively limit an amount of rotation of the plurality of beads with respect to the at least one lysing member.

87. The electrosurgical device of example 43, further comprising a plurality of protuberances formed on the at least one lysing member, wherein the plurality of protuberances are configured to confine each of the plurality of beads to a predetermined region relative to the at least one lysing member.

88. The electrosurgical device of example 87, wherein the plurality of protuberances comprise welds formed on the at least one lysing member.

89. The electrosurgical device of example 43, wherein the at least one lysing member comprises a single lysing rod.

90. The electrosurgical device of example 89, wherein the lysing rod comprises a leading edge for delivery of electrosurgical energy.

91. The electrosurgical device of example 90, wherein the lysing rod comprises only a single edge.

92. The electrosurgical device of example 91, wherein, other than the single edge, the lysing rod comprises an at least substantially smooth exterior surface.

93. The electrosurgical device of example 89, wherein the lysing rod comprises a polygonal shape in cross section.

94. The electrosurgical device of example 93, wherein the lysing rod comprises at least one of a pentagonal and a hexagonal shape in cross section.

95. The electrosurgical device of example 43, wherein each of the plurality of beads comprises an identical shape.

96. The electrosurgical device of example 43, wherein two opposing outer beads of the plurality of beads comprise a first shape, and wherein at least one inner bead of the plurality of beads comprises a second shape that differs from the first shape.

97. The electrosurgical device of example 43, wherein each of at least a subset of the plurality of beads comprises a substantially ellipsoidal shape.

98. The electrosurgical device of example 43, wherein each of at least a subset of the plurality of beads comprises an annular bead structure.

99. The electrosurgical device of example 98, wherein each of the at least a subset of the plurality of beads comprises a bead hub positioned within the annular bead structure.

100. The electrosurgical device of example 99, wherein each of the bead hubs is configured to couple the bead with the at least one lysing member.

101. The electrosurgical device of example 43, wherein each of at least a subset of the plurality of beads comprises a trailing end and a leading end, wherein the trailing end comprises a rougher surface than the leading end.

102. An electrosurgical device, comprising:
a lysing tip comprising a treatment side and an orientational-deployment side opposite from the treatment side, wherein the lysing tip further comprises:
a plurality of beads; and
at least one lysing member defining at least one lysing segment extending between each pair of adjacent beads, wherein the at least one lysing segment defines a coupling axis with the plurality of beads, and wherein the lysing tip comprises an open region lacking structure on the orientational-deployment side such that at least some of the plurality of beads protrudes from the treatment side and from the orientational-deployment side of the lysing tip.

103. An electrosurgical device, comprising:
a lysing tip comprising a treatment side and an orientational-deployment side opposite from the treatment side, wherein the lysing tip further comprises:
a plurality of beads;
at least one lysing member defining at least one lysing segment extending between each pair of adjacent beads, wherein the at least one lysing segment defines a coupling axis with the plurality of beads; and
a support member extending between a first outer bead of the plurality of beads and a second outer bead of the plurality of beads opposite from the first outer bead on the orientational-deployment side, wherein the support member is configured to facilitate coupling of the lysing tip to a surgical tool used to control the lysing tip during a surgical procedure within a patient's body.

104. The electrosurgical device of example 103, further comprising a grasping pad configured to engage at least one jaw of the surgical tool.

105. The electrosurgical device of example 104, wherein at least a portion of the grasping pad is electrically coupled to the at least one lysing member such that the grasping pad is configured to receive electrosurgical energy from the surgical tool and transfer the electrosurgical energy to the at least one lysing segment.

106. The electrosurgical device of example 104, wherein the grasping pad is formed on the support member.

107. The electrosurgical device of example 105, wherein the grasping pad comprises a hole configured to receive a projection extending from the at least one jaw of the surgical tool.

108. The electrosurgical device of example 107, wherein the grasping pad is coated with an insulating coating, wherein the hole is uncoated, and wherein the at least a portion of the grasping pad comprises the hole.

109. An electrosurgical system, comprising:
a lysing tip comprising a treatment side and an orientational-deployment side opposite from the treatment side, wherein the lysing tip further comprises:
a plurality of beads;
at least one lysing member defining at least one lysing segment extending between each pair of adjacent beads, wherein the at least one lysing member defines a coupling axis with the plurality of beads; and
a cannula configured for delivery of the lysing tip therethrough into a patient's body, wherein the cannula comprises a cannula axis, and wherein the system is configured such that the lysing tip can be delivered through the cannula with the coupling axis aligned with the cannula axis.

110. The electrosurgical system of example 109, further comprising a second cannula, wherein the second cannula comprises a lumen having a smaller cross-sectional dimension that the cannula such that the second cannula can fit within the cannula, and wherein the lysing tip is configured such that the plurality of beads is unable to be fully received within the second cannula with the coupling axis aligned with the cannula axis.

111. An electrosurgical system, comprising:
a lysing tip comprising a treatment side and an orientational-deployment side opposite from the treatment side, wherein the lysing tip further comprises:
a plurality of beads;
at least one lysing member defining at least one lysing segment extending between each pair of adjacent beads, wherein the lysing tip comprises a primary axis extending between a first outer bead of the plurality of beads and a second outer bead of the plurality of beads, and wherein each of the plurality of beads comprises a tip extending at least substantially perpendicular to the primary axis; and
a cannula configured for delivery of the lysing tip therethrough into a patient's body, wherein the cannula comprises a cannula axis, and wherein the system is configured such that the lysing tip can be delivered through the cannula with the primary axis aligned with the cannula axis.

112. An electrosurgical system, comprising:
a lysing tip comprising a treatment side and a grasping pad opposite from the treatment side, wherein the treatment side is configured to receive and deliver electrosurgical energy for tissue one or both of dissection and modification; and
a first instrument configured to selectively couple with the lysing tip, wherein the first instrument is configured to deliver electrosurgical energy to the treatment side of the lysing tip while the lysing tip is coupled with the first instrument, and wherein the first instrument is configured to selectively couple with the lysing tip at the grasping pad.

113. The electrosurgical system of example 112, wherein the lysing tip comprises:
a plurality of protrusions;
at least one lysing member defining at least one lysing segment between each pair of adjacent protrusions of the plurality of protrusions.

114. The electrosurgical system of example 112, wherein the lysing tip further comprises:
a plurality of beads; and
a lysing rod extending at least partially through each of the plurality of beads so as to define a plurality of lysing segments extending between adjacent beads of the plurality of beads.

115. The electrosurgical system of example 114, wherein the lysing tip further comprises a support member coupled to the lysing rod at opposite ends of the support member.

116. The electrosurgical system of example 115, wherein the lysing tip further comprises a grasping pad formed on the support member, and wherein the first instrument comprises at least one jaw configured to engage the grasping pad.

117. The electrosurgical system of example 116, wherein the at least one jaw comprises an upper jaw and a lower jaw, and wherein at least one of the upper jaw and the lower jaw is movable such that the upper jaw and the lower jaw are configured to open to receive the grasping pad and to close to fixedly couple the grasping pad in between the upper jaw and the lower jaw.

118. The electrosurgical system of example 116, wherein the at least one jaw comprises a projection, wherein the grasping pad comprises an opening configured to receive the projection.

119. The electrosurgical system of example 118, wherein the first instrument is configured to deliver electrosurgical energy from the projection, through the opening, and into the lysing rod.

120. The electrosurgical system of example 119, wherein the grasping pad comprises a non-conductive insulation, and wherein the at least one jaw comprises a non-conductive insulation.

121. The electrosurgical system of example 120, wherein the projection lacks the non-conductive insulation, and wherein the opening lacks the non-conductive insulation.

122. The electrosurgical system of example 120, wherein the non-conductive insulation comprises a coating.

123. The electrosurgical system of example 113, wherein the plurality of protrusions comprises a plurality of beads positioned along the at least one lysing member.

124. The electrosurgical system of example 114, wherein each of the plurality of beads is independently movable at least one of laterally and rotationally with respect to the at least one lysing member.

125. The electrosurgical system of example 114, wherein at least a subset of the plurality of beads protrudes both distally in a direction of the treatment side and proximally in a direction opposite of the direction of the treatment side relative to the at least one lysing member.

126. The electrosurgical system of example 114, wherein each of the plurality of beads protrudes both distally in a direction of the treatment side and proximally in a direction opposite of the direction of the treatment side relative to the at least one lysing member.

127. The electrosurgical system of example 112, wherein the first instrument comprises a jaw configured to receive the grasping pad of the lysing tip to couple the lysing tip to the first instrument.

128. The electrosurgical system of example 127, wherein the grasping pad comprises a magnet, and wherein the jaw comprises a magnetic element configured to engage the magnet.

129. The electrosurgical system of example 127, wherein the jaw comprises an insulated exterior surface, and wherein at least a portion of an interior surface of the jaw configured to engage the grasping pad is uninsulated to allow for delivery of electrosurgical energy through the jaw to the grasping pad and to the treatment side of the lysing tip.

130. The electrosurgical system of example 127, wherein the jaw is configured to open to facilitate receiving the grasping pad, and wherein the jaw is configured to close to grasp the grasping pad.

131. The electrosurgical system of example 127, wherein the jaw comprises a projection, wherein the grasping pad comprises a hole, and wherein the projection is configured to be received in the hole to facilitate a more stable coupling of the lysing tip with the first instrument.

132. The electrosurgical system of example 131, wherein the jaw is insulated, and wherein the projection is uninsulated to allow for delivery of electrosurgical energy through the projection to the grasping pad and to the treatment side of the lysing tip.

133. The electrosurgical system of example 112, further comprising a second instrument configured to facilitate coupling of the lysing tip to the first instrument.

134. The electrosurgical system of example 133, further comprising:
   a first cannula configured to deliver the first instrument and the lysing tip into a patient's body; and
   a second cannula configured to deliver the second instrument into the patient's body.

135. The electrosurgical system of example 133, wherein the second instrument lacks the ability to deliver electrosurgical energy.

136. The electrosurgical system of example 133, wherein the first instrument comprises a jaw, wherein the second instrument comprises a jaw, and wherein the jaw of the first instrument is identical to the jaw of the second instrument.

137. The electrosurgical system of example 112, further comprising a first cannula configured to deliver the first instrument and the lysing tip into a patient's body.

138. The electrosurgical system of example 112, further comprising a linking member positioned opposite from the treatment side, wherein the linking member is configured to facilitate coupling of the lysing tip with the first instrument.

139. The electrosurgical system of example 138, wherein the grasping pad extends from the linking member.

140. The electrosurgical system of example 112, wherein the first instrument comprises at least one of means for grasping the lysing tip and means for controlling the lysing tip during a surgical procedure.

141. The electrosurgical system of example 140, wherein the first instrument comprises means for grasping the lysing tip, and wherein the means for grasping the lysing tip comprises a pair of jaws configured to receive the grasping pad.

142. The electrosurgical system of example 141, wherein at least one jaw of the pair of jaws is movable.

143. The electrosurgical system of example 112, further comprising a tether coupled with the lysing tip, wherein the tether is configured to facilitate coupling of the lysing tip with the first instrument.

144. The electrosurgical system of example 143, wherein the tether is coupled with the grasping pad of the lysing tip.

145. The electrosurgical system of example 144, wherein the first instrument comprises a jaw configured to receive the grasping pad of the lysing tip to couple the lysing tip to the first instrument, and wherein the tether extends through an opening formed in the jaw.

146. The electrosurgical system of example 143, wherein the tether is configured to, upon being retracted, direct the lysing tip into an engagement feature of the first instrument.

147. The electrosurgical system of example 146, wherein the engagement feature comprises a jaw.

148. The electrosurgical system of example 112, wherein the first instrument comprises at least one jaw, wherein the at least one jaw is configured to engage the grasping pad of the lysing tip, and wherein the system is configured such that the first instrument delivers electrosurgical energy from the at least one jaw, through the grasping pad, and into a plurality of lysing segments on the treatment side.

149. The electrosurgical system of example 148, further comprising a slot formed in the at least one jaw, wherein the slot is configured to receive at least a portion of the grasping pad.

150. The electrosurgical system of example 149, wherein the at least one jaw is configured to open and shut, and wherein the slot is configured to enclose the grasping pad about at least 3 sides of the grasping pad and at least partially about a fourth side of the grasping pad when the at least one jaw is closed with the grasping pad positioned therein.

151. The electrosurgical system of example 149, wherein the at least one jaw comprises at least one of an insulating cover and an insulating coating, and wherein at least a portion of the slot lacks the at least one of an insulating cover and an insulating coating so as to allow for transfer of electrosurgical energy therethrough.

152. A method for use of an electrosurgical device, the method comprising the steps of:
   delivering a lysing tip through a first cannula into a patient's body;
   advancing the lysing tip beyond a distal opening of the first cannula;
   delivering a first instrument through a second cannula into the patient's body adjacent to the lysing tip;
   coupling the lysing tip with the first instrument;
   advancing a second instrument through the first cannula into the patient's body such that at least a distal end of the second instrument protrudes beyond the distal opening of the first cannula;
   using the first instrument to couple the lysing tip with the second instrument;
   releasing the lysing tip from the first instrument; and
   using the second instrument to perform a surgical procedure with the lysing tip.

153. The method of example 152, wherein the second instrument comprises at least one jaw configured to engage a first portion of the lysing tip, and wherein the step of using the first instrument to couple the lysing tip with the second instrument comprises advancing the first portion of the lysing tip into the at least one jaw.

154. The method of example 153, wherein the step of using the first instrument to couple the lysing tip with the second instrument further comprises closing the at least one jaw to secure the first portion of the lysing tip therein.

155. The method of example 153, wherein the first portion of the lysing tip comprises a grasping pad protruding from a proximal side of the lysing tip.

156. The method of example 155, wherein lysing tip comprises an energy delivery side opposite from the proximal side, and wherein the second instrument is configured to deliver electrosurgical energy through the grasping pad to the energy delivery side when the second instrument is coupled with the lysing tip.

157. The method of example 153, wherein the first instrument comprises at least one jaw configured to engage a second portion of the lysing tip distinct from the first portion.

158. The method of example 148, wherein the step of advancing the lysing tip beyond a distal opening of the first cannula is performed using the second instrument.

159. The method of example 148, wherein the second instrument is configured to deliver electrosurgical energy to the lysing tip when the second instrument is coupled with the lysing tip.

160. The method of example 159, wherein the first instrument lacks the ability to deliver electrosurgical energy.

161. An electrosurgical system, comprising:
- a lysing tip comprising a treatment side and an orientational-deployment side opposite from the treatment side, wherein the lysing tip further comprises:
  - a plurality of beads, wherein each of the plurality of beads extends from the treatment side towards the orientational-deployment side, and wherein the plurality of beads collectively defines a lysing tip axis extending between two outer beads of the plurality of beads; and
  - at least one lysing member defining at least one lysing segment extending between each pair of adjacent beads, wherein the at least one lysing member defines a coupling axis with the plurality of beads;
- a cannula comprising a lumen configured to deliver the lysing tip therethrough; and
- at least one actuation rod coupled with the lysing tip, wherein the at least one actuation rod is configured to reorient the lysing tip between a delivery configuration in which the lysing tip axis extends through the lumen and a treatment configuration in which the lysing tip axis extends at least substantially perpendicular to an axis of the lumen outside of a distal end of the cannula.

162. The system of example 161, wherein the lysing tip comprises an open region lacking structure on the orientational-deployment side proximal to the at least one lysing member and the plurality of beads.

163. The system of example 161, wherein the lysing tip is configured such that at least a subset of the plurality of beads protrude from the treatment side and at least a subset of the plurality of beads protrude from the orientational-deployment side.

164. The system of example 161, wherein the at least one lysing member comprises a lysing plate, and wherein the lysing plate extends along the lysing tip axis.

165. The system of example 164, wherein the lysing tip is configured such that the lysing plate extends through each of the plurality of beads, and such that the lysing plate alone supports each of the plurality of beads on the lysing tip.

166. The system of example 161, wherein the electrosurgical system is configured such that the lysing tip axis extends at least substantially parallel to the axis of the lumen in the delivery configuration.

167. The system of example 161, wherein the electrosurgical system is configured such that at least one of the two outer beads of the plurality of beads extends beyond a cross-sectional profile of an opening at the distal end of the cannula in the treatment configuration.

168. The system of example 167, where the electrosurgical system is configured such that both of the two outer beads of the plurality of beads extends beyond a cross-sectional profile of an opening at the distal end of the cannula in the treatment configuration.

169. The system of example 161, further comprising a second cannula, wherein the second cannula comprises a lumen having a smaller cross-sectional size than the cannula, and wherein the second cannula is configured to be received within the cannula.

170. The system of example 169, wherein the lysing tip is configured such that none of the plurality of beads is configured to be fully received within the second cannula in either the delivery or treatment configurations.

171. The system of example 161, wherein the at least one actuation rod comprises a first actuation rod and a second actuation rod.

172. The system of example 171, wherein the first actuation rod comprises a distal portion coupled to the lysing tip, wherein the distal portion extends at least substantially parallel to the lysing tip axis.

173. The system of example 172, wherein the distal portion extends at least substantially perpendicular to a proximal portion of the first actuation rod.

174. The system of example 173, wherein the at least one lysing member comprises a lysing plate, and wherein the distal portion is coupled directly to the lysing plate.

175. The system of example 174, wherein the distal portion is pivotably coupled to the lysing plate.

176. The system of example 175, further comprising a pivot member for coupling the lysing plate to the first actuation rod.

177. The system of example 161, further comprising a horizontal tunnel extending through each of the plurality of beads, wherein the at least one lysing member is positioned to extend at least partially through the horizontal tunnel.

178. The system of example 177, wherein the at least one lysing member comprises a lysing plate, and wherein the lysing plate extends through the horizontal tunnel to define a plurality of lysing segments between each pair of adjacent beads.

179. The system of example 177, wherein each of the plurality of beads comprises a vertical tunnel extending between an upper end of the bead and a lower end of the bead.

180. The system of example 179, further comprising a plurality of pins, wherein each of the plurality of pins extends through one of the vertical tunnels, and wherein each of the plurality of pins also extends through an opening formed in the lysing plate to secure the plurality of beads to the lysing plate.

181. The system of example 161, wherein the at least one actuation rod comprises a hinge structure.

182. The system of example 179, wherein the hinge structure is configured to allow the lysing tip to be rotated at least one of above and below a cross-sectional profile of an opening at the distal end of the cannula in the treatment configuration.

183. The system of example 182, wherein the at least one actuation rod comprises a first actuation rod and a second actuation rod, wherein the first actuation rod comprises a first hinge structure, and wherein the second actuation rod comprises a second hinge structure.

184. The system of example 183, wherein both the first and second hinge structures are configured to allow the lysing tip to be rotated either above or below the cross-sectional profile of the opening at the distal end of the cannula in the treatment configuration.

185. The system of example 161, further comprising a second cannula, wherein the second cannula comprises a lumen having a smaller cross-sectional size than the cannula, wherein the second cannula is configured to be received within the cannula, and wherein the lysing tip is configured such that the plurality of beads is configured to be fully received within the cannula and the second cannula in the delivery configuration.

186. The system of example 161, wherein the lysing tip further comprises a support member coupled to the at least one lysing member and extending along the orientational-deployment side of the lysing tip, wherein the support member is configured to facilitate coupling of the lysing tip with the at least one actuation rod.

187. The system of example 186, wherein the support member is coupled to the at least one lysing member adjacent to the two outer beads.

188. The system of example 187, wherein the support member is coupled to the at least one lysing member adjacent to respective inner surfaces of the two outer beads.

189. The system of example 186, wherein the support member is formed in a bow shape from a first end of the support member coupled with the at least one lysing member to a second end of the support member coupled with the at least one lysing member opposite from the first end.

190. The system of example 189, wherein the at least one actuation rod comprises a first actuation rod and a second actuation rod, wherein the support member comprises a first hole configured to receive a first coupling member for coupling the first actuation rod to the support member, and wherein the support member further comprises a second hole configured to receive a second coupling member for coupling the second actuation rod to the support member.

191. The system of example 190, wherein the first coupling member comprises a pin, and wherein the second coupling member comprises a pin.

192. The system of example 190, wherein the first hole is offset from the second hole with respect to at least one central axis of the lysing tip.

193. The system of example 192, wherein the first hole is offset from the second hole with respect to at least one of a central axis defined by the at least one lysing member and a central axis of the lysing tip extending between the treatment side and the orientational-deployment side of the lysing tip.

194. The system of example 193, wherein the first hole is positioned a first distance from the at least one lysing member, wherein the second hole is positioned a second distance from the at least one lysing member, and wherein the first distance differs from the second distance.

195. The system of example 186, wherein the at least one actuation rod comprises a first actuation rod and a second actuation rod, wherein the support member comprises a first hole configured to receive a first pin for coupling the first actuation rod to the support member, and wherein the support member further comprises a second hole configured to receive a second pin for coupling the second actuation rod to the support member.

196. The system of example 195, wherein the support member is formed with a first knob protruding from the support member, and wherein the first hole is formed in the first knob.

197. The system of example 196, wherein the support member is formed with a second knob protruding from the support member, and wherein the second hole is formed in the second knob.

198. The system of example 197, wherein the support member is formed in a bow shape from a first end of the support member coupled with the at least one lysing member to a second end of the support member coupled with the at least one lysing member opposite from the first end.

199. The system of example 161, wherein the at least one actuation rod comprises a lysing tip receptacle configured to at least partially receive the lysing tip when the lysing tip is repositioned from the treatment configuration to the delivery configuration.

200. The system of example 199, wherein the lysing tip further comprises a support member coupled to the at least one lysing member and extending along the orientational-deployment side of the lysing tip, wherein the support member is configured to facilitate coupling of the lysing tip with the at least one actuation rod, and wherein the lysing tip receptacle is configured to receive the support member.

201. The system of example 199, wherein the at least one actuation rod comprises a first actuation rod and a second actuation rod, and wherein the lysing tip receptacle comprises a cutout region formed in the first actuation rod.

202. The system of example 161, wherein the at least one actuation rod comprises a first actuation rod and a second actuation rod, wherein the first actuation rod comprises a distal portion and a proximal portion, wherein the second actuation rod comprises a distal portion and a proximal portion, and wherein the distal portions of the first and second actuation rods are configured to pivot with respect to the proximal portions of the first and second actuation rods.

203. The system of example 202, wherein the first actuation rod comprises a first hinge member configured to pivot the proximal portion of the first actuation rod with respect to the distal portion of the first actuation rod, wherein the second actuation rod comprises an opening configured to at least partially receive the first hinge member while the lysing tip is in the delivery configuration.

204. The system of example 203, wherein the first actuation rod further comprises a lysing tip receptacle configured to at least partially receive the lysing tip when the lysing tip is repositioned from the treatment configuration to the delivery configuration.

205. The system of example 161, wherein the lysing tip and the cannula are configured such that the lysing tip may be fully received within the cannula in the delivery configuration.

206. The system of example 205, wherein the electrosurgical system is configured such that the lysing tip axis extends at an angle with respect to the axis of the lumen of the cannula in the delivery configuration.

207. The system of example 161, wherein the at least one lysing member comprises a single lysing member, wherein the single lysing member defines a plurality of lysing segments, and wherein each lysing segment extends between an adjacent pair of beads of the plurality of beads.

208. The system of example 207, further comprising a plurality of spacers, wherein each spacer of the plurality of spacers is coupled with a lysing segment of the plurality of lysing segments.

209. The system of example 208, wherein each of the plurality of spacers is configured to confine each of the plurality of beads to a predetermined region relative to the single lysing member.

210. The system of example 207, further comprising a plurality of protuberances coupled with the single lysing member, wherein each of the plurality of lysing segments comprises a first protuberance at a first end of the lysing segment and a second protuberance at a second end of the lysing segment.

211. The system of example 207, wherein the single lysing member comprises a non-circular shape in cross section along at least a portion of the single lysing member.

212. The system of example 211, wherein the single lysing member comprises a non-circular shape in cross section only at locations corresponding with each of the plurality of beads.

213. The system of example 211, wherein the single lysing member comprises a non-circular shape in cross section along an entire length of the single lysing member.

214. The system of example 161, wherein each of the plurality of beads has an at least substantially identical length extending between the treatment side and the orientational-deployment side.

215. The system of example 161, wherein the at least one actuation rod comprises a first actuation rod and a second actuation rod, wherein at least one of the first actuation rod and the second actuation rod comprises a retraction guide configured to facilitate repositioning of the lysing tip between the treatment configuration and the delivery configuration.

216. The system of example 215, wherein the retraction guide is configured to provide a restorative force to the lysing tip by contacting the cannula when the lysing tip is repositioned from the treatment configuration to the delivery configuration.

217. The system of example 216, wherein the retraction guide comprises a spring positioned on the first actuation rod.

218. The system of example 216, wherein the retraction guide extends from the first actuation rod by a first distance, wherein at least one bead of the plurality of beads extends from the first actuation rod in the delivery configuration by a second distance, and wherein the first distance is at least one of approximately equal to and slightly greater than the second distance.

219. The system of example 218, wherein the first distance is between about 1% and about 10% greater than the second distance.

220. The system of example 161, further comprising a protective sleeve configured to encase the lysing tip during delivery.

221. The system of example 220, wherein the protective sleeve is removable such that the protective sleeve may be removed prior to treatment using the lysing tip.

222. The system of example 220, wherein the protective sleeve is made up of a biodegradable material.

223. The system of example 161, wherein the lysing tip further comprises an antenna configured to track a location of the lysing tip during a surgical procedure.

224. The system of example 223, wherein the antenna comprises a radiofrequency identification tag.

225. The system of example 223, wherein the lysing tip further comprises a sensor, and wherein the sensor is coupled with the antenna such that location data may be combined with sensor data from the sensor.

226. The system of example 225, wherein the sensor comprises a temperature sensor.

227. The system of example 161, further comprising a canal configured to selectively deliver fluids adjacent to the lysing tip during a surgical procedure.

228. The system of example 227, wherein the canal is selectively retractable and advanceable relative to the cannula.

229. The system of example 161, wherein the at least one lysing member comprises a first lysing member and a second lysing member, and wherein the first lysing member is electrically isolated from the second lysing member.

230. The system of example 229, wherein the lysing tip is configured to deliver bipolar electrosurgical energy, wherein the first lysing member comprises a positive lysing member configured to deliver positive electrosurgical energy, and wherein the second lysing member comprises a negative lysing member configured to deliver negative electrosurgical energy.

231. The system of example 229, wherein the first lysing member defines only a first lysing segment of the plurality of lysing segments, and wherein the second lysing member defines only a second lysing segment of the plurality of lysing segments.

232. The system of example 229, further comprising:
 a first tunnel formed in at least a first subset of the plurality of beads; and
 a second tunnel formed in at least a second subset of the plurality of beads, wherein the first lysing member extends through the first tunnel, and wherein the second lysing member extends through the second tunnel.

233. The system of example 232, wherein the first lysing member comprises a flexible wire and wherein the second lysing member comprises a flexible wire.

234. The system of example 233, further comprising means for maintaining a flexible lysing member in a rigid state to define a lysing segment.

235. The system of example 234, wherein the means for maintaining a flexible lysing member in a rigid state to define a lysing segment comprises at least one of a bead tunnel having a cross-sectional dimension less than a cross-sectional dimension of a lysing member extending therethrough and a plurality of protuberances.

236. An electrosurgical system, comprising:
 a lysing tip comprising a treatment side and an orientational-deployment side opposite from the treatment side, wherein the lysing tip comprises an upper side and a lower side opposite from the upper side, and wherein the lysing tip further comprises:
  a plurality of beads;
  at least one lysing member defining at least one lysing segment extending between each pair of adjacent beads, wherein the lysing tip comprises a primary axis extending between a first outer bead of the plurality of beads and a second outer bead of the plurality of beads, and wherein each of the plurality of beads comprises a tip extending at least substantially perpendicular to the primary axis; and
  an energy window positioned on at least one of the upper side and the lower side of the lysing tip, wherein the energy window is configured to selectively deliver energy therethrough to treat tissue during a surgical procedure with the lysing tip; and
 a cannula configured for delivery of the lysing tip therethrough into a patient's body, wherein the cannula comprises a cannula axis, and wherein the system is configured such that the lysing tip can be delivered through the cannula in a delivery configuration.

237. The system of example 229, wherein the system is configured such that the lysing tip can be delivered through the cannula in a delivery configuration with the primary axis aligned with the cannula axis.

238. The system of example 229, wherein the energy window comprises an energy window array defined by plurality of electrode termini.

239. The system of example 238, wherein each of the plurality of electrode termini are separated from one another such that the energy window is configured to treat tissue with the energy window to result in damaged tissue from the electrode termini and intermittent islands of undamaged tissue.

240. The system of example 229, further comprising a support member extending between the first outer bead of the plurality of beads and the second outer bead of the plurality of beads opposite from the first outer bead on the orientational-deployment side.

241. The system of example 240, further comprising a first actuation rod and a second actuation rod, wherein the first and second actuation rods are configured to reorient the lysing tip between a delivery configuration in which the primary axis extends through the lumen and a treatment configuration in which the primary axis extends at least substantially perpendicular to an axis of the lumen outside of a distal end of the cannula.

242. The system of example 241, wherein the first actuation rod is coupled to the support member adjacent to the first outer bead, and wherein the second actuation rod is coupled to the support member adjacent to the second outer bead.

243. The system of example 242, wherein the support member is formed in a bow shape from a first end of the support member to a second end of the support member opposite from the first end.

244. The system of example 243, wherein the support member is coupled with the at least one lysing member at the first end second end of the support member and at the second end of the support member.

245. The system of example 229, wherein the energy window comprises an energy window strip, and wherein the energy window strip is positioned to extend along respective upper surfaces of each of the plurality of beads.

246. The system of example 240, wherein the energy window strip comprises a plurality of electrode termini.

247. The system of example 246, wherein each of the plurality of electrode termini protrude from an upper surface of the energy window strip.

248. The system of example 240, further comprising an energy window cover configured to receive the energy window strip and couple the energy window strip with each of the plurality of beads.

249. The system of example 248, wherein the energy window cover comprises an insulation cover made up of a non-conductive material, and wherein the energy window strip is made up of a conductive material configured to receive and delivery energy therethrough.

250. The system of example 249, wherein the insulation cover comprises:
an elongated base configured to receive the energy window strip; and
a plurality of bead coupling members, wherein each of the plurality of bead coupling members is configured to couple with one of the plurality of beads.

251. The system of example 240, wherein the energy window strip is configured to deliver at least one of LASER, intense pulse light, resistive heating, radiant heat, ultrasound, and microwave energy.

252. The system of example 240, wherein the energy window strip is configured to deliver radiofrequency energy.

253. The system of example 238, wherein the energy window is configured to deliver bipolar electrosurgical energy, and wherein a first subset of the plurality of electrode termini are electrically isolated from a second subset of the plurality of electrode termini.

254. A method for delivery of an electrosurgical device into a patient for use during a surgical procedure, the method comprising the steps of:
delivering a lysing tip through a first cannula subcutaneously into a patient's body, wherein the lysing tip comprises:
a plurality of beads;
at least one lysing member defining at least one lysing segment extending between each pair of adjacent beads; and
a support member coupled with the at least one lysing member, wherein the support member is configured to facilitate coupling of the lysing tip to a surgical tool used to control the lysing tip during a surgical procedure within the patient's body;
advancing the lysing tip beyond a distal opening of the first cannula;
delivering the surgical tool into the patient's body adjacent to the lysing tip;
coupling the lysing tip with the surgical tool; and
delivering electrosurgical energy from the surgical tool to the at least one lysing member.

255. The method of example 254, wherein the support member extends between a first outer bead of the plurality of beads and a second outer bead of the plurality of beads opposite from the first outer bead on the orientational-deployment side.

256. The method of example 254, wherein the at least a proximal portion of the support member extends along the orientational-deployment side of the lysing tip, and wherein the step of coupling the lysing tip to the surgical tool comprises coupling the proximal portion of the support member with the surgical tool.

257. The method of example 256, wherein the support member defines a bow shape, wherein the support member comprises a grasping pad, wherein the surgical tool comprises at least one jaw, and wherein the step of coupling the lysing tip to the surgical tool comprises coupling the grasping pad with the at least one jaw.

258. The method of example 254, further comprising a tunnel extending at least partially through each of the plurality of beads, wherein the at least one lysing member is positioned to extend at least partially through the tunnel to define the at least one lysing segment between each pair of adjacent beads.

259. The method of example 254, wherein the step of delivering the surgical tool into the patient's body adjacent to the lysing tip comprises delivering the surgical tool through a second cannula.

260. The method of example 254, further comprising:
advancing a second surgical tool into the patient's body;
using the second surgical tool to couple the lysing tip with the first surgical tool;
releasing the lysing tip from the second surgical tool; and
using the first surgical tool to perform a surgical procedure with the lysing tip.

261. The method of example 254, wherein the lysing tip further comprises a plurality of spacers, and wherein each of the plurality of spacers is coupled with a respective lysing segment of the plurality of lysing segments.

262. A lysing tip, comprising:
- a treatment side and an orientational-deployment side opposite from the treatment side;
- a grasping pad on the orientational-deployment side, wherein the grasping pad is configured to receive and deliver electrosurgical energy;
- a plurality of beads;
- a lysing rod defining a plurality of lysing segments, wherein each of the plurality of lysing segments extends between a pair of adjacent beads of the plurality of beads; and
- a support member coupled to the lysing rod at opposite ends of the lysing rod, wherein the support member is configured to facilitate coupling of the lysing tip to a surgical tool used to control the lysing tip during a surgical procedure within a patient's body and deliver electrosurgical energy through the grasping pad and into the lysing rod.

263. The lysing tip of example 262, wherein the grasping pad is formed on the support member.

264. The lysing tip of example 263, wherein the grasping pad comprises a tab projecting from the support member.

265. The lysing tip of example 262, wherein the support member is coupled to the lysing rod between a first outer bead of the plurality of beads and a second outer bead of the plurality of beads opposite from the first outer bead on the orientational-deployment side.

266. The lysing tip of example 265, wherein the support member is formed in a bow shape from a first end of the support member coupled with the lysing rod to a second end of the support member coupled with the lysing rod opposite from the first end.

267. The lysing tip of example 262, further comprising a plurality of spacers, wherein each of the plurality of spacers is coupled with the lysing rod at a respective lysing segment of the plurality of lysing segments.

268. The lysing tip of example 267, wherein each of the plurality of spacers is fixedly coupled with the lysing rod.

269. The lysing tip of example 267, wherein each of the plurality of spacers comprises a slot configured to allow each of the respective spacers to be coupled with the lysing rod by advancing each of the respective spacers towards the lysing rod adjacent to the slot in a direction perpendicular to an axis of the lysing rod.

270. The lysing tip of example 267, wherein each of the plurality of spacers comprises a conductive material such that electrosurgical energy can be delivered through the spacers from the lysing rod.

271. The lysing tip of example 267, wherein each of the plurality of spacers is configured to confine at least one respective bead of the plurality of beads to a predetermined location on the lysing rod.

272. The lysing tip of example 271, wherein each of the plurality of spacers is configured to restrict an amount of rotation of at least one respective bead of the plurality of beads on the lysing rod.

273. The lysing tip of example 272, wherein each of the plurality of spacers comprises opposing beveled edges configured to selectively restrict rotation of adjacent beads on the lysing rod.

274. The lysing tip of example 271, wherein each of the plurality of spacers is in direct contact with two respective beads on opposite ends of the spacer.

275. The lysing tip of example 262, further comprising a plurality of protuberances configured to confine each of the plurality of beads to a predetermined region relative to the lysing rod, wherein each of the lysing segments comprises a first protuberance adjacent a first respective bead and a second protuberance adjacent a second respective beads.

276. The lysing tip of example 273, wherein the plurality of protuberances are configured to prevent any lateral movement of the plurality of beads on the lysing rod.

277. The lysing tip of example 262, wherein the lysing rod comprises a hollow rod.

278. The lysing tip of example 277, wherein the lysing rod comprises a first plurality of sections having non-circular cross-sections.

279. The lysing tip of example 278, wherein each of the first plurality of sections correspond with each of the plurality of lysing segments.

280. The lysing tip of example 278, wherein each of the plurality of sections is configured to confine each of the plurality of beads to a predetermined region relative to the lysing rod.

281. The lysing tip of example 278, wherein each of the plurality of sections comprises a flattened shape.

282. The lysing tip of example 281, wherein each of the plurality of sections comprises a leading edge extending towards the treatment side.

283. The lysing tip of example 278, wherein the lysing rod further comprises a second plurality of sections having circular cross-sections.

284. The lysing tip of example 283, wherein the second plurality of sections extend through tunnels extending at least partially through each of the plurality of beads.

285. The lysing tip of example 262, wherein the lysing rod extends at least partially through each of the plurality of beads.

286. The lysing tip of example 285, wherein the lysing rod defines a coupling axis with the plurality of beads, wherein each of the plurality of beads defines a bead axis extending from a leading end to a trailing end, and wherein the bead axis of each of the plurality of beads is at least substantially perpendicular to the coupling axis.

287. The lysing tip of example 286, wherein the lysing rod extends through at least a subset of the plurality of beads at a non-central location relative to a bead axis of each of the at least a subset of the plurality of beads.

288. The lysing tip of example 287, wherein the lysing rod extends through each of the plurality of beads at a non-central location relative to a bead axis of each of the plurality of beads.

289. The lysing tip of example 287, wherein the non-central location is positioned towards the leading end of each of the at least a subset of the plurality of beads.

290. The lysing tip of example 262, wherein each of the plurality of beads defines a bead axis extending from a leading end to a trailing end, wherein the plurality of beads comprises a first subset of beads having a first length extending along the bead axis of each of the first subset of beads, wherein the plurality of beads comprises a second subset of beads having a second length extending along the bead axis of each of the second subset of beads, and wherein the first length is greater than the second length.

291. The lysing tip of example 290, wherein the first subset of beads comprises a first outer bead positioned adjacent to a first end of the lysing rod and a second outer bead positioned adjacent to a second end of the lysing rod opposite from the first end.

292. The lysing tip of example 291, wherein each of the second subset of beads comprises a flattened trailing end, and wherein the flattened trailing end is positioned adjacent to the support member so as to accommodate the support member extending proximally of the trailing ends of each of the second subset of beads.

293. The lysing tip of example 292, wherein the support member comprises an insulated portion and a conductive portion.

294. The lysing tip of example 293, wherein the conductive portion comprises at least a portion of a grasping pad formed on the support member.

295. The lysing tip of example 294, wherein the conductive portion comprises an opening formed on the grasping pad.

296. The lysing tip of example 262, wherein each of at least a subset of the plurality of beads is configured so as to allow for rotation of each respective bead of the at least a subset of the plurality of beads about the lysing rod.

297. The lysing tip of example 296, wherein each of the plurality of beads is configured so as to allow for rotation of each respective bead of the plurality of beads about the lysing rod.

298. The lysing tip of example 262, wherein each of at least a subset of the plurality of beads comprises a trailing end having a rougher exterior surface that its respective leading end.

299. The lysing tip of example 298, wherein the at least a subset of the plurality of beads comprises a first outer bead positioned at a first end of the lysing rod and a second outer bead positioned at a second end of the lysing rod opposite from the first end.

300. The lysing tip of example 299, wherein the first outer bead is positioned adjacent to a first end of the lysing rod, and wherein the second outer bead is positioned adjacent to a second end of the lysing rod opposite from the first end of the lysing rod.

301. The lysing tip of example 262, wherein each of at least a subset of the plurality of beads comprises a plurality of faceted surfaces.

302. The lysing tip of example 301, wherein each of at least a subset of the plurality of faceted surfaces is positioned at an acute angle with respect to one another.

303. The lysing tip of example 302, each of at least a subset of the plurality of beads comprises a first faceted surface on an upper side of the bead and a second faceted surface on a lower side of the bead, wherein the first faceted surface and the second faceted surface defined a wedge shape at a leading end of the bead.

304. The lysing tip of example 262, wherein each of at least a subset of the plurality of beads is configured to move with respect to the lysing rod during a surgical procedure.

305. The lysing tip of example 304, wherein each of the at least a subset of the plurality of beads is configured to pivot on the lysing rod.

306. The lysing tip of example 305, wherein each of the at least a subset of the plurality of beads is configured to pivot on the lysing rod in at least two separate planes.

307. The lysing tip of example 262, wherein at least one of the plurality of beads comprises a hole separated from the lysing rod, and wherein the hole is configured to be coupled with means for maintaining retrievability of a free-floating lysing tip when the lysing tip is decoupled from a grasping/control instrument.

308. The lysing tip of example 262, wherein the means for maintaining retrievability of a free-floating lysing tip when the lysing tip is decoupled from a grasping/control instrument comprises a cord.

309. The lysing tip of example 262, further comprising:
a first coupling tip at a first end of the lysing rod; and
a second coupling tip at a second end of the lysing rod, wherein the first coupling tip and the second coupling tip are configured to secure the lysing rod to two outermost beads of the plurality of beads.

310. The lysing tip of example 309, wherein the first coupling tip differs from the second coupling tip.

311. The lysing tip of example 309, wherein the first coupling tip comprises a weld defining a cross-sectional dimension greater in at least one direction that a cross-sectional dimension of the lysing rod.

312. The lysing tip of example 262, wherein the lysing rod comprises at least one of a non-conductive coating and a non-conductive cover positioned at opposing ends of the lysing rod.

313. The lysing tip of example 312, further comprising:
a first coupling tip at a first end of the lysing rod; and
a second coupling tip at a second end of the lysing rod, wherein the first coupling tip and the second coupling tip are configured to secure the lysing rod to two outermost beads of the plurality of beads, and wherein the first coupling tip and the second coupling tip both comprise at least one of a non-conductive coating and a non-conductive cover.

314. The lysing tip of example 262, further comprising:
a first coupling tip at a first end of the lysing rod; and
a second coupling tip at a second end of the lysing rod, wherein the first coupling tip and the second coupling tip are configured to secure the lysing rod to two outermost beads of the plurality of beads, wherein the first coupling tip is positioned within a first outermost bead of the plurality of beads, and wherein the second coupling tip is positioned within a second outermost bead of the plurality of beads opposite from the first outermost bead.

315. The lysing tip of example 314, wherein each of the first outermost bead and the second outermost bead comprises two concentric tunnels, and wherein each of the first coupling tip and the second coupling tip is positioned and configured to engage a ledge positioned at a transition point between the two concentric tunnels.

316. The lysing tip of example 314, wherein each of the first outermost bead and the second outermost bead comprises a tunnel that tapers from a larger dimension to a smaller dimension at an inner side of the outermost beads, and wherein each of the first coupling tip and the second coupling tip is configured to engage a portion of their respective tunnel between the larger dimension and the smaller dimension.

317. The lysing tip of example 262, wherein the grasping pad comprises a plate having opposing flattened surfaces configured to engage opposing jaws of the surgical tool.

318. The lysing tip of example 262, further comprising a non-conductive sheath configured to cover at least a portion of the lysing tip, wherein the non-conductive sheath is configured to expose the plurality of lysing segments.

319. An electrosurgical system, comprising:
a lysing tip comprising:
a plurality of beads; and
a lysing member coupling the plurality of beads together, wherein the lysing member defines at least one lysing segment extending between each pair of adjacent beads of the plurality of beads; and a surgical tool configured to selectively engage the lysing tip and control the lysing tip during a surgical procedure, wherein the surgical tool comprises a pair of jaws configured to engage the lysing tip by grasping the lysing tip.

320. The electrosurgical system of example 319, wherein the electrosurgical system is configured such that the surgical tool is configured to selectively engage the lysing tip by grasping the lysing member.

321. The electrosurgical system of example 319, wherein a distal end of the surgical tool is configured to protrude distally beyond the lysing member when the lysing tip is engaged with the pair of jaws.

322. The electrosurgical system of example 320, wherein, when the lysing tip is engaged with the pair of jaws, the plurality of beads and the distal end of the surgical tool are configured to facilitate blunt dissection of tissue during a surgical procedure.

323. The electrosurgical system of example 320, wherein the distal end of the surgical tool is configured to protrude distally beyond the lysing member when the lysing tip is engaged with the pair of jaws by a distance at least substantially equal to a distance with which each of the plurality of beads protrudes distally from the lysing member.

324. The electrosurgical system of example 320, wherein a portion of the distal end of the surgical tool that protrudes distally beyond the lysing member when the lysing tip is engaged with the pair of jaws has a shape that is at least substantially identical to a shape of a portion of each of the plurality of beads that protrudes distally beyond the lysing member.

325. The electrosurgical system of example 319, wherein the lysing member comprises a lysing plate.

326. The electrosurgical system of example 319, further comprising a slot defined by at least one of the pair of jaws, wherein the slot is configured to receive the lysing member.

327. The electrosurgical system of example 326, wherein the lysing member comprises a lysing plate, and wherein the slot has a size when the pair of jaws is closed that is at least substantially identical to a size of the lysing plate that is configured to be received in the slot such that the lysing plate can be rigidly received within the slot.

328. The electrosurgical system of example 319, wherein the surgical tool is configured to deliver electrosurgical energy to the lysing member through the pair of jaws when the lysing tip is coupled with the surgical tool.

329. The electrosurgical system of example 319, wherein the lysing member comprises a lysing rod.

330. The electrosurgical system of example 329, wherein the lysing rod is configured to be received in a slot formed within at least one jaw of the pair of jaws.

331. The electrosurgical system of example 330, wherein an upper jaw of the pair of jaws comprises an overhang portion that protrudes distally of a lower jaw of the pair of jaws such that a distal end of the surgical tool is wholly defined by the upper jaw.

332. The electrosurgical system of example 330, wherein the lysing rod is configured to be loosely received in the slot such that the lysing tip is allowed to rotate with respect to the surgical tool.

333. The electrosurgical system of example 329, wherein the lysing tip is configured to be coupled with the surgical tool such that, while coupled with the lysing tip, a distal end of the surgical tool protruding distally beyond the lysing rod, has a shape that at least substantially mimics the shapes of each of the plurality of beads.

334. The electrosurgical system of example 329, wherein each of the plurality of beads comprises a hole extending to the lysing rod.

335. The electrosurgical system of example 334, wherein each of the holes of each of the plurality of beads comprises a substantially vertical tunnel extending from an upper surface of each of the plurality of beads to the lysing rod.

336. The electrosurgical system of example 334, wherein each of the holes of each of the plurality of beads comprises a binding material directly coupling each of the plurality of beads to the lysing rod.

337. The electrosurgical system of example 329, further comprising a grasping plate coupled with the lysing rod, wherein the surgical tool is configured to selectively engage the lysing tip and control the lysing tip during a surgical procedure by grasping the grasping plate.

338. The electrosurgical system of example 337, wherein the surgical tool comprises an upper jaw and a lower jaw defining a receiving slot, wherein the lysing plate comprises an upper surface and a lower surface, and wherein the grasping plate is configured to be received in the receiving slot such that the upper surface engages a first inner surface of the upper jaw and such that the lower surface engages a second inner surface of the lower jaw.

339. The electrosurgical system of example 337, wherein the lysing rod is coupled to the grasping plate such that the lysing rod fits within a groove formed in a distal surface of the grasping plate.

340. The electrosurgical system of example 339, wherein the lysing rod is coupled to the grasping plate by way of a snap-fit engagement between a central portion of the lysing rod and the groove.

341. The electrosurgical system of example 337, wherein each of the plurality of beads comprises a trailing end and a leading end, wherein the trailing end of each of the plurality of beads comprises a rougher surface than the leading end.

342. The electrosurgical system of example 337, wherein each of the plurality of beads is at least partially rotatable with respect to the lysing rod.

343. The electrosurgical system of example 342, wherein each of the plurality of beads is at least partially rotatable with respect to each other bead of the plurality of beads.

344. The electrosurgical system of example 337, wherein a first outer end of the lysing rod terminates within a first outer bead of the plurality of beads, and wherein a second outer end of the lysing rod terminates within a second outer bead of the plurality of beads.

345. The electrosurgical system of example 344, wherein the lysing rod comprises opposing coupling tips positioned on the first outer end and the second outer end.

346. The electrosurgical system of example 345, wherein each of the first outer bead and the second outer bead comprises an inner tunnel and an outer tunnel, and wherein the outer tunnel comprises a larger cross-sectional dimension than the inner tunnel such that each of the coupling tips is able to fit within the outer tunnel but unable to fit within the inner tunnel.

347. The electrosurgical system of example 337, wherein the grasping plate comprises at least one of a conductive opening and a conductive projection, wherein the surgical tool comprises at least one of a conductive opening and a conductive projection, and wherein the conductive opening or projection of the grasping plate is configured to selectively engage the conductive projection or opening of the surgical tool to allow for delivery of electrosurgical energy from the surgical tool, through the grasping plate, and into the lysing rod.

348. The electrosurgical system of example 347, wherein the grasping plate comprises a conductive opening, wherein the surgical tool comprises a pair of jaws comprising a conductive projection extending from one of the jaws of the pair of jaws, and wherein the grasping plate is insulated other than the conductive opening.

349. The electrosurgical system of example 348, wherein the grasping plate comprises a plurality of conductive openings, wherein the surgical tool comprises a plurality of conductive projections extending from one of the jaws, and wherein each of the plurality of conductive projections is configured to be received in a respective conductive opening of the plurality of conductive openings.

350. The electrosurgical system of example 319, wherein the plurality of beads comprises a first outer bead positioned at a first end of the lysing member and a second outer bead positioned at a second end of the lysing member opposite from the first end.

351. The electrosurgical system of example 350, wherein the first outer bead comprises a first rounded outer proximal corner, and wherein the second outer bead comprises a second rounded outer proximal corner positioned opposite from the first rounded outer proximal corner.

352. The electrosurgical system of example 351, wherein each of the first outer bead and the second outer bead comprises a flattened proximal surface.

353. The electrosurgical system of example 352, where each of the flattened proximal surfaces extends into a rounded o 354. The electrosurgical system of example 350, wherein each of the first outer bead and the second outer bead comprises an ellipsoidal shape extending from a proximal tip to a distal tip of each of the first outer bead and the second outer bead.

355. The electrosurgical system of example 354, wherein each of the first outer bead and the second outer bead comprises a hole, wherein the hole is configured to couple with a safety line that is configured to extend from the lysing tip within a patient's body to a location outside of the patient's body during a surgical procedure.

356. The electrosurgical system of example 355, wherein the safety line comprises at least one of a cord, a suture, and a hook.

357. The electrosurgical system of example 355, wherein the hole comprises a thru-hole, and wherein the hole is positioned in a proximal portion of each of the first outer bead and the second outer bead proximally of the lysing member.

358. The electrosurgical system of example 357, wherein the safety line comprises a loopable element configured to extend through the hole.

359. An electrosurgical system, comprising:
    a lysing tip comprising:
        a plurality of beads; and
        a lysing member coupling the plurality of beads together, wherein the lysing member defines at least one lysing segment extending between each pair of adjacent beads of the plurality of beads; and
    a surgical tool configured to selectively engage the lysing tip and deliver electrosurgical energy to the lysing member during a surgical procedure.

360. The electrosurgical system of example 359, wherein the lysing tip further comprises a shaft extending proximally from the lysing tip, wherein the shaft is electrically coupled with the lysing member, and wherein the surgical tool comprises a conductive slot configured to engage the shaft such that, when the shaft is engaged with the conductive slot, the surgical tool is able to deliver electrosurgical energy to the lysing member through the shaft.

361. The electrosurgical system of example 360, wherein the lysing tip further comprises a support member coupled with the lysing member.

362. The electrosurgical system of example 361, wherein the shaft is coupled with the support member.

363. The electrosurgical system of example 362, wherein the shaft comprises a conductive inner core, and wherein at least a portion of the shaft comprises an insulating outer shell.

364. The electrosurgical system of example 361, wherein the support member defines a bow shape, wherein the support member comprises a first end positioned adjacent to a first outer bead of the plurality of beads and coupled to the lysing member, and wherein the support member comprises a second end positioned adjacent to a second outer bead of the plurality of beads opposite from the first outer bead and coupled to the lysing member.

365. The electrosurgical system of example 359, further comprising a tether extending from the lysing tip.

366. The electrosurgical system of example 365, wherein the surgical tool comprises an opening configured to receive the tether so as to facilitate coupling the lysing tip to the surgical tool.

367. The electrosurgical system of example 366, wherein the surgical tool comprises at least one jaw configured to receive a portion of the lysing tip.

368. The electrosurgical system of example 367, wherein the opening is positioned in the at least one jaw.

369. The electrosurgical system of example 368, wherein the lysing tip further comprises a grasping pad configured to be received in the at least one jaw, wherein the tether extends from the grasping pad, and wherein the tether is configured to allow the grasping pad to be pulled into the at least one jaw by pulling the tether proximally.

370. The electrosurgical system of example 359, further comprising at least one magnet configured to guide the lysing tip to a coupling region of the surgical tool.

371. The electrosurgical system of example 370, wherein the coupling region comprises a pair of jaws formed on a distal end of the surgical tool.

372. The electrosurgical system of example 371, wherein the at least one magnet is positioned on at least one jaw of the pair of jaws.

373. The electrosurgical system of example 371, wherein the lysing tip further comprises a grasping pad configured to be received in the pair of jaws to couple the lysing tip with the surgical tool, and wherein the at least one magnet comprises a first magnet positioned on the grasping pad and a second magnet positioned on at least one jaw of the pair of jaws.

374. The electrosurgical system of example 359, wherein the surgical tool comprises at least one of an opening and a projection, wherein the lysing tip comprises at least one of a projection and an opening configured to mate with the at least one of an opening and a projection of the surgical tool to lock the lysing tip in place on the surgical tool during a surgical procedure.

375. The electrosurgical system of example 374, wherein the surgical tool comprises an upper jaw and a lower jaw, wherein the at least one of an opening and a projection extends from at least one of the upper jaw and the lower jaw, and wherein the lysing tip is configured to be received and engaged in between the upper jaw and the lower jaw during a surgical procedure.

376. The electrosurgical system of example 375, wherein the lysing tip comprises a support member extending adjacent to and proximal of the plurality of beads, and wherein the at least one of a projection and an opening of the lysing tip is formed on the support member.

377. The electrosurgical system of example 376, wherein the lysing tip comprises a first projection extending from an upper surface of the support member and a second projection extending from a lower surface of the support member, wherein the upper jaw comprises a first opening configured to receive the first projection, and wherein the lower jaw comprises a second opening configured to receive the second projection.

378. The electrosurgical system of example 377, wherein at least one of the first projection and the second projection is configured lock the lysing tip in place relative to the surgical tool at a preconfigured rotational orientation.

379. The electrosurgical system of example 378, wherein the at least one of the first projection and the second projection comprises a faceted surface, and wherein the surgical tool comprises an opening comprising a shape configured to mate with the faceted surface.

380. The electrosurgical system of example 378, wherein the at least one of the first projection and the second projection is configured to allow for locking the lysing tip in place relative to the surgical tool at any of a plurality of preconfigured rotational orientations.

381. The electrosurgical system of example 378, wherein the first projection is configured to lock the lysing tip in place relative to the surgical tool at a preconfigured rotational orientation, and wherein the second projection is configured to be received in the second opening so as to allow the lysing tip to rotate with respect to the surgical tool while the lysing tip is coupled with the surgical tool.

382. The electrosurgical system of example 381, wherein the upper jaw is configured to move with respect to the lower jaw such that the lysing tip can be rotated while the second projection is received within the second opening and the first projection is withdrawn from the first opening and then the upper jaw closed to insert the first projection into the first opening and lock the lysing tip at a particular rotational orientation.

383. A lysing tip, comprising:
a plurality of beads comprising a first outer bead and a second outer bead opposite from the first outer bead; and
a lysing rod extending along a treatment side of the lysing tip and extending at least partially through each of the plurality of beads to couple the plurality of beads to one another, wherein the lysing rod defines at least one lysing segment extending between each pair of adjacent beads of the plurality of beads, and wherein the lysing rod is configured such that a central portion of the lysing rod protrudes further distally from the treatment side than opposing portions of the lysing rod immediately adjacent to the first outer bead and the second outer bead.

384. The lysing tip of example 383, wherein the lysing rod extends in a bowed shape along the treatment side of the lysing tip.

385. The lysing tip of example 384, wherein the plurality of beads further comprises at least one middle bead positioned between the first outer bead and the second outer bead, and wherein the at least one middle bead protrudes distally from the treatment side to a greater extent than either the first outer bead or the second outer bead.

386. The lysing tip of example 384, further comprising a support member extending along a side of the lysing tip opposite from the treatment side, wherein the support member is configured to facilitate coupling of the lysing tip to a surgical tool used to control the lysing tip during a surgical procedure within a patient's body.

387. The lysing tip of example 386, wherein the support member extends in a bowed shape along the side of the lysing tip opposite from the treatment side, and wherein the bowed shape of the support member extends in an opposite direction relative to the bowed shape of the lysing rod.

388. The lysing tip of example 387, wherein the support member further comprises a tongue coupled with at least one central lysing segment of the lysing rod, wherein the tongue is configured to maintain the central portion of the lysing rod in a position protruding further distally from the treatment side than opposing portions of the lysing rod.

389. The lysing tip of example 388, wherein the tongue is coupled with a single lysing segment of the lysing rod.

390. The lysing tip of example 388, further comprising a groove formed in the tongue, wherein the at least one central lysing segment is positioned within the groove.

391. The lysing tip of example 388, wherein the tongue is positioned in contact with two beads on opposing sides of the tongue such that the tongue defines a length of a center lysing segment of the plurality of lysing segments.

392. The lysing tip of example 391, further comprising a plurality of spacers positioned on the lysing rod so as to confine each of the plurality of beads to predetermined locations on the lysing rod.

393. The lysing tip of example 392, wherein the center lysing segment lacks a spacer, and wherein each of the lysing segments other than the center lysing segment comprises a spacer positioned thereon.

394. A lysing tip, comprising:
a plurality of beads;
at least one lysing rod defining at least one lysing segment extending between each pair of adjacent beads;
a tunnel extending at least partially through each of the plurality of beads, wherein the at least one lysing member is positioned to extend at least partially through the tunnel to define the at least one lysing segment between each pair of adjacent beads; and
a plurality of sleeves positioned on the at least one lysing rod, wherein each of the plurality of sleeves is positioned within a bead of the plurality of beads in between the bead and the at least one lysing rod.

395. The lysing tip of example 394, wherein the plurality of sleeves comprises:
a pair of outer bead sleeves positioned within two opposing outer beads of the plurality of beads; and
at least one inner bead sleeve positioned within at least one inner bead positioned between the two opposing outer beads, wherein the pair of outer bead sleeves differs in structure from the at least one inner bead sleeve.

396. The lysing tip of example 394, wherein each of the plurality of sleeves comprises a material configured to at least partially insulate each of the plurality of beads from heat from the at least one lysing rod.

397. The lysing tip of example 396, wherein each of the plurality of sleeves comprises at least one of a ceramic material and a high-temperature thermoplastic.

398. The lysing tip of example 397, wherein each of the plurality of sleeves comprises at least one of an alumina, a carbide, a nitride, quartz silica, a silicate, an yttria, a zirconia, a thermoset plastic, and a high-performance thermoplastic.

399. The lysing tip of example 394, wherein at least a subset of the plurality of sleeves is configured to rotate about the at least one lysing rod such that beads coupled with each of the at least a subset of the plurality of sleeves can rotate on its respective sleeve with respect to the at least one lysing rod.

400. The lysing tip of example 399, wherein each of the plurality of sleeves is configured to allow each of the plurality of beads to rotate about the at least one lysing rod, and wherein each of the plurality of beads is configured to pivot with respect to the at least one lysing rod as it passes through tissue during a surgical procedure.

401. The lysing tip of example 394, wherein each of the plurality of sleeves comprises a raised band, and wherein each of the raised bands is configured to prevent one of the beads from moving laterally along the at least one lysing rod.

402. The lysing tip of example 401, wherein the plurality of sleeves comprises:
a pair of outer bead sleeves positioned within two opposing outer beads of the plurality of beads, wherein each of the pair of outer bead sleeves comprises a raised band formed on an outer edge of the outer bead sleeve; and
at least one inner bead sleeve positioned within at least one inner bead positioned between the two opposing outer beads, wherein each of the at least one inner bead sleeve comprises a raised band spaced apart from two opposing ends of each of the at least one inner bead sleeve.

403. The lysing tip of example 401, wherein the plurality of sleeves comprises a pair of outer bead sleeves positioned within two opposing outer beads of the plurality of beads, and wherein each of the pair of outer bead sleeves comprises an inner tunnel comprising an internal ledge at a transition between a smaller diameter portion of the inner tunnel and a larger diameter portion of the inner tunnel.

404. The lysing tip of example 394, further comprising a plurality of protuberances positioned on the at least one lysing rod, wherein each of at least a subset of the plurality of sleeves comprises a first protuberance positioned adjacent a first end of the sleeve and a second protuberance positioned adjacent a second end of the sleeve opposite from the first end so as to confine the sleeve to a predetermined location on the at least one lysing rod.

405. The lysing tip of example 394, further comprising at least one spacer positioned in between at least two adjacent beads of the plurality of beads, wherein the at least one spacer is configured to confine at least one sleeve of the plurality of sleeves to a predetermined location on the at least one lysing rod.

406. The lysing tip of example 394, wherein the at least one lysing rod comprises at least one hollow lysing rod.

407. The lysing tip of example 406, wherein the at least one hollow lysing rod comprises at least one flattened section extending between at least two adjacent beads of the plurality of beads.

408. The lysing tip of example 407, wherein the at least one flattened section comprises a leading distal edge extending at least substantially towards a treatment side of the lysing tip.

409. The lysing tip of example 394, wherein the plurality of sleeves comprises a pair of outer bead sleeves positioned within two opposing outer beads of the plurality of beads, wherein each of the pair of outer bead sleeves comprises an inner tunnel configured to receive the at least one lysing rod, and wherein the inner tunnel of each of the outer bead sleeves comprises a taper from a larger diameter to a smaller diameter.

410. The lysing tip of example 409, wherein coupling tips are formed on opposing ends of the at least one lysing rod, and wherein the taper of each of the inner tunnels of the outer bead sleeves is configured to engage one of the coupling tips.

411. The lysing tip of example 394, wherein the at least one lysing rod extends along a treatment side of the lysing tip, and wherein the lysing tip further comprises a support member extending along a side of the lysing tip opposite from the treatment side.

412. The lysing tip of example 411, wherein the support member defines a bow shape, and wherein the support member is coupled at opposite ends of the support member to the at least one lysing rod.

413. The lysing tip of example 412, wherein the at least one lysing rod extends through openings in the support member formed at the opposite ends of the support member.

414. The lysing tip of example 394, wherein at least one of the plurality of beads comprises at least one facet comprising a flattened region formed on the at least one of the plurality of beads.

415. The lysing tip of example 394, further comprising a support member extending along a side of the lysing tip opposite from the treatment side, wherein the support member extends proximally behind each of a plurality of middle beads positioned between two opposing outer beads positioned at opposite ends of the at least one lysing rod.

416. The lysing tip of example 415, wherein the lysing tip is configured to perform in a relaxed configuration in which each of the middle beads does not contact the support member and a flexed configuration in which at least one of the middle beads contacts the support member.

417. The lysing tip of example 415, wherein at least a subset of the plurality of beads is configured to rotate about the at least one lysing rod, wherein the lysing tip is configured such that each of the middle beads does not contact the support member in a relaxed configuration, and wherein the lysing tip is configured such that at least one of the middle beads contacts the support member following sufficient rotation of the at least one of the middle beads about the at least one lysing rod so as to prevent further rotation.

418. The lysing tip of example 394, wherein each of the plurality of beads comprises at least one of a plastic, a gelatin, and a hydrogel material.

419. The lysing tip of example 418, wherein each of the plurality of beads is overmolded onto one of the plurality of sleeves.

420. The lysing tip of example 394, wherein each of at least a subset of the plurality of beads comprises an at least substantially annular bead structure.

421. The lysing tip of example 420, wherein each of the at least a subset comprises an annular bead structure having at least one of a circular shape and an oval shape in cross-section.

422. The lysing tip of example 420, wherein the plurality of beads comprises a first outer bead, a second outer bead positioned opposite from the first outer bead, and at least one middle bead positioned in between the first outer bead and the second outer bead, wherein the at least one middle bead defines a partial annular shape.

423. The lysing tip of example 422, wherein the at least one middle bead comprises opposite ends each terminating in a knob at a proximal side of the at least one middle bead.

424. The lysing tip of example 420, wherein each of the at least a subset comprises a bead hub positioned within the annular bead structure, and wherein each of the bead hubs is configured to couple the annular bead structure with one of the plurality of sleeves.

425. The lysing tip of example 424, wherein each of the at least a subset further comprises at least one spoke extending from the bead hub to the annular bead structure.

426. The lysing tip of example 424, wherein each of the at least a subset further comprises a bead hub frame extending continuously from the bead hub to the annular bead structure without protruding laterally beyond an upper profile of the annular bead structure.

427. The lysing tip of example 420, wherein the at least one lysing rod comprises a plurality of deformed regions corresponding with the plurality of sleeves so as to prevent each of the plurality of sleeves from being removed from a predefined region on the at least one lysing rod.

428. The lysing tip of example 420, wherein the plurality of beads comprises a first outer bead, a second outer bead positioned opposite from the first outer bead, and at least one middle bead positioned in between the first outer bead and the second outer bead, wherein each of the first outer bead and the second outer bead defines a full annular structure extending in a full perimeter about a respective sleeve of the plurality of sleeves, and wherein the at least one middle bead defines a partial annular structure extending in a partial perimeter about a respective sleeve the plurality of sleeves.

429. The lysing tip of example 428, wherein each of the at least one middle bead comprises knobs formed at opposing ends of the partial annular structure.

430. The lysing tip of example 428, wherein the at least one lysing rod extends along a treatment side of the lysing tip, wherein the lysing tip further comprises a support member extending along a side of the lysing tip opposite from the treatment side, and wherein the at least one middle bead is configured to operate in a relaxed configuration in which the at least one middle bead is spaced apart from the support member, a first flexed configuration in which the at least one middle bead rotates about the lysing rod in a first direction and a first terminal end of the at least one middle bead contacts the support member to inhibit further rotation in the first direction, and a second flexed configuration in which the at least one middle bead rotates about the lysing rod in a second direction and a second terminal end of the at least one middle bead opposite from the first terminal end contacts the support member to inhibit further rotation in the second direction.

431. The lysing tip of example 420, wherein the plurality of beads comprises a first outer bead, a second outer bead positioned opposite from the first outer bead, and at least one middle bead positioned in between the first outer bead and the second outer bead, wherein each of the plurality of beads defines a full annular structure extending in a full perimeter about a respective sleeve of the plurality of sleeves.

432. The lysing tip of example 431, wherein each of the at least one middle bead comprises a full annular structure comprising a rounded leading end and a flattened trailing end.

433. The lysing tip of example 432, wherein the first outer bead and the second outer bead comprise a rounded leading end and a rounded trailing end.

434. The lysing tip of example 431, wherein each of the at least a subset comprises a bead hub positioned within the annular bead structure, wherein each of the bead hubs is configured to couple the annular bead structure with one of the plurality of sleeves, and wherein the first outer bead and the second outer bead are coupled directly to an interior surface of the full annular structure.

435. The lysing tip of example 420, wherein each of the plurality of beads comprises an annular structure, and wherein the annular structure comprises an annular band structure.

436. The lysing tip of example 435, wherein the annular band structure is defined by an upper surface extending in a full perimeter about the annular band structure, wherein the annular band structure is further defined by a lower surface extending in a full perimeter about the annular band structure, and wherein the upper surface is at least substantially parallel to the lower surface about the full perimeter.

437. The lysing tip of example 435, wherein the annular band structure comprises a resiliently flexible material such that the annular band structure can deform during a surgical procedure and automatically return to a relaxed configuration.

438. The lysing tip of example 437, wherein each of the plurality of beads comprises a bead hub positioned within the annular band structure, wherein each of the bead hubs is configured to couple the annular band structure with one of the plurality of sleeves.

439. The lysing tip of example 438, wherein each of the plurality of beads further comprises at least two spokes extending between the bead hub and the annular band structure.

440. The lysing tip of example 439, wherein the at least two spokes comprises only a first spoke extending between an upper portion of the annular band structure and a second spoke extending between a lower portion of the annular band structure, and wherein the first spoke and the second spoke are positioned and configured to allow the annular band structure to compress during a surgical procedure.

441. The lysing tip of example 440, wherein the first spoke and the second spoke are positioned and configured to allow the annular band structure to compress between an upper portion and a lower portion of the annular band structure and to compress between a distal portion and a proximal portion of the annular band structure.

442. The lysing tip of example 437, wherein the annular band structure is configured to compress during a surgical procedure to reduce a cross-sectional profile of the annular band structure between an upper end of the annular band structure and a lower end of the annular band structure.

443. The lysing tip of example 442, wherein the annular band structure is further configured such that, upon encountering sufficiently dense tissue at a distal tip of the annular band structure, the at least one lysing rod advances in a distal direction relative to the annular band structure.

444. The lysing tip of example 442, wherein the annular band structure is configured to elongate between a distal end and a proximal end of the annular band structure as the annular band structure compresses to reduce the cross-sectional profile.

445. A system comprising the lysing tip of example 394, wherein the system further comprises:
   a cannula configured to deliver the lysing tip therethrough; and
   a deployment assembly configured to reposition the lysing tip from a delivery configuration and a treatment configuration.

446. The system of example 445, wherein the deployment assembly comprises a pair of actuation rods coupled to the lysing tip, wherein the pair of actuation rods is configured to pivot the lysing tip between the delivery and treatment configurations.

447. The system of example 446, wherein, in the delivery configuration, an axis of the at least one lysing rod extends along an axis of the cannula, and wherein, in the treatment configuration, the axis of the at least one lysing rod extends at least substantially perpendicular to the axis of the cannula outside of a distal opening of the cannula.

448. A system for delivery of tissue modification energy during a surgical procedure, the system comprising:
   a tissue modification tip comprising an energy window configured to deliver energy therethrough for modification of patient tissue during a surgical procedure;
   at least one cannula configured to deliver the tissue modification tip therethrough; and
   a deployment assembly comprising at least one actuation rod, wherein the at least one actuation rod is configured to pivot the tissue modification tip between a delivery configuration in which an axis of the energy window extends along an axis of the cannula and a treatment configuration in which the axis of the energy window extends at least substantially perpendicular to the axis of the cannula outside a distal opening of the at least one cannula.

449. The system of example 448, wherein the at least one cannula comprises an inner cannula and an outer cannula.

450. The system of example 449, wherein the tissue modification tip is configured to be fully received within the outer cannula in the delivery configuration, and wherein the tissue modification tip is configured to be unable to be fully received within the inner cannula in the delivery configuration.

451. The system of example 448, wherein the energy window comprises an energy window array comprising a plurality of isolated energy window termini.

452. The system of example 451, wherein the energy window is configured to deliver electrosurgical energy through each of the plurality of isolated energy window termini.

453. The system of example 452, wherein the energy window is configured to deliver coagulation electrosurgical energy through each of the plurality of isolated energy window termini.

454. The system of example 451, wherein the energy window is configured to deliver pulsed electrosurgical energy through each of the plurality of isolated energy window termini.

455. The system of example 454, wherein the pulsed electrosurgical energy is configured such that, upon moving the tissue modification tip through a patient's tissue, intermittent islands of unmodified tissue are created in between tissue modified by the energy window.

456. The system of example 451, wherein at least a first subset of the plurality of isolated energy window termini is both physically and electrically isolated from at least a second subset of the plurality of isolated energy window termini.

457. The system of example 456, wherein each of the first subset of the plurality of isolated energy window termini is configured to deliver a first modality of energy, and wherein the second subset of the plurality of isolated energy window termini is configured to deliver a second modality of energy that differs from the first modality.

458. The system of example 457, wherein the first modality comprises an electrosurgical energy of a first frequency, and wherein the second modality comprises an electrosurgical energy of a second frequency distinct from the first frequency.

459. The system of example 448, wherein the at least one actuation rod comprises:
   a central actuation rod coupled to a central portion of the tissue modification tip; and
   a side actuation rod coupled at a first end of the side actuation rod to the tissue modification tip adjacent a first end of the tissue modification tip and coupled to the central actuation rod at a second end of the side actuation rod opposite from the first end of the side actuation rod.

460. The system of example 448, further comprising at least one canal configured to extend through the at least one cannula to deliver fluid to a surgical site adjacent to the tissue modification tip during a surgical procedure.

461. A system for delivery of tissue modification energy during a surgical procedure, the system comprising:
   a tissue modification tip comprising an energy window configured to deliver energy therethrough for modification of patient tissue during a surgical procedure;
   a grasping pad; and
   a first instrument configured to selectively couple with the tissue modification tip, wherein the first instrument is configured to selectively couple with the tissue modification tip at the grasping pad.

462. The system of example 461, wherein the energy window comprises an elongated energy window extending along an upper surface of the tissue modification tip.

463. The system of example 462, wherein the tissue modification tip comprises a plurality of bars extending across the elongated energy window, and wherein the plurality of bars is configured to separate the elongated energy window into a plurality of isolated energy windows.

464. The system of example 463, wherein the elongated energy window comprises a primary axis extending from a first side of the elongated energy window to a second side of the elongated energy window opposite from the first side, and wherein each of the plurality of bars extends across the elongated energy window in a direction at least substantially perpendicular to the primary axis.

465. The system of example 461, wherein the energy window comprises a plurality of isolated energy window termini formed on an upper surface of the tissue modification tip.

466. The system of example 461, wherein the grasping pad is electrically coupled with the energy window, and wherein the first instrument is configured to deliver energy to the energy window through the grasping pad while the tissue modification tip is coupled with the first instrument.

467. The system of example 461, further comprising an energy conduit coupled with the energy window.

468. The system of example 467, wherein the energy conduit comprises a wire extending from the energy window and configured to extend through a lumen formed in the first instrument.

469. The system of example 461, wherein the energy window is configured to deliver at least one of LASER, intense pulse light, resistant heating, radiant heat, thermochromic, ultrasound, and microwave energy.

470. The system of example 461, wherein the tissue modification tip further comprises at least one of an energy window tongue and an energy window slot configured to couple with a corresponding slot or tongue of the first instrument, and wherein the at least one of an energy window tongue and an energy window slot is configured to deliver energy therethrough to the energy window from the first instrument.

471. The system of example 470, wherein the tissue modification tip comprises an energy window tongue formed on the grasping pad, wherein the first instrument comprises a pair of jaws configured to grasp the grasping pad, wherein the first instrument comprises an energy window slot configured to receive the energy window tongue, and wherein the energy window slot is formed on at least one of the pair of jaws.

472. An electrosurgical system, comprising:
a lysing tip configured for delivery of electrosurgical energy, wherein the lysing tip comprises:
a first lysing tip portion comprising an energy delivery side configured to receive and deliver electrosurgical energy for one or more of tissue dissection and modification and an orientational-deployment side opposite from the energy delivery side;
a second lysing tip portion pivotably coupled with the first lysing tip portion and comprising an energy delivery side configured to receive and deliver electrosurgical energy for one or more of tissue dissection and modification and an orientational-deployment side opposite from the energy delivery side, wherein the lysing tip is configured to be repositioned between a delivery configuration in which the energy delivery side of the first lysing tip portion is positioned adjacent to the energy delivery side of the second lysing tip portion and a treatment configuration in which the energy delivery side of the first lysing tip portion and the energy delivery side of the second lysing tip portion collectively define an energy delivery side of the lysing tip; and
a deployment assembly coupled with the lysing tip, wherein the deployment assembly is configured to allow for selective repositioning between the delivery configuration and the treatment configuration.

473. The system of example 472, wherein each of the first tip portion and the second tip portion comprises a plurality of protrusions and at least one recession positioned between at least two adjacent protrusions in the plurality of protrusions.

474. The system of example 473, wherein the lysing tip comprises at least one lysing member forming a lysing segment between each two adjacent protrusions.

475. The system of example 473, wherein the lysing tip is configured such that at least a subset of the plurality of protrusions of the first tip portion nests within at least a subset of the at least one recession of the second tip portion in the delivery configuration.

476. The system of example 472, wherein the first tip portion is configured to extend at least substantially parallel to the second tip portion in the delivery configuration.

477. The system of example 472, wherein the first tip portion is configured to extend adjacent to the second tip portion in the treatment configuration such that the orientational-deployment side of the first tip portion extends at least substantially co-planar relative to the orientational-deployment side of the second tip portion.

478. The system of example 472, wherein the lysing tip is configured such that the first tip portion may be approximated with the second tip portion during a surgical procedure to clamp patient tissue therebetween.

479. The system of example 472, wherein the lysing tip is configured to operate in an intermediate configuration between the treatment configuration and the delivery configuration, wherein, in the intermediate configuration, the orientational-deployment sides of the first and second tip portions extend at an acute angle relative to one another, and wherein the lysing tip is configured to deliver electrosurgical energy to both the first and second tip portions in the intermediate configuration.

480. The system of example 472, wherein the first tip portion comprises at least one lysing segment configured to deliver electrosurgical energy therethrough, wherein the second tip portion comprises at least one lysing segment configured to deliver electrosurgical energy therethrough, and wherein the at least one lysing segment of the first tip portion is electrically isolated from the at least one lysing segment of the second tip portion.

481. The system of example 480, wherein the lysing tip comprises a bipolar lysing tip.

482. The system of example 472, wherein the lysing tip comprises a bipolar lysing tip, wherein the first tip portion comprises at least one lysing segment configured to deliver electrosurgical energy therethrough, wherein the second tip portion comprises at least one lysing segment configured to deliver electrosurgical energy therethrough, and wherein the lysing tip is configured such that, in the treatment configuration, each lysing segment of the first and second tip portions is configured to deliver electrosurgical energy of an opposite polarity relative to each adjacent lysing segment of the first and second tip portions.

483. A method for electrosurgically treating patient tissue, the method comprising the steps of:
delivering a lysing tip through a first cannula in a delivery configuration, wherein the lysing tip comprises:
a first lysing tip portion comprising an energy delivery side configured to receive and deliver electrosurgical energy for one or both of tissue dissection and modification and an orientational-deployment side opposite from the energy delivery side;
a second lysing tip portion pivotably coupled with the first lysing tip portion and comprising an energy delivery side configured to receive and deliver electrosurgical energy for tissue dissection and/or modification and an orientational-deployment side opposite from the energy delivery side, wherein at least one of the energy delivery side and the orientational-deployment side of both the first lysing tip portion and the second lysing tip portion faces an inner wall of the cannula in the delivery configuration;
reconfiguring the lysing tip to a treatment configuration by pivoting the first lysing tip portion relative to the second lysing tip portion; and
delivering electrosurgical energy to the first and second lysing tip portions to treat patient tissue.

484. The method of example 483, wherein the lysing tip is configured in the delivery configuration such that the energy delivery side of the first lysing tip portion faces the energy delivery side of the second lysing tip portion.

485. The method of example 484, wherein the step of reconfiguring the lysing tip to a treatment configuration comprises pivoting the first lysing tip portion relative to the second lysing tip portion such that the first lysing tip portion extends at an acute angle relative to the second lysing tip portion.

486. The method of example 485, further comprising:
positioning at least one of a duct and a blood vessel of a patient in between the first lysing tip portion and the second lysing tip portion; and approximating the first and second lysing tip portions to clamp the at least one of a duct and a blood vessel therebetween.

487. The method of example 484, wherein the step of reconfiguring the lysing tip to a treatment configuration comprises pivoting the first lysing tip portion relative to the second lysing tip portion such that the first lysing tip portion is aligned with the second lysing tip portion and such that the energy delivery sides of the first and second lysing tip portions extend in at least substantially the same direction.

488. The method of example 484, wherein the step of reconfiguring the lysing tip to a treatment configuration comprises pivoting the first lysing tip portion relative to the second lysing tip portion such that the first lysing tip portion and the second lysing tip portion are at least substantially perpendicular to an axis of the first cannula.

489. The method of example 488, wherein, in the treatment configuration, at least one of the first and second lysing tip portions extend beyond a cross-sectional profile of the first cannula.

490. The method of example 489, wherein, in the treatment configuration, both the first and second lysing tip portions extend beyond the cross-sectional profile of the first cannula.

491. A method for performing an electrosurgical procedure, the method comprising the steps of:
delivering a lysing tip through an entrance incision into a patient's body in a delivery configuration, wherein the lysing tip comprises:
a plurality of protrusions; and
at least one lysing segment positioned between at least two adjacent protrusions in the plurality of protrusions;
reconfiguring the lysing tip to a treatment configuration; and
passing the lysing tip to a target tissue area within the patient's body.

492. The method of example 491, wherein the step of delivering a lysing tip through an entrance incision into a patient's body in a delivery configuration comprises delivering the lysing tip through a first cannula into the patient's body in the delivery configuration.

493. The method of example 492, wherein the lysing tip extends at least substantially along an axis of the first cannula in the delivery configuration, and wherein the step of reconfiguring the lysing tip to a treatment configuration comprises pivoting the lysing tip outside of a distal end of the first cannula such that at least one end of two opposing ends of the lysing tip extends beyond a cross-sectional profile of the first cannula.

494. The method of example 491, further comprising setting a threshold temperature for operation of the lysing tip.

495. The method of example 494, wherein the threshold temperature comprises at least one of a threshold temperature of patient tissue and a threshold temperature of at least a portion of the lysing tip.

496. The method of example 491, further comprising setting an energy level for delivery of electrosurgical energy to the lysing tip.

497. The method of example 491, wherein the step of delivering the lysing tip comprises inserting the lysing tip through the entrance incision through a first cannula and releasing the lysing tip, and wherein the step of reconfiguring the lysing tip to a treatment configuration comprises delivering a grasping/control instrument into the patient's body adjacent to the lysing tip and coupling the lysing tip with the grasping/control instrument.

498. The method of example 491, further comprising delivering electrosurgical energy to the at least one lysing segment.

499. The method of example 491, further comprising:
obtaining sensor data;
comparing the sensor data with a threshold; and
upon detecting that a parameter of the sensor data has exceeded the threshold, reducing energy delivered to the lysing tip.

500. The method of example 499, wherein the sensor data comprises temperature data, and wherein the threshold comprises a temperature threshold.

501. The method of example 491, further comprising receiving location data associated with the lysing tip during a surgical procedure.

502. The method of example 501, wherein the step of receiving location data comprises receiving RFID tag data from an RFID tag located on the lysing tip.

503. The method of example 501, further comprising receiving temperature data from a temperature sensor on the lysing tip.

504. The method of example 503, further comprising combining the temperature data and the location data.

505. The method of example 504, further comprising creating an image using both the temperature data and the location data.

506. The method of example 505, wherein the image allows a user to determine which regions within a patient's body have been adequately treated using the lysing tip.

507. The method of example 505, wherein the image allows a user to determine which regions within a patient's body have exceeded a threshold temperature resulting from use of the lysing tip.

508. The method of example 491, wherein the entrance incision comprises a first length, wherein the lysing tip comprises a greatest dimension, and wherein the first length is less than the greatest dimension of the lysing tip.

509. The method of example 508, wherein the greatest dimension of the lysing tip is defined between a first outer protrusion of the plurality of protrusions and a second outer protrusion of the plurality of protrusions opposite from the first outer protrusion.

510. The method of example 509, wherein the step of delivering the lysing tip comprises inserting the lysing tip through the entrance incision through a first cannula in the delivery configuration and extending the lysing tip through a distal opening of the first cannula, and wherein the step of reconfiguring the lysing tip to the treatment configuration comprises rotating the lysing tip within the patient's body such that the greatest dimension is greater than a cross-sectional diameter of the first cannula and such that the lysing tip cannot be received back into the first cannula in the treatment configuration.

511. The method of example 510, wherein the step of delivering the lysing tip comprises inserting the lysing tip through the entrance incision through a first cannula extending over a second cannula.

512. The method of example 511, wherein the lysing tip is configured such that it may not be received within the second cannula in the delivery configuration.

513. The method of example 491, further comprising creating a path to a target organ using the lysing tip.

514. The method of example 513, wherein the step of creating a path to the target organ comprises activating an electrosurgical generator and delivering electrosurgical energy from the electrosurgical generator to the at least one lysing segment.

515. The method of example 513, further comprising identifying critical tissue that is not to be treated using the lysing tip, and wherein the step of creating the path to the target organ comprises creating a path to the target organ that avoids the critical tissue.

516. The method of example 513, further comprising expanding the path to the target organ using the lysing tip.

517. The method of example 516, wherein the plurality of protrusions comprises a first outer protrusion and a second outer protrusion opposite from the first outer protrusion, wherein the first outer protrusion extends in a first direction, wherein the second outer protrusion extends in a second direction, and wherein the first direction extends at an angle relative to the second direction.

518. The method of example 517, wherein the step of expanding the path to the target organ comprises using a side-to-side fanning motion to expand the path.

519. The method of example 491, further comprising:
creating a path to a target organ using the lysing tip;
reconfiguring the lysing tip from the treatment configuration to the delivery configuration;
withdrawing the lysing tip from the patient's body through the entrance incision;
inserting a tissue modification tip comprising an energy window configured to deliver energy therethrough into the patient's body; and
extending the tissue modification tip through the path to the target tissue area.

520. The method of example 519, further comprising at least one of removing an organ and accessing an organ at the target tissue area using the lysing tip.

521. The method of example 520, further comprising using the tissue modification tip to achieve hemostasis at the target tissue area.

The method of example 520, wherein the organ comprises at least one of a muscle, a parotid gland, a salivary gland, a thyroid gland, a lung, a heart, a liver, a pancreas, a spleen, a gallbladder, a kidney, an adrenal gland, a prostate, an ovary, a uterus, a bladder, a blood vessel, a nerve, a lymph node, and a bone.

522. The method of example 491, further comprising:
reconfiguring the lysing tip from the treatment configuration to the delivery configuration; and
withdrawing the lysing tip from the patient's body.

523. The method of example 522, wherein the step of reconfiguring the lysing tip from the treatment configuration to the delivery configuration comprises rotating the lysing tip such that a primary axis of the lysing tip extends at least substantially along a direction of withdrawal of the lysing tip.

524. The method of example 523 wherein the step of reconfiguring the lysing tip from the treatment configuration to the delivery configuration comprises rotating the lysing tip such that a primary axis of the lysing tip extends at least substantially along an axis of a cannula, and wherein the step of withdrawing the lysing tip comprises withdrawing the lysing tip through the cannula.

525. The method of example 491, further comprising creating a path to a site of herniated tissue using the lysing tip.

526. The method of example 525, further comprising dissecting tissue around the herniated tissue using the lysing tip to prepare the site for excision of the herniated tissue.

527. The method of example 526, further comprising using the lysing tip to excise at least a portion of the herniated tissue.

528. The method of example 527, further comprising applying energy to tissue remaining at the site following excision of the herniated tissue.

529. The method of example 528, wherein the step of applying energy to remaining tissue at the site following excision of the herniated tissue comprises applying energy using at least one of the lysing tip and a separate tissue modification tip.

530. The method of example 528, further comprising:
binding at least some of the remaining tissue; and
using at least one of the lysing tip and a separate tissue modification tip to induce supportive fibrosis at the site.

531. The method of example 491, CNS access further comprising creating a path to at least one of the brain, spinal cord, and adjacent proximal nerves.

532. The method of example 491, further comprising creating a path to a peripheral nerve using the lysing tip.

533. The method of example 532, further comprising using the lysing tip to remove at least one of a tumor and fibrotic tissue from the peripheral nerve.

534. The method of example 533, wherein the step of using the lysing tip to remove at least one of a tumor and fibrotic tissue from the peripheral nerve is performed without delivering electrosurgical energy to the at least one lysing segment.

535. The method of example 534, wherein the step of creating a path to a peripheral nerve using the lysing tip is performed at least in part while delivering electrosurgical energy to the at least one lysing segment.

536. The method of example 533, further comprising, following the step of using the lysing tip to remove at least one of a tumor and fibrotic tissue from the peripheral nerve:
activating the lysing tip so as to deliver electrosurgical energy through the at least one lysing segment; and
inducing hemostasis at a site of removal of the at least one of a tumor and fibrotic tissue using the lysing tip.

537. The method of example 491, further comprising using the lysing tip to create at least a portion of a tissue flap.

538. The method of example 537, wherein the tissue flap comprises at least one of a skin flap, a muscle flap, and a mucosal flap.

539. The method of example 538, further comprising using the tissue flap in a breast reconstruction procedure wherein the tissue flap comprises at least one of a latissimus dorsi flap and a transverse rectus abdominus myocutaneous flap.

540. The method of example 491, using the lysing tip to create at least a portion of a tissue graft.

541. The method of example 541, wherein the tissue graft comprises at least one of a skin graft, fat graft, fascial graft, vascular graft, connective tissue graft, and mucosal graft.

542. The method of example 491, further comprising:
creating a path to a target organ having a tumor using the lysing tip; and
removing at least a portion of the tumor from the target organ.

543. The method of example 542, further comprising:
activating an electrosurgical generator to deliver electrosurgical energy to the at least one lysing segment; and
using the lysing tip to induce hemostasis following removal of the at least a portion of the tumor from the target organ.

544. The method of example 491, further comprising creating a tip deployment pocket within the patient's body.

545. The method of example 544, wherein the tip deployment pocket comprises a width running along or at least substantially parallel to a length of the entrance incision, and wherein the width of the tip deployment pocket is greater than the length of the entrance incision.

546. The method of example 545, wherein the lysing tip comprises a lysing tip length between a first outer protrusion of the plurality of protrusions and a second outer protrusion of the plurality of protrusions opposite from the first outer protrusion, and wherein the width of the tip deployment pocket is greater than or equal to the lysing tip length.

547. The method of example 546, wherein the width of the width of the tip deployment pocket is at least about 150% of the lysing tip length.

548. The method of example 544, wherein the tip deployment pocket comprises a rectangular shape.

549. The method of example 544, wherein the tip deployment pocket comprises a circular shape.

550. The method of example 544, wherein the step of creating a tip deployment pocket comprises:
inserting a blunt instrument through the entrance incision; and
using the blunt instrument to separate tissue adjacent to the entrance incision into upper and lower planes defining the tip deployment pocket.

551. The method of example 544, wherein the step of creating a tip deployment pocket is performed without using the lysing tip, and wherein the step of creating a tip deployment pocket is performed before the step of delivering a lysing tip through an entrance incision into a patient's body.

552. The method of example 551, wherein the step of delivering a lysing tip through an entrance incision into a patient's body comprises delivering the lysing tip through a cannula with an elongated axis of the lysing tip extending along an axis of the cannula.

553. The method of example 552, wherein the step of reconfiguring the lysing tip from the delivery configuration to the treatment configuration comprises:
extending the lysing tip out of a distal end of the cannula into the tip deployment pocket; and
rotating the lysing tip such that the elongated axis extends at an at least substantially perpendicular angle relative to the axis of the cannula in the tip deployment pocket.

554. The method of example 553, wherein the step of rotating the lysing tip comprises rotating the lysing tip such that at least one end of the lysing tip defining the elongated axis extends beyond a cross-sectional profile of the cannula.

555. The method of example 554, wherein the step of rotating the lysing tip comprises rotating the lysing tip such that both opposing ends of the lysing tip defining the elongated axis extend beyond a cross-sectional profile of the cannula.

556. The method of example 553, further comprising using the lysing tip to create a path to at least one of an apocrine gland and an eccrine gland.

557. The method of example 556, further comprising:
activating an electrosurgical generator to deliver electrosurgical energy to the at least one lysing segment; and
using the lysing tip to apply electrosurgical energy to the at least one of an apocrine gland and an eccrine gland to incapacitate the at least one of an apocrine gland and an eccrine gland.

558. The method of example 544, further comprising using a fluid delivery canal to deliver fluid within the patient's body to a region adjacent to the lysing tip during a surgical procedure using the lysing tip.

559. The method of example 544, further comprising:
using the lysing tip to create a path to a hair follicle region;
activating an electrosurgical generator to deliver electrosurgical energy to the at least one lysing segment of the lysing tip; and
using the lysing tip to apply electrosurgical energy to one or more hair follicles in the hair follicle region, wherein the electrosurgical energy results in the one or more hair follicles being incapacitated.

560. The method of example 544, wherein the entrance incision is between about 2 mm and about 12 mm in length, wherein the tip deployment pocket comprises a width running along or at least substantially parallel to the length of the entrance incision, and wherein the width of the tip deployment pocket is greater than the length of the entrance incision.

561. The method of example 560, wherein the width of the tip deployment pocket is greater than a length of the lysing tip extending between a first outer protrusion of the plurality of protrusions and a second outer protrusion of the plurality of protrusions opposite from the first outer protrusion.

562. The method of example 560, wherein the width of the tip deployment pocket is about 1 cm.

563. The method of example 562, wherein the tip deployment pocket comprises a rectangular shape, wherein a length of the tip deployment pocket extending at least substantially perpendicular to the width is between about 1 cm and about 2 cm.

564. The method of example 560, further comprising:
using the lysing tip to create a first path from the tip deployment pocket to a first cellulite treatment zone; and
using the lysing tip to treat cellulite in the first cellulite treatment zone.

565. The method of example 564, further comprising using the lysing tip to create a second path from the tip deployment pocket to the first cellulite treatment zone.

566. The method of example 565, wherein the second path is angled relative to the first path.

567. The method of example 564, further comprising:
using the lysing tip to create a second path from the tip deployment pocket to a second cellulite treatment zone spaced apart from the first cellulite treatment zone; and
using the lysing tip to treat cellulite in the second cellulite treatment zone.

568. The method of example 564, wherein the step of using the lysing tip to treat cellulite in the first cellulite treatment zone comprises:
manipulating the first cellulite treatment zone to move a top portion of the first cellulite treatment zone into the first path; and
advancing the lysing tip into the first cellulite treatment zone to treat cellulite in the top portion of the first cellulite treatment zone.

569. The method of example 568, wherein the step of using the lysing tip to treat cellulite in the first cellulite treatment zone further comprises:
manipulating the first cellulite treatment zone to move a bottom portion of the first cellulite treatment zone into the first path; and
advancing the lysing tip into the first cellulite treatment zone to treat cellulite in the bottom portion of the first cellulite treatment zone.

570. The method of example 564, wherein the step of using the lysing tip to treat cellulite in the first cellulite treatment zone comprises:
  delivering electrosurgical energy to the at least one lysing segment; and
  using the electrosurgical energy to denature tissues in the in the first cellulite treatment zone.

571. The method of example 564, wherein a single entrance incision is used to treat cellulite in a first plurality of cellulite treatment zones along the patient's first leg, and further comprising:
  forming a second entrance incision;
  forming a second tip deployment pocket; and
  using the lysing tip to treat cellulite in a second plurality of cellulite treatment zones along the patient's second leg from the second entrance incision.

572. The method of example 544, wherein the step of creating a tip deployment pocket comprises creating the tip deployment pocket adjacent to the entrance incision.

573. The method of example 544, further comprising:
  reconfiguring the lysing tip from the treatment configuration to the delivery configuration; and
  withdrawing the lysing tip through the entrance incision.

574. The method of example 573, wherein the step of reconfiguring the lysing tip from the treatment configuration to the delivery configuration comprises rotating the lysing tip such that an elongated axis of the lysing tip extends at least substantially in a withdrawal direction.

575. The method of example 574, wherein the withdrawal direction extends along an axis of a cannula, and wherein the step of withdrawing the lysing tip comprises withdrawing the lysing tip through the cannula.

576. The method of example 491, further comprising creating a tip deployment pocket within at least one of a patient's neck and head, wherein the surgical procedure comprises at least one of a facelift and a necklift procedure.

577. The method of example 576, further comprising forming at least one treatment path using the lysing tip from the tip deployment pocket along at least one of a patient's face and neck.

578. The method of example 577, wherein the step of forming at least one treatment path comprises forming a plurality of overlapping treatment paths using the lysing tip from the tip deployment pocket along the at least one of the patient's face and neck.

579. The method of example 578, further comprising activating the at least one lysing segment to deliver electrosurgical energy to tissue adjacent to the at least one treatment path using the lysing tip.

580. The method of example 577, further comprising:
  withdrawing the lysing tip from the entrance incision;
  inserting a tissue modification tip comprising an energy window configured to deliver energy therethrough through the entrance incision; and
  using the tissue modification tip to modify tissue adjacent to the at least one treatment path to tighten the tissue adjacent to the at least one treatment path.

581. The method of example 580, wherein the energy window is positioned on an upper surface of the tissue modification tip.

582. The method of example 581, wherein the step of using the tissue modification tip to modify tissue adjacent to the at least one treatment path comprises positioning the energy window to face an upper surface of the at least one treatment path closer to an exterior surface of the patient's skin.

583. The method of example 581, wherein the step of using the tissue modification tip to modify tissue adjacent to the at least one treatment path comprises positioning the energy window to face a lower surface of the at least one treatment path further from an exterior surface of the patient's skin.

584. The method of example 491, further comprising using the lysing tip to dissect the patient's scalp.

585. The method of example 491, further comprising:
  forming a plurality of entrance incisions;
  inserting the lysing tip within each of the entrance incisions; and
  using the lysing tip to dissect the patient's scalp adjacent to each of the entrance incisions.

586. The method of example 491, further comprising creating a tip deployment pocket adjacent to the patient's scalp.

587. The method of example 586, further comprising:
  inserting the lysing tip in the tip deployment pocket; and
  after inserting the lysing tip in the tip deployment pocket, reconfiguring the lysing tip from the delivery configuration to the treatment configuration in the tip deployment pocket.

588. The method of example 587, further comprising:
  forming a plurality of entrance incisions adjacent to the patient's scalp;
  forming a plurality of tip deployment pockets adjacent to the plurality of entrance incisions;
  deploying the lysing tip in each of the plurality of tip deployment pockets; and
  forming a scalp dissection path using the lysing tip from each of the tip deployment pockets to separate the patient's scalp from its underlying structure.

589. The method of example 491, wherein the electrosurgical procedure comprises installing at least one of a biomedical implant and a cosmetic implant within the patient, and further comprising creating a path to a location adjacent to an implant zone where the at least one of a biomedical implant and a cosmetic implant will be installed using the lysing tip.

590. The method of example 589, further comprising using the lysing tip to create an implant pocket in tissue in the implant zone, wherein the implant pocket is configured to receive the at least one of a biomedical implant and a cosmetic implant.

591. The method of example 590, wherein the at least one of a biomedical implant and a cosmetic implant comprises a biomedical implant, and wherein the biomedical implant comprises at least one of a pump, a pacemaker, a neurological implant, a drug delivery device, a tracking implant, and an ID chip.

592. The method of example 590, wherein the at least one of a biomedical implant and a cosmetic implant comprises a cosmetic implant, and wherein the cosmetic implant comprises at least one of a skin implant, a breast implant, a face implant, and a muscle implant.

593. The method of example 590, further comprising:
  forming a tip deployment pocket; and
  deploying the lysing tip in the tip deployment pocket by inserting the lysing tip in the tip deployment pocket and reconfiguring the lysing tip from the delivery configuration to the treatment configuration in the tip deployment pocket.

594. The method of example 593, wherein the tip deployment pocket is formed adjacent to the implant zone.

595. The method of example 593, wherein the tip deployment pocket is formed adjacent to the entrance incision.

596. The method of example 593, further comprising advancing the at least one of a biomedical implant and a cosmetic implant to the implant zone and inserting the at least one of a biomedical implant and a cosmetic implant in the implant pocket.

597. The method of example 491, wherein the electrosurgical procedure comprises at least one of a capsulotomy and a capsulectomy.

598. The method of example 597, further comprising using the lysing tip to create a path to an implant having a capsule of scar tissue adjacent to the implant.

599. The method of example 598, further comprising using the lysing tip to separate at least a portion of the capsular fibrous tissue from the implant.

600. The method of example 598, wherein the implant comprises a breast implant.

601. The method of example 598, wherein the implant comprises a hip implant.

602. An electrosurgical lysing tip, comprising:
a first outer protrusion;
a second outer protrusion opposite from the first outer protrusion;
at least one inner bead positioned in between the first outer protrusion and the second outer protrusion, wherein each of the at least one inner bead defines an inner protrusion;
at least one lysing member defining at least one lysing segment between each pair of adjacent protrusions; and
a support member extending between the first outer protrusion and the second outer protrusion, wherein the support member is configured to facilitate coupling of the lysing tip to a surgical tool used to control the lysing tip during a surgical procedure within a patient's body.

603. The electrosurgical lysing tip of example 602, wherein the first outer protrusion is defined by a first outer bead, and wherein the second outer protrusion is defined by a second outer bead positioned on an opposite end of the lysing tip relative to the first outer bead.

604. The electrosurgical lysing tip of example 603, wherein each of the first outer bead and the second outer bead comprises a leading end protruding distally of the at least one lysing member, and wherein each of the first outer bead and the second outer bead comprises a trailing end protruding proximally from the support member.

605. The electrosurgical lysing tip of example 603, wherein the first outer bead is non-rigidly coupled to the support member at a first end of the support member, and wherein the second outer bead is non-rigidly coupled to the support member at a second end of the support member opposite from the first end.

606. The electrosurgical lysing tip of example 603, wherein the first outer bead and the second outer bead each comprises an inner recess, and wherein each inner recess is configured to receive a respective portion of the support member therein.

607. The electrosurgical lysing tip of example 606, wherein each inner recess is configured to receive a respective end portion of the support member such that each opposing end of the support member terminates in an inner recess.

608. The electrosurgical lysing tip of example 606, wherein each inner recess is configured to loosely receive a respective portion of the support member therein such that the first outer bead and the second outer bead can move relative to the support member during a surgical procedure.

609. The electrosurgical lysing tip of example 602, wherein the first outer protrusion comprises an integral portion of the support member at a first end of the support member, and wherein the second outer protrusion comprises an integral portion of the support member at a second end of the support member opposite from the first end.

610. The electrosurgical lysing tip of example 602, wherein the first outer protrusion and the second outer protrusion each comprises a shape that at least substantially mimics the shapes of each of the at least one inner bead along a leading end of the first outer protrusion and the second outer protrusion.

611. The electrosurgical lysing tip of example 602, wherein the first outer protrusion is defined by a first outer bead, wherein the second outer protrusion is defined by a second outer bead positioned on an opposite end of the lysing tip relative to the first outer bead, and wherein the first outer bead and the second outer bead each comprises an at least substantially ellipsoidal shape.

612. The electrosurgical lysing tip of example 611, wherein each of the at least one inner bead comprises a leading end having an at least substantially ellipsoidal shape.

613. The electrosurgical lysing tip of example 612, wherein each of the at least one inner bead further comprises a flattened trailing end.

614. The electrosurgical lysing tip of example 613, wherein each of the at least one inner bead comprises a flattened trailing end that terminates adjacent to the support member.

615. An electrosurgical system, comprising:
a lysing tip comprising:
a plurality of beads; and
a lysing member extending through each of the plurality of beads such that each of the plurality of beads protrudes beyond the lysing member; and
a surgical tool configured to selectively couple with the lysing tip, wherein the surgical tool comprises a pair of jaws configured to selectively engage at least a portion of the lysing tip.

616. The electrosurgical system of example 615, wherein the lysing member comprises a first coupling tip formed at a first end of the lysing member and a second coupling tip formed at a second end of the lysing member opposite from the first end, and wherein the surgical tool is configured to selectively engage the lysing tip at the first coupling tip and the second coupling tip.

617. The electrosurgical system of example 616, wherein the lysing member comprises a lysing rod comprising an at least substantially circular cross-section, and wherein the first and second coupling tips comprise enlarged portions of the lysing rod.

618. The electrosurgical system of example 616, wherein the first coupling tip comprises an enlarged end, wherein the second coupling tip comprises a second enlarged end, wherein a first jaw of the pair of jaws is configured to engage the first coupling tip at the first end, and wherein a second jaw of the pair of jaws is configured to engage the second coupling tip at the second end.

619. The electrosurgical system of example 615, wherein each of the plurality of beads is configured to rotate with respect to the lysing member.

620. The electrosurgical system of example 615, further comprising a plurality of spacers coupled with the lysing member, wherein each of the plurality of spacers is positioned between a pair of adjacent beads of the plurality of beads.

621. The electrosurgical system of example 620, further comprising a first outer spacer positioned in between a first outer bead of the plurality of beads and an adjacent bead and a second outer spacer positioned in between a second outer bead of the plurality of beads opposite from the first outer bead and an adjacent bead.

622. The electrosurgical system of example 615, wherein the surgical tool is configured to deliver electrosurgical energy to the lysing member when the lysing tip is selectively engaged with the surgical tool.

623. The electrosurgical system of example 622, wherein the surgical tool is configured to deliver electrosurgical energy to the lysing tip through at least one jaw of the pair of jaws.

624. The electrosurgical system of example 615, wherein each of the plurality of beads comprises an at least substantially ellipsoidal leading end.

625. The electrosurgical system of example 624, wherein each of the plurality of beads comprises a flattened trailing end.

626. An electrosurgical lysing tip, comprising:
a plurality of beads;
at least one lysing member extending at least partially through each of the plurality of beads to couple the plurality of beads together, wherein the at least one lysing member defines at least one lysing segment between each pair of adjacent beads of the plurality of beads;
a treatment portion coupled with the at least one lysing member;
a base portion removably couplable with the treatment portion and configured such that, following an electrosurgical procedure with the electrosurgical lysing tip, the treatment portion may be removed from the base portion and a new treatment portion with a new at least one lysing member and a new plurality of beads coupled with the base portion for a subsequent electrosurgical procedure.

627. The electrosurgical lysing tip of example 626, wherein the base portion comprises at least one hole configured to couple the base portion with a deployment assembly of a surgical instrument.

628. The electrosurgical lysing tip of example 626, wherein the base portion and the treatment portion together define a support member for the electrosurgical lysing tip, wherein the support member is configured to facilitate coupling of the electrosurgical lysing tip to a surgical instrument used to control the lysing tip during an electrosurgical procedure within a patient's body.

629. The electrosurgical lysing tip of example 628, wherein the treatment portion is configured to mate with the base portion such that the treatment portion defines a distal portion of the support member and the base portion defines a proximal portion of the support member.

The features, structures, steps, or characteristics disclosed herein in connection with one embodiment may be combined in any suitable manner in one or more alternative embodiments.

The term dissection may indicate the separation of tissues or of one tissue plane from another (ref: Free Online Medical Dictionary). Some also consider dissection to comprise separation of a single tissue into portions. Much of the bodies of animals and humans are formed from embryonic fusion planes. Many of the organs of the human or animal body may be categorized from the embryonic fusion planes from whence they came. The interfaces between organs may often be referred to as 'tissue planes.' Such planes may be considered substantially planar depending upon the size of a comparative planar living or inanimate object (such as a surgical instrument). Some embodiments disclosed herein may comprise cannula-delivered tissue dissectors (CDTD). Other embodiments disclosed herein may be used without a cannula and may therefore be considered non-cannula-delivered tissue dissectors (non-CDTD). Some embodiments may be used either with or without cannulas and therefore, depending upon the systems/procedure, may be considered CDTD or non-CDTD. Both the CDTD and non-CDTD embodiments disclosed herein may perform the functions of sharp dissection, blunt dissection, electrosurgical cutting and/or coagulation simultaneously without a surgeon having to switch instruments. Tissue modification may also be carried out.

Sharp dissection has been referred to by some as separation of tissues by means of the sharp edge of a knife or scalpel or with the inner sharp edge of scissors. Blunt dissection has been defined by Webster as surgical separation of tissue layers by means of an instrument without a cutting edge or by the fingers.

The term 'minimally invasive surgery' has been used to describe a procedure (surgical or otherwise) that is less invasive than open surgery used for the same purpose. Some minimally invasive procedures typically involve use of laparoscopic and/or endoscopic devices and manual and/or remote/computerized manipulation of instruments with indirect observation of the surgical field through an endoscope or similar device, and are carried out through the skin or through a body cavity or anatomical opening. This may result in shorter hospital stays, or allow outpatient treatment (reference: Wikipedia).

Sometimes minimally invasive surgery is known as "keyhole" surgery and may be performed using one or more trocars and one or more laparoscopes and/or endoscopes and/or cannulae to access tissues within the body.

The term 'open surgery' is used to indicate cutting skin and tissues to 'open the body' so that the surgeon has direct access to the structures or organs involved. An incision may be of the size that permits a surgeon's hands to enter the patient's body. The structures and tissues involved may be seen and touched and may be directly exposed to the air of the operating room.

The term "cannula," as used herein, is intended to encompass any tube or tubular structure that is configured to be inserted into the body of a human or animal during a surgical procedure and facilitate selective movement of a surgical device and/or related components for performing delivery of the surgical device and/or surgical procedures with the surgical device. Tubular structures that contain fixed structures/elements therein, such as needle drivers or grasping instruments, are not considered cannulas as that term is used herein. Although often "trocars" are used in connection with cannulas, the term cannula, as used herein, is intended to encompass a trocar alone if such a trocar is capable of being used to insert a medical device into a body.

It may be advantageous to have a spot coagulator extend from an embodiment of the CDTD at such a distance and/or location that allows complete viewing and/or contact of a bleeding area with a portion of the spot coagulator (for example the distal end point of a tip of the coagulator). Such a probe may be deployable and may obtain electrical energy off of a conductive element located between the lysing elements of the tip and the plug.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1a is a perspective view of an embodiment of a system for delivery of a lysing tip through a cannula in a treatment configuration.

FIG. 1b is a perspective view of the embodiment previously depicted in FIG. 1a in a partially retracted configuration, in between the delivery and treatment configurations.

FIG. 1c is a perspective view of the embodiment previously depicted in FIG. 1a in the delivery configuration.

FIG. 1d is an upper view of the lysing tip in FIG. 1a and the distal portions of the cannulas.

FIG. 1e is an upper view of lysing tip of the embodiment shown in FIG. 1a.

FIG. 1f is a rear perspective view of the lysing tip and actuation arms of the embodiment shown in FIG. 1a.

FIG. 1g is perspective view of the protrusion base of the embodiment shown in FIG. 1a.

FIG. 1h is a perspective view of the lysing member of the embodiment shown in FIG. 1a.

FIG. 1i is a side view of a hand assembly that may be used with the embodiment shown in FIG. 1a.

FIG. 1j is perspective view of the embodiment shown in FIG. 1a used in connection with a single cannula.

FIG. 2a is a perspective view of an embodiment of a system for delivery of a lysing tip through a cannula in a treatment configuration.

FIG. 2b is a perspective view of the embodiment previously depicted in FIG. 2a in a partially retracted configuration, in between the delivery and treatment configurations.

FIG. 2c is a perspective view of the embodiment previously depicted in FIG. 2a in the delivery configuration.

FIG. 2d is an upper view of the lysing tip in FIG. 2a and the distal portion of the cannulas.

FIG. 2e is a perspective view of the embodiment previously depicted in FIG. 2a used in connection with a single cannula.

FIG. 3a is a perspective view of an embodiment of a system for delivery of a lysing tip through a cannula in a treatment configuration.

FIG. 3b is a perspective view of the embodiment previously depicted in FIG. 3a in a partially retracted configuration, in between the delivery and treatment configurations.

FIG. 3c is a perspective view of the embodiment previously depicted in FIG. 3a in the delivery configuration.

FIG. 3d is an upper view of the lysing tip in FIG. 3a and the distal portion of the cannulas.

FIG. 3e is a perspective view of the embodiment previously depicted in FIG. 3a used in connection with a single cannula.

FIG. 4a is a perspective view of an embodiment of a system for delivery of a bipolar lysing tip through a cannula in a treatment configuration.

FIG. 4b is a perspective view of the embodiment previously depicted in FIG. 4a in a partially retracted configuration, in between the delivery and treatment configurations.

FIG. 4c is a perspective view of the embodiment previously depicted in FIG. 4a in the delivery configuration.

FIG. 4d is an upper view of the lysing tip in FIG. 4a and the distal portion of the cannulas.

FIG. 4e is a perspective view of the protrusion base of the embodiment previously depicted in FIG. 4a.

FIG. 4f is a perspective view of the lysing members of the embodiment previously depicted in FIG. 4a.

FIG. 4g is a rear perspective view of the embodiment previously depicted in FIG. 4a including the rear of the lysing tip and the actuation rods.

FIG. 4h is a perspective view of the embodiment previously depicted in FIG. 4a used in connection with a single cannula.

FIG. 5a is a perspective view of an embodiment of a system for delivery of a lysing tip through a cannula in a treatment configuration.

FIG. 5b is a perspective view of the embodiment previously depicted in FIG. 5a in a partially retracted configuration, in between the delivery and treatment configurations.

FIG. 5c is a perspective view of the embodiment previously depicted in FIG. 5a in the delivery configuration.

FIG. 5d is an upper view of the lysing tip in FIG. 5a and the distal portion of the cannulas.

FIG. 5e is a perspective view of the embodiment previously depicted in FIG. 5a used in connection with a single cannula.

FIG. 6a is a perspective view of an embodiment of a system for delivery of a lysing tip through a cannula in a treatment configuration.

FIG. 6b is a perspective view of the embodiment previously depicted in FIG. 6a in a partially retracted configuration, in between the delivery and treatment configurations.

FIG. 6c is a perspective view of the embodiment previously depicted in FIG. 6a in the delivery configuration.

FIG. 6d is an upper view of the lysing tip in FIG. 6a and the distal portion of the cannulas.

FIG. 6e is a perspective view of the embodiment previously depicted in FIG. 6a used in connection with a single cannula.

FIG. 7a is a perspective view of an embodiment of a system for delivery of a lysing tip through a cannula via a grasping/control instrument.

FIG. 7b is an upper plan view of the embodiment previously depicted in FIG. 7a.

FIG. 7c is a close-up side view of the embodiment previously depicted in FIG. 7a wherein a lysing tip is reattached.

FIG. 7d is an upper plan view of the lysing tip of the embodiment previously depicted in FIG. 7a.

FIG. 7e is a side view of the embodiment previously depicted in FIG. 7a, wherein the lysing tip is uncoupled from the grasping/control instrument.

FIG. 7f is a side view of the grasping/control instrument of the embodiment previously depicted in FIG. 7a.

FIG. 8a is a perspective view of an embodiment of a system for delivery of a lysing tip through a single cannula via a grasping/control instrument further comprising a tether.

FIG. 8b is a close-up side view of the distal end of the embodiment previously depicted in FIG. 8a wherein the tip is coupled to the instrument tip.

FIG. 8c is a close-up side view of the distal end of the grasping/control instrument of the embodiment previously depicted in FIG. 8a.

FIG. 8d is a close-up, cross-sectional side view of the distal end of the embodiment previously depicted in FIG. 8a wherein the tip is coupled to the instrument tip.

FIG. 8e is a close-up perspective view of the distal end of the embodiment previously depicted in FIG. 8a wherein the tip is uncoupled from the instrument tip yet tethered.

FIG. 8f is a close-up perspective view of the distal end of the embodiment previously depicted in FIG. 8a wherein the tip is uncoupled from the instrument tip yet tethered and upside down.

FIG. 10a is a perspective view of yet another embodiment of a system for delivery of a lysing tip through a cannula in a treatment configuration.

FIG. 10b is an upper plan, close-up view of the embodiment previously depicted in FIG. 10a in a treatment configuration.

FIG. 10c is a close-up upper plan view of the embodiment previously depicted in FIG. 10a showing beads, protuberances, and lysing tip.

FIG. 10d is a side view through the tunnel of a bead of the embodiment previously depicted in FIG. 10a.

FIG. 10e is a close-up, upper plan view of the lysing tip depicted in FIG. 10c illustrating the lysing tip in a stressed/deformed state.

FIG. 11a is a perspective view of an embodiment of a system for delivery of a lysing tip through a cannula in a treatment configuration.

FIG. 11b is an upper plan, close-up view of the embodiment previously depicted in FIG. 11a in a treatment configuration.

FIG. 11c is a close-up upper plan view of the embodiment previously depicted in FIG. 11a showing beads, a spacer, and lysing tip.

FIG. 11d is a side view through the tunnel of a bead with facets comprising the embodiment previously depicted in FIG. 11a.

FIG. 11e is a close-up upper plan view of the lysing tip depicted in FIG. 11c illustrating the lysing tip in a stressed/deformed state with spacers.

FIG. 11f is an upper view of the embodiment previously depicted in FIG. 11b illustrating that tip may not fit within one or more cannulas.

FIG. 12dx comprises a perspective view of a lysing member/lysing rod having a pentagonal cross section that is twisted along its length.

FIG. 12h comprises a perspective view of a spacer to a lysing tip with a hole through its length having a circular cross-section with non-beveled ends.

FIG. 12i comprises a perspective view of a spacer to a lysing tip with a hole through its length having a circular cross-section with beveled ends.

FIG. 12j comprises a perspective view of a spacer to a lysing tip with a hole through its length having a circular cross-section with beveled ends and holes.

FIG. 12k comprises a perspective view of a spacer to a lysing tip with a hole through its length having a circular cross-section arced along its length.

FIG. 12L comprises a perspective view of a spacer to a lysing tip with opposing loops connected by a rod in a relaxed state.

FIG. 12m comprises a perspective view of a spacer to a lysing tip with opposing loops connected by a rod in a stressed state.

FIG. 12n comprises a perspective view of a spacer to a lysing tip with a hole through its length having a triangular cross-section.

FIG. 12o comprises a perspective view of a spacer to a lysing tip with a hole through its length having a rectangular cross-section.

FIG. 12p comprises a perspective view of a spacer to a lysing tip with a hole through its length having a pentagonal cross-section.

FIG. 12px comprises a perspective view of a spacer to a lysing tip with a hole through its length having a pentagonal cross section that is twisted along its length.

FIG. 12q comprises a perspective view of a spacer to a lysing tip with a hole through its length having a hexagonal cross-section.

FIG. 12r comprises a perspective view of a spacer to a lysing tip with a hole through its length having a blade-shaped cross-section with rounded edges.

FIG. 12s comprises a perspective view of a spacer to a lysing tip with a hole through its length having a blade-shaped cross-section with flat edges.

FIG. 12t comprises a perspective view of a spacer to a lysing tip with a hole through its length having a spindle cross-section.

FIG. 12aa is a perspective view of a bead having a spherical shape.

FIG. 12bb is a perspective view of a bead having a wheel shape.

FIG. 12cc is a perspective view of a bead having a dodecahedron shape.

FIG. 12dd is a perspective view of a bead having a substantially ellipsoidal shape.

FIG. 12ee is a perspective view of a bead having a substantially ellipsoidal shape with facets.

FIG. 12ff is a perspective view of a bead having a substantially ellipsoidal shape able to accept a sleeve.

FIG. 12gg is a perspective view of a bead having a partially ellipsoidal shape with a flat proximal end and facets.

FIG. 12hh is a perspective view of a bead having a partially ellipsoidal shape with two flat surfaces on its proximal end.

FIG. 12ii is an upper view of a bead having a partially ellipsoidal shape with convex proximal end.

FIG. 12jj is an upper view of a bead having a partially ellipsoidal shape with an asymmetric proximal end with facets.

FIG. 12kk is an upper view of a bead having a partially ellipsoidal shape with an angular cut-out on its proximal end.

FIG. 12LL is an upper view of a bead having a partially ellipsoidal shape with a concave proximal end.

FIG. 12mm is a side view, from the outside, of an outer bead having a substantially annular shape.

FIG. 12nn is a side view, from the inside, of bead depicted in FIG. 12mm.

FIG. 12oo is a side view of a deformable bead having a substantially annular shape.

FIG. 12pp is a side view of a middle bead having a substantially annular shape and knobs on its proximal end.

FIG. 12qq is a side view of a middle bead having a substantially annular shape and a cross-member at its proximal end.

FIG. 12rr is a side perspective view of a bead comprising a slot configured to engage a lysing member.

FIG. 13a is a perspective view of an embodiment of a system for delivery of a lysing tip comprising a bar through a cannula in a treatment configuration.

FIG. 13b is a perspective view of the embodiment previously depicted in FIG. 13a in a partially retracted configuration, in between the delivery and treatment configurations.

FIG. 13c is a perspective view of the embodiment previously depicted in FIG. 13a in the delivery configuration.

FIG. 13d is an upper view of the lysing tip in FIG. 13a and the distal portion of the cannulas.

FIG. 13e is a perspective view of the lysing tip of the embodiment previously depicted in FIG. 13a.

FIG. 13f is an upper view of the assembled lysing tip with actuation arms of the embodiment previously depicted in FIG. 13a.

FIG. 13g is an upper view of the embodiment previously depicted in FIG. 13a, more specifically of the lysing tip without actuation arms.

FIG. 13h is an upper view of the lysing plate comprising the embodiment.

FIG. 13i is a side view of the lysing tip.

FIG. 14a is an upper perspective view of an alternative embodiment of a lysing tip delivered through one or more cannulas in the treatment configuration.

FIG. 14b is an upper perspective view of the embodiment in FIG. 14a in a partially deployed configuration, between the treatment and delivery configurations.

FIG. 14c is an upper perspective view of the embodiment in FIG. 14a in a delivery configuration.

FIG. 14d is an upper view of the lysing tip in FIG. 14a and the distal portion of the cannulas.

FIG. 14e is a perspective view of the lysing tip of the embodiment previously depicted in FIG. 14a.

FIG. 14f is a side view of the lysing tip of the embodiment previously depicted in FIG. 14a.

FIG. 14g is an upper view of the embodiment previously depicted in FIG. 14a, more specifically of the lysing tip without actuation arms.

FIG. 14h is an upper view of the lysing tip with certain components removed to view structures beneath.

FIG. 14i is a perspective view of lysing tip in the delivery configuration being too large to enter the inner cannula but of sufficient dimensions to enter the outer cannula.

FIG. 14j is an upper perspective view of FIG. 14i.

FIG. 14k is a perspective view of the lysing tip of FIG. 14j in the delivery configuration with an inner cannula having a diameter smaller than tip width of the lysing tip.

FIG. 14L is a perspective view of the embodiment of FIG. 14k without the outer cannula.

FIG. 14m is a perspective view of the lysing tip of FIG. 14k in the delivery configuration with an inner cannula having a diameter smaller than tip width of the lysing tip which is covered by a protective sleeve.

FIG. 14n is a perspective view of the embodiment of FIG. 14L without the outer cannula with the lysing tip covered by a protective sleeve.

FIG. 14o is a perspective view of an alternative embodiment to that depicted in FIG. 14a in which a treatment portion may be removed from the lysing tip.

FIG. 14p is a perspective view of cross section taken along line A-A from FIG. 14r.

FIG. 14q is a perspective view of the treatment portion of the embodiment depicted in FIG. 14o.

FIG. 14r is an exploded perspective view of the lysing tip of the embodiment of FIG. 14o.

FIG. 14s is an exploded, side perspective cross-sectional view taken along line A-A from FIG. 14r.

FIG. 14t is an exploded, side cross-sectional view taken along line A-A from FIG. 14r.

Figure 15A:
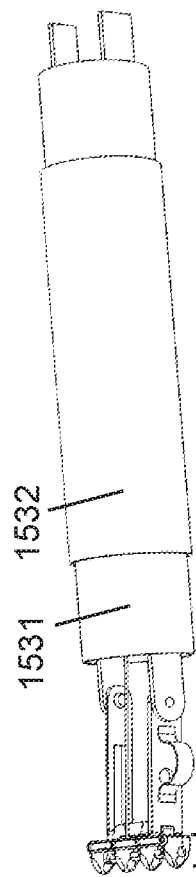

FIG. 15a is an upper perspective view of an alternative embodiment of a lysing tip delivered through one or more cannulas in the treatment configuration, said lysing tip being configured with one or more energy windows.

Figure 15B:
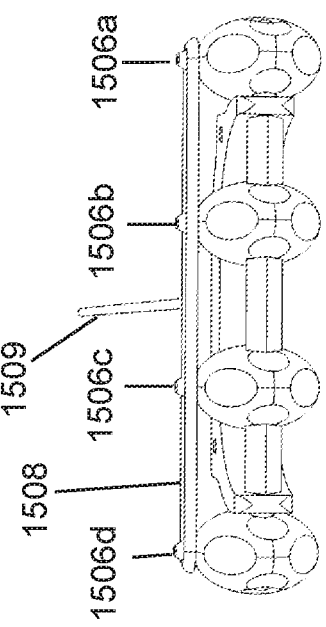

FIG. 15b is an upper view of the embodiment previously depicted in FIG. 15a, more specifically of the lysing tip with one or more energy windows and actuation arms.

Figure 15C:
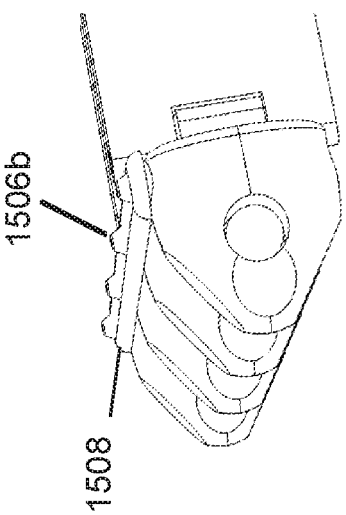

FIG. 15c is a front view of lysing tip of the embodiment previously depicted in FIG. 15a with energy window strip.

Figure 15D:
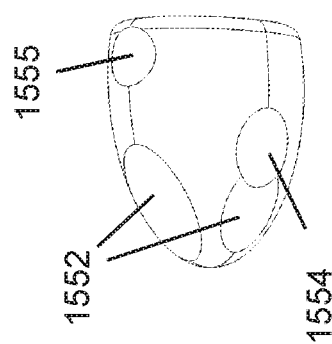

FIG. 15d is a close-up side view of lysing tip of the embodiment previously depicted in FIG. 15a with energy window strip.

Figure 15E:
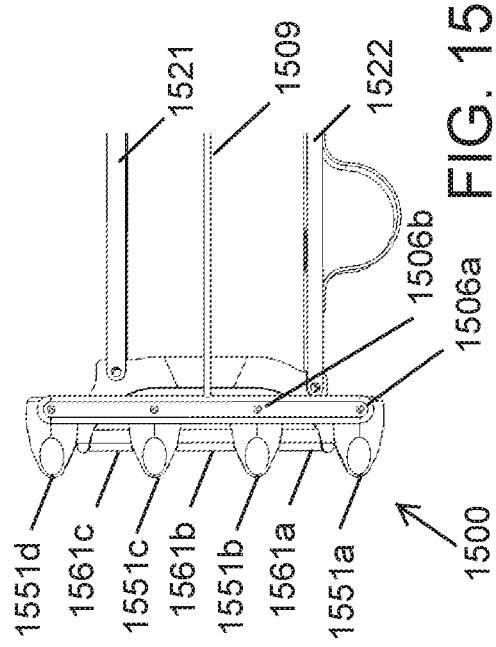

FIG. 15e is a close-up perspective view of a bead of the embodiment previously depicted in FIG. 15a.

Figure 15F:
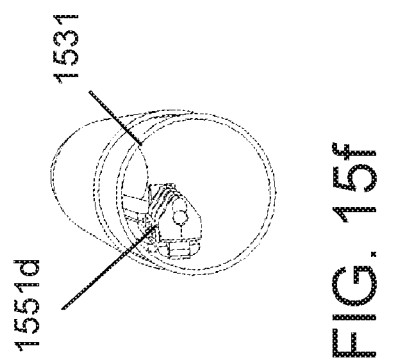

FIG. 15f is a front view showing lysing tip of the embodiment previously depicted in FIG. 15a with energy window recessed within one or more cannulas.

FIG. 15g is an exploded view of an energy window.

FIG. 15h is a front view of the insulation cover of the embodiment previously depicted in FIG. 15a.

FIG. 15i is a close-up sectioned side view of the outer bead showing the insertion of the insulation cover through the bead.

FIG. 15j is a perspective view of a bipolar lysing tip of the embodiment of FIG. 15a.

FIG. 15k is an upper plan view of a bipolar lysing tip of the embodiment of FIG. 15a.

FIG. 16a is an upper perspective view of a bipolar embodiment of a CDTD system in the treatment configuration.

FIG. 16b is a perspective view of the embodiment previously depicted in FIG. 16a in a partially retracted configuration, in between the delivery and treatment configurations.

FIG. 16c is a perspective view of the embodiment previously depicted in FIG. 16a in the delivery configuration.

FIG. 16d is an upper view of the lysing tip in FIG. 16a and the distal portion of the cannulas.

FIG. 16e is a perspective view of the lysing tip of the embodiment previously depicted in FIG. 16a.

FIG. 16f is an upper view of the lysing tip of the embodiment previously depicted in FIG. 16a.

FIG. 16g is a perspective view of the lysing tip of the embodiment previously depicted in FIG. 16a.

FIG. 16h is a rear view of the beads and wiring of the embodiment previously depicted in FIG. 16a.

Figure 17A:
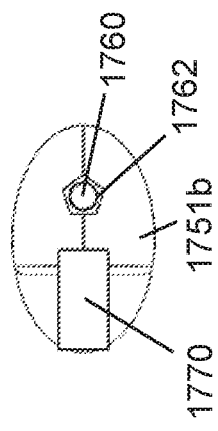

FIG. 17a is an upper plan view of an embodiment of a lysing tip.

Figure 17B:
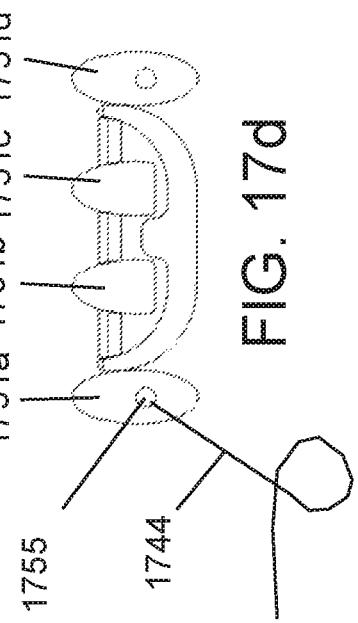

FIG. 17b is a cross sectional view of the embodiment previously depicted in FIG. 17a at the location shown in FIG. 17a.

Figure 17C:
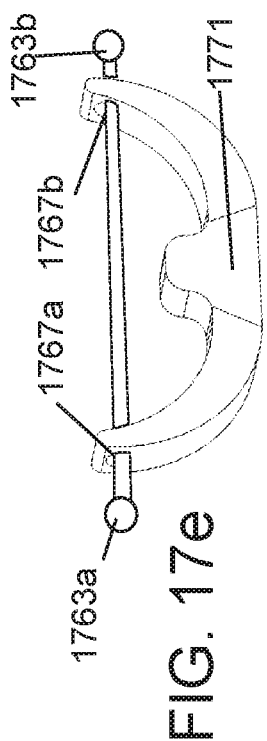

FIG. 17c is an upper plan view of yet another embodiment of a lysing tip.

Figure 17D:
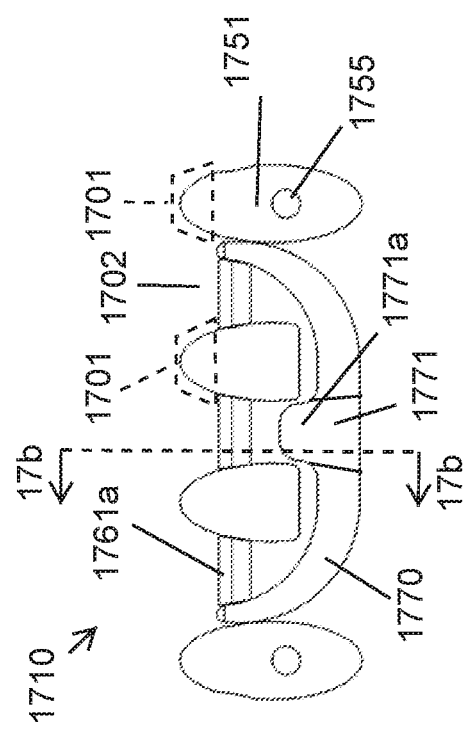

FIG. 17d is an upper plan view of still another embodiment of a lysing tip.

Figure 17E:
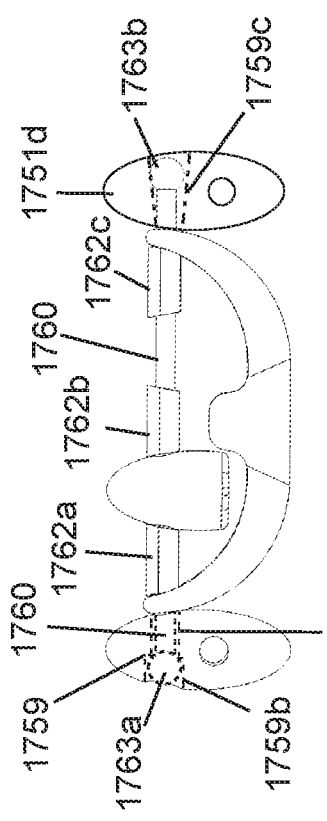

FIG. 17e is a perspective view of the structural member coupled with lysing rod.

FIG. 17f is a partial breakaway view of the delivery of lysing tip and grasping/control instrument inside a body, said lysing tip to be received and held by a second instrument until the grasping/control instrument grasps and controls lysing tip for the surgical procedure.

FIG. 17g is a perspective view of the interaction between a lysing tip, its grasping/control instrument, and a temporary holding/grasping instrument.

FIG. 17h is a side view of a lysing tip and its associated grasping control instrument without a non-conductive sheath.

FIG. 17i is a side view of a lysing tip and its associated grasping control instrument covered by a non-conductive sheath.

FIG. 17j is an upper view of a lysing tip depicting middle beads held via friction fit and protuberances.

FIG. 17k is a front view of a lysing tip depicting deformed lysing rod between beads.

Figure 17L:
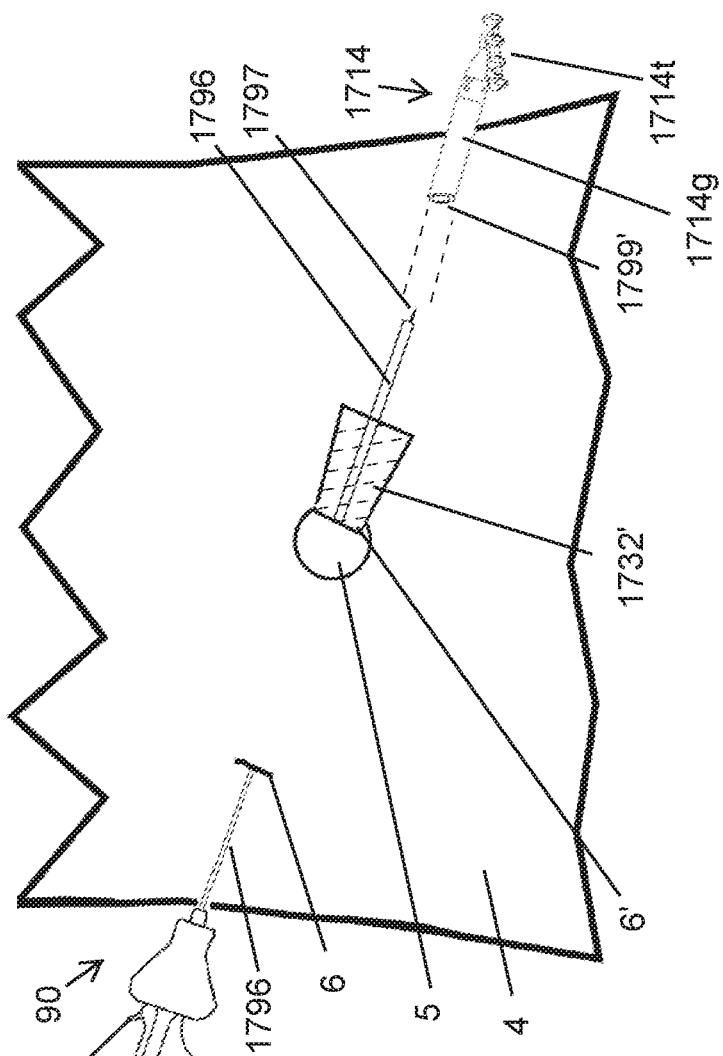

FIG. 17L is a view of the abdomen depicting the construction of a surgical device to be used therein.

Figure 17M:
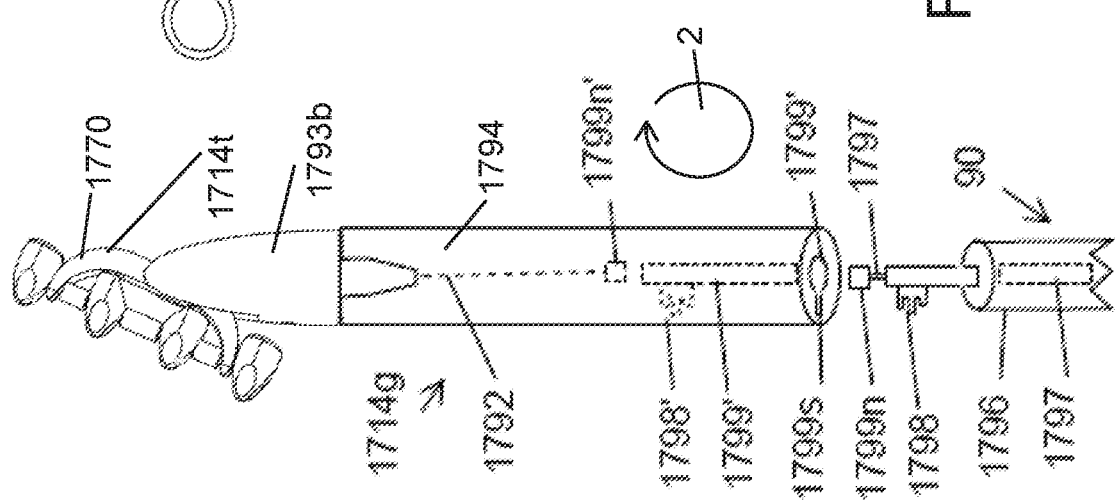

FIG. 17m is a top plan view of a modular lysing tip depicting internal components of a locking mechanism.

Figure 18C:
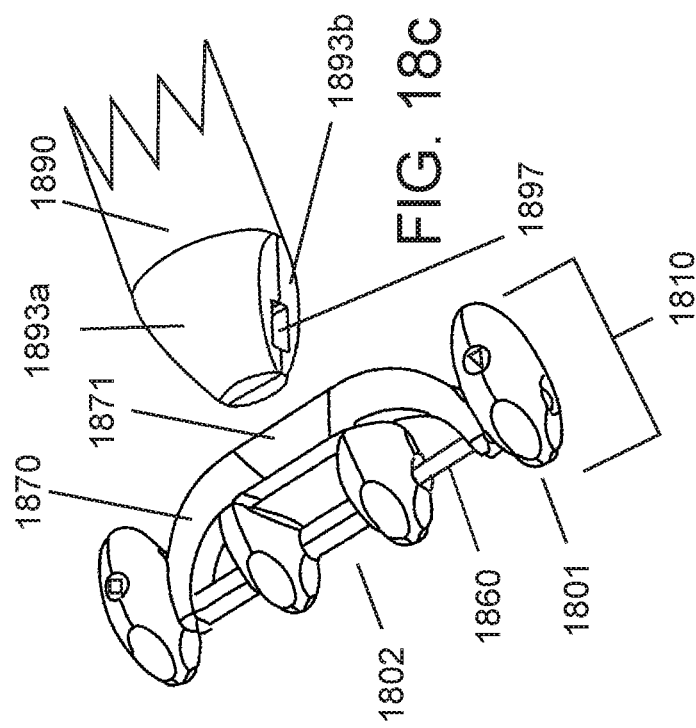
Figure 18E:
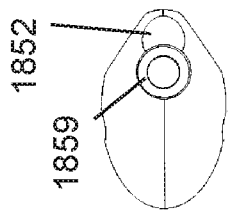
Figure 18D:
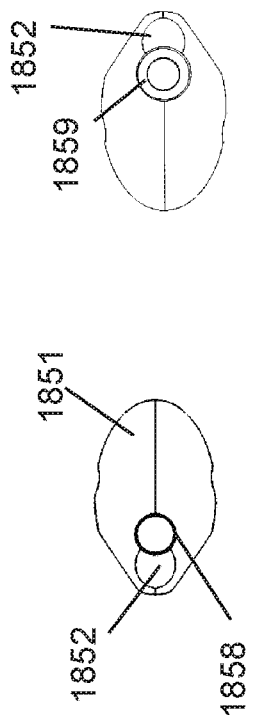
Figure 18A:
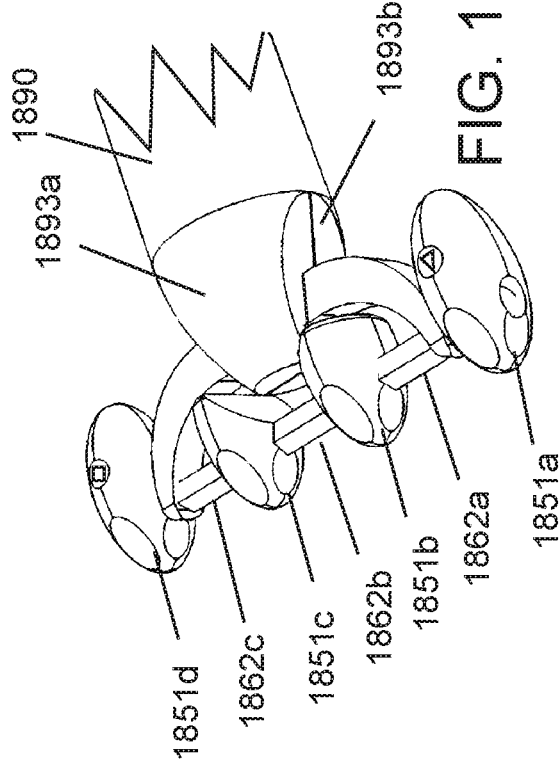

FIG. 18a is a perspective view of a system comprising a lysing tip and grasping/control instrument, coupled.

Figure 18B:
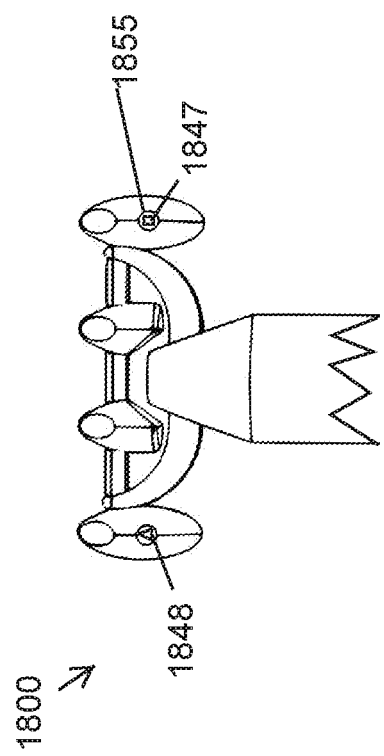

FIG. 18b is an upper plan view of a lysing tip and grasping control instrument, coupled.

FIG. 18c is a perspective view of a lysing tip and grasping/control instrument, uncoupled.

FIG. 18d is a side view of an outer bead, being the inside view of the outer bead.

FIG. 18e is a side view of an outer bead, being the outside view of the outer bead.

Figure 19C:
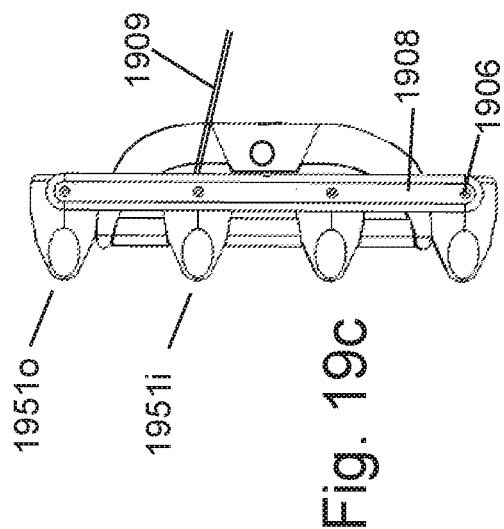
Figure 19D:
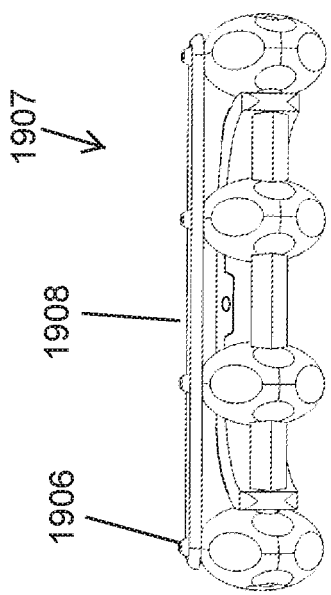
Figure 19A:
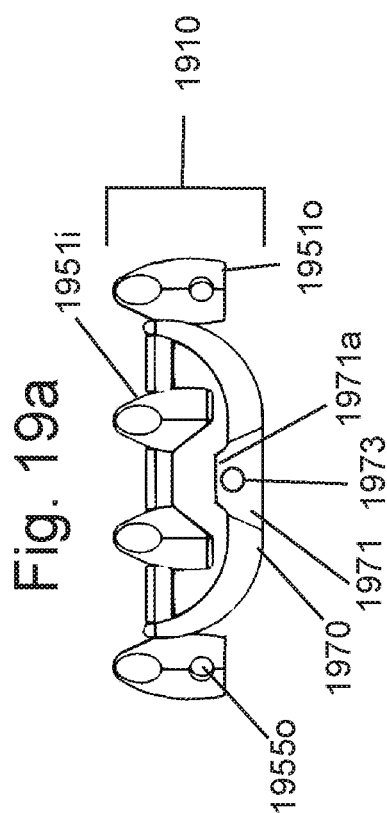

FIG. 19a is an upper plan view of a lysing tip comprising a tab.

Figure 19B:
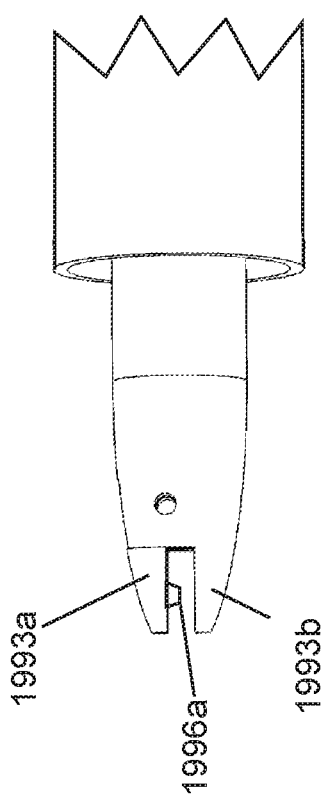

FIG. 19b is a side view of a grasping control instrument configured to couple with the lysing tip in FIG. 19a.

FIG. 19c is top view of the lysing tip of the embodiment of FIG. 19a coupled with an energy strip.

FIG. 19d is front view of the lysing tip of the embodiment of FIG. 19a coupled with an energy strip.

FIG. 20a is a perspective view of system comprising a lysing tip comprising two outer beads and configured to be used with a corresponding grasping/control instrument that defines a third inner bead when coupled.

FIG. 20b is a perspective view of the embodiment in FIG. 20a, with lysing tip uncoupled from its corresponding grasping/control instrument.

FIG. 20c is an upper plan view of the embodiment of FIG. 20a, with lysing tip and its corresponding grasping/control instrument.

Figure 20F:
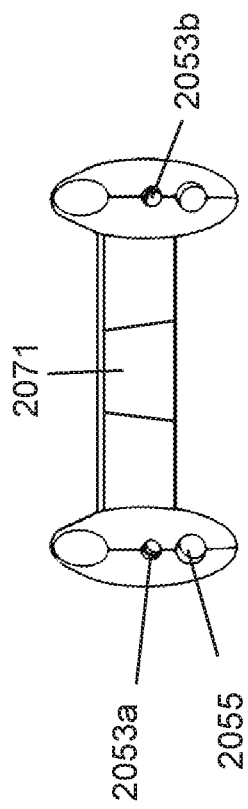
Figure 20G:
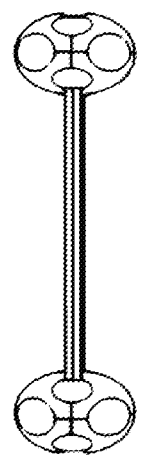
Figure 20H:
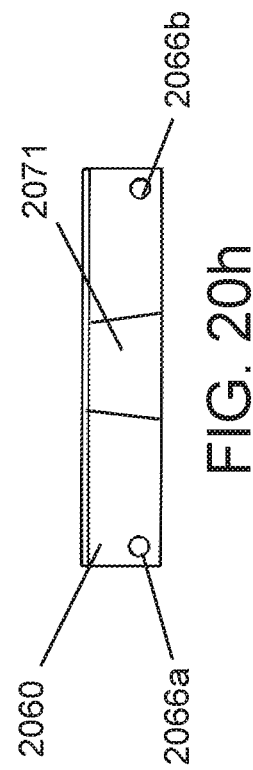
Figure 20D:
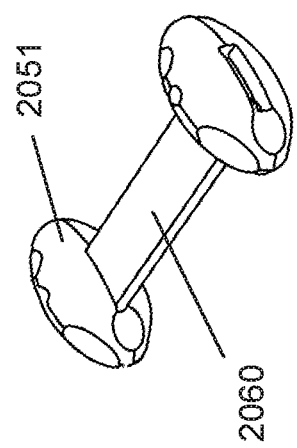

FIG. 20d is a perspective view of the embodiment of FIG. 20a of the lysing plate and its associated side beads.

Figure 20E:
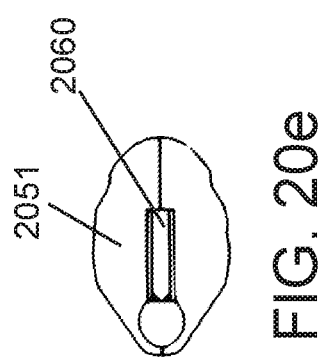

FIG. 20e is a side view of the embodiment of FIG. 20a of the lysing tip illustrating the positioning of lysing plate within bead.

FIG. 20f is an upper view of the embodiment of FIG. 20a of the lysing plate and associated side beads.

FIG. 20g is a front view of the embodiment of FIG. 20a of lysing plate and associated side beads.

FIG. 20h is an upper view of the embodiment of FIG. 20a of lysing plate.

FIG. 20i is a perspective view of an alternative embodiment to the device depicted in of FIG. 20a in which the lysing member comprises a circular cross section.

FIG. 20j is a side view of a bead from the embodiment of FIG. 20i depicting a hole that makes contact with lysing member and a rod tunnel that does not extend through bead.

FIG. 20k is a side view of a bead from the embodiment of FIG. 20i depicting a hole that makes contact with lysing member and a rod tunnel that does extend through bead.

FIG. 20L is a top view of the lysing tip of FIG. 20i comprising only a rod and beads.

FIG. 20m is a top view of the lysing tip of FIG. 20i comprising a spacer and beads.

FIG. 20n is a top view of the lysing tip of FIG. 20i comprising a rod, partial spacer and beads.

FIG. 20o is a side view of a grasping control instrument depicted in FIG. 20i with a modified distal jaw shape comprising an overbite shape.

FIG. 21a is a perspective view of an alternative embodiment of a system comprising a 2-bulb lysing tip and its associated grasping/control instrument, coupled.

FIG. 21b is a perspective view of the lysing tip and its associated grasping/control instrument, uncoupled.

FIG. 21c is a side view of the embodiment depicted in FIG. 21a.

FIG. 21d is an upper plan view of a lysing tip coupled with a grasping/control instrument depicting hidden lines of internal components of a bead on one side.

FIG. 21e is an upper exploded view showing beads removed from lysing segment.

FIG. 22a is a perspective view of an alternative embodiment of a system comprising a 2-bulb lysing tip with beads rounded on the proximal ends and its associated grasping/control instrument, coupled.

FIG. 22b is a perspective view of the lysing tip and its associated grasping/control instrument, uncoupled.

FIG. 22c is a side view of the embodiment depicted in FIG. 22a.

FIG. 22d is an upper plan view of a lysing tip coupled with a grasping/control instrument.

FIG. 22e is an upper exploded view showing beads removed from lysing segment.

FIG. 23a is an upper plan view of an alternative embodiment of a system comprising a 2-bulb lysing tip illustrating use of cords for retrieval.

FIG. 23b is a side view of the embodiment depicted in FIG. 23a of the lysing tip and its associated grasping/control instrument, uncoupled.

FIG. 23c is a perspective view of the embodiment depicted in FIG. 23a.

FIG. 23d is an upper view of the grasping plate and lysing member of the embodiment depicted in FIG. 23a.

FIG. 24a is a perspective view of a lysing tip configured to couple with an electrosurgical pencil.

FIG. 24b is an upper view of the lysing tip of FIG. 24a coupled to an electrosurgical pencil.

FIG. 24c is a perspective view of an alternative lysing tip configured to couple to an electrosurgical pencil.

FIG. 25a is a perspective view of an embodiment of a system for delivery of a lysing tip through a single cannula via a grasping/control instrument further comprising a tether.

FIG. 25b is a close-up side view of the embodiment depicted in FIG. 25a of the distal end of the embodiment previously depicted in FIG. 25a wherein the tip is coupled to the instrument tip.

FIG. 25c is a close-up side view of the embodiment depicted in FIG. 25a of the distal end of the grasping/control instrument of the embodiment previously depicted in FIG. 25a.

FIG. 25d is a close-up, cross-sectional side view of the distal end of the embodiment previously depicted in FIG. 25a wherein the tip is coupled to the instrument tip.

FIG. 25e is a close-up perspective view of the distal end of the embodiment previously depicted in FIG. 25a wherein the tip is uncoupled from the instrument tip yet tethered and may contain magnets.

FIG. 26a is an elevated view of a lysing tip comprising a non-axial configuration in which the middle spacer is removed.

FIG. 26b is an elevated view of a lysing tip comprising a non-axial configuration in which the middle spacer is present.

Figure 27B:
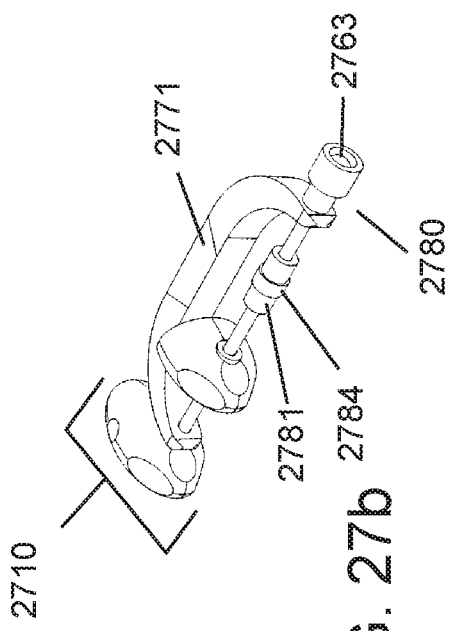
Figure 27C:
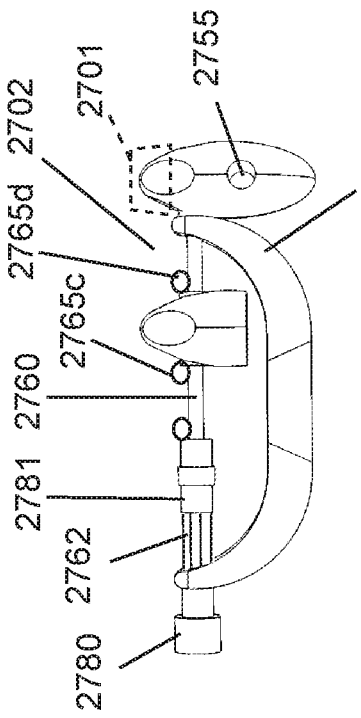
Figure 27A:
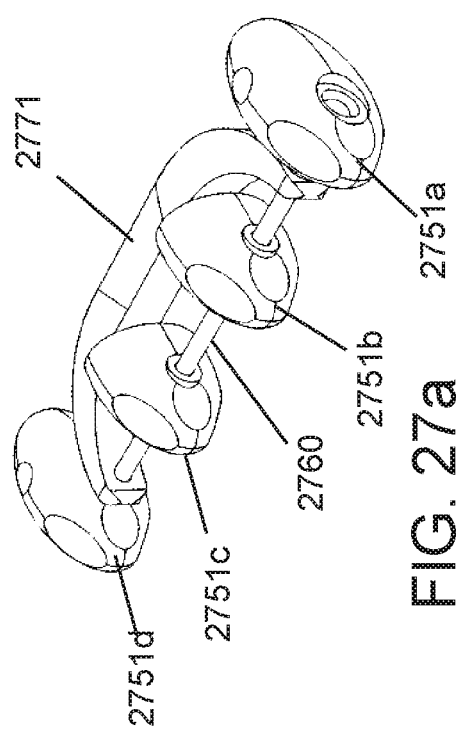

FIG. 27a is an upper plan perspective view of an alternative embodiment for a lysing tip comprising beads with associated sleeves.

FIG. 27b is a perspective view of a lysing tip showing two beads removed to expose internal components.

FIG. 27c is an upper plan view showing two beads removed to expose internal components.

FIG. 27d is the exploded perspective view of one end of a lysing tip to show how a bead is coupled with a lysing rod.

FIG. 27e is a perspective view of a side bead.

FIG. 27f are perspective views of an outer sleeve illustrating the two ends of the sleeve.

FIG. 27g is a side view of an outer bead.

FIG. 27h is a side perspective view of a middle bead coupled to lysing rod.

FIG. 27i is the exploded perspective view of a middle bead to show how a bead is coupled with a lysing rod and sleeve.

FIG. 27j is a perspective view of an outer sleeve illustrating the outer tunnel being tapered.

FIG. 28a is an upper plan perspective view of an alternative embodiment for a lysing tip.

FIG. 28b is an upper view of the lysing tip of the embodiment of FIG. 28a.

FIG. 28c is a distal view of the embodiment of FIG. 28a.

FIG. 28d is side view of the lysing tip of the embodiment of FIG. 28a.

Figure 28F:
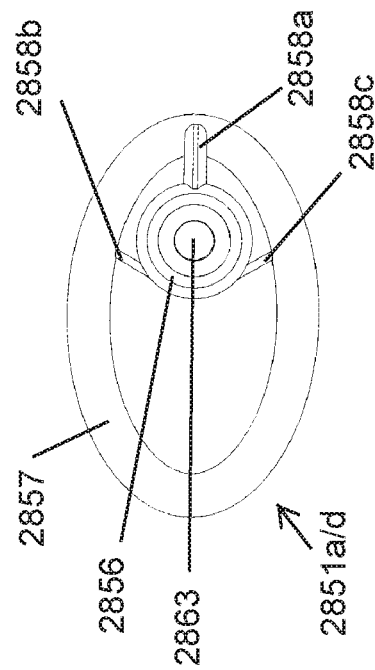
Figure 28H:
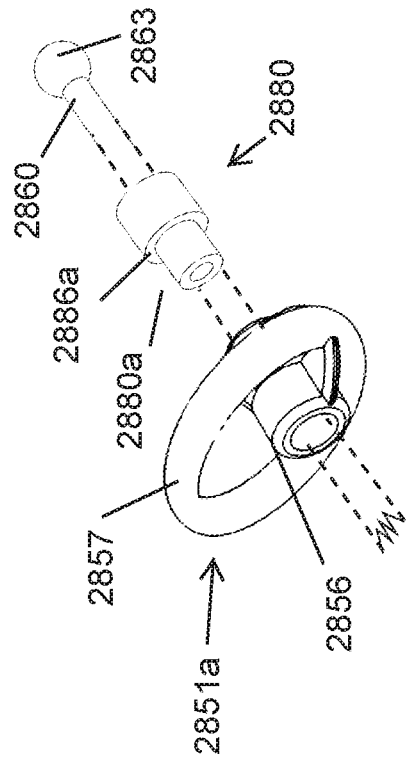
Figure 28E:
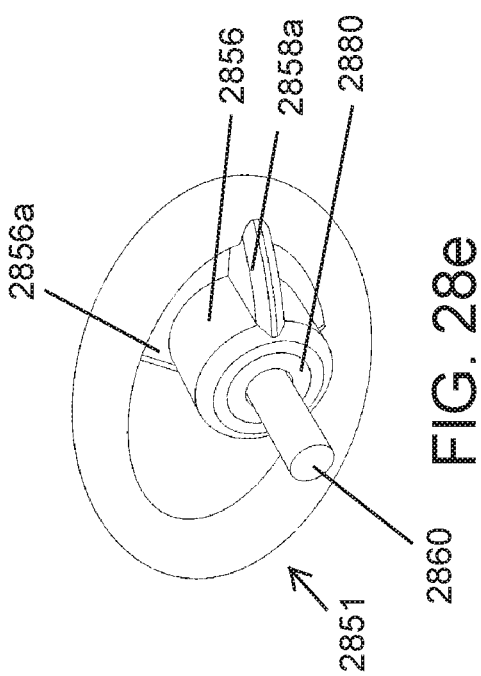

FIG. 28e is a perspective view of a side bead of the embodiment of FIG. 28a.

FIG. 28f is a side view of the annular bead of the embodiment of FIG. 28a.

Figure 28G:
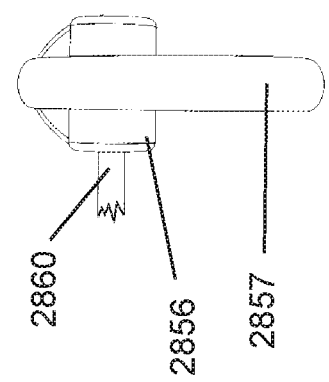

FIG. 28g is an upper view of a side bead coupled to lysing rod.

FIG. 28h is the exploded perspective view of a side bead to show how a bead is coupled with a lysing rod and sleeve.

Figure 28J:
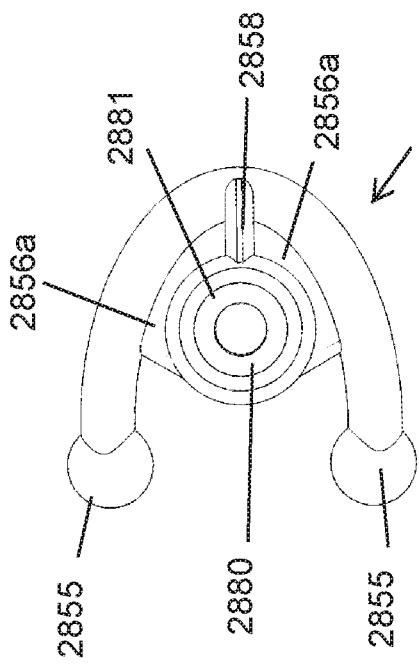
Figure 28I:
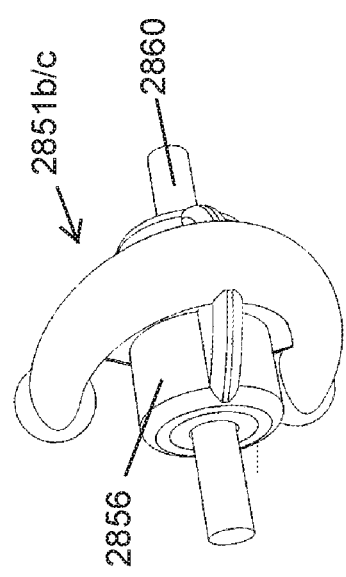

FIG. 28i is a side perspective view of a middle bead coupled to lysing rod.

FIG. 28j is a side view of a middle bead.

Figure 28L:
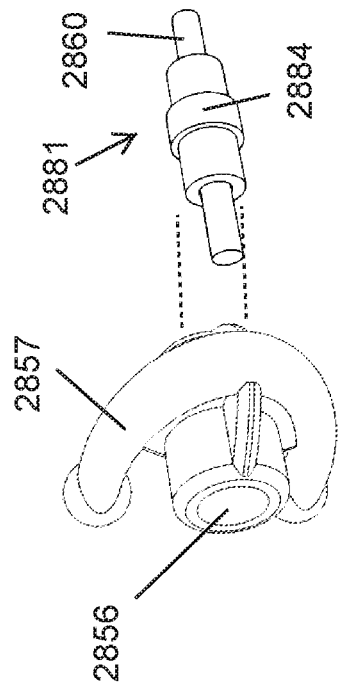
Figure 28K:
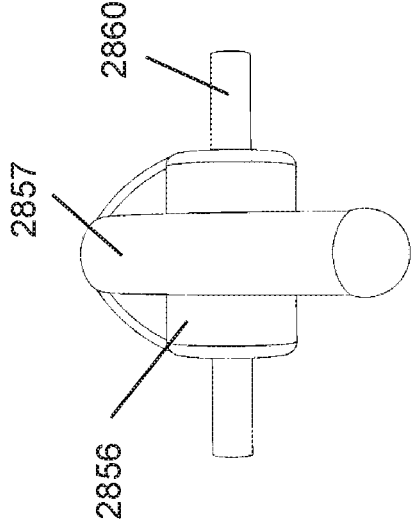

FIG. 28k is an upper view of a middle bead coupled to lysing rod.

FIG. 28L is a perspective exploded view of a bead and corresponding sleeve coupled to lysing rod.

FIG. 29a is an upper plan perspective view of an alternative embodiment for a lysing tip.

FIG. 29b is an upper view of the lysing tip of the embodiment of FIG. 29a.

FIG. 29c is a side view of the embodiment of FIG. 29a.

FIG. 29d is side view of the middle bead of the embodiment of FIG. 29a.

Figure 29E:
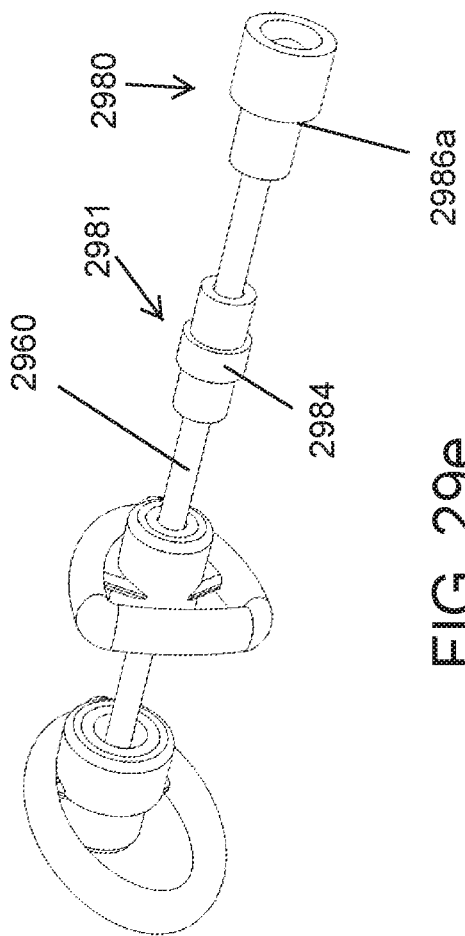

FIG. 29e is a perspective view of the lysing rod and its components with 2 beads removed to expose internal components.

Figure 29F:
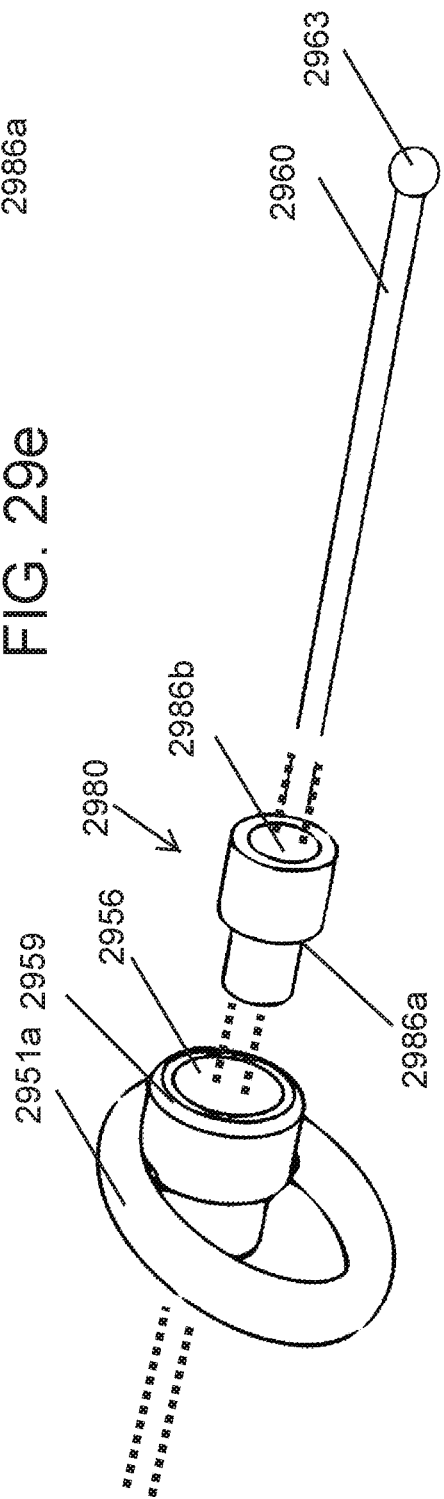

FIG. 29f is a perspective exploded view of an outer annular bead of the embodiment of FIG. 29a demonstrating how it is coupled with lysing rod and sleeve.

FIG. 30a is an upper plan perspective view of an alternative embodiment for a lysing tip.

FIG. 30b is an upper view of the lysing tip of the embodiment of FIG. 30a.

FIG. 30c is a side view of the embodiment of FIG. 30a.

FIG. 30d is side view of the middle bead of the embodiment of FIG. 30a and corresponding sleeve coupled to lysing rod.

FIG. 30e is a perspective view of an outer bead in an uncompressed state.

FIG. 30f is a perspective view of an outer bead in a compressed state.

FIG. 30g is a perspective view of an outer sleeve of the embodiment of FIG. 30a.

FIG. 30h is a side view of an outer bead in an uncompressed state.

FIG. 30i is a side view of an outer bead in a compressed state.

FIG. 30j is an upper view of an outer bead in an uncompressed state.

FIG. 30k is an upper view of an outer bead in a compressed state.

FIG. 31a is a perspective view of an embodiment of a system for delivery of a lysing tip through a cannula in a treatment configuration.

FIG. 31b is a close-up perspective view of the embodiment depicted in FIG. 31a comprising the middle beads depicted in FIG. 28a.

FIG. 31c is a close-up perspective view of the embodiment depicted in FIG. 31a comprising the middle beads depicted in FIG. 27a.

FIG. 31d is a close-up perspective view of the embodiment depicted in FIG. 31a comprising the middle beads depicted in FIG. 29a.

FIG. 31e is a close-up perspective view of the embodiment depicted in FIG. 31a comprising the middle beads depicted in FIG. 30a.

FIG. 32a is a perspective view of an embodiment of a TMT coupled to a cannula with actuating rods and canal in the treatment configuration.

FIG. 32b is a perspective view of the embodiment of FIG. 32a in between the treatment and delivery configurations without canal.

FIG. 32c is a perspective view of the embodiment of FIG. 32a in the delivery configuration without canal.

FIG. 33a is a perspective view of a TMT comprising an energy bar coupled to a grasping/control instrument with energy conduit visible.

FIG. 33b is a side view of the embodiment depicted in FIG. 33a with TMT uncoupled from grasping/control instrument with energy conduit visible.

FIG. 33c is a perspective view of a cover to the TMT depicted in FIG. 33a.

FIG. 33d is a perspective view of the energy bar and members to the TMT depicted in FIG. 33a.

FIG. 33e is a perspective view of a TMT and its associated grasping/control instrument and an alternative embodiment of an energy conduit.

FIG. 33f is a top plan view of the embodiment depicted in FIG. 33a depicting the energy window tip in a delivery configuration and coupled to a modular instrument tip.

FIG. 34a is an upper view of a dissector/tissue clamp system in the treatment/dissection configuration.

FIG. 34b is an upper view of the dissector/tissue clamp system depicted in FIG. 34a with jaws in an intermediate configuration.

FIG. 34c is an upper view of the dissector/tissue clamp system depicted in FIG. 34a with jaws clamped.

FIG. 34d is an upper view of the dissector/tissue clamp system depicted in FIG. 34a in the delivery configuration.

FIG. 34e is an upper view of the dissector/tissue clamp system depicted in FIG. 34a with outer cannula removed.

FIG. 34f is an exploded view of the parts of the tip of the embodiment depicted in FIG. 34a.

Figure 34G:
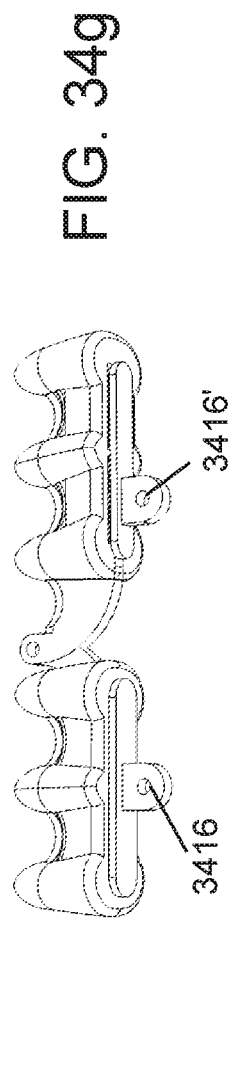

FIG. 34g is a rear perspective view of the parts depicted in FIG. 34f coupled.

Figure 34H:
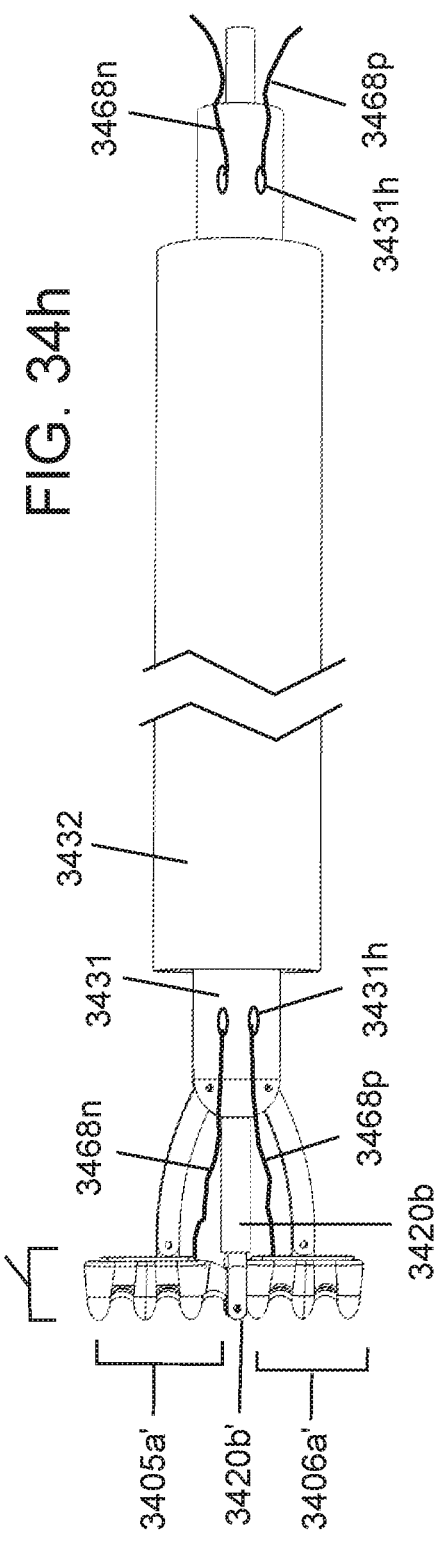

FIG. 34h is an example of a bipolar embodiment of the system depicted in FIG. 34a.

Figure 34I:
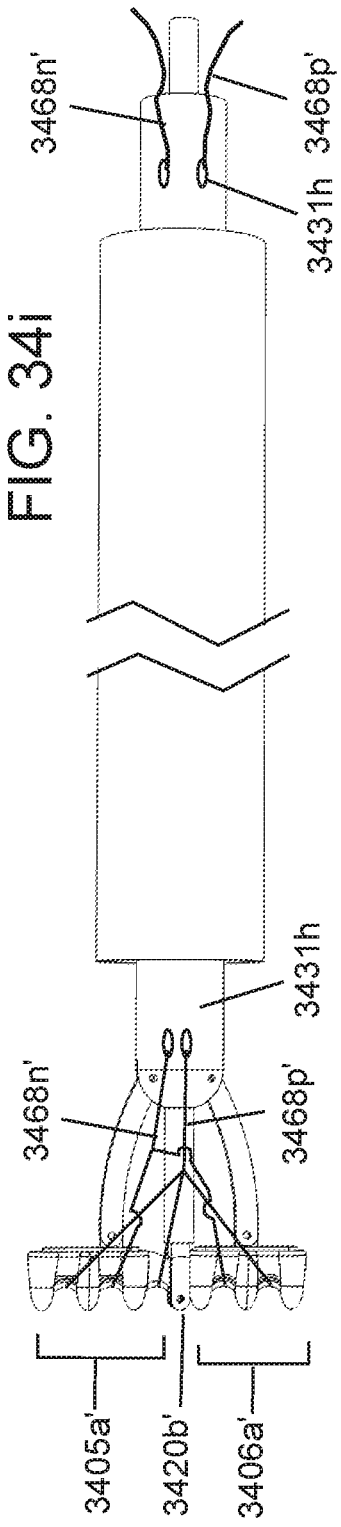

FIG. 34i is an alternative embodiment of the bipolar system depicted in FIG. 34h.

FIG. 35a is a perspective view of an alternative embodiment of a system comprising a rotatable lysing tip and associated grasping/control instrument and cannula.

FIG. 35b is a perspective view of the embodiment of FIG. 35a with lysing tip rotated.

FIG. 35c is a close-up side rear view of the lysing tip of the embodiment of FIG. 35a with upper jaw removed.

FIG. 35d is the side view of the support member of the embodiment of FIG. 35a showing the upper and lower projections.

FIG. 35e is a perspective view of the upper jaw of the embodiment of FIG. 35a.

FIG. 35f is a top view of an alternative to the embodiment of FIG. 35a in a delivery configuration in which the upper and lower protrusions are moved away from the centerline of the support member.

Figures 36A, 36B, 36C, 36D, 36E:
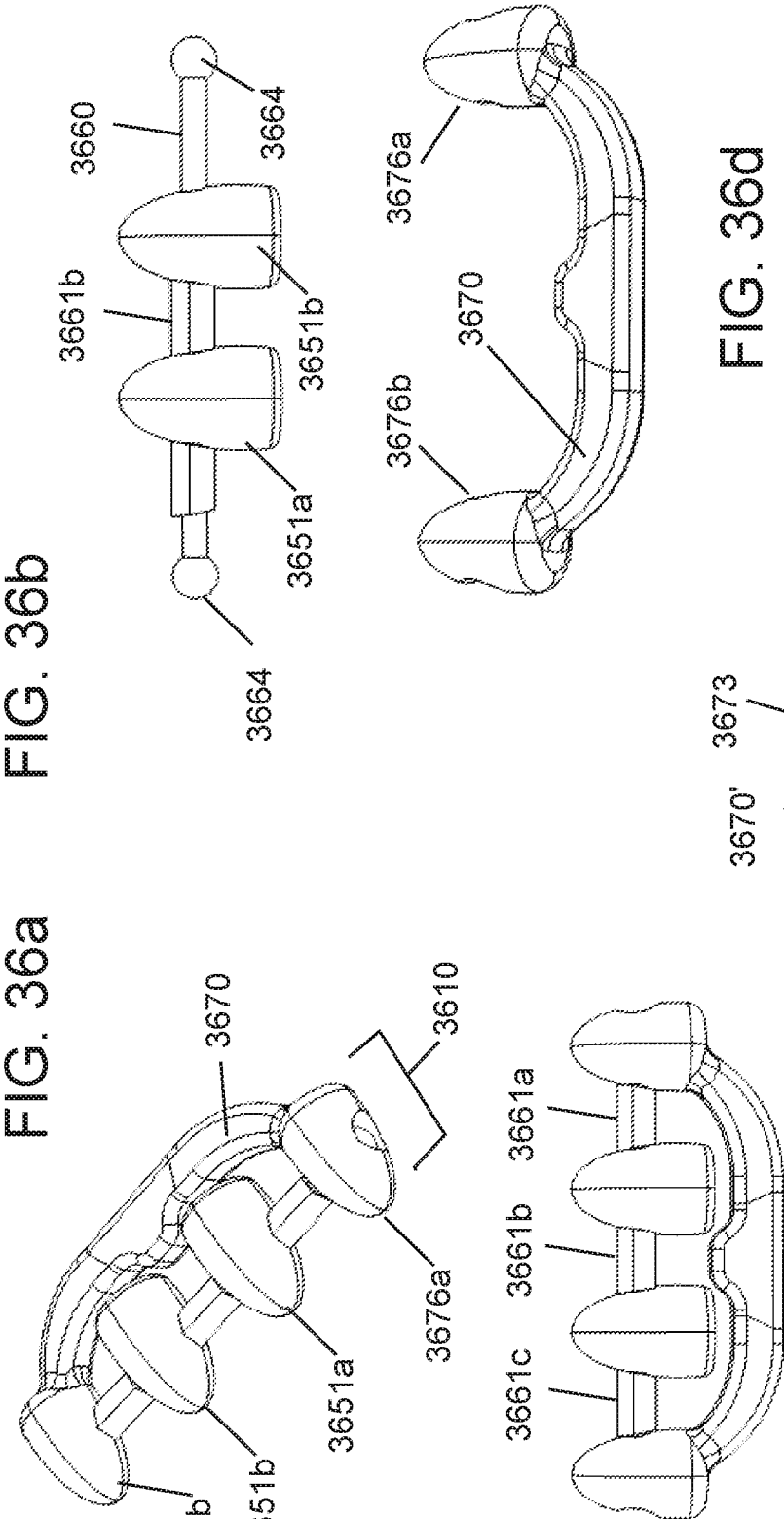

FIG. 36a is an alternative embodiment of a lysing tip comprising two outer protrusions extending from a support member and two inner beads positioned along a lysing member.

FIG. 36b is an upper plan view of various components of the lysing tip of the embodiment depicted in FIG. 36a.

FIG. 36c is an upper plan view of the lysing tip of the embodiment depicted in FIG. 36a.

FIG. 36d is an upper plan view of certain components of the lysing tip of the embodiment depicted in FIG. 36a.

FIG. 36e is a side view of the embodiment depicted in FIG. 36a.

Figure 37A:
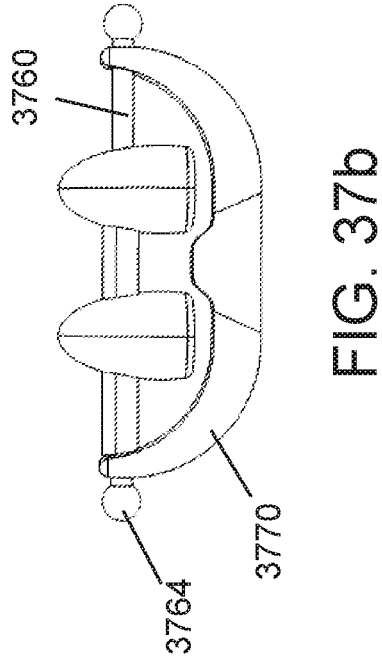

FIG. 37a is an alternative embodiment of a lysing tip comprising two beads that may cover the end tips of the support member.

Figure 37C:
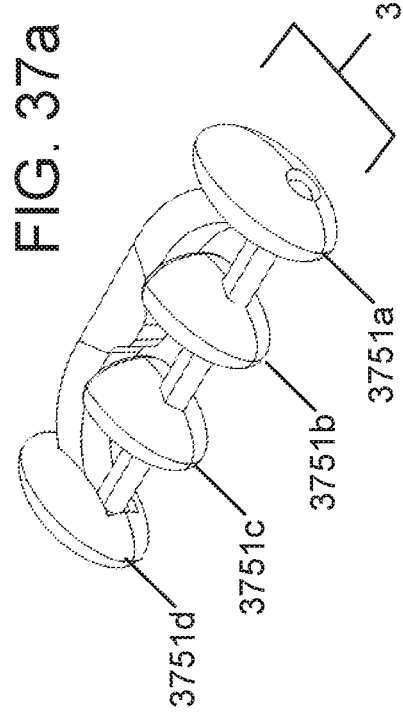
Figure 37B:
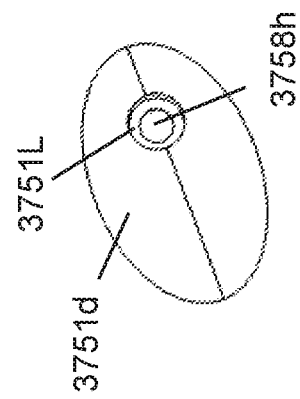

FIG. 37b is an upper plan view of certain components of the lysing tip of the embodiment depicted in FIG. 37a.

FIG. 37c is an upper plan view of the lysing tip of the embodiment depicted in FIG. 37a.

Figure 37D:
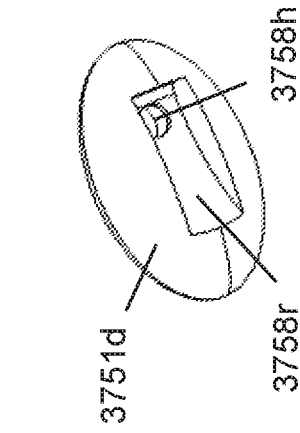

FIG. 37d is a side view of the side bead of the embodiment depicted in FIG. 37a, said view being from the inside.

Figure 37E:
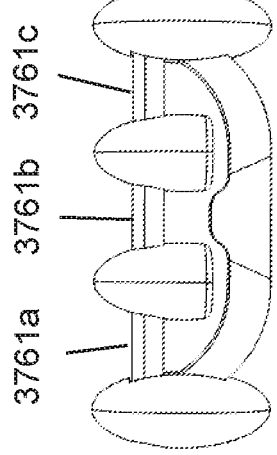

FIG. 37e is a side view of the side bead of the embodiment depicted in FIG. 37a, said view being from the outside.

FIG. 38a is an upper view of a lysing member with associated beads.

FIG. 38b is an exploded upper view of an alternative embodiment to the lysing tip of FIG. 38a in proximity to its modular grasping/control device.

FIG. 38c is an upper view of the embodiment of FIG. 38b in the delivery configuration.

FIG. 39a is a perspective view of an embodiment comprising a modular tip further comprising a support member that slides through a slot within said modular tip.

FIG. 39b is an upper view of the embodiment depicted in FIG. 39a in the treatment configuration.

FIG. 39c is an upper view of a midline cross section of the embodiment depicted in FIG. 39b in the treatment configuration comprising a piston engaging and bracing the support member.

FIG. 39d is an upper view of the embodiment depicted in FIG. 39a in the delivery configuration depicting an alternative mechanism to brace the support member during a surgical procedure.

FIG. 39e is an upper view of the embodiment depicted in FIG. 39a in the delivery configuration depicting an alternative mechanism to fix the support member during a surgical procedure.

FIG. 40 is a flow chart illustrating one implementation of a method for an energy feedback loop.

FIG. 41 is a flow chart illustrating one implementation of a method for separating and modifying tissues.

FIG. 42 is a flow chart illustrating one implementation of a method for accessing an organ.

FIG. 43 is a flow chart illustrating one implementation of a method for hernia repair.

FIG. 44 is a flow chart illustrating one implementation of a method for accessing the central nervous system.

FIG. 45 is a flow chart illustrating one implementation of a method for removing tissue from a peripheral nerve.

Figure 46:
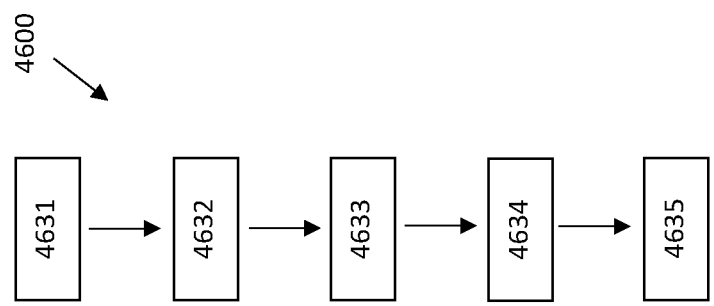

FIG. 46 is a flow chart illustrating one implementation of a method for creating a flap.

Figure 47:
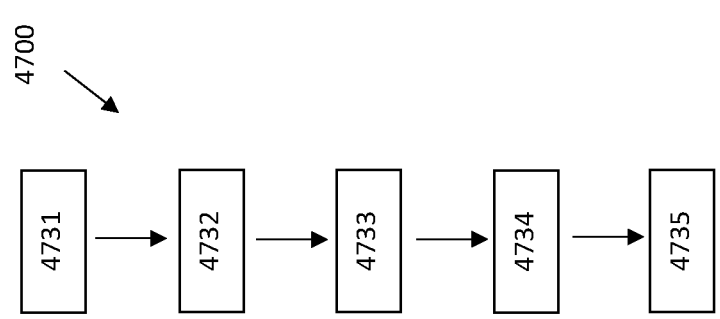

FIG. 47 is a flow chart illustrating one implementation of a method for creating a graft.

Figure 48:
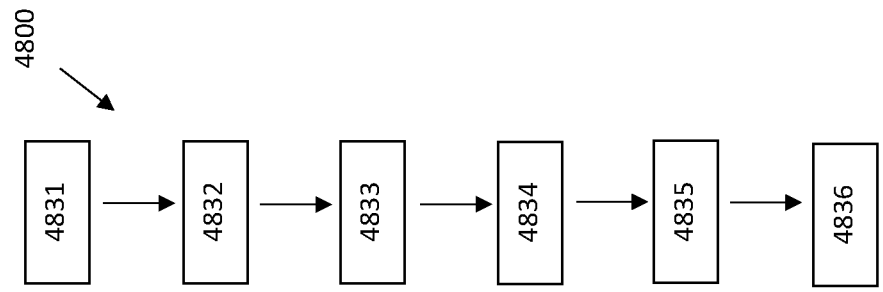

FIG. 48 is a flow chart illustrating one implementation of a method for removing tissue/tumor from an organ.

FIG. 49 is a flow chart illustrating one implementation of a method for removing an organ.

FIG. 50 is a flow chart illustrating one implementation of a method for removing scar and/or fibrotic tissue.

FIG. 51 is a flow chart illustrating one implementation of a method for treatment of apocrine glands.

FIG. 52 is a flow chart illustrating one implementation of a method for treatment of eccrine glands.

FIG. 53 is a flow chart illustrating one implementation of a method for reduction of hair.

FIG. 54a is a perspective view of surgical site involving cellulite treatment.

FIG. 54b is a perspective view of surgical site involving cellulite treatment.

FIG. 55 is a flow chart illustrating one implementation of a method for treatment of cellulite.

FIG. 56 is a flow chart illustrating one implementation of a method for face dissection and/or face lifting.

FIG. 57 is a flow chart illustrating one implementation of a method for neck dissection and/or neck lifting.

Figure 58:
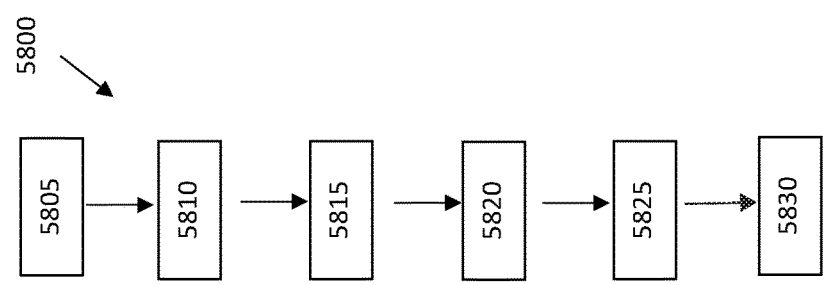

FIG. 58 is a flow chart illustrating one implementation of a method for dissection of the brow and/or brow lifting.

Figure 59:
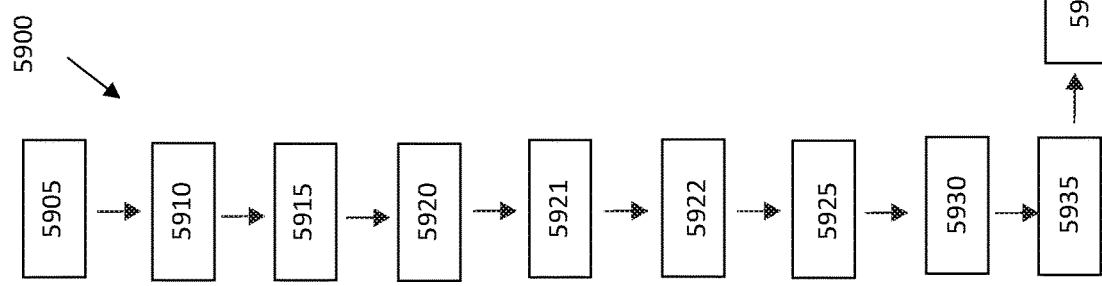

FIG. 59 is a flow chart illustrating one implementation of a method for creating pockets for implants.

Figure 60:
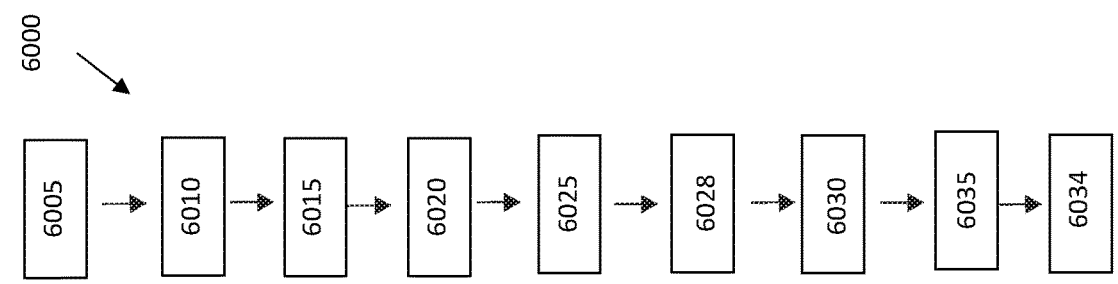

FIG. 60 is a flow chart illustrating one implementation of a method for capsulotomy.

Figure 61:
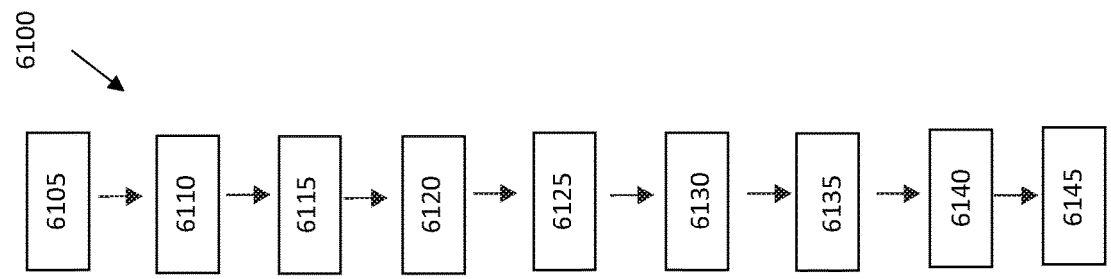

FIG. 61 is a flow chart illustrating one implementation of a method for body lifting and skin excision.

DETAILED DESCRIPTION

Further details regarding various embodiments will now be provided with reference to the drawings.

FIGS. 1a-j depict an embodiment of a CDTD 100 comprising a plurality of protrusions 101 and recessions 102 positioned in between adjacent protrusions. In the depicted embodiment, recessions 102 comprise lysing segments 103a, 103b, and 103c. Thus, a lysing segment is positioned in each of the recessions 102 positioned in-between adjacent protrusions 101. In the depicted embodiment, these three lysing segments 103a, 103b, and 103c are collectively defined by a lysing member 103. However, other embodiments are contemplated in which separate lysing members may be used for each of the lysing segments positioned between adjacent protrusions.

In this embodiment, the lysing member 103 comprises a lysing plate. However, other embodiments are contemplated in which separate lysing members may be used for each of the lysing segments 103a/103b/103c positioned between adjacent protrusions 101.

In the depicted embodiment, the cannulas 131 and 132 may comprise hollow tubes, which may comprise insulating and/or supportive coating(s) and/or cover overlying other conductive materials. The first/inner/device cannula 131 may be considered a device cannula that is coupled with device/lysing tip 110 and may or may not be used with a second/outer cannula. The second/outer cannula 132 could be associated with a trocar and may be used primarily for surgical introduction of first/inner/device cannula 131 into body. In alternative embodiments and implementations even first/inner/device cannula 131 may be omitted for certain procedures. With respect to such embodiments, other structural elements may be added to provide rigidity and/or to assist with delivery and/or use of the device during a procedure.

It should be understood that in some embodiments or implementations, such devices can be used in connection with only a single cannula as shown in FIG. 1j. Such an embodiment or implementation may be useful because: (A) the surgeon may not be working in a closed cavity that requires insufflation (for example, skin, fat, muscle); (B) it may allow the manufacture of a larger tip configuration than the smallest cannula's constraining dimensions allowing for larger, thicker, stronger components than would otherwise be permitted to fit in the smaller volume or pass through a smaller cross-sectional area, or (C) it may allow smaller diameter entrance incision/wound as cannulas have a thickness component.

Each of the protrusions 101 extends from a common base 105 such that the protrusions 101 are coupled with one another. In some embodiments, each of the protrusions 101 is integrally coupled with each of the other protrusions 101. Thus, in some embodiments, each of the protrusions may be defined by base 105. Alternatively, separate protrusions 101 may be coupled with or formed on base 105. A linking member 115 may be an integral part of or a monolithic component with lysing member 103. Alternatively, linking member 115 could be coupled to the lysing member 103. Linking member 115 may be used to facilitate a desired coupling between lysing tip 110—which, in the embodiment of FIG. 1e, comprises protrusions 101, recessions 102, lysing member(s) 103 (which may comprised of lysing segments 103a/103b/103c), linking member 115, and hinges 116/117 that may adhered to or otherwise coupled with linking member 115—and one or more elements used to facilitate delivery and/or deployment of lysing tip 110 through cannulas 131 and/or 132 such as actuation rods 121, 122, 123, and/or 124. In some embodiments, linking member 115 may be a separate component from lysing tip 110 and may be used to couple lysing tip 110 to a hinge and/or actuation rod. Linking member 115 preferably is at least partially covered and in some embodiments fully covered by an insulating material so that the electrosurgical energy is delivered to lysing member 103 without delivering electrosurgical energy to the rear of lysing tip 110. In alternative embodiments, a wire or wires may extend through an insulator or insulating portion of linking member 115 and connect with a conducting portion of linking member 115 and/or lysing member 103. This wire or wires could extend through or along one or both of the actuation rods and/or within the first/inner/device cannula 131 to supply electrosurgical energy to linking member 115 from the hand assembly.

In some embodiments and implementations, linking member 115 may be non-conductive and as such hinges 116 and 117 may be electrically coupled to lysing member 103. Alternatively, hinges 116 and 117 may be non-conductive as well, and in such case, the lysing member 103 may be electrically coupled to electrosurgical energy source by other means such as wire for example.

Retraction guide 125 is preferably near tip 110 at or near the distal end of one of actuation rods 121/122. In the depicted embodiment, retraction guide 125 is positioned near the distal end of actuation rod 122 adjacent to (immediately proximal of) tip 110. In some embodiments, retraction guide 125 may comprise a resilient material, such as a spring, so that it provides a restorative force during retraction of tip 110 into cannula 131. Preferably, retraction guide 125 is positioned and configured so as to extend from actuation rod 122 laterally by a distance at least approximately equal to, in some embodiments slightly greater than, the distance one or more of the protrusions 101 that extend laterally relative to actuation rod 122 in the retracted/folded configuration. In some embodiments, retraction guide 125 may extend in this direction a distance equal to, or slightly greater than, the largest protrusion 101 (in embodiments in which each of the protrusions are not identical and/or do not project an equal distance).

In the depicted embodiment, protrusions 101 are fixed with respect to base 105 and the rest of lysing tip 110. In this embodiment, protrusions 101 are fixed three-dimensionally with respect to base 105 and the rest of lysing tip 110. In other embodiments discussed later, protrusions 101 may not be coupled to a common base. Similarly, in other embodiments discussed later, protrusions 101 may be movable rather than fixed three-dimensionally. For example, in some embodiments, protrusions 101 may be rotatable with respect to a lysing member, a base, and/or another portion of lysing tip 110.

System 100 may be configured to allow for repositioning of lysing tip 110 between a delivery configuration and a treatment configuration. In the delivery configuration, protrusions 101 may be configured to extend in a direction that is at least substantially perpendicular to the cannula axis, and lysing tip 110 may be configured to extend in a direction that is at least substantially parallel to the cannula axis. In other embodiments, lysing tip 110 may be configured to extend at an acute angle relative to the cannula axis so long as the axis of lysing tip 110 fits within the lumen of the cannula such as shown in FIG. 11f as an example. In addition, in the depicted embodiment, lysing tip 110 may be configured such that an energy delivery side of lysing tip 110 in front of protrusions 101 and recessions 102, which energy delivery side will ultimately deliver electrosurgical energy for dissecting tissue, faces an interior surface of a lumen of first/inner/device cannula 131 through which lysing tip 110 is delivered. Following delivery of lysing tip 110 through a distal end of first/inner/device cannula 131 and/or second/outer cannula 132, system 100 may be configured to reposition lysing tip 110 to the treatment configuration in which the energy delivery side extends at least substantially perpendicular to the cannula axis.

Lysing tip 110 may comprise an orientational-deployment side opposite from the energy delivery side. The orientational-deployment side of lysing tip 110 may be configured to allow lysing tip 110 to be repositioned between the delivery configuration and the treatment configuration described above. A deployment assembly may be coupled with the orientational-deployment side of lysing tip 110. This deployment assembly may be configured to allow for selective repositioning between the delivery and treatment configurations. In the depicted embodiment, the deployment assembly may comprise linking member 115 and one or more pivot members, such as pivot members 116 and 117. Pivot members 116 and/or 117 may comprise various elements configured to allow for selective pivoting, rotation, and/or angulation of lysing tip 110, such as joints, ball pivots, hinges, pins, groove/slot pairs, etc.

Pivot members 116 and 117 may be coupled with linking member 115 at one end and may be coupled with distal (to the surgeon) portions 121 and 122 of actuation rods, respectively. Thus, upon advancing one or both of proximal actuation rods 123 and 124, lysing tip 110 may be advanced in its delivery configuration down one or more cannulas, such as first/inner/device cannula 131 and/or second/outer cannula 132. In some embodiments, appropriate wires or other transmission lines for delivery of electrosurgical energy may be positioned to extend adjacent and/or through one or more of the various actuation rods. Alternatively, in some embodiments, electrosurgical energy may be delivered directly through one or more actuation rods. In some embodiments, wires or other transmission lines for delivery of electrosurgical energy may instead, or additionally, extend though other regions of lumens of first/inner/device cannula 131 and/or second/outer cannula 132. Actuation rods 121, 122, 123 and/or 124 may comprise any suitable material depending on whether electrosurgical energy is being delivered through them. For example, a metal or other conductive material may be used if electrosurgical energy is to be delivered through the actuation rods, or a plastic or other insulating material may be used if electrosurgical energy is to be delivered through separate wiring or other suitable transmission lines. Actuation rods may be divided into more segments, with or without pivots, than proximal or distal, for example, 3 segments. In some embodiments, actuation rods may be insulated with a non-conductive material but may have a conductive core for delivery of electrosurgical energy.

In this embodiment, spot coagulator ("SC") is comprised of SC shaft 142 and SC tip 141 may be seen in the deployed view. SC shaft 142 may be comprised of a metal insulated with a non-conductor. In the depicted embodiment, SC shaft 142 is slidably coupled to the first/inner/device cannula 131. The more distal end of the SC is the SC tip 141 and the more proximal (toward the surgeon) end of the SC is SC shaft 142. In this depicted embodiment the SC tip 141 extends from the SC shaft 142 and is conductive and not insulated along at least a portion of the tip. In some embodiments, the entire tip may be conductive. A spot coagulator may be helpful by allowing the surgeon not to exchange other instruments during the operative procedure to stem bleeding blood vessel(s); it may be beneficial during some surgical procedures to have spot coagulator coagulation capabilities within the same instrument. In the depicted embodiment the SC tip 141 may be restricted to 25 mm protrusion beyond the distalmost portion of lysing tip 110, which may comprise one end of the protrusions 101 on lysing tip 110. In various contemplated embodiments, a bend in the SC shaft 142 and/or size mismatch and/or tether, etc., may also be used to limit the distance SC tip 141 may protrude. In other contemplated embodiments, no elements may restrict the working movement range of the SC shaft 142. The SC shaft 142 may derive its electrical energy from separate wiring and/or parasitization off of one or more of the actuation rods. In the depicted embodiment, SC shaft 142 may comprise one or more non-insulated area(s) that may be brought into an actuation rod or other energetic source within the first/inner/device cannula 131. An implementation using the depicted embodiment may involve pushing distally SC either directly or indirectly on the SC shaft 142 distally (possibly via through handle assembly 160). Electrosurgical energy, such as suitable electrosurgical waveform, may be delivered when the electrosurgical generator is activated, via the handle assembly 160 into the SC shaft 142 and thereupon to SC tip 141 and then into target tissue. In the depicted embodiment SC shaft 142 may comprise stainless steel and may be round in cross-section. Also in the depicted embodiment, the exterior of the SC shaft 142 may be insulated. The electrical insulator may comprise, for example, porcelain, ceramics, glass-ceramics, plastics, various halogenated carbon molecules, polytetrafluoroethylene, carbon, graphite, and graphite-fiberglass composites and the like. In some embodiments, the conductive material may comprise: steel, nickel, alloys, palladium, gold, tungsten, silver, copper, platinum and/or any other conductive metal that does not give off toxic residua at operating temperatures. In other contemplated embodiments, the conductive material may comprise cermets and the like. In the depicted embodiment, SC tip 141 is shaped like a sphere. In other embodiments, the SC tip may be shaped like the frustum of a cone, pyramid, polyhedron, ellipsoid, as well as a wide variety of geometric shapes. In some embodiments, SC shaft 142 may be oval, flat, rectangular or geometric in cross-section or substantially flattened. In alternative embodiments, SC tip 141 may be pointed, bullet shaped, or geometric in cross section; more angulate and/or pointed tips may disperse electrical energy more readily and allow greater precision than larger, more rounded tip designs. In the depicted embodiments of the SC shaft 142, the electrical insulator may comprise polytetrafluoroethylene. In alternative embodiments the electrical insulator may comprise, for example, polyether etherketone and/or polysulfone and/or another electrically nonconductive polymers (with thermal stability in the operating range) and/or materials that are both electrically non-conductive and of low thermal conductivity. In contemplated embodiments the electrical insulator may comprise, for example, porcelain, ceramics, glass-ceramics, plastics, various halogenated carbon molecules, polytetrafluoroethylene, carbon, graphite, and graphite-fiberglass composites and the like. Although the depicted embodiment shows a manually deployed SC, other contemplated embodiments may allow deployment to be (including but not limited to): motorized and/or spring activated and/or screw driven and/or ratchet style and/or cog style and/or pneumatic and/or hydraulic, etc. In the depicted embodiment, the SC tip 141 and SC shaft 142 together may measure about, 2 mm in diameter and be of a suitable length to match the given system including the handle assembly. In some embodiments, the insulation thickness may range from about 0.1 mm to 3 mm. Embodiments are contemplated wherein sizes of about one-fifth to about five times these dimensions may have possible uses. It is also contemplated in some veterinary embodiments tip sizes of about one-tenth to 20 times the aforementioned dimensions having possible uses.

System 100 comprises two separate cannulas, namely, a first/inner/device cannula 131 which preferably comprises a lumen of sufficient diameter to allow folded lysing tip 110 (in a delivery configuration) to be positioned within the lumen of first/inner/device cannula 131, and a second/outer cannula 132, which may have a larger cross-sectional diameter; the first/inner/device cannula 131 may be delivered within second/outer cannula 132.

In some embodiments and implementations, lysing tip 110 may be configured such that its protrusions 101 and/or another portion of lysing tip 110 are too large to fit within the lumen of first/inner/device cannula 131, even in the delivery configuration. Thus, lysing tip 110 in its delivery configuration may be positioned just outside (immediately distal) of first/inner/device cannula 131 and within second cannula 132 during delivery and retraction. Any of the embodiments described herein may be configured such that the tip 110 cannot be fully received within first/inner/device cannula 131. This embodiment may be useful because it permits the tip to be as large as possible given the dimension constraints of the second/outer cannula and not the first/inner/device cannula thus reducing the expense of further miniaturizing and/or allows for thicker/stronger components.

By providing two co-axial cannulas, proximal actuation rods 123 and 124 may be prevented, or at least substantially prevented, from inordinate bending and/or being separated from one another or otherwise system 100 may be configured to maintain better control over lysing tip 110 during deployment. Thus, preferably, actuation rods 123 and 124 are also delivered through first/inner/device cannula 131. Some embodiments may further comprise one or more additional joints and/or pivot members positioned proximally relative to pivot members 116 and 117. For example, some such embodiments may comprise hinges and/or pivot members that are positioned within one or both of proximal actuation rods 123/124, and one or both distal actuation rods 121/122 such as hinges 127 and 128. Hinges 127/128 may allow for one or both of distal actuation rods 121/122 to be pivoted/rotated in a desired direction once hinges 127/128 have exited or are approximately coincident with or near the terminal end of first/inner/device cannula 131.

In the depicted embodiment, hinge 127 may be actuated by providing actuating means comprising two cords 129a and 129b that extend from actuation rod 121. Cords 129a and 129b may be coupled with lysing tip 110 such that forces from cords 129a and 129b may be transferred to lysing tip 110 to result in pivoting of hinge 127. By selectively pulling on one of the cords 129a and 129b, tip 110 may be rotated in a desired direction and by selectively pulling on another of the cords 129a and 129b, tip 110 may be rotated in a different desired direction. Of course, any number of cords may be used to fine tune the pivotability of lysing tip 110 as desired. Cords 129a and 129b may comprise any suitable material, such as wiring, plastic, metal, string, biopolymer, etc. Cord attachment areas 121u and 121L on distal actuation rod 121 may be used to affix cords 129a and 129b. Such cord attachment areas may comprise an opening for insertion of the cord which may include a plug or weld to secure the cord. In other embodiments, the cord attachment area 121u or 121L may comprise a weld against the surface of distal actuation rod 121.

The deployment assembly of system 100 may further comprise a handle assembly 160 that may be used to selectively deploy lysing tip 110 and control various aspects of its delivery and/or use during surgery. Handle assembly 160 comprises a body 161 coupled with a pistol grip 162. First/inner/device cannula 131 may extend from and be coupled with handle assembly 160. A rocker assembly 165 or another such control means may be provided for actuation of various features/functions/elements in system 100. For example, rocker assembly 165 may be coupled with cords 126a/126b and 129a/129b such that, upon pressing rocker assembly 165 along a top portion of the assembly, a first cord or set of cords 126b and 129b may be pulled causing the tip 110 to rotate upwards. Similarly, rocker assembly 165 may be further configured such that, upon pressing rocker assembly 165 along a bottom portion of the assembly the other cord or set of cords 126a and 129a may be pulled causing the tip to rotate downwards. Upon pushing one of cords 126a/129a, the other of cords 126b/129b may be moved in an opposite direction, since pushing one end of rocker assembly 165 may result in an opposite movement of the opposite end of rocker assembly 165. In this manner, lysing tip 110 may be selectively moved in one direction or another as desired. In an alternative embodiment, a more rigid cord or wire may be used to push an actuation rod into a desired position.

In this particular embodiment, hinges 127 and 128 may be positioned between or at the ends of actuation rods 121/123 and/or 122/124, respectively, and may allow for rotation of lysing tip 110 above and/or below the cross-sectional profile of first/inner/device cannula 131. Alternatively, hinges 127 and 128 or other means for facilitating movement of the tip outside of the cross-sectional profile of the first/inner/device cannula 131 may be positioned along the length of one or more actuation rods such as 123 or 124 in which case distal actuation rods may be omitted.

An electrosurgical actuation button 167 may be provided, which a surgeon may use to initiate transmission of electrosurgical energy to lysing tip 110. More particularly, electrosurgical actuation button 167 may be used to initiate transmission of electrosurgical cutting or blended energy to lysing member/plate 103. Button 167 may be positioned on rocker assembly 165 if desired, as shown in FIG. 1i. Pressing or otherwise actuation of button 167 may result in delivery of such energy from an electrosurgical generator coupled with handle assembly 160. Handle assembly 160 may also be used in connection with any of the other embodiments disclosed herein.

Figure 1F:
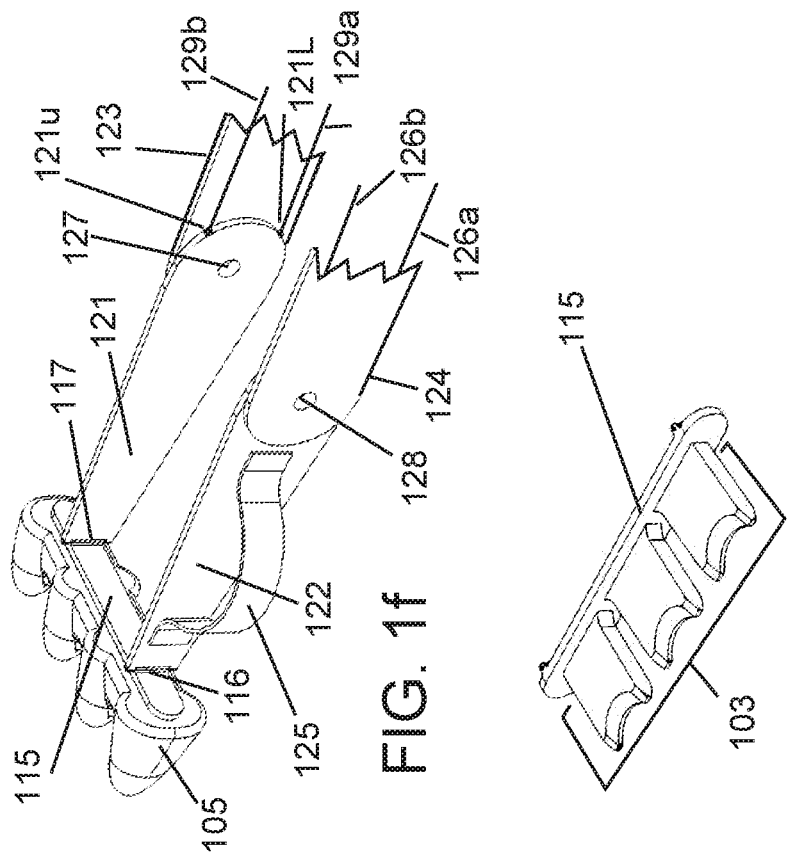
Figure 1H:
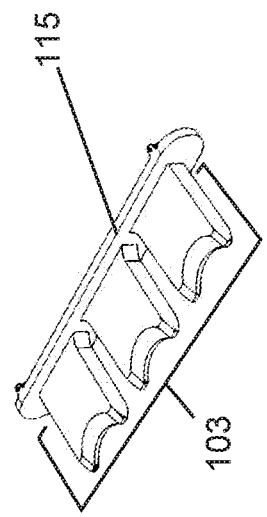
Figure 1E:
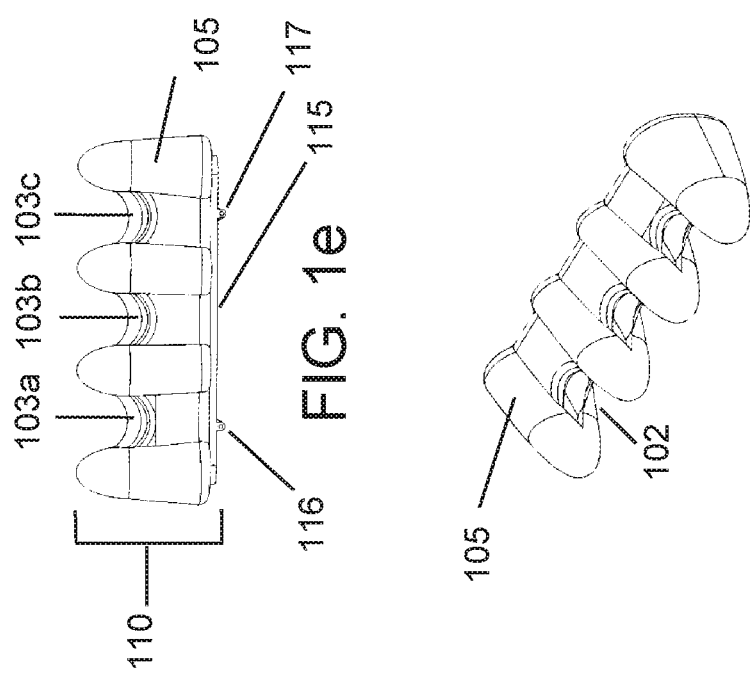
Figure 1G:
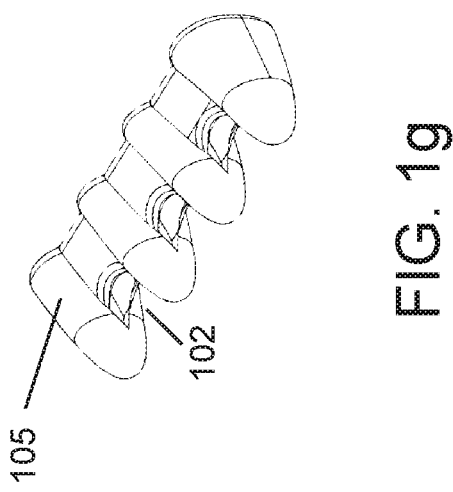

Lysing member 103 is shown removed from the rest of lysing tip 110 in FIGS. 1g and 1h. As shown in FIG. 1h, lysing member 103 may be configured to define three separate lysing segments, as shown in the figure. In other embodiments, however, lysing member 103 may be separated into three distinct and separated segments. This may be useful for certain applications, such as, for example, for embodiments using bipolar electrosurgical energy, such that each separate segment may be activated with electrosurgical energy separately.

Handle assembly 160 may further comprise one or more other actuation controls. For example, as also shown in FIG. 1i, handle assembly 160 may comprise a first actuation rod control 168 and a second actuation rod control 169. In some embodiments, one or both of first and second actuation rod controls 168 and 169 may comprise a ratchet to allow a surgeon to more precisely control the distance with which lysing tip 110 is extended and/or allow for locking lysing tip 110 in place with respect to first/inner/device cannula 131 and/or second/outer cannula 132. In some embodiments, one or both of first and second actuation rod controls 168 and 169 may have a manual control element, such as a finger control element as shown, or another grip, button, trigger, or other suitable control element. First and second actuation rod controls 168/169 may be directly or indirectly connected to proximal actuation rods 123/124 to effect movement and positioning of lysing tip 110.

In some embodiments, handle assembly 160 may be configured to be rotatable with respect to the first/inner/device cannula 131 and/or the second/outer cannula 132 such that the lysing tip 110 may be selectively rotated within a patient's body. In other words, system 100 may be configured such that some or all of the elements of the system other than first/inner/device cannula 131 and/or second/outer cannula 132, or in some embodiments some or all elements within first/inner/device cannula 131 and/or second/outer cannula 132 (such as, in some embodiments, just lysing tip 110), may be selectively rotated from handle assembly 160 to allow lysing tip 110 to be selectively rotated as needed during surgery.

It should be understood that handle assembly 160 may be used in connection with one or more of the other systems disclosed herein. Of course, those of ordinary skill in the art will appreciate that any other handle assembly, gun, or other available control mechanism may also be used, as desired.

Some embodiments may be configured such that lysing tip 110 is not aligned with the axis of cannulas 131 or 132 in the delivery configuration. More particularly the axis of lysing tip 110 may be positioned at an acute angle with respect to the axis of cannulas 131 or 132. In other embodiments, lysing tip 110 may be configured to extend at an acute angle relative to the cannula axis so long as the axis of lysing tip 110 fits within the lumen and/or lumens of one and/or both cannulas.

It should be understood that embodiments are contemplated wherein the dimensions of the tip relative to a cannula 131 may vary as for example, as shown in FIGS. 14*k* and 14L. In other words, the lysing tip 110 in the axial deployment configuration may be unable to be received within cannula 131 such as shown in FIG. 14L or may be unable to be received within an inner cannula of two delivery cannulas as shown in FIG. 14*k*. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

Although in the embodiments previously depicted, the protrusions typically extended along an axis of the cannula and were parallel to one another along the lysing tip, other embodiments are contemplated in which non-axial protrusions may instead be provided. In some such embodiments such as those depicted in FIGS. 26*a*/26*b*, for example, the two outermost protrusions/beads may extend at an angle of between about 60 degree and 90 degrees relative to each other. In some embodiments, adjacent beads/protrusions may be configured to extend relative to each other at an angle between about 20 to 40 degrees. It is contemplated that it may be desirable for some implementations and embodiments to provide, non-axial tips extending in a direction or directions falling within this range in order to, for example, allow a surgeon to effectively perform both a to and fro, and a side-to-side ("windshield wiper") motion using the CDTD. Such side or non-axial protrusions may be useful to enable a surgeon to avoid entangling the dissector in tissue during one or both such motions.

FIGS. 2*a*-2*e* depict an alternative embodiment of a CDTD system 200 comprising a plurality of protrusions 201 and recessions 202 positioned in between adjacent protrusions. In the depicted embodiment, a lysing member 203 (comprised of lysing segments 203*a*/203*b*/203*c*) is positioned so as to extend in recessions 202 and define a plurality of lysing segments. Thus, a lysing segment 203*a*/203*b*/203*c* is positioned in each of the recessions 202 positioned in-between adjacent protrusions 201. Lysing member 203 is further electrically coupled to linking member 215. System 200 further comprises first/inner/device cannula 231 and second/outer cannula 232, the first or both which may be used to deliver lysing tip 210, as previously mentioned.

Some embodiments may comprise an energy window 206 located proximally to protrusions 201. In the depicted embodiment, energy window system 206 may comprise electrode termini 206*a*/206*b*/206*c*/206*d* which may be supplied energy from an energy source via conduits (not shown) that may comprise, for example, wires and/or fiber optic filaments and/or the like. Energy window 206 may be configured in any manner to accommodate any energy modality, including, but not limited to, laser, intense pulse light, resistive heating, radiant heat, thermochromic, ultrasound, mechanical, and/or microwave.

In some embodiments, each of the various electrode termini 206*a*/*b*/*c*/*d* may comprise separate elements each of which may be coupled with lysing tip 210. In such embodiments, it may be preferred to have an electrical conduit such as a wire coupled along tip 210 between each adjacent termini 206*a*/*b*/*c*/*d*. Alternatively, a ribbon and/or band or other suitable coupling element (not shown) may define or contain each of the various termini. Such coupling elements may be coupled with lysing tip 210 in any suitable manner.

System 200 only differs from system 100 in that it lacks a spot coagulator and possesses an energy window(s).

FIGS. 3*a*-3*e* depict another alternative embodiment of a CDTD system 300 comprising a plurality of protrusions 301 and recessions 302 positioned in between adjacent protrusions 301. In the depicted embodiment, a lysing member 303, and its associated lysing segments 303*a*/303*b*/303*c*, is positioned so as to extend in recessions 302 and define a plurality of lysing segments. Thus, a lysing segment is positioned in each of the recessions 302 positioned in-between adjacent protrusions 301. System 300 further comprises first/inner/device cannula 331 and may comprise second/outer cannula 332, which may be used to deliver lysing tip 310, as previously mentioned.

System 300 only differs from system 100 in that it possesses unitary/unhinged actuation rods, a canal, and rotational stop means and that system 300 lacks a spot coagulator.

System 300 may comprise canal(s) 304 which may be positioned to supply one or more fluids to the surgical site around or near lysing tip 310 via a port located adjacent to the internal device cannula and/or lysing tip (show in FIG. 3*a* only). Canal 304 may be configured to be extended and withdrawn as needed. In alternative embodiments, other fluids that may pass down canal 304 may include, but not be limited to, cold nitrogen gas, fluorocarbons, etc., which might cool and/or freeze tissue to alter it in a desired fashion.

Most notably, system 300 comprises means for fixing the rotational orientation of lysing tip 310 with respect to first/inner/device cannula 331. In some embodiments the rotational fixing means may also provide proximal support to lysing tip 310 during a surgical procedure. More particularly, in the depicted embodiment, this rotational fixing means comprises opposing slots 333*a* and 333*b* formed in the distal end of first/inner/device cannula 331, which slots are sized, shaped, and configured to receive at least a portion of actuation rods 323/324 when deployed distally. Other examples of rotational fixing means 333a/333b include hooks, catches, etc. In addition, in another example of a rotational fixing means, corresponding features on the deployment side of lysing tip 310 may engage the distal end or special features designed in the distal end of first/inner/device cannula 331. In some embodiments, such fixing may also provide direct support restricting proximal movement. In alternative embodiments, rotational fixing means may comprise grooves on the inside of the cannula lumen of raised rails or channels in the material from which cannulas are made; said grooves engage one or both actuation rods for support.

FIG. 3d shows how portions of the actuation rods 323/324 engage rotational fixing means 333a/333b.

FIG. 3a is an isometric view depicting how, in the treatment configuration, lysing tip 310 extends, at both opposing ends, beyond the cross-sectional profile of first/inner/device cannula 331. Also, in this particular embodiment, lysing tip 310 is coupled with actuation rods 323/324 at points that are greater than the inner diameter of the cross-sectional profile of first/inner/device cannula 331 in the treatment configuration.

Retraction guide 325 is preferably near tip 310 at or near the distal end of one of actuation rods 323/324. In the depicted embodiment, retraction guide 325 is positioned near the distal end of actuation rod 324 adjacent to (immediately proximal of) lysing tip 310. In some embodiments, retraction guide 325 may comprise a spring and/or be made up of a resilient material so that it provides a restorative force during retraction of lysing tip 310 into first/inner/device cannula 331. Preferably retraction guide 325 may be shaped to (A) if made of a non-resilient material, have a sufficient slope so that the edge closest to the cannula does not have its proximal movement impeded but rather cause a lateral movement of the actuation rods and tip toward the opposite side of the cannula or (B) if made of a resilient material, upon contacting the distal end of the cannula, retraction guide 325 deforms in a manner that permits proximal movement and then provides a restorative force that guides the lateral movement of the actuation rods and tip to the opposite side of the cannula. Preferably, retraction guide 325 is positioned and configured so as to extend from actuation rod 324 laterally by a distance at least approximately equal to, in some embodiments slightly greater than, the distance one or more of the protrusions 301 that extend laterally relative to actuation rod 324 in the retracted/folded configuration. In some embodiments, retraction guide 325 may extend in this direction a distance equal to, or slightly greater than, the largest protrusion 301 (in embodiments in which each of the protrusions are not identical and/or do not project an equal distance).

In the depicted embodiment, each of the protrusions 301 extends from a common base 305 such that the protrusions 301 are coupled with one another. In some embodiments, each of the protrusions 301 is integrally coupled with each of the other protrusions 301. Linking member 315 may be coupled to base 305 and/or lysing member 303.

It should be understood that embodiments are contemplated wherein the dimensions of the tip relative to a cannula 331 may vary as for example, as shown in FIGS. 14k and 14L. In other words, the lysing tip 310 in the axial deployment configuration may be unable to be received within cannula 331 such as shown in FIG. 14L or may be unable to be received within an inner cannula of two delivery cannulas as shown in FIG. 14k. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision required for a certain procedure. For example, plastic surgeons may usually attempt to minimize scarring with minimum entrance incision widths, thus, in treating cellulite, the width of the entrance incision and lysing tip profile using embodiments contemplated herein may be 3 to 6 mm. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

In the depicted embodiment, 347 represents an antenna configured to deliver a signal to a receiver unit. In some embodiments, antenna 347 may comprise radiofrequency identification (RFID) TAG. In some embodiments the RFID tag may comprise an RFID transponder. In other embodiments the RFID tag may comprise a passive tag. It should be understood that antenna 347 is not depicted in every one of the other figures; any of the embodiments described herein may comprise one or more such elements. Other embodiments may comprise one or more antenna on any other suitable location on the embodiment, including but not limited to on the protrusions or otherwise on the tip, and on the shaft. In embodiments in which antenna 347 comprises an RFID transponder, the RFID transponder may comprise a microchip, such as a microchip having a rewritable memory. In some embodiments, the tag may measure less than a few millimeters. In some embodiments a reader may generate an alternating electromagnetic field which activates the RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body", which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 347 may comprise a Bluetooth antenna. In such embodiments, multiple corresponding Bluetooth receivers at known locations may be configured to sense signal strengths from the Bluetooth antenna 347 and triangulate such data in order to localize the signal from the Bluetooth antenna 347 and thereby locate the lysing tip within a patient's body. Other embodiments may be configured to use angle-based, electronic localization techniques and equipment in order to locate the antenna 347. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the lysing tip relative to a patient and/or a particular organ or other surgical site on the patient may be determined. In some embodiments, a display screen with appropriate software may be coupled with the RFID or other localization technology to allow a surgeon to visualize at least an approximate location of the tag/antenna, and therefore the lysing tip, relative to the patient's body.

Some embodiments may be further configured such that data from the antenna(s) may be used in connection with sensor data from the device. For example, some embodiments comprising one or more sensors 348 may be further configured with one or more RFID tags. As such, data from the one or more sensors may be paired or otherwise used in connection with data from the one or more RFID tags or other antennas. For example, some embodiments may be configured to provide information to a surgeon regarding one or more locations on the body from which one or more sensor readings were obtained. In some embodiments, temperature sensors may include thermistors and/or thermocouples. To further illustrate using another example, information regarding tissue temperature may be combined with a location from which such tissue temperature(s) were taken. In this manner, a surgeon may be provided with specific information regarding which locations within a patient's body have already been treated in an effective manner and thus which locations need not receive further treatment using the device.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently treated. For example, a display of a patient's liver may change colors at locations on the display that correspond with regions of the liver that have experienced a sufficient degree of fibrosis or other treatment. Such regions may, in some embodiments, be configured such that pixels corresponding to particular regions only light up after the corresponding tissue in that region reaches a particular threshold temperature.

Such sensor 348 may be coupled with an antenna, which may send and/or receive one or more signals to/from a processing unit. Alternatively, or additionally, data from such sensors resulting from tissue and/or fluid analysis using such sensors may be stored locally and transmitted later. As yet another alternative, such a signal may be transmitted following surgery. In such implementations, the signals need not necessarily be transmitted wirelessly. In fact, some embodiments may be configured to store data locally, after which a data module, such as a memory stick, may be removed from the device and uploaded to a separate computer for analysis.

Some embodiments may be configured such that lysing tip 310 is not aligned with the axis of cannulas 331 or 332 in the delivery configuration. More particularly the axis of lysing tip 310 may be positioned at an acute angle with respect to the axis of cannulas 331 or 332. In other embodiments, lysing tip 310 may be configured to extend at an acute angle relative to the cannula axis so long as the axis of lysing tip 310 fits within the lumen and/or lumens of one and/or both cannulas.

FIGS. 4a-4h depict an alternative embodiment of a CDTD system 400 comprising a plurality of protrusions 401 and recessions 402 positioned in between adjacent protrusions. In the depicted embodiment, a lysing member 403, comprised of lysing segments 403a/403b, is positioned so as to extend in recessions 402 and define a plurality of lysing segments. Thus, a lysing segment 403a/403b is positioned in each of the recessions 402 positioned in-between adjacent protrusions 401. System 400 further comprises first/inner/device cannula 431 and second/outer cannula 432, the first or both which may be used to deliver lysing tip 410, as previously mentioned.

System 400 differs from system 100 in that it lacks a spot coagulator, is configured for bipolar electrosurgical energy delivery, has 3 protrusions and 2 lysing segments, and has electrically isolated linking members 415a/415b.

An external power cord may bring electrosurgical energy from an electrosurgical generator to a hand assembly 160, such as that illustrated in FIG. 1i, (which is electrically connected) to proximal actuation rods 423/424 which are physically and electrically via contact coupled to distal actuation rods 421/422 and thus to linking members 415a/415b (via pivot members 416/417) and thus to their respective electrically conductive lysing segments 403a/403b, mounted in the recessions 402 in between protrusions, such as protrusions 401. For example, electrosurgical current (comprised of alternating current adjusted to perform certain functions) may flow from electrosurgical generator via proximal actuation rod 423 to distal actuation rod 421 to its physically-connected/electrically-coupled/respective linking member 415a and thus to its physically-connected/electrically-coupled/respective electrically conductive lysing segment 403a. The electrosurgical current may then travel into the adjacent/target tissue of the patient via lysing segment 403a and then back into lysing segment 403b and may then return to the electrosurgical generator via linking member 415b via distal actuation rod 422 via proximal actuation rod 424. By virtue of the linking members 415a/415b being separated and/or insulated from each other, the current may not short circuit within lysing tip 410. Retraction guide 425 is preferably near tip 410 at or near the distal end of one of actuation rods 421/422.

The tip shown in this embodiment has three relative protrusions 401, lysing member 403 (and associated lysing segments 403a/403b, pointing along the main axis of the CDTD in treatment mode. In other embodiments, the bipolar CDTD lysing tip 410 may have one or more non-axial protrusions and one or more non-axial relative recessions. In some embodiments, the tip may have between 3 and 100 axial and/or non-axial protrusions and/or relative recessions. It should be understood that the number of protrusions need not match the number of lysing elements or recessions. In some embodiments, lysing elements may be located at the termini of conductive elements. In some embodiments, lysing elements may also be made partially or completely of a cermet material. In an embodiment, the modular bipolar CDTD tip 410 may measure about 12 to 15 mm in width and/or about 3 mm in thickness. Embodiments are contemplated wherein sizes of about one-fifth to about five times these dimensions may have possible uses. It is also contemplated, for example in some veterinary embodiments, tip sizes of about one-tenth to 20 times the aforementioned dimensions may have possible uses. In some embodiments, wherein electrical insulation and/or polymeric insulating coating is present on such parts, for example, but not limited to, distal and proximal actuation rods and linking member portions 415a/415b, such insulation may measure about 0.5 mm in thickness; in some contemplated embodiments, the insulation thickness may range from 0.01 mm to 3 mm. In other contemplated embodiments, electroconductive leads may course from an electrosurgical generator via first/inner/device cannula 431 to energize various lysing elements located in bipolar CDTD tip 410. In some embodiments leads may comprise wires and/or conductive conduits.

FIG. 4g is a posterior elevated perspective view of the two bipolar lysing segments of the embodiment depicted in FIG. 4a. In this embodiment, lysing element 403 may be comprised of even numbers of oppositely charged (when activated) individual lysing segments 403a/403b. In this embodiment, individual bipolar CDTD lysing segments 403a/403b may comprise surgical grade stainless steel positioned within all and/or a portion of one or more pieces of ceramic and/or other thermally resistant, non-conductive housing. In some embodiments, one or more individual lysing elements may comprise electroconductive materials including but not limited to cermets, steel, nickel, alloys, palladium, gold, tungsten, titanium, silver, copper, and/or platinum. In the depicted embodiment, the lysing elements may measure about 2 mm in length, and about 0.5 mm in thickness/diameter. In the depicted embodiment, the axial lysing elements are concave and crescentic in shape. However, in other contemplated embodiments lysing elements may comprise straight and/or convex and/or a variety of shapes.

In some contemplated embodiments there need not be equal numbers of oppositely signed and/or charged individual lysing elements, for example, there may be 3 positive and 2 negative individual lysing elements. Uniformity of flux on activation may be achieved by modifying the size and/or position of lysing elements with respect to each other among other methods known in the art.

The relative static permittivity of some ceramics may range from about 5 to 10; this may cause some leakage of current in an undesirable path between closely approximated opposing electrodes during activation. Use of other materials, for example, those having over of relative static permittivities of 5 may undesirably alter the resultant plasma field. The relative static permittivity of the intervening materials housing the opposing electrodes may be enhanced by coating and/or surrounding and/or injection molding thermoresistant polymers of a low relative static permittivity into the housing and/or around one or more portions of bipolar lysing segments 403a/403b to reduce the effective static permittivity of the tip. In an embodiment, the thermoresistant polymer of low relative static permittivity 2.1 may be polytetrafluoroethylene. In other contemplated embodiments, thermoresistant polymers may include polyether etherketone (@3.3) and/or polysulfone (@3.1) and the like may be useful.

In the depicted embodiments, the electrical insulator comprises polytetrafluoroethylene. In other contemplated embodiments, the electrical insulator may comprise an electrically nonconductive polymer with a high melting temperature. In some embodiments, the nonconductive polymer may comprise for example, polyether etherketone and/or polysulfone, etc. In other contemplated embodiments, the electrical insulator may comprise an electrically nonconductive and/or thermally nonconductive polymer.

It should be understood that embodiments are contemplated wherein the dimensions of the tip relative to a cannula 431 may vary as for example, as shown in FIGS. 14k and 14L. In other words, the lysing tip 410 in the axial deployment configuration may be unable to be received within cannula 431 such as shown in FIG. 14L or may be unable to be received within an inner cannula of two delivery cannulas as shown in FIG. 14k. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

As of the year 2000, the bipolar mode had traditionally been used primarily for coagulation (reference: "The Biomedical Engineering Handbook, Electrosurgical Devices" J Eggleston, W Maltzahn, Ch 81, CRC Press 2000). However, more recent modifications to bipolar electrosurgical outputs may have facilitated the use of bipolar cutting instruments (reference: ValleyLab, Hotline, vol. 4, issue 4 pg. 1), examples of such outputs may include Macrobipolar settings (Reference: ValleyLab ForceTriad Users Guide 2006, chapter/sections: 9-13, 9-16, 9-24).

Some embodiments may be configured such that lysing tip 410 is not aligned with the axis of cannulas 431 or 432 in the delivery configuration. More particularly the axis of lysing tip 410 may be positioned at an acute angle with respect to the axis of cannulas 431 or 432. In other embodiments, lysing tip 410 may be configured to extend at an acute angle relative to the cannula axis so long as the axis of lysing tip 410 fits within the lumen and/or lumens of one and/or both cannulas.

FIGS. 5a-5e depict still another embodiment of a CDTD system 500. FIG. 5a depicts system 500 in a treatment configuration. System 500 again comprises a plurality of protrusions 501 and recessions 502 positioned in between adjacent protrusions 501. In the depicted embodiment, a lysing member 503, comprised of lysing segments 503a/503b/503c, is positioned so as to extend in recessions 502 and define a plurality of lysing segments. Thus, a lysing segment is positioned in each of the recessions 502 positioned in-between adjacent protrusions 501. System 500 further comprises first/inner/device cannula 531 and second/outer cannula 532, which may be used to deliver lysing tip 510 therethrough.

System 500 differs from those previously described in that system 500 comprises an intermediate hinge member 522 that is pivotably coupled at one end 525a to a first actuation rod 521 and pivotably coupled at the opposite end 525b to lysing tip 510. More particularly, intermediate hinge member 522 is pivotably coupled 525b at the opposite end to base 505 via linking member 515. In addition, system 500 comprises a pivot member 523 that is also coupled to lysing tip 510, but is coupled to lysing tip 510 at a mid-point of lysing tip 510 between its opposing ends via linking member 515. Pivot member 523 may also be coupled to actuation rod 520.

FIG. 5c depicts system 500 in a delivery configuration with lysing tip 510 folded up in alignment with the axis of first/inner/device cannula 531 and/or second/outer cannula 532. FIG. 5b depicts another perspective view of system 500 in an interim position between the treatment configuration and the delivery configuration that depicts the rear or proximal side of lysing tip 510. As better seen in this figure, the rear of lysing tip 510 comprises a common base 505 from which each of the protrusions 501 extends. Lysing tip 510 again comprises a base 505 coupled to linking member 515. In addition, it can be seen from FIG. 5b that both intermediate hinge member 522 and pivot member 523 are coupled to lysing tip base 505 via linking member 515.

Some embodiments may be configured such that lysing tip 510 is not aligned with the axis of cannulas 531 or 532 in the delivery configuration. More particularly the axis of lysing tip 510 may be positioned at an acute angle with respect to the axis of cannulas 531 or 532. In other embodiments, lysing tip 510 may be configured to extend at an acute angle relative to the cannula axis so long as the axis of lysing tip 510 fits within the lumen and/or lumens of one and/or both cannulas.

FIGS. 6a-6e depict yet another alternative embodiment of a CDTD system 600. FIG. 6a is a perspective view depicting system 600 in a treatment configuration. System 600 again comprises a plurality of protrusions 601 and recessions positioned in between adjacent protrusions 601. In the depicted embodiment, a lysing member 603 is positioned so as to extend in the recessions and define a plurality of lysing segments 603a/603b/603c. Thus, a lysing segment is positioned in each of the recessions positioned in-between adjacent protrusions 601. System 600 further comprises first/inner/device cannula 631 and/or second/outer cannula 632, which may be used to deliver lysing tip 610 therethrough.

Although, like system 500, system 600 comprises an intermediate hinge member 622, system 600 differs from system 500 in that system 600 comprises an intermediate hinge member 622 that is pivotably coupled at one end 625a to a first actuation rod 621 but is pivotably coupled at the opposite end 625b to a mid-point or near mid-point of lysing tip 610 rather than adjacent to an end of lysing tip 610. More particularly, intermediate hinge member 622 is pivotably coupled to a mid-point or near mid-point of base 605 via linking member 615. Pivot member 623 may be coupled to actuation rod 620.

System 600 also differs from system 500 in that pivot member 623 is coupled to an end of lysing tip 610 rather than to a mid-point of lysing tip 610 as in system 500. Because of these pivot/coupling points, lysing tip 610 only extends beyond the cross-sectional profile of first/inner/device cannula 631 and/or second/outer cannula 632 at one end (the end opposite from pivot member 623), as shown in FIG. 6a.

FIG. 6c depicts system 600 in a delivery configuration with lysing tip 610 folded up in alignment with the axis of first/inner/device cannula 631. FIG. 6b better depicts the opposing hinges of intermediate hinge member 622, namely first hinge 625a and opposite hinge 625b.

FIGS. 7a-7f depict an alternative embodiment of a CDTD system 700. System 700 comprises a lysing tip 710 that is configured to be completely separated from any other element of the system. In this manner, lysing tip 710 may be delivered through one cannula 732 and then coupled with a grasping/control instrument 790 (see FIG. 7f) that may be used to control the lysing tip 710 within the body of a patient during a surgical procedure. In some embodiments and implementations, a second cannula, positioned through the same incision or another incision at another site on the patient's body, such as the cannula 1735 in FIGS. 17f & 17g, may be used to deliver a transfer grasping instrument, such as transfer grasping instrument 1796 as depicted in FIGS. 17f and 17g, that may be used to facilitate coupling of lysing tip 710 to the grasping/control instrument 790, which grasping/control instrument 790 may be delivered through the same cannula 732 through which the lysing tip 710 is delivered. Alternatively, the lysing tip 710 may be delivered though a second cannula along with a transfer grasping instrument used to couple the lysing tip 710 to grasping/control instrument 790 delivered through the first cannula 732, which grasping/control instrument 790 may be used to control lysing tip 710 and perform the surgical procedure. In alternative embodiments, the transfer grasping instrument may comprise at the distal end other means for grasping the lysing tip 710 such as a hook and/or magnet and/or glue.

Lysing tip 710 may comprise a plurality of protrusions comprising bulbs 701. A lysing member 703 may be positioned in recessions 702 for delivering electrosurgical energy. Each of the segments of lysing member 703 may be considered lysing segments 703a/703b/703c. In the depicted embodiment, each of the lysing segments is collectively defined by a single lysing member 703. However, other embodiments are contemplated in which separate lysing members may be used for each of the lysing segments positioned between adjacent protrusions.

It should be understood that in some embodiments or implementations, such systems 700 can be used in connection without any cannula as shown in FIG. 7f. Such an embodiment or implementation may be useful because: (A) the surgeon may not be working in a closed cavity that requires insufflation (for example, skin, fat, muscle); (B) it may allow the manufacture of a larger tip configuration than the smallest cannula's constraining dimensions allowing for larger, thicker, stronger components than would otherwise be permitted to fit in the smaller volume or pass through a smaller cross-sectional area, or (C) it may allow smaller diameter entrance incision/wound as cannulas have a thickness component.

Each of the protrusions 701 extends from a common base 705 such that the protrusions 701 are coupled with one another. In some embodiments, each of the protrusions 701 is integrally coupled with each of the other protrusions 701 along base 705. A linking member 715 may be coupled to base 705 and/or lysing member 703. In this particular embodiment, linking member 715 comprises a grasping pad 718. The structure of grasping pad 718 preferably comprises a plate-like shape having opposing surfaces that match or may be grooved to match the jaws of grasping/control instrument 790. In the depicted embodiment, the surfaces are flat and define parallel planes. Grasping pad 718 may be an integral part of linking member 715 or be a separate element coupled with linking member 715. Grasping pad 718 may be used to facilitate a desired coupling between lysing tip 710—which comprises protrusions 701, recessions 702, lysing member(s) 703, and/or linking member 715 and a grasping/control instrument 790 used to control lysing tip 710 during a surgical procedure, which instrument may also be delivered through cannula 732. Pad 718, in this embodiment, comprises hole 718c (shown in FIG. 7e only) which may be used for an alternative means of grasping or otherwise holding the lysing tip 710 in position for grasping/control instrument 790 to grasp lysing tip 710. Such additional means may include threading cord and/or suture and/or wire through the hole or otherwise hooking hole 718c or the like. Additionally, hole 718h (shown in FIG. 7d only) may be used to receive a projection 796a (shown in FIG. 7f only) mounted on the tip of grasping/control instrument to ensure a more stable coupling. In some embodiments, the surface of tab 718 may be completely electrically insulated except where contact is made with upper or lower jaw 793/794. In alternative embodiments, the entire surfaces of jaws 793/794 and the entire tab may be insulated except within hole 718h (shown in FIG. 7d) and at projection 796a (shown in FIG. 7f) which may serve as a conduit for electrosurgical energy.

Grasping/control instrument 790 may comprise means for grasping and/or controlling lysing tip 710. "Controlling" herein may be described as including, but not limited to, the physical movement of lysing tip in any direction and/or orientation and the conduction of electrosurgical energy to lysing tip. Such grasping/control instrument 790 may comprise grasping means fixed jaw 794, grasping means moveable upper jaw 793, and shaft 791 that may be comprised of additional means to grasp and/or permit the flow of electrosurgical energy to the tip 710, such as wires, actuation rods, and the like. In some embodiments, grasping/control instrument 790 may further comprise a means for controlling lysing tip 710 during a surgical procedure. Grasping/control instrument jaws 793/794 may comprise, for example, closable jaws that may be configured to grasp or otherwise engage linking member 715 via pad 718. An actuator (not shown) may be provided for controlling/actuating such jaws, or another means for grasping lysing tip 710. Grasping/control instrument 790 may be electroconductive in some embodiments such that electrosurgical energy may be delivered through jaws 793/794 to lysing tip 710. In some such embodiments, insulation, such as an insulating cover, may be used to cover conductive areas of grasping/control instrument 790. In some embodiments, the insulation (if present) on grasping/control instrument 790 may extend to at least partially onto jaws 793/794 to avoid delivering electrosurgical energy to undesired tissues. In other embodiments, electrosurgical energy may be delivered through another element of the system and, thus, grasping/control instrument jaws 793/794 may only be used to physically control tip 710 and need not be formed from a conductive material (although still may be if desired).

In some embodiments and implementations, grasping/control instrument 790 may be replaced with a device such as second transfer/grasping tip, such as transfer grasping instrument 1796 as depicted in FIGS. 17f and 17g, that may be used to facilitate coupling of lysing tip 710. In some such embodiments and/or implementations, the lysing tip 710 may be delivered through a separate cannula, which may comprise various elements previously mentioned for delivery of the lysing tip 710. Alternatively, the lysing tip 710 may be delivered through the same cannula that is ultimately used to grasp and/or control the lysing tip 710 during surgery. In other words, the lysing tip 710 may be pushed out of the distal end of cannula 732, after which grasping/control instrument 790 may be used to grasp or otherwise couple to lysing tip 710 and used to perform a surgical procedure.

The embodiment in FIG. 7 is similar to the embodiment in FIG. 17 in respect that the lysing tip may be passed down the inner cannula and grasped by a second grasping instrument entering the body from another cannula whereupon the second grasping instrument such as a needle driver and/or hemostat and/or clamp and/or the like may grasp the front of a forward portion of the lysing tip and feed pad 718 back into receiving slot 797 defined by upper and lower jaws 793 and 794.

In FIGS. 8a-f, a system 800 is depicted which may allow for maintaining control of a free-floating lysing tip and/or facilitating coupling of the free-floating lysing tip with a jaw of a grasping control instrument. In system 800, a tether 844 extends through an opening 893h formed in a jaw 893 of the grasping/control instrument 891. Examples of tethers may be cords, bands, wires, sutures or the like. As used herein, "free-floating" lysing tips are lysing tips that are releasably coupled with the instrument(s) that are used to energize and/or control the lysing tips during a surgical procedure. Tether 844 may further be configured to be coupled with free-floating, tabbed lysing tip 810. In the depicted embodiment, tether 844 couples with grasping tab 818. More particularly, grasping tab 818 comprises an opening 818h configured to receive the tether 844 as shown in the cross-sectional view of FIG. 8d. In some embodiments, the opening 818h may comprise a blind opening. Alternatively, opening 818h may comprise a through-hole. In some embodiments, tether 844 may comprise a distal bulb 844c and/or stop that prevents tether 844 from pulling through the opening 818h. In the depicted embodiment, bulb 844c is configured to be received in a recess 818h' formed in grasping tab 818. Recess 818h' may be a portion of opening 818h having a larger dimension.

In the depicted embodiment, by pulling on tether 844 either manually or by way of a mechanism, tip 810 may be configured to be directed into the jaws 893/894 of grasping/control instrument 891. In still other embodiments, tether 844 may be coupled with tip 810 without also extending through one or both of jaws 893/894. In this manner the tip 810 may be retrieved simply by pulling on the tether 844. In other embodiments, a tether 844 may extend through other portions of the grasping instrument, such as the bottom jaw 894 and/or both jaws 893/894 and/or through the center of the grasping/control instrument 891. The tether may be packaged with a tether already attached or medical personnel at the procedure may choose an appropriate tether to thread and catch in the lysing tip and thread through the jaw with the through-hole.

In some embodiments, one or more cannulas 832 may be used to deliver and/or retrieve lysing tip 810. For example, instrument 891 and lysing tip 810 may be delivered within cannula 832. Alternatively, instrument 891 and lysing tip

810 may be delivered without using a cannula in some embodiments and implementations.

In some embodiments such as that depicted in FIG. 8*f*, one or more magnets 892*g* on/in one or more jaws 893/894 of grasping control instrument 891 may be used to guide lysing tip 810 towards a desired location such as within jaws 893/894. In some embodiments, one or more magnets 892*t* may be positioned along grasping tab 818. In alternative embodiments, one or more magnets may be positioned along grasping tab 818 and/or along one or both of jaws 893/894 (892*t* and 892*g* respectively).

Figure 9:
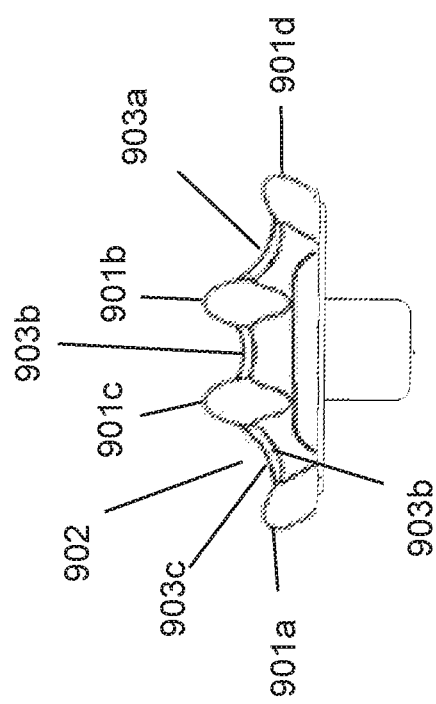
FIG. 9 is an upper plan view of a non-axial lysing tip.

FIG. 9 depicts a lysing tip comprising non-axial and/or substantially non-axial protrusions and a proximal tab. In this embodiment, one or more protrusions 901*a*/901*b*/901*c*/901*d*, recessions 902, and/or lysing member(s) 903*a*/903*b*/903*c* may not be in an axial configuration. In all other respects, the lysing tip of FIG. 9 may be similar to that tip depicted in FIGS. 7*a*-7*f*. In alternative embodiments, the lysing tips may be configured to all point in the same non-axial direction. In still other embodiments, each corresponding protrusion or pair of protrusions may be configured to point in the same direction. In still other embodiments, lysing segments and/or protrusions may be configured to point perpendicular or substantially perpendicular to the axis.

FIGS. 10*a*-10*h* depict an embodiment of a CDTD 1000 comprising a plurality of protrusions 1001 comprising the distal tips of beads 1051, comprising individual beads 1051*a*/1051*b*/1051*c*/1051*d*, coupled with one another by way of a single lysing member 1060, in the depicted embodiment, a lysing rod 1060, extending through tunnels 1054 extending through each of the respective beads 1051*a*/1051*b*/1051*c*/1051*d*. In this embodiment, lysing rod 1060 comprises a lysing rod 1060 that defines three separate lysing segments 1060*a*/1060*b*/1060*c* formed between each bead, and, as described above, may be used to deliver electrosurgical energy during a surgical procedure. Also, like the previously-described embodiments, the areas between each of the adjacent beads 1051 may define recessions 1002 positioned in between adjacent protrusions (defined by beads 1051). In the depicted embodiment, each of the lysing segments is collectively defined by a single lysing rod 1060. However, other embodiments are contemplated in which separate lysing members may be used for each of the lysing segments positioned between adjacent protrusions.

Beads 1051, or any of the other beads described herein, are preferably made from a suitable inert, biocompatible, and non-conductive material, for example, such as a suitable plastic, alumina, zirconia, silicon nitride, silicon carbide, glass, graphite, silicate, diamond, carbon-containing compounds, cermet, or ceramic material or the like, or a combination of one or more of the foregoing.

In the depicted embodiment, lysing rod 1060 is positioned through beads 1051 at a location such that beads 1051 may be non-symmetrical and/or eccentric relative to tunnels 1054. In other words, as best shown in FIG. 10*c*, tunnels 1054 may be positioned to extend through a non-central location within beads 1051. Moreover, in the depicted embodiment, beads 1051 are non-symmetrical relative to an axis extending through the side-to-side centers of beads 1051 (perpendicular to the long axis of the beads). In addition, as shown in the figures, the distal/forward tip of beads 1051 may have a more narrowed end to act more as a wedge for purposes of acting as a blunt dissector between tissues and tissue planes; the proximal/non-distal/back portions being less narrowed and/or larger in volume may create a desirable drag effect thus orienting the bead in a desirable direction for dissection. Whereas the rear/proximal end of beads 1051 may take many shapes that may be larger and/or more prominent than that of the front/distal end of the beads. As in FIG. 10*d*, the forward tip may be narrowed by use of facets 1052; three are visible and numbered and the fourth is on the opposite side of the one facing the reader. As described later in FIGS. 12*aa-rr*, a wide variety of alternative bead shapes are possible including, for example, ovoid shapes, spherical shapes, wheel shapes, bullet shapes or other shapes having a flat terminal end (such as, for example, frusto-shaped), wing shapes, etc. As can be seen from some of the examples shown in FIGS. 12*aa-rr*, in some embodiments, beads may be symmetrical relative to the openings for receiving the rod. In some embodiments, beads 1051 may be faceted on the top, bottom, sides, front and/or back such as illustrated in FIGS. 10*c* and 10*d*, at facet 1052. Facets are preferably formed on the distal/front/leading portions of the bead to facilitate tip movement through/between tissue layers.

In some embodiments, the tunnels 1054 may be positioned in a non-central location within beads 1051. For example, in some preferred embodiments, the tunnels 1054 may be positioned in a forward or distal location relative to a central axis of beads 1051. This may be preferable to allow the lysing tip 1010 to be directed through tissue in a desired manner, such as without allowing the beads 1051 to rotate on their respective tunnels in an undue manner. However, some embodiments may be configured to allow a certain amount of such rotation so that the tip can be maneuvered through patient tissue in a flexible manner.

In some alternative embodiments, the forward or distal portions 1001 of beads relative to tunnels 1054 may also, or alternatively, be wider than such that beads 1051 have a trailing end that may be longer and/or more narrow, which may yield desired aerodynamics and/or maneuverability; this may be similar to a 'kite-tail' effect.

Preferably, the entire surface of the beads may be smooth, however, some faceting features may provide for a surface that is less smooth. For example, providing a smooth front end and a smooth trailing end may allow the lysing tip to be moved in a forward direction and then in a rearward direction back and forth without catching an undesirable amount of tissue on beads to inhibit such movement. However, as mentioned elsewhere in this disclosure, in some embodiments, the trailing end may comprise a flat surface such that the entire bead comprises a frusto-ellipsoidal shape or another similar shape. Preferably, at least the forward or distal surface of the beads is smooth and defines an ellipsoidal shape or another shape having an at least substantially smooth forward surface. In alternative embodiments, various portions of the bead may be textured or given surface irregularities that may yield a desired dissection orientation such as for example having the non-proximal/rear portion of the bead roughened on the surface to create drag from the rear.

In some embodiments, it may be desirable to allow beads 1051 to rotate on lysing rod 1060. Thus, beads 1051 may not be fixed three-dimensionally with respect to lysing rod 1060 and/or one or more other elements of lysing tip 1010. In some such embodiments, beads 1051 may be at least partially rotatable with respect to the entire lysing tip 1010. For example, the beads may rotate about the rod upon encountering tissue similar to that of a vegetable/fruit peeler. In embodiments in which beads 1051 are rotatable in this manner, it may be desirable to use a lysing rod having a circular cross section. Other embodiments are contemplated in which, instead of being rotatable, the beads may be otherwise movable with respect to one or more elements of a lysing tip 1010. In any such embodiments, such beads may be considered not three-dimensionally fixed with respect to the lysing rod and/or lysing tip.

In the depicted in FIG. 10c, protuberances 1065a/1065b/1065c/1065d/1065e/1065f formed on the lysing rod 1060 may be created to restrict lateral movement of the beads, and depending upon the distance from a bead, may restrict or partially restrict rotational movement of the beads around the axis of lysing rod 1060. In the preferred implementation, a LASER or arc welder may be used to heat the conductive material comprising lysing rod 1060 causing liquefaction that cools into a non-uniform structure that increases an outer diameter measurement of lysing rod 1060. Thus, in such embodiments and implementations, protuberances 1065a/b/c/d may comprise "welds" that deform lysing rod 1060. In alternative embodiments, "welds" may comprise added material to lysing rod 1060 through welding techniques in said locations and may be located at any cross-sectional orientation including facing proximally or distally. In alternative embodiments, crimps that mechanically deform the metal at or substantially adjacent to beads may be utilized to hold beads at particular locations on lysing rod 1060. In additional embodiments, lysing rod 1060 may be deformed at locations where beads 1051 are desired and couple at those locations via a friction fit between the bead tunnel and the lysing rod 1060.

Although allowing rotation of beads on a lysing rod may be desired for certain surgical procedures, it may be desirable to prevent or at least inhibit such rotation in other embodiments. Thus, in some such embodiments, tunnels 1054 and/or the lysing rod 1060 may comprise a non-circular shape in cross-section to prevent or at least inhibit such rotation. In alternative embodiments, beads 1051 may effectively be welded to the lysing rod 1060 as an alternative method to inhibit rotation. Each bead may comprise hole 1055 that may be positioned perpendicular to lysing rod hole 1054; holes 1055 may be available as a platform/location to add other features/components such as providing a location for coupling of a cord as described below in connection with other embodiments and/or locating a sensor and/or RFID location component and/or being used for placement of luminescent and/or light production element(s) for visualization, for example, tritium and the like.

In alternative embodiments, hole 1055d' may be moved to fully or partially intersect tunnel 1054 thus allowing communication with lysing rod 1060; thus a weld, plug (for example 1055p), glue, insert or other method of fixation may be inserted via hole 1055d' to attach to lysing rod 1060 thus restricting lateral movement of a bead. To reduce escape of electrosurgical energy through hole 1055d', an insulator comprised of epoxy, plastic, ceramic or the like may be placed in part or all of the remaining hole 1055d'. This alternative embodiment may be applied to other embodiments herein.

In alternative embodiments, the lysing rod may lack coupling tips at its outermost portions. Instead any number of bead holes 1055d' may be made at any number of angles to intersect the lysing rod 1060 and/or its tunnel 1054 to deposit a material that restrains the lysing rod within the bead 1051 (for example, materials may include welds, glues, epoxies, plugs, and the like). In such embodiments, tunnel 1054 may be a blind tunnel not requiring full passage through bead 1051 as bead 1051 may be fixed/restrained internally (See for example FIGS. 20j/k showing side views of beads 2051a' and 2051a". FIG. 20k shows full passage of tunnel 2054 which intersects with hole 2055' (illustrated with dashed lines designating hole 2055'). FIG. 20j illustrates tunnel 2054' which intersects with hole 2055' (illustrated with dashed lines designating hole 2055') not extending to the outside of outer bead 2051a" (2054' illustrated with dashed lines). This feature of this embodiment may be applied to other embodiments herein. Beads may comprise facets 2052.

The shape of lysing member/lysing rod 1060 may also be important as to the most efficient and safe means to transfer electrosurgical energy from the lysing rod to the tissue(s). Since electrosurgical energy on/under a surface tends to move toward edges of an object, a lysing rod with a circular cross section may force current to the opposing lysing rod tips and/or protuberances creating hot spots at/near adjacent beads and/or protuberances. Therefore, it may be beneficial for lysing rod 1060 to comprise a non-circular cross section with substantially uniform edges along its length from which electrosurgical energy may uniformly be transferred to tissues. In contemplated embodiments, a pentagonal or hexagonal cross-sectional shape may be preferable. In other embodiments, spacers with non-circular cross-sections may accumulate less debris and/or eschar on lysing rod and/or spacer because debris may have a more difficult time adhering to an angled edge when forces are applied to the debris.

As shown in FIG. 10b, actuation rods 1021 and 1022 exit distally from inner/device cannula 1031. The distal terminations of actuation rods 1021 and 1022 may contain holes in the distal area through which lysing rod 1060 may extend. Actuation rods 1021/1022 may terminate on the outermost side of outer beads 1051a and 1051d. In alternative embodiments, actuation rods 1021/1022 may be coupled to the lysing rod 1060 between the two outer pairs of beads such as that shown in FIG. 17a.

Lysing rod 1060 may be held in position by features located on the ends of lysing rod 1060, namely coupling tips 1063 and 1064. Coupling tips 1063/1064 may have diameters larger than the inner diameter of their corresponding holes 1026 in actuation rods 1021/1022 respectively. The coupling tips may take various shapes. In FIG. 10c, coupling tip 1063 comprises the shape of a mushroom cap and coupling tip 1064 comprises the shape of a ball. In alternative embodiments, other shapes may be used to couple the ends of lysing rod 1060 that effectively prevent lysing rod 1060 from sliding through either hole 1026. Coupling tips 1063/1064 may be made by for example by liquefying the ends by LASER and/or other heating and/or other metal modification methods; and in other embodiments, coupling tips may be separate structural elements such as screw-on nuts or the like. In some embodiments, it may be desirable to provide features and/or elements that inhibit or limit the ability of the electrosurgical energy to discharge from the opposing ends of the lysing rod. Thus, in some such embodiments, coupling tips 1063/1064 may be coated or covered with a suitable insulating material such as an epoxy with non-conductive properties; this may apply to all embodiments herein.

Figure 10F:
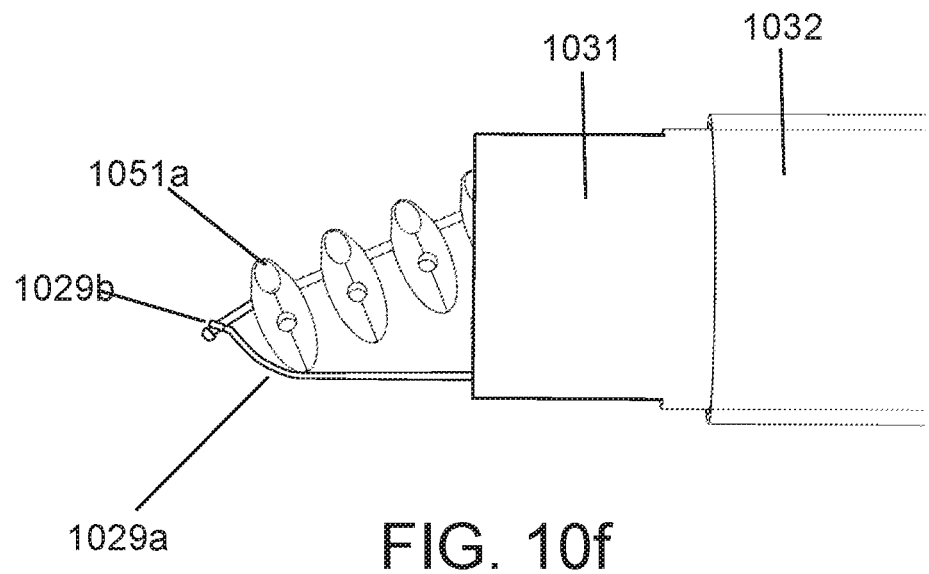
FIG. 10f is an upper view of the embodiment previously depicted in FIG. 10a with lysing tip in delivery configuration.
Figure 10G:
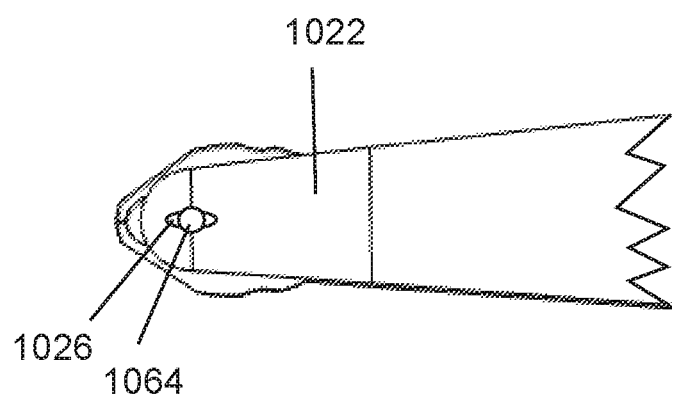
FIG. 10g is a side view of the embodiment previously depicted in FIG. 10a illustrating the coupling of the lysing member to the actuation rod.

FIGS. 10f and 10g demonstrate how the lysing tip 1010 transitions between the delivery and treatment configurations. As shown in FIG. 10f actuation rod 1022 comprises a first bend 1029a which allows the rear portion of bead 1051a to be received within a widened defined area defined by bend 1029a to allow lysing tip 1010 to pivot from a treatment configuration to a delivery configuration. As can be seen in this figure, some embodiments may be configured such that lysing tip 1010 is not aligned with the axis of cannulas 1031 or 1032 in the delivery configuration. More particularly the axis of lysing tip 1010 is positioned at an acute angle with respect to the axis of cannulas 1031 or 1032. In some embodiments, a second bend 1029b may be provided at or near the distal end of actuation rod 1022 which second bend may be in the opposite direction of first bend 1029a, As shown in FIG. 10g, hole 1026 is positioned in the middle of second bend 1029b; second bend 1029b being part of hole 1026 may allow additional rotational movement of lysing rod 1060 as it pivots more toward the delivery configuration.

Figure 10H:
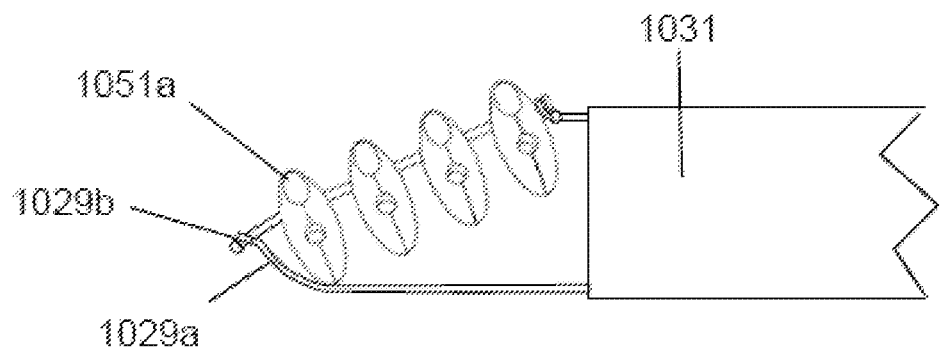
FIG. 10h is an upper view of the embodiment previously depicted in FIG. 10f illustrating that tip may not fit within one or more cannulas.

As shown in FIG. 10g, opening 1026 may be elongated in the direction of or at least substantially in the direction of the axis of actuation rod 1022 such that as lysing tip 1010 is repositioned between the treatment and delivery configurations, the portion of lysing rod 1060 adjacent to coupling tip 1064 can move/pivot within opening 1026 to allow lysing tip 1010 to similarly pivot with respect to the axis of cannulas 1031 and/or 1032. The shape of opening 1026 may be oval and/or rectangular or the like. In other words, in the present embodiment, holes 1026 may be elongated shapes, for example, in the form of ovals or rectangles that facilitate the folding away of the lysing tip 1010 against the actuation rods 1021 and 1022. In some such embodiments or in alternative embodiments internal beveling around the holes 1026 may facilitate movement between treatment and delivery configurations. In some embodiments and implementations such as depicted in FIG. 10h, lysing tip 1010 may be configured such that its beads 1051 are too large to fit within the lumen of first/inner/device cannula 1031, even in the delivery configuration. Thus, lysing tip 1010 in its delivery configuration may be positioned just outside (immediately distal) of first/inner/device cannula 1031 but within second/outer cannula 1032 during delivery.

In the present embodiment, coupling tips 1063/1064 are not the same shape and may be different as pre-formed lysing rods 1060 may be delivered to the assembly line with mushroom-style coupling tips at one end, and ball-style coupling tips may be the preferred method to create coupling tips on a production line to fix the beads 1051 and lysing rod 1060 into position relative to actuation rods 1021/1022.

In the present embodiment, actuation rods 1021 and 1022 are not comprised of any pivotable hinges but are comprised of bends at various locations along actuating rods to facilitate deployment and control of lysing tip 1010. In alternative embodiments, hinges and/or control cords may be placed along the length of actuation rods to facilitate movement in other directions.

FIG. 10h depicts an alternative configuration similar to that of FIG. 10f. However, in the configuration of FIG. 10h, the lysing tip 1010 is configured such that it cannot be fully received within cannula 1031. In some embodiments and implementations, cannula 1031 may comprise an inner cannula in which case an outer cannula (not shown in FIG. 10h) may also be used. Preferably, in such configurations the lysing tip 1010 may be fully received within the outer cannula in its delivery configuration.

FIG. 10e is a top view illustrating system 1000 that lysing rod 1060 may deform when tip 1010 encounters resistance during a surgical procedure. In the figure, the center beads 1051b/1051c are pushed proximally deforming lysing rod 1060.

System 1000 comprises means for fixing or guiding the 'rotational orientation' of lysing tip 1010 with respect to first/inner/device cannula 1031. In some embodiments the rotational fixing means may also provide proximal support to lysing tip 1010 during a surgical procedure. Rotational fixing means 1033 is configured to engage actuation rods 1021/1022. More particularly, in the depicted embodiment, rotational fixing means 1033 comprises opposing slots 1033a and 1033b formed in the distal end of first/inner/device cannula 1031, which slots are sized, shaped, and configured to receive at least a portion of actuation rods 1021/1022 when deployed distally. Other examples of rotational fixing means 1033 include hooks, catches, etc. In addition, in another example of a rotational fixing means, corresponding features on the deployment side of lysing tip 1010 may engage the distal end or special features designed in the distal end of first/inner/device cannula 1031, in some embodiments 1033a and/or 1033b, and such seating may provide direct support restricting proximal movement and/or fixing the tip against rotation.

Each bead may have a height BH as illustrated in FIG. 10d and a length BL extending perpendicular to the axis of the lysing rod 1060. Each bead also has a width BW as shown in FIG. 10e. Similarly, lysing tip 1010 may have a length TL which preferably extends in the same direction as the axis of lysing rod 1060 and a tip width TW extending perpendicular to the tip length TL as shown in FIG. 10e and a tip height TH as shown in FIG. 10d. In some embodiments, the tip height TH may be identical to the bead height BH. However, in other embodiments, the tip height may differ from the bead height.

FIGS. 11a-11e depict various views similar to those depicted in FIGS. 10a-10h for an alternative embodiment of a CDTD system 1100. System 1100 differs from system 1000 in that spacers 1162a/1162b/1162c may be positioned between bead pairs 1151a/1151b, 1151b/1151c, and 1151c/1151d. System 1100 is comprised of first/inner/device cannula 1131 and second/outer cannula 1132 through which lysing tip 1110 may be deployed or retrieved via actuation rods 1121 and 1122. In the depicted embodiment, each of the respective lysing segments between each bead pair comprises a spacer 1162 (1162a/1162b/1162c) that may be configured to space the various beads 1151 apart, provide stability to the lysing tip, and/or protect the respective lysing segments (which, in the depicted embodiment, are collectively defined by a single lysing member/lysing rod 1160). Preferably, spacers 1162 comprise a conductive material, such as a suitable biocompatible metal, that can receive electrosurgical energy from the lysing member 1160 and deliver it to various body tissues during a surgical procedure. Preferably, spacer(s) 1162 are therefore in direct contact with lysing member 1160. In some embodiments, a single spacer 1162 may both extend between the various beads 1151 and extend through the tunnels 1154 through the beads 1151. Lysing rod 1160 terminates on its opposing ends at coupling tips 1163 and 1164 that may hold the bead/lysing rod/spacer components in position between actuation rods 1121 and 1122. Each bead may comprise hole 1155 that may be positioned perpendicular to lysing rod hole 1154; holes 1155 may be available as a platform/location to add other features/embodiments and/or to be used for cord/suture attachments for lysing tip manipulation and/or removal and/or be used for placement of luminescent and/or light production for visualization, for example, tritium and the like. Each bead 1151 may comprise one or more facets 1152.

Spacers 1162a/1162b/1162c may be coupled with lysing rod 1160 by, for example, sliding spacers 1162 comprising a lumen along the axis of lysing rod 1160. Alternatively, spacers 1162 may be coupled with lysing rod 1160 by placing spacers 1162 over lysing rod 1160 in a direction perpendicular to the axis of the lysing rod at a desired location using a slot or other opening formed along a portion of a perimeter spacer 1162. For example, spacers may be provided with a slit extending along their respective axes. Such spacers may then be coupled with a lysing rod by aligning the slit with the lysing rod and pressing the spacer towards the lysing rod to snap it in place. In some embodiments and implementations, spacers 1162 may be crimped or otherwise fixedly coupled with lysing rod 1160 at a desired location. In some embodiments, this fixed coupling may be configured to prevent the relative movement between lysing rod 1160 and spacer 1162 possibly reducing hot spots caused from high current density flow in certain areas between lysing rod 1160 and spacer 1162. These exemplary methods for applying spacers to a lysing rod and/or another lysing member may be apply to any of the other embodiments utilizing spacers.

In some contemplated embodiments spacers may be comprised of insulating materials (such as ceramic, glass, plastic and the like) that may have holes (illustrated in FIG. 12*j*) and/or be porous and/or have breaks and/or have separations such that energy from lysing member(s) within may be released into target tissues.

In some such embodiments, beads 1151 may be at least partially rotatable with respect to the entire lysing tip 1110. In embodiments in which beads 1151 are rotatable in this manner, it may be desirable to use a lysing rod having a circular cross section. It may also be desirable to either omit spacers 1162 or form them without the beveled edges as shown in 12*i* and 12*j*.

Spacers 1162 may be used to prevent rotation of beads 1151 or to selectively limit the amount of rotation of beads 1151 on a lysing member 1160. For example, if spacers 1162 extend the entire distance or at least substantially the entire distance between each adjacent bead, spacers may prevent rotation or, depending upon the distance between spacers and adjacent beads, may be used to allow for a predetermined amount of such rotation. Similarly, the opposing ends of spacers 1162 may be shaped to match or at least substantially match the shape of the adjacent bead(s) again to either prevent or control rotation.

The shape of lysing member/lysing rod 1160 and/or spacers 1162 may also be important so as to provide selective energy-to-tissue delivery. Electrosurgical energy on/under a surface may tend to move toward edges of an object. In some embodiments, therefore, it may be beneficial for lysing rod 1160 and/or spacer 1162 to comprise a non-circular cross section with acute or substantially acute cross-sectional angles along its perimeter thus creating a lysing rod with edges that may increase electrosurgical energy discharge in those areas. In contemplated embodiments, a pentagonal or hexagonal cross-sectional shape may be preferable. Additionally, spacers with non-circular cross-sections may accumulate less debris and/or eschar on lysing rod and/or spacer because debris may have a more difficult time adhering to an angled edge.

System 1100 is otherwise similar to system 1000. For example, system 1100 comprises areas between each of the adjacent beads 1151 that define recessions 1102 positioned in between adjacent protrusions 1101 (defined by distal/leading portions of beads 1151). In addition, lysing rod 1160 defines lysing segments that are positioned between each of the adjacent beads 1151.

In some embodiments, the tunnels 1154 may be shaped and/or sized such that the lysing rod 1160 alone can provide the needed rigidity and structure to separate beads 1151 without providing spacers.

In some embodiments and implementations such as depicted in FIG. 11*f*, lysing tip 1110 may be configured such that its beads 1151 are too large to fit within the lumen of first/inner/device cannula 1131, even in the delivery configuration. Thus, lysing tip 1110 in its delivery configuration may be positioned just outside (immediately distal) of first/inner/device cannula 1131 but within second/outer cannula 1132 during delivery.

Figure 12D:
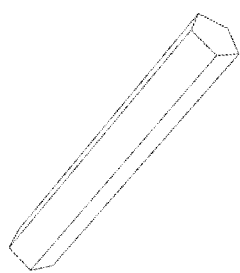
FIG. 12d comprises a perspective view of a lysing member/lysing rod with a pentagonal cross-section.
Figure 12G:
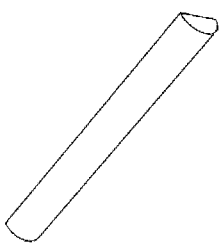
FIG. 12g comprises a perspective view of a lysing member/lysing rod with a half-circle cross-section.
Figure 12C:
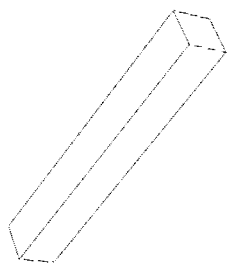
FIG. 12c comprises a perspective view of a lysing member/lysing rod with a rectangular cross-section.
Figure 12F:
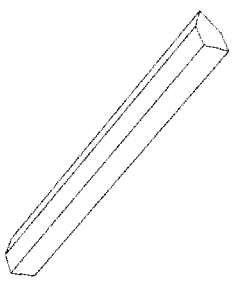
FIG. 12f comprises a perspective view of a lysing member/lysing rod with a wedge cross-section.
Figure 12B:
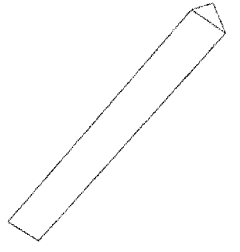
FIG. 12b comprises a perspective view of a lysing member/lysing rod with a triangular cross-section.
Figure 12E:
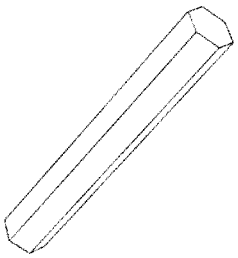
FIG. 12e comprises a perspective view of a lysing member/lysing rod with a hexagonal cross-section.
Figure 12A:
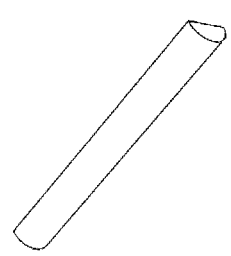
FIG. 12a comprises a perspective view of a lysing member/lysing rod with a circular cross-section.
Figure 12D:
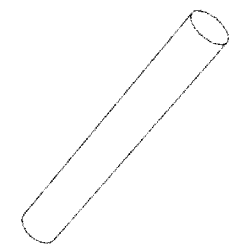

FIGS. 12*a*-12*rr* depict 3 general components of the lysing tip and various potential shapes: Lysing rod (FIGS. 12*a*-12*g*), spacers (FIGS. 12*h*-12*t*), and beads (FIGS. 12*aa*-12*rr*).

FIGS. 12*a*-12*g* depict various examples of cross-sectional shapes of wires or other lysing members. In some embodiments, these shapes may be formed by crimping a wire or other suitable lysing member into the desired shape. Crimping the lysing member may be particularly useful in connection with certain embodiments and/or implementations of the invention, as it may facilitate a preferred coupling between various other elements of the CDTD system, such as the beads and/or spacers. Crimping may also, or alternatively, be useful in providing for a preferred delivery of electrosurgical energy through the wire/lysing member. Other methods of shaping the lysing member may include but not be limited to cutting, polishing, forging or forming by extrusion. In additional embodiments, various coatings may be applied to lysing rods that may reduce adhesion of heated biological material to the lysing rod or spacers.

FIG. 12*a* comprises a lysing rod having a circular cross-section. The shape of lysing member/lysing rods may also be important as to the most efficient and safe means to transfer electrosurgical energy from the lysing members to the tissue(s). Electrosurgical energy on/under a surface may tend to move toward edges of an object. This shape may be useful for allowing a useful distribution of a coating to the surface of the lysing rod that may be used to reduce char buildup and/or modify ease of movement of a lysing tip through tissue. FIG. 12*b* comprises a lysing rod having a triangular cross-section; this may be useful for maximizing electrosurgical energy discharge and minimizing char build-up about the lysing rod. FIG. 12*c* comprises a lysing rod having a square cross-section. FIG. 12*d* comprises a lysing rod having a pentagonal cross-section along its length while FIG. 12*dx* comprises a lysing rod having a pentagonal cross-section that is twisted along its length. FIG. 12*e* comprises a lysing rod having a hexagonal cross-section. FIG. 12*f* comprises a lysing rod having a wedge-shaped cross-section. FIG. 12*g* comprises a lysing rod having a semi-circular or frusto-circular cross-section.

FIGS. 12*h*-12*t* depict various shapes for spacers that may be used in connection with one or more of the embodiments disclosed herein. Each may have a hole through which lysing members may extend. As illustrated in these figures, FIG. 12*h* illustrates a spacer having flat ends and a cylindrical shape. FIG. 12*i* illustrates a spacer having a circular cross-section and tapered ends which may be useful for allowing a desired distribution of a coating to the surface of the spacer to reduce char buildup and/or modify ease of movement of a lysing tip through tissue. FIG. 12*j* comprises various openings, such as holes, for delivery of electrosurgical energy therethrough; this may allow for making spacers of a non-conductive material and still deliver such energy therethrough. FIG. 12*k* illustrates an alternative spacer that is arced. FIGS. 12L (resting) and 12*m* (stressed) illustrate an alternative spacer having opposing loops with central openings configured to allow for receipt of a wire or other lysing rod therethrough and a flexible connector extending between the two loops. As shown in FIG. 12*m*, once coupled with adjacent beads (not shown), the flexible connector may bend to serve as a brace and space apart the adjacent beads. This spacer may also be configured such that the opposing loops may be flexed to the side to allow for coupling of adjacent beads and receipt of a lysing rod therethrough (not shown). FIG. 12*n* illustrates a cross-sectional view of another spacer having a triangular cross-sectional shape and an opening for receipt of a lysing rod therethrough. FIG. 12*o* illustrates a cross-sectional view of another spacer having a rectangular cross-sectional shape and an opening for receipt of a lysing rod therethrough. FIG. 12*p* illustrates a cross-sectional view of another spacer having a pentagonal cross-sectional shape along its length and an opening for receipt of a lysing rod therethrough while FIG. 12*px* comprises a spacer having a pentagonal cross-section that is twisted along its length and an opening for receipt of a lysing rod therethrough. Spacers with twisted features may acquire less debris along its surface and may tend to rotate thus multiple sides of a spacer are exposed to charred tissue. FIG. 12*q* illustrates a cross-sectional view of another spacer having a hexagonal cross-sectional shape and an opening for receipt of a lysing rod therethrough. FIG. 12*r* illustrates a blade-style cross-sectional shape with smooth, rounded outer surfaces that meet at the distal edge and an opening for receipt of a lysing wire or other lysing rod therethrough. FIG. 12*s* illustrates a cross-sectional view of another spacer having a blade cross-sectional shape (differing from FIG. 12*r* in that outer surfaces are formed by intersecting planar/flat surfaces) and an opening for receipt of a lysing wire or other lysing rod therethrough. FIG. 12*t* illustrates a cross-sectional view of another spacer having a spindle cross-sectional shape and an opening for receipt of a lysing wire or other lysing rod therethrough.

The cross-sectional shape of the exterior surface of spacers 12-4 may also be important as to the most efficient and safe means to transfer electrosurgical energy from spacers to the tissue(s). Electrosurgical energy on/under a surface may tend to move toward edges of an object, so a spacer with an exterior surface having a circular cross section may force current to the opposing spacer ends creating hot spots at/near adjacent beads. Therefore, it may be beneficial for spacers to comprise an exterior surface having a non-circular cross section with one or more substantially uniform edges along its length from which electrosurgical energy may uniformly be transferred to tissues. In contemplated embodiments, a pentagonal or hexagonal cross-sectional shape may be preferable. Additionally, spacers with non-circular cross-sections may accumulate less debris and/or eschar on lysing rod and/or spacer because debris may have a more difficult time adhering to an angled edge. In some embodiments, one or more (in some embodiments, all) of the spacers may comprise a leading edge for delivery of electrosurgical energy from the lysing member(s). In some such embodiments, one or more of the spacers may comprise only a single such leading edge. In some such embodiments, the spacer(s) may comprise a smooth, or at least substantially smooth, exterior surface, other than the single leading edge. For example, the spacer(s) (or, in some embodiments, the lysing member/rod itself) may comprise a circular or oval shape in cross section with a flattened leading end terminating in a leading edge. This may be useful for controlling the delivery of electrosurgical energy.

Because the spacers may be configured to receive the lysing member/rod therethrough, the spacers may also comprise an opening extending therethrough for receiving the lysing member/rod. Thus, the spacers may also have an interior cross-sectional shape, which may differ from the shape of the exterior surface. For example, it may be useful to form the spacers with an opening having a cross-sectional shape that matches the cross-sectional shape of the lysing member/rod. Thus, if the lysing member/rod comprises a circular or polygonal shape in cross-section, the spacer(s) may comprise an opening having a similar cross-sectional shape. In some embodiments, the shape of the exterior surface of the spacers may therefore be used to primarily dictate preferred delivery locations for the electrosurgical energy.

FIGS. 12*aa*-12*rr* show 12-5 alternative shapes for beads positioned along a lysing tip. As illustrated in these figures, bead shapes that may be useful may include spheres (FIG. 12*aa*), wheel shapes (FIG. 12*bb*), dodecahedron shapes (FIG. 12*cc*). In other embodiments, bead shapes may be bullet-shaped or partially or substantially ellipsoidal (FIGS. 12*dd*-12*ff*) and may have facets (FIGS. 12*ee* and 12*ff*). In other contemplated embodiments, beads of various geometries may be cut off having flat or slightly curved proximal surfaces or further shaped by geometric cuts (FIGS. 12*gg*-12LL) (herein, this may be referred to as "frusto-shaped"). In other contemplated embodiments, bead shapes and/or tunnels through them may be uniform spherical and/or centered. In other contemplated embodiments, beads may have skeleton features supported by a hub that may be adjacent to the lysing rod or adjacent to or formed around a ceramic sleeve through which a lysing rod is extended (FIGS. 12*mm*-12*rr*). 12-6 In some contemplated embodiments, providing a rough trailing end may create frictional drag on that portion of the bead thus helping reorient the front end of the bead for further tissue passage. Thus, in some embodiments, the trailing end may have a rougher surface than the front end. For example, in some embodiments, the trailing end, or at least a portion of the trailing end, of one or more beads may be sanded with a rougher sanding material than the leading end, may be formed with ridges, grooves, or other roughening elements, or may otherwise be made with a less smooth surface for this purpose. In some contemplated embodiments such as that depicted in FIG. 12*rr*, a bead may comprise a slot beginning at its trailing end and terminating within the bead 12*rr* so as to allow for receipt of a lysing rod therein. In some such embodiments, a hole 1255 may be positioned to extend through the bead and may at least partially intersect with slot 1253. Thus a weld, plug, glue, insert or other method of fixation may be inserted via hole 1255 to attach to a lysing rod thus restricting movement of a bead and/or rotation of the bead with respect to its lysing rod.

In alternative embodiments, beads may comprise a conductive material such as metal and coated with an insulator; for example, a bead shaped such as FIG. 12*rr* but made of metal (internally) may be pressed over a lysing rod with increased pressure closing the slot behind the lysing rod causing the bead to remain in place along a lysing rod.

FIGS. 13*a*-13*i* depict another embodiment of a CDTD system 1300 comprising a plurality of beads 1351 positioned on lysing member 1360 which comprises lysing plate 1360. It should be noted that in the embodiments of 13*a*-13*i*, beads 1351 are supported laterally by lysing plate 1360. It should also be noted that beads 1351 lack a base, such as base 105 for system 100, and instead define a lysing tip that lacks structure immediately behind the beads for support. It should also be noted that lysing tip 1310 comprises beads 1351 (1351*a*/1351*b*/1351*c*/1351*d*) that project both distally and proximally relative to lysing plate 1360.

System 1300 may be configured to allow for repositioning of lysing tip 1310 between a delivery configuration and a treatment configuration. In the delivery configuration, the axis of each of the elongated beads 1351 towards the treatment side may be configured to extend in a direction that is at least substantially perpendicular to the cannula axis and lysing tip 1310 (the axis between the two outer beads 1351*a*/1351*d*) may be configured to extend in a direction that is at least substantially parallel to the cannula axis. In addition, in the depicted embodiment, lysing tip 1310 may be configured such that an energy delivery side of lysing tip 1310 in front of protrusions 1301 defined by the leading/proximal tips of beads 1351 and the relative recessions 1302, which energy delivery side will ultimately deliver electrosurgical energy for dissecting tissue, faces an interior surface of a lumen of cannula 1331 through which lysing tip 1310 is delivered. Following delivery of lysing tip 1310 through a distal end of cannula 1331, system 1300 may be configured to reposition lysing tip 1310 to the treatment configuration in which the energy delivery side extends at least substantially perpendicular to the cannula axis.

As shown in FIG. 13*d*, system 1300 comprises two separate cannulas, namely, a first or first/inner/device cannula 1331 which preferably comprises a lumen of sufficient diameter to allow folded lysing tip 1310 (in a delivery configuration) to be positioned within the lumen of first/inner/device cannula 1331, and a second cannula 1332, which may have a larger cross-sectional diameter. In some embodiments and implementations, lysing tip 1310 may be configured such that its beads 1351 are too large to fit within the lumen of first/inner/device cannula 1331, even in the delivery configuration. Thus, lysing tip 1310 in its delivery configuration may be positioned just outside (immediately distal) of first/inner/device cannula 1331 but within second/outer cannula 1332 during delivery. By providing two co-axial cannulas, actuation rods 1321 and 1322 and/or actuation rod pairs 1321/1323 and 1322/1324 may be prevented, or at least substantially prevented, from being separated from one another or otherwise system 1300 may be configured to maintain better control over lysing tip 1310 during deployment. Thus, preferably, actuation rods 1321/1322 and/or actuation rod pairs 1321/1323 and 1322/1324 are also delivered through first/inner/device cannula 1331. Retraction 1325 is preferably near tip 1310 at or near the distal end of one of actuation rods 1321/1322.

In this embodiment, distal actuation rods 1321 and 1322 are formed with two bends that bring the distal end of the actuation rods perpendicular with the main axis of the actuation rods but parallel to the elongated axis of the lysing plate 1360 in the treatment configuration. This configuration may be advantageous during the delivery configuration to optimize the volume needs within cannulas. In the present embodiment, actuation rods 1321 and 1322 may have cutouts in the distal tips allowing for lysing plate 1360 to be received in the distal tips of actuation rods 1321/1322. Alternatively, the lysing plate 1360 may comprise recesses that permit the actuation rods 1321/1322 to seat within the lysing plate 1360.

Lysing tip 1310 may comprise an orientational-deployment side opposite from the energy delivery side. The orientational-deployment side of lysing tip 1310 may be configured to allow lysing tip 1310 to be repositioned between the delivery configuration and the treatment configuration described above. A deployment assembly may be coupled with the orientational-deployment side of lysing tip 1310. This deployment assembly may be configured to allow for selective repositioning between the delivery and treatment configurations. In the depicted embodiment, the deployment assembly may comprise one or more pivot members, such as pivot members 1316 and 1317. Pivot members 1316 and/or 1317 may comprise various elements configured to allow for selective pivoting, rotation, and/or angulation of lysing tip 1310, such as joints, ball pivots, hinges, pins, groove/slot pairs, etc., such that lysing tip 1310 can be pivoted, rotated, or "folded" between its deployment and treatment configurations.

Pivot members 1316 and 1317, such as pins or the like, may be coupled at one end to the lysing plate 1360 at holes 1368*a* and 1368*b* and may be further coupled with actuation rods 1322 and 1321, respectively. In some embodiments, pivot members 1316/1317 may therefore be configured to be received in holes formed in both lysing plate 1360 and corresponding aligned holes formed within actuations rods 1321/1322. Thus, upon advancing one or both of actuation rods 1322 and 1323, lysing tip 1310 may be advanced in its delivery configuration down first/inner/device cannula 1331. In some embodiments, appropriate wires or other transmission lines for delivery of electrosurgical energy may be positioned to extend through one or more of the various actuation rods. Alternatively, in some embodiments, electrosurgical energy may be delivered directly through one or more actuation rods. In some embodiments, wires or other transmission lines for delivery of electrosurgical energy may instead, or additionally, extend though other regions of lumen, as previously described. Actuation rods 1321 and/or 1322 and/or actuation rod pairs 1321/1323 or 1322/1324 may comprise any suitable material depending on whether electrosurgical energy is being delivered through them. For example, a metal or other conductive material may be used if electrosurgical energy is to be delivered through the actuation rods, or a plastic or other insulating material may be used if electrosurgical energy is to be delivered through separate wiring or other suitable transmission lines.

Some embodiments may further comprise one or more additional joints and/or pivot members positioned proximally relative to pivot members 1316 and 1317. For example, some such embodiments may comprise hinges and/or pivot members 1327/1328 that are positioned within one or both of actuation rod pairs 1321/1323 or 1322/1324, as previously described in FIGS. 1*a-j*. Such hinges may allow for one or both of distal actuation rods 1321/1322 to be pivoted/rotated in a desired direction once lysing tip 1310 has exited the terminal end of cannula 1331 and/or 1332.

System 1300 differs from Systems 800 and 900 in that lysing member 1360 comprises a plate 1360. Plate 1360 may extend through horizontal tunnels 1352 within the various beads 1351. Beads 1351 may also have vertical tunnels 1355. Thus, beads 1351 may be more permanently coupled with plate 1360 by way of holes within plate 1360, such as 1369*a*/1369*b*/1369*c*/1369*d* formed within plate 1360 configured to correspond to holes 1355 located in beads 1351. In some embodiments, pins, screws, rivets or the like or epoxy, or metallic welds may extend through vertical tunnels 1355 and holes 1369*a*/1369*b*/1369*c*/1369*d* to affix the two elements together. In alternative embodiments, holes 1369*a*/1369*b*/1369*c*/1369*d* may be replaced by bevels. Thus, in some embodiments, horizontal and/or vertical tunnels may not be needed. However, in other embodiments, plate 1360 may comprise beveled or narrowed regions configured to fit within such tunnels formed within beads 1351. Because use of a plate 1360 may provide more rigidity than certain other embodiments, use of spacers may not be needed for lysing tip 1300.

System 1300 comprises areas between each of the adjacent protrusions 1301 (defined by the distal/front ends of adjacent beads 1351*a-d*) that define recessions 1302. Plate 1360 may define lysing segments 1360*a*/1360*b*/1360*c* that are positioned between each of the adjacent beads 1351*a-d*. Each of these lysing segments may be collectively defined by a single lysing member/plate 1360 or, in other embodiments, separate lysing members/plates may be used for each of the lysing segments positioned between adjacent protrusions/beads.

As shown in FIG. 13d, the hinge structure may allow for rotation of lysing tip 1310 above and/or below the cross-sectional profile of cannula 1331 and/or 1332 and may allow lysing tip 1310 to extend beyond the cross-sectional profile of cannula 1331 and/or 1332 along one or both of the opposing ends of the lysing tip 1310.

It should be understood that embodiments are contemplated wherein the dimensions of the tip relative to a cannula 1331 may vary as for example, as shown in FIGS. 16k and 16L. In other words, the lysing tip 1310 in the axial deployment configuration may be unable to be received within cannula 1331 such as shown in FIG. 16L or may be unable to be received within an inner cannula of two delivery cannulas as shown in FIG. 16k. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

Another embodiment is depicted in FIGS. 14a-14n. System 1400 comprises lysing tip 1410 comprising recessions 1402 created by adjacent protrusions 1401. Lysing tip 1410 further comprises a support member 1470 defining a bow shape through which holes 1472 and 1473 extend vertically. In the depicted embodiment, hole 1472 is offset from hole 1473 on support member 1470, such as with respect to the lysing rod 1460, for example. This may facilitate a preferred pivoting of lysing tip 1410 between treatment and delivery configurations. Holes 1472/1473 may configured to receive pins for coupling lysing tip 1410 to actuation rods 1422 and 1421 respectively. Support member 1470 and/or holes 1472/1473, in some embodiments, may not be symmetrical with respect to one or more points and/or axes, such as one or more central axes of lysing tip 1410, such as the axis defined by lysing rod 1460 and/or the center axis of the lysing tip 1410 from a plan view extending between the treatment and deployment/orientation sides of the lysing tip 1410, in order to facilitate movement between the treatment and delivery configurations. For example, in the depicted embodiment, if an XY grid is imposed over FIG. 14g with the Y-axis bifurcating lysing rod 1460 and the X-axis touches the lower most feature of support member 1470, then holes 1472 and 1473 may not have the same y-coordinate. In other words, holes 1472 and 1473 may be positioned at different distances from lysing rod 1460 or are non-symmetrical with respect to lysing rod 1460. Furthermore, in some embodiments, holes 1472/1473 may be positioned at different distances from the center of support member 1470.

Support member 1470 may be preferably insulated, except within one or both sets of its two sets of holes, to prevent unwanted delivery of electrosurgical energy to tissues; thus, electrosurgical energy is directed to support member holes at which lysing rod 1460 becomes energized for energy delivery.

In the depicted embodiment, knobs 1475a and 1475b are provided on support member 1470 in order to provide additional material support such that holes 1472 and 1473 can be formed in a desired location. In this embodiment, holes 1472 and 1473 may be positioned within and/or adjacent to knobs 1475a and 1475b respectively.

Lysing tip receptacle 1421a on distal actuation rod 1421 comprises a cutout formed in the distal control arm into which the bottom of support member 1470 recesses. In other embodiments, the lysing tip receptacle may instead comprise a recess that is not fully cut out.

Actuation rod 1422 further comprises opening 1422a such that when lysing tip 1410 is in the delivery configuration, fastening member of hinge 1427 enters opening 1422a to facilitate maximum proximal movement of the actuation rods relative to each other.

As shown in FIG. 14c, system 1400 comprises two separate cannulas, namely, an outer cannula 1432 which preferably comprises a lumen of sufficient diameter to allow folded lysing tip 1410 (in a delivery configuration) to be positioned within the lumen of cannula 1432, and a first inner/device cannula 1431 which comprises a lumen of sufficient diameter to allow folded lysing tip 1410 (in a delivery configuration) to be positioned within the lumen of cannula 1431. In certain embodiments, such as in FIGS. 14i and 14j, lysing tip 1410 in the delivery configuration may have one or more cross-sectional dimensions that may exceed the inner diameter of inner/device cannula 1431 and thus may not retract partially or fully into inner/device cannula 1431. However, in some such embodiments, lysing tip 1410 may still retract fully into outer cannula 1432 during deployment or retraction. More particularly, lysing tip 1410 may be configured such that its beads 1451a/b/c/d are too large to fit within the lumen of inner/device cannula 1431, even in the delivery configuration. Thus, lysing tip 1410 in its delivery configuration may be positioned just outside (immediately distal) of inner/device cannula 1431 but within outer cannula 1432 during delivery.

Any of the embodiments described herein may be configured such that the tip 1410 cannot be fully received within second cannula 1432 as shown in FIG. 14c. Or alternatively, any of the embodiments disclosed herein such that the entire tip may be fully received within first/inner/device cannula 1431. This embodiment may be useful because it permits the tip to be as large as possible given the dimension constraints of the outer cannula and not the inner cannula thus reducing the expense of further miniaturizing.

Some embodiments may be configured such that lysing tip 1410 is not aligned with the axis of cannulas 1431 or 1432 in the delivery configuration. More particularly the axis of lysing tip 1410 may be positioned at an acute angle with respect to the axis of cannulas 1431 or 1432. In other embodiments, lysing tip 1410 may be configured to extend at an acute angle relative to the cannula axis so long as the axis of lysing tip 1410 fits within the lumen and/or lumens of one and/or both cannulas such as illustrated in FIG. 10f or 11f.

By providing two co-axial cannulas, actuation rods 1421 and 1422 may be prevented, or at least substantially prevented, from being separated from one another or otherwise system 1400 may be configured to maintain better control over lysing tip 1410 during deployment. Thus, preferably, actuation rods 1421 and 1422 are delivered through both cannulas 1431 and 1432.

Lysing rod 1460 extends through all beads and terminates in outer beads 1451a/1451d coupling all beads with lysing rod 1460 and structural member 1470 via coupling tips 1463 terminating within outer beads 1451a/1451d. In this embodiment, the configuration of the tunnels in the middle and end beads may capture corresponding elements as described in previous embodiments. In some embodiments, it may be desirable to provide features and/or elements that inhibit or limit the ability of the electrosurgical energy to discharge from the opposing ends of the lysing rod 1460 at coupling tips 1463/1464. Thus, in some such embodiments, coupling tips 1463/1464 may be coated or covered with a suitable insulating material such as an epoxy with non-conductive properties. Alternatively, outer bead hole 1454 at the end with the larger-opening may be capped or plugged with an element configured to be received or otherwise engage the larger opening of the bead. Preferably, this element will have non-conductive properties similar to the insulating material previously referenced.

In this embodiment, spacers 1462a/1462b/1462c may be positioned between bead pairs 1451a/1451b, 1451b/1451c, and 1451c/1451d. In the depicted embodiment, each of the respective lysing segments between each bead pair comprises a spacer 1462 (1462a/1462b/1462c) that may be configured to space the various beads 1451a/b/c/d apart, provide stability to the lysing tip, and/or protect the respective lysing segments (which, in the depicted embodiment, are collectively defined by a single lysing member/lysing rod 1460). Preferably, spacers 1462 comprise a conductive material, such as a suitable biocompatible metal, that can receive electrosurgical energy from the lysing member 1460 and deliver it to various internal body tissues during a surgical procedure. Preferably, spacer(s) 1462 are therefore in direct contact with lysing member 1460. In some embodiments, a single spacer 1462 may both extend between the various beads 1451a/b/c/d and extend through the tunnels 1454 through the beads 1451a/b/c/d. In some contemplated embodiments, spacers may be comprised of insulating materials (such as ceramic, glass, plastic and the like) that may have holes and/or be porous and/or have breaks and/or have separations such that energy from lysing member(s) within may be released into target tissues to have effect such as that illustrated in FIG. 12j. As discussed earlier, in some embodiments, spacers may have a circular cross-sectional profile which may facilitate adhesion of surface coatings which may have functions, including but not limited to, such as reduction in char buildup and/or ease of movement of lysing tip through tissue. However, in some embodiments electrical discharge may be enhanced across the length of the lysing member 1460 via a cross sectional profile with acute or substantially acute angles, for example, pentagonal or hexagonal shapes. Additionally, spacers with non-circular cross-sections may accumulate less debris and/or eschar on lysing rod and/or spacer because debris may have a more difficult time adhering to an angled edge.

Beads 1451a-d may be positioned along lysing rod 1460 differently in alternative embodiments. For example, in FIG. 14h, in some embodiments, spacers 1462a-c may be removed and protuberances 1465c/1465d such as welds may be placed on each side of the middle beads 1451b/c and may face proximally, distally or therebetween. In alternative embodiments, spacers 1462a-c may be removed and lysing rod 1460 may be deformed on each side of the middle beads 1451b/c such that the beads may not slide past the deformation. With respect to such embodiments, these deformations may also be considered protuberances as this term is used herein. In alternative embodiments, spacers 1462a-c may be removed and lysing rod 1460 may be deformed, such as flattening, making ellipsoidal in cross section, or otherwise modified, prior to coupling with the middle bead(s) such that the outer diameter of lysing rod 1460 may couple via friction fit with the inner tunnel surface of middle beads 1451b/c. In alternative embodiments, spacers 1462a-c may be deformed on lysing rod 1460 to a degree that spacers may no longer rotate around lysing rod 1460 and the new cross-sectional shape of spacers 1462a-c may have a beneficial effect.

In the current embodiment, outer beads 1451a and 1451d are the approximate same length as middle beads 1451b and 1451c; this shorter outer bead configuration may allow for more complete folding of the lysing tip during the delivery configuration.

Retraction guide 1425 is preferably near tip 1410 at or near the distal end of one of actuation rods 1421/1422. In the depicted embodiment, retraction guide 1425 is positioned near the distal end of actuation rod 1422 adjacent to (immediately proximal of) tip 1410. In some embodiments, retraction guide 1425 may comprise a resilient material, such as a spring, so that it provides a restorative force during retraction of tip 1410 into cannula 1431. Preferably, retraction guide 1425 is positioned and configured so as to extend from actuation rod 1422 laterally by a distance at least approximately equal to, in some embodiments slightly greater than, the distance one or more of the protrusions 1401 that extend laterally relative to actuation rod 1422 in the retracted/folded configuration. In some embodiments, retraction guide 1425 may extend in this direction a distance equal to, or slightly greater than, the largest protrusion 1401 (in embodiments in which each of the protrusions are not identical and/or do not project an equal distance).

It should be understood that embodiments are contemplated wherein the dimensions of the tip relative to a cannula 1431 may vary as for example, as shown in FIGS. 14k and 14L. In other words, the lysing tip 1410 in the axial deployment configuration may be unable to be received within cannula 1431 such as shown in FIG. 14L or may be unable to be received within an inner cannula of two delivery cannulas as shown in FIG. 14k. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

Some embodiments could be configured to allow for treatment to take place from the tip at a non-perpendicular angle relative to the axis of the cannula. In some such embodiments, this non-perpendicular angle may even allow the tip to be withdrawn in this treatment configuration. Thus, such embodiments may be configured such that some deployment configurations may also be considered treatment configurations. In alternative embodiments, the lysing tip may be reconfigured to rotate 180 degrees allowing for angling of the tip in either direction relative to the normal of the axis of the cannula. Thus, in this manner a lysing tip could be used to treat in a first lateral direction and also a second lateral direction opposite to the first lateral direction such as in FIGS. 14b, 14k, and/or 14/L.

In the current embodiment, hinges 1427/1428 couple actuation rod pairs 1421/1423 and 1422/1424 allowing a pivoting movement in both vertical directions.

Some embodiments may utilize a protective sleeve 1499 which sleeve 1499 may serve to protect the tip (either a lysing tip or tissue modification tip (TMT)) during deployment such as those depicted in FIGS. 14k-n. In some embodiments the protective sleeve 1499 may comprise a biodegradable material such as gelatin. Preferably the protective sleeve 1499 is positioned about the distal end of the tip during deployment. In embodiments in which the protective sleeve 1499 is biodegradable, the sleeve 1499 may begin to degrade once deployed in the body. Alternatively, the protective sleeve 1499 may not be biodegradable in which case the sleeve may be withdrawn from the tip by another instrument. In some embodiments, the sleeve 1499 may be withdrawn by positioning the sleeve covered tip within the body and then withdrawing the tip to remove the sleeve. In other embodiments, the lysing tip 1410 may be configured to rotate up to 180 degrees to a point to allow the sleeve to be withdrawn. In alternative embodiments, sleeve 1499 may comprise a weakened seam 1499' such that when lysing tip 1410 is rotated, the weakened seam 1499' breaks allowing sleeve 1499 to disengage lysing tip 1410. For example, weakened seam 1499' may comprise a series of cuts or scorings. In some embodiments, the sleeve 1499 may be made up of a material configured to utilize body fluids to provide a slippery or non-frictional surface.

In the depicted embodiment, 1447 represents an antenna configured to deliver a signal to a receiver unit. Antennae 1447 may be located within hole 1455. In some embodiments, antenna 1447 may comprise radiofrequency identification (RFID) TAG. In some embodiments the RFID tag may comprise an RFID transponder. In other embodiments the RFID tag may comprise a passive tag. It should be understood that antenna 1447 is not depicted in every one of the other figures; any of the embodiments described herein may comprise one or more such elements. Other embodiments may comprise one or more antenna on any other suitable location on the embodiment, including but not limited to on the protrusions or otherwise on the tip, and on the shaft. In embodiments in which antenna 1447 comprises an RFID transponder, the RFID transponder may comprise a microchip, such as a microchip having a rewritable memory. In some embodiments, the tag may measure less than a few millimeters. In some embodiments a reader may generate an alternating electromagnetic field which activates the RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. In some such embodiments, the alternating electromagnetic field may be in the shortwave (13.56 MHz) or UHF (865-869 MHz) frequency. Examples of potentially useful systems and methods for mapping/tracking a surgical instrument in relation to a patient's body may be found in U.S. Patent Application Publication No. 2007/0225550 titled "System and Method for 3-D Tracking of Surgical Instrument in Relation to Patient Body", which is hereby incorporated by reference in its entirety.

In some embodiments, a transmission unit may be provided that may generate a high-frequency electromagnetic field configured to be received by an antenna of the RFID tag or another antenna. The antenna may be configured to create an inductive current from the electromagnetic field. This current may activate a circuit of the tag, which may result in transmission of electromagnetic radiation from the tag. In some embodiments, this may be accomplished by modulation of the field created by the transmission unit. The frequency of the electromagnetic radiation emitted by the tag may be distinct from the radiation emitted from the transmission unit. In this manner, it may be possible to identify and distinguish the two signals. In some embodiments, the frequency of the signal from the tag may lie within a range of the frequency of the radiation emitted from the transmission unit. Additional details regarding RFID technology that may be useful in connection with one or more embodiments discussed herein may be found in, for example, U.S. Patent Application Publication No. 2009/0281419 titled "System for Determining the Position of a Medical Instrument," the entire contents of which are incorporated herein by specific reference.

In other embodiments, antenna 1447 may comprise a Bluetooth antenna. In such embodiments, multiple corresponding Bluetooth receivers at known locations may be configured to sense signal strengths from the Bluetooth antenna 1447 and triangulate such data in order to localize the signal from the Bluetooth antenna 1447 and thereby locate the lysing tip within a patient's body. Other embodiments may be configured to use angle-based, electronic localization techniques and equipment in order to locate the antenna 1447. Some such embodiments may comprise use of directional antennas, which may be useful to increase the accuracy of the localization. Still other embodiments may comprise use of other types of hardware and/or signals that may be useful for localization, such as WIFI and cellular signals, for example.

One or more receiver units may be set up to receive the signal from the tag. By evaluating, for example, the strength of the signal at various receiver units, the distances from the various receiver units may be determined. By so determining such distances, a precise location of the lysing tip relative to a patient and/or a particular organ or other surgical site on the patient may be determined. In some embodiments, a display screen with appropriate software may be coupled with the RFID or other localization technology to allow a surgeon to visualize at least an approximate location of the tag/antenna, and therefore the lysing tip, relative to the patient's body.

Some embodiments may be further configured such that data from the antenna(s) may be used in connection with sensor data from the device. For example, some embodiments comprising one or more sensors 1448 may be further coupled with one or more RFID tags. One or more sensors 1448 may be located within one or more holes 1455. As such, data from the one or more sensors may be paired or otherwise used in connection with data from the one or more RFID tags or other antennas. For example, some embodiments may be configured to provide information to a surgeon regarding one or more locations on the body from which one or more sensor readings were obtained. In some embodiments, temperature sensors may include thermistors and/or thermocouples. To further illustrate using another example, information regarding tissue temperature may be combined with a location from which such tissue temperature(s) were taken. In this manner, a surgeon may be provided with specific information regarding which locations within a patient's body have already been treated in an effective manner and thus which locations need not receive further treatment using the device.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently treated. For example, a display of a patient's liver may change colors at locations on the display that correspond with regions of the liver that have experienced a sufficient degree of fibrosis or other treatment. Such regions may, in some embodiments, be configured such that pixels corresponding to particular regions only light up after the corresponding tissue in that region reaches a particular threshold temperature.

Such sensor 1448 may be coupled with an antenna, which may send and/or receive one or more signals to/from a processing unit. Alternatively, or additionally, data from such sensors resulting from tissue and/or fluid analysis using such sensors may be stored locally and transmitted later. As yet another alternative, such a signal may be transmitted following surgery. In such implementations, the signals need not necessarily be transmitted wirelessly. In fact, some embodiments may be configured to store data locally, after which a data module, such as a memory stick, may be removed from the device and uploaded to a separate computer for analysis.

In alternative embodiments which may be helpful for skin/cosmetic procedures, the TD tip and/or the anticipated and/or previous paths may be visualized using for example an internal camera such as an endoscopic or laparoscopic camera, and/or an external camera such as an infrared camera, (for example, a FLIR camera), an RFID tag or other antenna. In some implementations, such a device or devices may be positioned on the TD. In other implementations such a device or devices may be separate from the TD. A real time display may be created using the data of the cameras and/or antennae and/or tags, for example, showing the exact location of the tip and the during- and post-passage temperature effects. In alternative embodiments, the software presenting the visual information may hold (or slow the decay back to the body temperature) the color (designating temperature) at its maximum value during the remainder of the procedure so that the surgeon will know where the TD tip has been.

In some embodiments, system 1400 may comprise canal(s) 1404 (only depicted in FIG. 14*d*) which may be positioned to supply one or more fluids to the surgical site around or near lysing tip 1410 via a port located adjacent to the internal device cannula and/or lysing tip. Canal 1404 may be configured to be extended and withdrawn as needed. In alternative embodiments, other fluids that may pass down canal 1404 may include, but not be limited to, cold nitrogen gas, fluorocarbons, etc., which might cool and/or freeze tissue to alter it in a desired fashion.

FIGS. 14*o*-14*t* depict an example of a modular lysing tip 1410' comprising a treatment portion 1411' of lysing tip and a reusable base portion 1470L. Treatment portion 1411', which may be disposable in some embodiments, is reversibly coupled with base portion 1470L. Thus, upon completing an electrosurgical procedure, the user may remove treatment portion 1411', and its accompanying lysing rod 1460 and beads 1451, from base portion 1470L and reattach a new treatment portion for a subsequent surgery.

In the depicted embodiment, treatment portion 1411' may be coupled with base portion 1470L aligning a seat 1470*u*' formed in upper support member 1470*u* of treatment portion 1411' with a locking portion comprising a pair of opposing flanges 1470*f* each of which comprises a hooked end portion 1470*h*. Seat 1470*u*' in some embodiments may comprise a narrowed region of upper support member 1470*u*. Thus, upon inserting seat 1470*u*' between opposing flanges 1470*f*, hooked end portions 1470*h* engage an upper surface of upper support member 1470*u* in the region of seat 1470*u*' as depicted in FIG. 14*t*. As best illustrated in FIG. 14*r*, base portion 1470L may comprise a lower support member configured to mate with upper support member 1470*u* such that together they define a full support member as previously described. In addition, because the upper support member 1470*u* of treatment portion 1411' will likely be used only once or otherwise less than base portion 1470L, preferably, holes 1472 and 1473 are formed in base portion 1470L. As previously described holes 1472 and 1473 may be used to facilitate coupling of lysing tip 1410' with a deployment assembly as depicted in FIG. 14*o*.

After performing an electrosurgical procedure using lysing tip 1410', upper support member 1470*u* may be removed from base portion 1470L by, for example, pulling seat 1470*u*' out of the locking portion of base portion 1470L. In some cases, a user may pull or pry opposing flanges 1470*f* apart either by hand or by use of a suitable tool during this decoupling process. FIGS. 14*p*, 14*s*, and 14*t* are cross sectional views taken at line A-A depicted in FIG. 14*r*.

FIGS. 15*a*-15*k* depict an alternative embodiment of a CDTD system 1500 comprising beads 1551*a/b/c/d* coupled with a bow/support member 1570 and further comprising an energy window made up of a plurality of electrode termini 1506*a*/1506*b*/1506*c*/1506*d* for delivering energy such as RF. Bow/support member 1570 may be coupled to actuation arms 1521 and 1522 and delivered through cannulas 1531 and 1532 may be employed. In some embodiments the RF energy delivered by the termini 1506*a*/1506*b*/1506*c*/1506*d* may be distinct from the RF energy delivered by the lysing segments between the adjacent beads. Beads may comprise facets 1552 and tunnels 1554. More particularly, in the depicted embodiment, the energy window comprises an energy window strip 1507 which is preferably made of a conductive material. Energy window strip 1507 comprises a plurality of energy window termini 1506*a*/1506*b*/1506*c*/1506*d* protruding from the energy window strip 1507. An insulation cover 1508 may be configured to be coupled with energy window strip 1507. In some embodiments insulation cover 1508 may be molded onto energy window strip 1507. Alternatively the insulation cover 1508 may be configured to receive the energy window strip 1507 or otherwise be coupled with energy window strip 1507. Preferably, the insulation cover 1508 comprises a non-conductive material. In the depicted embodiments, the insulation cover 1508 comprises an elongated base configured to cover the energy window strip but allow the energy window termini 1506*a*/1506*b*/1506*c*/1506*d* to protrude through the insulation cover 1508. In addition, the insulation cover 1508 comprises a plurality of protruding bead coupling members 1508', each of which is configured to extend into and be coupled with one of the beads of the tip via hole 1555 (as shown in FIG. 15*i*, a cross-sectional view down/through the center of outer bead 1551*d*). Energy delivery conduit 1509 such as a wire may be coupled with the energy window strip 1507. Preferably, the energy delivery conduit 1509 is insulated from the energy delivery conduit that delivers energy to the lysing segments 1561*a*/1561*b*/1561*c* such that a distinct type of energy may be delivered therethrough.

In other embodiments, energy window may be configured to utilize energy of different modalities, including, but not limited to, laser, intense pulse light, resistive heating, radiant heat, thermochromic, ultrasound, mechanical, and/or microwave.

In some embodiments, system 1500 may be configured to utilize bipolar radiofrequency energy as depicted in FIGS. 15*j* (energy conduits not shown) and 15*k*. In the depicted embodiment, each electrode termini may be physically independent of the other, however, electrode termini pairs 1506*a*'/1506*c*' and 1506*b*'/1506*d*' may each be electrically coupled to a positive energy conduit 1509*n* and a negative energy conduit 1509*p*, respectively. In some embodiments, the energy conduits may comprise wires.

FIGS. 16*a*-16*h* depict an alternative embodiment of a CDTD system 1600 comprising a plurality of protrusions 1601 and recessions 1602 positioned in between adjacent protrusions. System 1600 is structurally similar to system 1400, however, system 1600 is a bipolar device. System 1600 further comprises first/inner/device cannula 1631 and second/outer cannula 1632, the first or both which may be used to deliver lysing tip 1610, as previously mentioned. System 1600 is configured for bipolar electrosurgical energy delivery, has 3 protrusions defined by beads outer beads 1651*a*/1651*b* and middle bead 1652, and 2 lysing segments 1668*ps*/1668*ns* defined by two electrically isolated lysing members 1668*pm*/1668*nm*.

In the embodiment of FIG. 16*f*, negative lysing member 1668*nm* is configured to extend through a tunnel 1658*n* formed in bead 1652. Similarly, positive lysing member 1668*pm* is configured to extend through a separate tunnel 1658*p* formed in 1652. Positive lysing member 1668*pm* and negative lysing member 1668*nm* may extend from their respective tunnels all the way back to an electrosurgical generator and/or surgical instrument. In other embodiments lysing members 1668*pm*/1668*nm* may instead terminate within bead 1652 or may terminate somewhere in between bead 1652 and its ultimate electrical coupling with an electrosurgical energy source. For example, in some embodiments, a wire or another electrical conductor may be coupled to lysing members 1668*pm*/1668*nm*.

In some such embodiments, the lysing tip comprises means for maintaining a flexible lysing member in a rigid state. Examples of such means may include a weld, melt, crimp, bend, narrowing of tunnel, and the like. In a more particular example of such a means, protuberance 1668*b* may be formed adjacent to one or more of the openings of tunnel 1658*p* or 1658*n* such that lysing members 1668*pm*/1668*nm* may be pulled through their respective tunnels and tightened or kept taught after which protuberances 1668*b* may be formed to keep their respective lysing members in a rigid or substantially rigid state. In another embodiment, bead 1652 may be formed in two pieces and coupled together after positioning lysing members 1668*nm*/1668*pm* through their respective tunnels. In some such embodiments, the tunnels may be formed at least in part with a diameter equal to or less than that of lysing member 1668*nm*/1668*pm* such that upon applying both pieces together the lysing members may be prevented from being withdrawn from their respective tunnels.

In FIG. 16*e*, the wiring comprising lysing member 1668*p*/1668*n* has been removed in order to show the actuation rods 1621/1622 from the cannula distally to the lysing tip 1610.

Lysing tip 1610, more particularly structural member 1670, in the delivery configuration, seats inside groove 1621*a*.

An external power cord may bring electrosurgical energy from an electrosurgical generator to a hand assembly, such as that illustrated in FIG. 1, system 1600, (which is electrically connected) to lysing member 1668*pm*/1668*nm* (which may be insulated through cannula lumen) directly to lysing tip 1610. In this embodiment, each lysing member 1668*pm*/1668*nm* enters its respective tunnel 1658*p*/1658*n* through the rear of center bead 1652, and exits an opposite side of bead 1652 wherein lysing member 1668*pm*/1668*nm*, preferably no longer be insulated after exiting 1652, defines lysing segments 1668*ps*/1668*ns* whereupon each enters its respective outer bead 1651*a*/1651*b* and terminates within beads 1651*a* or 1651*b* as previously described herein via coupling tips 1663.

The tip shown in this embodiment has three relative protrusions 1601, lysing members 1668*pm*/1668*nm* (and associated lysing segments 1668*ps*/1668*ns*), with beads 1651*a*/1651*b*/1652 pointing along the main axis of the CDTD in treatment configuration. In other embodiments, the bipolar CDTD lysing tip 1610 may have one or more non-axial protrusions and one or more non-axial relative recessions. In some embodiments, the tip may have between 3 and 100 axial and/or non-axial protrusions and/or relative recessions. It should be understood that the number of protrusions need not match the number of lysing elements or recessions. In some embodiments, lysing elements may be located at the termini of conductive elements. In some embodiments, lysing elements may also be made partially or completely of a cermet material. In an embodiment, the modular bipolar CDTD tip 1610 may measure about 15 mm in length (TL in FIG. 10*e*) and/or about 3 mm in height (TH in FIG. 10*d*). Embodiments are contemplated wherein sizes of about one-fifth to about five times these dimensions may have possible uses. It is also contemplated, for example in some veterinary embodiments, tip sizes of about one-tenth to 20 times the aforementioned dimensions may have possible uses. In other contemplated embodiments, electroconductive leads may course from an electrosurgical generator via first/inner/device cannula 1631 to energize various lysing elements located in bipolar CDTD tip 1610. In some embodiments leads may comprise wires and/or conductive conduits.

FIG. 16*g* is an anterior elevated perspective view of lysing tip 1610. In this embodiment, individual lysing segments 1668*ps*/1668*ns* may comprise surgical grade conductive metals and/or alloys positioned within all and/or a portion of one or more pieces of ceramic and/or other thermally resistant, non-conductive housing. In some embodiments, one or more individual lysing elements/segments may comprise electroconductive materials including but not limited to cermets, steel, nickel, alloys, palladium, gold, tungsten, titanium, silver, copper, and/or platinum. In the depicted embodiment, the lysing elements may measure about 2 mm in length, and about 0.5 mm in diameter/thickness.

In this embodiment, the configuration of the tunnels in the end beads may capture corresponding elements as described in previous embodiments. For example, certain beads may comprise hole 1655 that may be positioned perpendicular to lysing rod hole 1658; holes 1655 may be available as a platform/location to add other features/components such as providing a location for coupling of a cord as described below in connection with other embodiments and/or locating a sensor and/or RFID location component and/or being used for placement of luminescent and/or light production element(s) for visualization, for example, tritium and the like.

In some contemplated embodiments there need not be equal numbers of oppositely signed and/or charged individual lysing elements. Uniformity of flux on activation may be achieved by modifying the size and/or position of lysing elements with respect to each other among other methods known in the art.

The relative static permittivity of some ceramics may range from about 5 to 10; this may cause some leakage of current in an undesirable path between closely approximated opposing electrodes during activation. Use of other materials, for example, those having over of relative static permittivities of 5 may undesirably alter the resultant plasma field. The relative static permittivity of the intervening materials housing the opposing electrodes may be enhanced by coating and/or surrounding and/or injection molding thermoresistant polymers of a low relative static permittivity into the housing and/or around one or more portions of bipolar lysing segments 1668ns/1668ps to reduce the effective static permittivity of the tip. In an embodiment, the thermoresistant polymer of low relative static permittivity 2.1 may be polytetrafluoroethylene. In other contemplated embodiments, thermoresistant polymers may include polyether etherketone (@3.3) and/or polysulfone (@3.1) and the like may be useful.

In the depicted embodiments, the electrical insulator on lysing member 1668nm/1668pm and/or support member 1670 may comprise polytetrafluoroethylene. In other contemplated embodiments, the electrical insulator may comprise an electrically nonconductive polymer with a high melting temperature. In some embodiments, the nonconductive polymer may comprise for example, polyether etherketone and/or polysulfone, etc. In other contemplated embodiments, the electrical insulator may comprise an electrically nonconductive and/or thermally nonconductive polymer.

In some embodiments and implementations, lysing tip 1610 may be configured such that its beads 1651a/b and 1652 are too large to fit within the lumen of first/inner/device cannula 1631, even in the delivery configuration. Thus, lysing tip 1610 in its delivery configuration may be positioned just outside (immediately distal) of first/inner/device cannula 1631 but within second/outer cannula 1632 during delivery.

FIGS. 17a-17m depict yet another embodiment of a CDTD or a non-CDTD system 1700. System 1700 comprises a lysing tip 1710 that is configured to be completely separable from any other element of the system. In this manner as depicted in FIGS. 17f-g, lysing tip 1710 may be delivered through a first/primary cannula 1732, which may comprise, for example, a trocar, and then coupled with a first surgical tool, such as a grasping/control instrument 1790 that can be used to control and/or energize the lysing tip 1710 within the body of a patient during a surgical procedure. In some embodiments and implementations, a second cannula may be used to deliver a second surgical tool, such as a transfer/grasping instrument 1796, that may be used to facilitate coupling of lysing tip 1710 to the grasping/control instrument 1790, which instrument may be delivered through the same cannula 1732 through which the lysing tip 1710 is delivered. In some embodiments, grasping/control instrument 1790 may have the same configuration as grasping/transfer instrument 1796. In alternative embodiments, transfer/grasping instrument 1796 may be configured differently from grasping control instrument 1790 in that, for example, it may not have the capability to transfer energy to lysing tip 1710 yet may have a different tip design in order to facilitate grasping/holding lysing tip 1710 between two beads or other protrusions. Alternatively, the lysing tip 1710 may be delivered though a second unattached cannula 1735 along with a grasping/transfer instrument 1796 used to couple the lysing tip 1710 to the first surgical tool delivered through the first/primary cannula, which other surgical tool may be used to control lysing tip 1710 and perform the surgical procedure. As shown in the FIG. 17f, lysing tip 1710 is positioned within outer cannula 1732 with an axis extending between the outermost beads 1751a/1751d in lysing tip 1710 aligned with a primary axis of cannula 1732 and with a treatment side of lysing tip 1710 (opposite from grasping pad 1771) facing an internal surface of cannula 1732.

In some implementations of methods using system 1700, the lysing tip may be reconfigured from a delivery configuration to a treatment configuration by delivering lysing tip 1710 through a cannula at least substantially along a treatment axis of the lysing tip extending between opposing outer beads and then rotating the lysing tip once outside the distal end of the cannula. In some such implementations the step of reconfiguration the lysing tip from delivery to treatment configuration may further comprise grasping a portion of the lysing tip such as the grasping pad in a manner such that the treatment axis is at least substantially perpendicular to an axis of the grasping instrument. Thus, the lysing tip may be grasped from a direction at least substantially perpendicular to the grasping direction in the treatment configuration during delivery.

In alternative implementations, a standard 3-5 mm diameter grasping instrument with handle (without a lysing tip attached) may be directed into the body cavity, possibly via a trocar of accepting diameter or via an incision in the skin, and exit extracorporeally via another trocar (for example, of larger diameter at umbilicus), whereupon the grasper may open its and receive the lysing tip at an angle that permits the grasper to pull lysing tip into the body cavity through the larger trocar. Once inside the body cavity, the lysing tip may be reconfigured from a delivery configuration to a treatment configuration.

Lysing tip 1710 may comprise a plurality of protrusions 1701 comprising beads 1751 and recessions 1702 between each bead pair. Lysing member 1760, which in the depicted embodiment comprises a lysing rod 1760 enclosed by spacers 1762a/1762b/1762c positioned in recessions 1702, delivers electrosurgical energy. Each of the portions of lysing member 1760 extending between adjacent beads 1751 may be considered lysing segments 1760a/1760b/1760c. In the depicted embodiment, each of the lysing segments or spacers 1762a/1762b/1762c is collectively defined by a single lysing member 1760. However, other embodiments are contemplated in which separate lysing members may be used for each of the lysing segments positioned between adjacent beads. FIG. 17c depicts lysing tip 1710 with bead 1751c removed in order to show internal components and to show tunneling within outer beads 1751a and 1751d.

In FIG. 17j, spacers 1762a/1762b/1762c may be removed and replaced with protuberances 1765a/1765b positioned on opposing sides of one or more of the beads, such as middle bead 1751b, as a means to inhibit or limit the lateral movement of middle bead 1751b and/or any other beads, as desired. Additionally depicted in FIG. 17j is an embodiment in which lysing rod 1760 is roughened or otherwise deformed between points 1767L and 1767R. In some such embodiments, this may be done by adding material to the lysing rod and/or adding material to the inside of the bead tunnel 1754 in a manner that the diameter of sufficient portions of lysing rod 1760 is increased to or slightly greater the internal diameter of tunnel 1754 of bead 1751c such that when bead 1751c is slid into its position between points 1767L and 1767R, bead 1751c may tend to remain in place via friction fit. Alternatively, the portions of lysing rod 1760 configured to extend through bead tunnel 1754 may be roughened by removing material from lysing rod 1760 such as by sanding and/or blasting. In these configurations, lysing rod 1760 may also act as the lysing segments. In FIG. 17j, although both protuberances and friction fit are shown and spacers removed, this is done primarily for purposes of illustration, thus, as those of ordinary skill in the art will appreciate, in practice, only one of the options may likely be used. The roughening described herein may be useful for example in order to prevent or inhibit rotation of the beads on the lysing rod. In some embodiments, the amount of roughening may be used selectively to select the amount and/or ease of rotation.

In alternative embodiments, hole 1055d' may be moved to fully or partially intersect tunnel 1054 thus allowing communication with lysing rod 1060; thus a weld, plug (for example 1055p), glue, insert or other method of fixation may be inserted via hole 1055d' to attach to lysing rod 1060 thus restricting lateral movement of a bead. To reduce escape of electrosurgical energy through hole 1055d', an insulator comprised of epoxy, plastic, ceramic or the like may be placed in part or all of the remaining hole 1055d'. This alternative embodiment may be applied to other embodiments herein.

FIG. 17k illustrates a front/elevation view of an alternative embodiment in which lysing tip 1710 may be configured without a solid lysing rod and/or without spacers and/or welds (that may face distally, proximally, or therebetween) and the like. In such embodiments, internal bead tunnels 1754 and support member holes 1767a/1767b may be configured to accommodate hollow lysing rod 1760a. Between beads, hollow lysing rod 1760a may be deformed 1760a' in a manner to prevent lateral movement of beads and/or prevent rotation of beads, as shown in FIG. 17k. Hollow lysing rod 1760a' may be deformed minimally or to a point that it is substantially flat. In such embodiments, it may be preferable for the front edge to point distally as the leading front edge. In such embodiments, screw 1709 may secure one or both ends of the hollow lysing rod 1760a within outer beads 1751a/1751d. In alternative embodiments, hollow lysing rod 1760a may be replaced with solid lysing rod 1760 and deformed adjacent to middle beads in the manner suggested in this paragraph. The configurations of this alternative embodiment may be available for any other similar embodiment contemplated herein.

In alternative embodiments that may comprise lysing rod 1760, spacers 1762a/b/c may be deformed on the lysing rod 1760 so as to become immovable, either in addition to deforming the lysing rod itself or as an alternative to deforming the lysing rod.

As previously mentioned, beads 1751 may be coupled with one another by way of a single lysing member 1760 extending through tunnels 1754 extending through each of the respective beads 1751. In the depicted embodiment, beads 1751 each comprise a non-symmetrical shape and/or may be eccentric relative to tunnels 1754. However, in this embodiment, as shown in the figures, the opposing outer beads 1751a and 1751d have a shape that differs from the shape of the beads in between the outer beads, namely beads 1751b and 1751c Of course, as previously mentioned, in some embodiments, all of the beads may have the same, or substantially the same, shape/size. In other embodiments, each of the beads may have a different shape to accommodate a particular type of surgery, for example. More particularly, beads 1751b and 1751c have a similar distal or frontal shape (from the perspective of the treatment side of tip 1710) but have a flattened, thus shorter, rear end so as to accommodate a support member 1770, which in this embodiment comprises a bow 1770. Support member, as described in greater detail below, may be used to facilitate temporary coupling of lysing tip 1710 to a surgical tool, such as a driver. In some embodiments, support member 1770 may also be used to facilitate delivery of electrosurgical energy into lysing tip 1710. Support member 1770 may be preferably fully or partially insulated, except for regions on which it is desired to transfer electrosurgical energy such as (1) at one or more surfaces of grasping pad 1771, (2) within the 2 distal support member holes (as shown in FIG. 17e, 1767a/1767b), and/or (3) the opposing distal ends of support member 1770, in some cases distal of lysing rod 1760 in order to deliver electrosurgical energy not only through lysing rod 1760 but also through these distal ends of support member 1770. Support member 1770 may be fully or partially insulated in order to prevent electrosurgical energy from transferring to tissue from the support member 1770; more particularly, insulating support member 1770 directs electrosurgical energy to lysing member 1760 through support member holes 1767a/1767b. In some embodiments, support member 1770 may comprise for example a non-conductive material such as a ceramic and/or flexible ceramics (for example, "Flexiramics®"). In some such embodiments, one or more electrical conduits such as a wire may be embedded within and/or extend through or otherwise be coupled with the support member 1770 so as to deliver electrosurgical energy to lysing member 1760.

Support member 1770 may be used to provide a frame or support structure for lysing tip 1710 and/or used to provide a feature, such as grasping pad 1771. In the depicted embodiment, the grasping pad 1771 is defined in part by a tab 1771a, to allow an endoscopic tool having a grasping tip, such as grasping tip jaws 1796a/1796b of grasping/control instrument 1790, to grasp and manipulate lysing tip 1710. If the tip ends of support member 1770 are coated with nonconductive insulation, such coating might increase the width of relative protrusion 1701 and perform similar to a protrusion bluntly dissecting/separating tissues, however, if said tips are not so coated, the area of relative protrusion 1701 may be limited to what is illustrated as said tip may perform in a manner similar to lysing rod 1760 cutting and/or coagulating tissues.

Support member 1770 in the current embodiment comprises a bow shape comprising two opposing end tips comprising holes or other openings through which lysing rod 1760 extends. The two tips of support member 1770 may extend far enough distally to provide sufficient material to form the lysing rod through-holes. Alternatively, openings comprising slots or the like may be formed at one or both of the two opposing tips of support member 1770 if desired.

In the depicted embodiment, the tunnels 1754 are positioned in a non-central location within each of beads 1751. More particularly, the tunnels 1754 in this particular embodiment are positioned in a forward or distal location relative to a central axis of each of beads 1751, including outer beads 1751a and 1751d, which may have a ellipsoidal or similar shape, and internal beads 1751c and 1751d, which may have a similar ellipsoidal front tip but have a flattened and/or shortened rear end, as shown in the figures. As previously mentioned, this may be preferable for some embodiments, particularly embodiments in which beads 1751 can at least partially rotate on the lysing rod or other lysing member 1760 to allow the lysing tip 1710 to be directed through tissue in a desired manner.

Preferably, the entire surfaces of the beads 1751, or at least outer beads 1751*a* and 1751*d*, may be smooth. Or, at least all surfaces that may be expected to contact tissue during a surgical procedure may be smooth. For example, providing a smooth front end and a smooth trailing end may allow the lysing tip to be moved in a forward direction and then in a rearward direction back and forth without catching an undesirable amount of tissue on beads to inhibit such movement. However, as shown in FIGS. 17*a*-17*m*, in some embodiments, the trailing end of some beads, such as internal beads 1751*b* and 1751*c*, may comprise a flat surface such that each internal bead comprises a frusto-shaped or another similar shape. In other contemplated embodiments, providing a rough trailing end may create frictional drag on that portion of the bead thus helping reorient the front end of the bead for further tissue passage. Thus, in some embodiments, the trailing end may have a rougher surface than the front end. Preferably, at least the forward or distal surface of each bead is smooth and defines a substantially and/or partially ellipsoidal shape or another shape having a smooth forward surface. In alternative embodiments, the distal/forward tip of beads 1751 may have a more narrowed end to act more as a wedge for purposes of acting as a blunt dissector between tissues and tissue planes. The forward tips may be narrowed by use of facets (such as those facets 1052 in FIG. 10*d*). Facets are preferably formed on the distal/front/leading portions of the bead to facilitate tip movement through/between tissue layers. As described in FIGS. 12*aa*-*rr*, a wide variety of alternative bead shapes are possible including, for example, ovoid shapes, spherical shapes, wheel shapes, bullet shapes or other shapes having a flat terminal end (such as, for example, frusto-ellipsoidal), wing shapes, etc. In some embodiments, beads may be faceted on the top, bottom, sides, front and/or back such as illustrated in FIGS. 10*c*/10*d*, at facet 1052.

As previously mentioned, in some embodiments, it may be desirable to allow beads 1751 to rotate, at least partially, on lysing member 1760. Thus, beads 1751 may not be fixed three-dimensionally with respect to lysing member 1760 and/or one or more other elements of lysing tip 1710. In some such embodiments, beads 1751 may be at least partially rotatable with respect to the remainder of lysing tip 1710. In embodiments in which beads 1751 are rotatable in this manner, it may be desirable to use a lysing member having a circular cross section. It may also be desirable to form spacers 1762*a*/1762*b*/1762*c* in ways that facilitate such rotation and/or restrict it in some manner. Thus, in some embodiments, one or more of spacers 1762*a*/*b*/*c* may also be rotatable with respect to lysing member 1760. In some such embodiments, spacers 1762 may be configured to rotate with beads 1751.

In the depicted embodiment, each of the spacers 1762*a*/*b*/*c* is positioned about one of the respective lysing segments defined by lysing member 1760 which may be configured to space the various beads 1751 apart, provide stability to the lysing tip, and/or protect the respective lysing segments (which, in the depicted embodiment, are collectively defined by a single lysing member 1760). Preferably, spacers 1762*a*/*b*/*c* comprise a conductive material, such as a suitable biocompatible metal, that can receive electrosurgical energy from the lysing member 1760 and deliver it to various internal body tissues during a surgical procedure. Preferably, spacer(s) 1762*a*/*b*/*c* are therefore in direct contact in one or more pre-determined locations on lysing member 1760. In other embodiments, a single spacer may both extend between the various beads 1751 and extend through the tunnels through the beads 1751 rather than using separate spacers for each lysing segment.

One or more of the beads 1751, such as preferably one or both of the outer beads 1751*a* and 1751*d*, may further comprise a hole 1755. Hole(s) 1755 may, together with a cord 1744 (which may be a suture), for example, comprise an example of means for maintaining retrievability of a free-floating lysing tip when the lysing tip is decoupled from a grasping/control instrument. In preferred embodiments and/or implementations, cord 1744 or another loopable element may be looped through one or more such hole(s) and then may extend through one or more cannulas used to deliver lysing tip 1710 proximally back to a surgeon. In this manner, in the event of a failure to grasp or otherwise couple lysing tip 1710 to a grasping/control instrument, such as grasping/control instrument 1790, lysing tip 1710 may be retrieved from within a patient's body by pulling on suture 1744 to retract lysing tip 1710 though cannula 1732. In some embodiments, hole 1755 may also or alternatively be used to maintain position of lysing tip 1710 while awaiting delivery of a grasping/control instrument 1790 for performing surgical procedures. Upon properly coupling lysing tip 1710 with an appropriate tool for grasping and/or controlling lysing tip 1710, such as grasping/control instrument 1790, a surgeon may cut suture 1744, preferably near a knot or other feature used to form a loop around hole 1755. If a suture 1744 or other similar material/element is used that is sufficiently flexible and non-disruptive, this shorter loop may be configured to be present during a surgical procedure using lysing tip 1710 without unduly interfering with the procedure. In alternative embodiments, holes 1755 may be available as a platform/location to add other features/components such as providing a location for coupling of a cord as described below in connection with other embodiments and/or locating a sensor and/or RFID location component and/or being used for placement of luminescent and/or light production element(s) for visualization, for example, tritium and the like. In alternative embodiments, hole 1755' may be moved to fully or partially intersect tunnel 1754 thus allowing communication with lysing rod 1760; thus a weld, plug, glue, insert or other method of fixation may be inserted via hole 1755' to attach to lysing rod 1760 thus restricting lateral movement of a bead and/or rotation of the bead with respect to lysing rod 1760. However, in some embodiments one or more of the beads along with the lysing rod 1760 may be configured to rotate at least partially with respect to the support member 1770. To reduce escape of electrosurgical energy through hole 1755', an insulator comprised of epoxy, plastic, ceramic or the like may be placed in part or all of the remaining hole 1755'. This alternative embodiment may be applied to other embodiments herein.

Preferably, lysing member 1760 terminates within outer beads 1751*a* and 1751*d*. Thus, it may be desirable to melt, tip, ball, crimp, fold, tie, or otherwise couple the ends of lysing member 1760 within outer beads 1751*a* and 1751*d* at opposing lysing member coupling tips 1763*a* and 1763*b*. Preferably, lysing tip 1710 is configured such that each of beads 1751 are rotatable independent of one another. However, depending upon how opposing lysing member coupling tips 1763*a* and 1763*b* are configured, rotation of outer bead 1751*a* may transfer, at least to a certain extent, to outer bead 1751*d*, and vice versa.

In some embodiments, it may be desirable to provide features and/or elements that inhibit or limit the ability of the electrosurgical energy to discharge from the opposing ends of the lysing rod 1760 at coupling tips 1763*a*/*b*. Thus, in some such embodiments, coupling tips 1763*a*/*b* may be coated or covered with a suitable insulating material such as an epoxy with non-conductive properties. Alternatively, outer bead hole 1754 at the end with the larger-opening may be capped or plugged with an element configured to be received or otherwise engage the larger opening of the bead. Preferably, this element will have non-conductive properties similar to the insulating material previously referenced.

Coupling tip 1763a/1763b may be configured to engage a ledge 1759 positioned at a transition point between two concentric tunnels (1759a/1759b), more particularly, outer tunnel 1759b may comprise a larger diameter or other cross-sectional dimension than inner tunnel 1759a such that lysing member 1760 may extend through inner tunnel 1759a but coupling tip 1763a due to its larger size may be configured to extend through outer tunnel 1759b without passing through inner tunnel 1759a. In other embodiments, there may be a single tunnel 1759c that tapers from a larger dimension on the outer side of bead 1751 to a smaller dimension toward the inside of the bead relative to the lysing tip 1710.

As shown in FIG. 17a, grasping pad 1771 of support member 1770 may be situated along a central portion of support member 1770 along the rear or proximal end of lysing tip 1710. In some embodiments, grasping pad 1771 may comprise a plate with opposing flattened surfaces configured to allow a surgical tool with a grasping tip, such as jaws 1796a and 1796b in FIGS. 17f and 17g, to grasp and/or manipulate/control support member 1770 and therefore lysing tip 1710.

In some embodiments, at least a portion of support member 1770 and/or grasping pad 1771 may comprise a conductive material and support member 1770 and/or grasping pad 1771 may be configured to receive electrosurgical energy, such as from a grasping/control instrument 1790 or another surgical tool, and deliver such energy to lysing member 1760. For example, in some such embodiments, electrosurgical energy may be delivered through grasping jaws 1793a/1793b, into grasping pad 1771, down through the frame of support member 1770, and into lysing member 1760. In other embodiments, grasping pad 1771 may be insulated and electrosurgical energy may instead be delivered to lysing tip 1710 in another manner.

FIGS. 17a-e illustrate a tab 1771a extending distal from grasping pad 1771, which comprises an extended central region. Such central region may be useful to allow for greater surface area for grasping by jaws or other elements of a grasping tip from a surgical tool, such as jaws 1796a/1796b of grasping/control instrument 1790.

In embodiments comprising a free-floating lysing tip (can be uncoupled from any control instrument or cannula), including the embodiments of FIGS. 17-31 and 35-38, certain preferred embodiments may have a size of about 12 to 18 mm from the end of one protrusion and/or bead to the opposite protrusion/bead on the opposite end; the length of the largest outer beads (BL as illustrated in FIGS. 10d/10e) may range from about 3 mm to 12 mm; the height BH as illustrated in FIGS. 10d/10e) of the largest outer beads may range from 2 mm to 10 mm. In some embodiments, this dimension may be defined by the distance from the upper end of one or more (in some embodiments, each) beads to the lower end of one or more beads. In some free-floating embodiments, the lysing tip may have a width TW as illustrated in FIGS. 10d/10e of about 4.5 mm from the proximal end of the lysing tip to the distal end of the lysing tip. However, it should be understood that a wide variety of alternative shapes and/or sizes may be usable depending upon the particular surgical procedure involved.

Similarly, in embodiments comprising a fixed lysing tip (coupled to one or more actuation rods), certain preferred embodiments may have a size of about 15 mm from the end of one protrusion and/or bead to the opposite protrusion/bead on the opposite end, may have a size of about 3 mm from the upper end of the lysing tip to the lower end of the lysing tip. In some embodiments, this dimension may be defined by the distance from the upper end of one or more (in some embodiments, each) protrusions/beads to the lower end of one or more protrusions/beads. In some free-floating embodiments, the lysing tip may have a size of about 3.5 mm from the proximal end of the lysing tip to the distal end of the lysing tip. However, it should be understood that a wide variety of alternative shapes and/or sizes may be usable depending upon the particular surgical procedure involved.

In FIGS. 17h-i, a non-conductive sheath 1795 may be deployed to cover the outer surface and/or conductive surfaces of shaft and tip/jaws 1793a/1793b of grasping/control instrument 1790 to electrically isolate the electrically conductive surfaces of grasping/control instrument 1790. In the current embodiment, conducting wire 1768 may carry electrosurgical energy from the energy source to lysing tip 1710. In other embodiments, the embodiment of FIG. 17h/17i may also have an insulated grasping pad 1771, since wire 1768 is provided for delivery of electrosurgical energy. In other contemplated embodiments, sheath 1795 may electrically isolate the grasping control instrument, but permit electrical contact between the jaws of grasping control instrument 1790 and the grasping plate of lysing tip 1710. However, it should be understood that the shape of grasping pad 1771 may be used in conductive or non-insulated embodiments.

FIG. 17b is a cross-sectional view taken along line 17b-17b in FIG. 17a illustrating spacer 1762b, middle bead, 1751b, support member 1770, and lysing rod 1760. FIG. 17e is a perspective view of support member 1770 (and grasping pad 1771) comprising holes 1767a/1767b through which lysing rod 1760 extends and comprises coupling tips 1763a/1763b on its opposing ends.

An alternative system for use of a lysing tip 1714t with a modular grasping instrument tip 1714g is shown in FIGS. 17L and 17m. In some embodiments, modular instrument tip 1714g and lysing tip 1714t may be permanently coupled to one another as described below. Alternatively, in other embodiments lysing tip 1714t may be removable from modular instrument tip 1714g. When the instrument tip 1714g and lysing tip 1714t may be combined, they may be referred to herein as a modular grasper/tip 1714. Modular instrument tip 1714g comprises a locking lumen 1799' that is configured to be coupled with a distal end of a pushrod 1797 and shaft 1796 of a modular grasping/control instrument 90.

In an example of a procedure using the system of FIG. 17L, a surgeon may initially place a trocar 1732' at a desired location such as through an incision 6' positioned through the umbilicus 5. A second incision 6, which may be a smaller incision than incision 6', may be made at a location spaced apart from incision 6'. In some embodiments and implementations, incision 6 may be between about 2.5 and about 5 mm. Shaft 1796 of instrument 90 may then be extended through incision 6 and then subsequently through incision 6' and trocar 1732'. Modular grasping instrument 1714g may then be coupled with the distal end of shaft 1796 and push rod 1797. Once lysing tip 1714t is coupled with modular grasping instrument tip 1714g, instrument 90 may then be pulled proximally to introduce lysing tip 1714t within patient 4. In embodiments in which lysing tip 1714t is removable from modular grasping instrument tip 1714g, lysing tip 1714t may be coupled with the distal end of instrument tip 1714g prior to proximally pulling instrument 90 and its distal tip back into the cavity of human or animal body 4. Once modular instrument tip 1714g has been coupled with instrument 90, handle 91 may be used to control one or more aspects of lysing tip 1714t. For example, actuation of handle 91 may result in locking lysing tip 1714t at a particular rotational orientation relative to shaft 1796 as described in connection with FIG. 17M. Alternatively, handle 91 or another actuation element of instrument 90 may be used to rotate lysing tip 1714t between delivery and treatment configurations. Instrument 90 may also be used to deliver electrosurgical energy to lysing tip 1714t. For example, as shown in FIG. 17L, energy connector 92 which may comprise a conductive post may be used to facilitate an electrical connection with an electrosurgical generator. The electrosurgical energy from this generator may extend through shaft 1796 via pushrod 1797 and be coupled with one or more lysing members of lysing tip 1714t as previously described.

FIG. 17M depicts a more detailed view of the interface between modular grasping instrument 1714g and distal tip of shaft 1796 and pushrod 1797 of instrument 90. As shown in this figure the distal end of shaft 1796 may comprise a locking feature 1798. Locking lumen 1799' within modular instrument tip shaft 1794 comprises a slot 1799s configured to receive locking feature 1798 at a predetermined rotational configuration. Upon aligning locking feature 1798 with slot 1799s, shaft 1796 and pushrod 1797 may be advanced into locking lumen 1799'. After advancing shaft locking feature 1798 to its terminal end 1798' within coupling rod 1792, upon rotation 2 of modular instrument tip shaft 1794, locking feature 1798 securely couples shaft 1796 to coupling rod 1792. During the same time period, pushrod 1797 and its accompanying pushrod locking feature 1799n was advanced to a locking chamber 1799n' in which pushrod 1797 and its accompanying pushrod locking feature 1799n may have been rotated to lock pushrod locking feature 1799n in place within locking chamber 1799n'. In some embodiments, the extent of the rotation of pushrod locking feature 1799n may be the same as the extent of rotation of locking feature 1798 which may in some embodiments be 90 degrees. In some embodiments, pushrod locking feature 1799n may comprise a plate or an elongated box or any other feature not having rotational symmetry about the axis pushrod 1797. Locking chamber 1799n' may comprise for example a box or other similar feature given to engage pushrod locking feature 1799n upon rotation of pushrod 1797.

Locking chamber 1799n' is coupled with coupling rod 1792 which in turn may be coupled with one or both jaws. Thus, upon advancing or retracting pushrod 1797, coupling rod 1792 advances or retracts to open or close the jaws so as to capture support member 1770 within jaws 1793a (not shown)/1793b.

Any of the preliminary steps for coupling a lysing tip with an instrument and/or inserting the lysing tip into a patient discussed in connection with FIGS. 17L and 17m may be performed in connection with any of the surgical methods described in connection with FIGS. 40-50.

FIGS. 18a-18e depict another embodiment of a CDTD system or a non-CDTD system. Although, other embodiments are contemplated in which system 1800 may comprise a CDTD system. System 1800 comprises a lysing tip 1810 that is configured to be completely separable from any other element of the system. Lysing tip 1810 may comprise a plurality of protrusions 1801 comprising beads 1851a-d and recessions 1802 between each bead pair. Lysing member 1860, which in the depicted embodiment comprises a lysing rod 1860, is enclosed or may be partially enclosed by spacers 1862a/1862b/1862c positioned in recessions 1802, delivers electrosurgical energy. Each of the portions of lysing member 1860 extending between adjacent beads 1851 may be considered lysing segments as discussed previously herein. In the depicted embodiment, each of the lysing segments or spacers 1862a/b/c is collectively defined by a single lysing member 1860. However, other embodiments are contemplated in which separate lysing members may be used for each of the lysing segments positioned between adjacent beads. Spacers may be configured and/or attached as described and illustrated in FIGS. 18a-18e to immovably fix spacers 1862a/b/c on a lysing rod 1860.

Spacers 1862a/1862b/1862c may be coupled with lysing rod 1860 by, for example, sliding spacers 1862a/b/c comprising a lumen along the axis of lysing rod 1860. Alternatively, spacers 1862a/b/c may be coupled with lysing rod 1860 by placing spacers 1862a/b/c over lysing rod 1860 in a direction perpendicular to the axis of the lysing rod at a desired location using a slot or other opening formed along a portion of a perimeter spacer 1862a/b/c. In some embodiments and implementations, spacers 1862a/b/c (two of a potential three shown in FIG. 18c) may be crimped or otherwise fixedly coupled with lysing rod 1860 at a desired location. In some embodiments, this fixed coupling may be configured to prevent the relative movement between lysing rod 1860 and spacer 1862a/b/c possibly reducing hot spots caused from high current density flow in certain areas between lysing rod 1860 and spacer 1862a1b/c. These exemplary methods for applying spacers to a lysing rod and/or another lysing member may be apply to any of the other embodiments utilizing spacers.

In some contemplated embodiments spacers may be comprised of insulating materials (such as ceramic, glass, plastic and the like) that may have holes and/or be porous and/or have breaks and/or have separations such that energy from lysing member(s) within may be released into target tissues to have effect such as that illustrated in FIG. 12j.

In some such embodiments, beads 1851 may be at least partially rotatable with respect to the entire lysing tip 1810. In embodiments in which beads 1851 are rotatable in this manner, it may be desirable to use a lysing rod having a circular cross section. It may also be desirable to either omit spacers 1862a/b/c or form them without the beveled edges best shown in FIGS. 12h, 12n, etc.

Spacers 1862a/b/c may be used to prevent rotation of beads 1851 or to selectively limit the amount of rotation of beads 1851 on a lysing member 1860. For example, if spacers 1862a/b/c extend the entire distance or at least substantially the entire distance between each adjacent bead, spacers may prevent rotation or, depending upon the distance between spacers and adjacent beads, may be used to allow for a predetermined amount of such rotation. Similarly, the opposing ends of spacers 1862a/b/c may be shaped to match or at least substantially match the shape of the adjacent bead(s) again to either prevent or control rotation.

System 1800 differs from system 1700 only in the manner as to how lysing tip 1810, specifically at grasping plate 1871, is grasped by grasping/control instrument 1890. Specifically, in FIGS. 18a-e, the grasping/control instrument 1890 comprises a tip with upper jaw 1893a and lower jaw 1893b, configured in such a manner to create, when shut, a receiving slot 1897 into which the grasping pad 1871 of support member 1870 may be grasped. The dimensions of the receiving slot 1897, such as the width and/or height of receiving slot 1897 may correspond with the dimensions of the support member 1870 at its grasping pad 1871 such that there will be a rigid coupling between the jaws and support member during the surgical procedure. FIG. 18*d* illustrates ledge 1859 within bead 1851 which may engage coupling tips positioned on opposing ends of lysing rod 1860. Support member 1870 may be preferably insulated, except within its holes, to prevent unwanted delivery of electrosurgical energy to tissues; thus, electrosurgical energy is directed to support member holes at which lysing rod 1860 becomes energized for energy delivery.

In this embodiment, facets 1852 may be positioned at the distal ends of the beads and the configuration of the tunnels in the end beads may capture corresponding elements as described in previous embodiments. For example, certain beads may comprise hole 1855 that may be positioned perpendicular to lysing rod hole 1858; holes 1855 may be available as a platform/location to add other features/embodiments (for example, antennae 1847 and/or sensor 1848) and/or to be used for cord/suture attachments for lysing tip manipulation and/or removal and/or be used for placement of luminescent and/or light production for visualization, for example, tritium and the like.

This description is intended to apply to holes in other embodiments herein similar to 1855.

In FIGS. 19*a-d*, an alternative structure for the support member 1970 of lysing tip 1910 is depicted, however, all other features of the embodiments depicted in all FIG. 17 and FIG. 18 may be the same in regards to or may apply to the embodiment depicted in FIG. 19. In FIG. 19, support member 1970 comprises a grasping pad 1971 with tab 1971*a*, however, in the depicted embodiment, grasping pad 1971 comprises an opening 1973 which may be either a blind hole or a through-hole. Opening 1973 may be configured to receive a corresponding projection 1996*a* formed on one or both of jaws of the tip of a grasping/control instrument, such as that in FIG. 19*b*, jaws 1993*a*/1993*b*, to facilitate a secure coupling during the surgical procedure. In addition, corresponding projection 1996*a* may be used to deliver energy from grasping/control instrument 1993 directly to the opening 1973 of support member 1970 which may be especially beneficial if jaws 1993*a*/1993*b* and grasping pad 1971 are coated with non-conductive insulation and projection 1996*a* and the tunnel of opening 1973 are not so coated with a non-conductive coating. Thus, in some embodiments projection 1996*a* may comprise a conductive, uncoated projection protruding from coated jaws.

In FIGS. 19*c* and 19*d*, an alternative embodiment of a non-CDTD system is illustrated comprising inner beads 1951*i* and outer beads 1951*o* coupled with a bow/support member 1970 and further comprising an energy window made up of a plurality of electrode termini 1906 for delivering energy such as RF. This embodiment is similar to that depicted in FIG. 15*a-k*. In some embodiments the RF energy delivered by the termini 1906 may be distinct from the RF energy delivered by the lysing segments between the adjacent beads. More particularly, in the depicted embodiment, the energy window comprises an energy window strip 1907 which is preferably made of a conductive material. Energy window strip 1907 comprises a plurality of energy window termini 1906 protruding from the energy window strip 1907. An insulation cover 1908 may be configured to be coupled with energy window strip 1907. In some embodiments insulation cover 1908 may be molded onto energy window strip 1907. Alternatively the insulation cover 1908 may be configured to receive the energy window strip 1907 or otherwise be coupled with energy window strip 1907. Preferably, the insulation cover 1908 comprises a non-conductive material. In the depicted embodiments, the insulation cover 1908 comprises an elongated base configured to cover the energy window strip but allow the energy window termini 1906 to protrude through the insulation cover 1908. In addition, the insulation cover 1908 comprises a plurality of protruding bead coupling members (not shown here, but as depicted in FIG. 15*h*, bead coupling member 1508'), each of which is configured to extend into and be coupled with one of the beads of the tip via hole 1955*o* (as shown in FIG. 15*i*, a cross-sectional view down/through the center of outer bead 1551*d*). Energy delivery conduit 1909 such as a wire may be coupled with the energy window strip 1907. Preferably, the energy delivery conduit 1909 is insulated from the energy delivery conduit that delivers energy to the lysing segments such that a distinct type of energy may be delivered therethrough.

In other embodiments, the energy windows may be configured to utilize energy of different modalities, including, but not limited to, laser, intense pulse light, resistive heating, radiant heat, thermochromic, ultrasound, mechanical, and/or microwave.

In alternative embodiments, the energy window strip 1907 may be configured to be positioned on the bottom of the device, thus mounted on the bottom of beads 1951*i*/1951*o*. However, in various implementations, a surgeon may simply invert the tip of a top-mounted energy strip 1907 so that it points in the opposite direction (for example, away from the surface skin and toward the subcutaneous tissues. This inward/subcutaneous direction of energy may be useful in directing energy toward the subcutaneous deposits in cellulite and other cosmetic conditions.

FIGS. 20*a*-20*o* depict another embodiment of a CDTD or non-CDTD system 2000. System 2000 comprises protrusions 2001 and recessions 2002. System 2000 comprises a lysing tip 2010 that is configured to be completely separable from any other element of the system, however, lysing tip 2010 is configured to work in conjunction with the substantially ellipsoidal-shape at the distal end of jaws 2093*a*/2093*b* of grasping/control instrument 2090, as this preferably insulated shape may serve the same functions as beads 2051*a*/2051*b* as previously discussed. Lysing tip 2010 comprises two beads 2051*a*/2051*b* positioned at opposite end of lysing member 2060. In the depicted embodiment, lysing member 2060 comprises plate 2060 which may comprise grasping pad 2071. Upon being grasped by grasping/control instrument 2090 to perform a surgical procedure, the distal tip 2093 of grasping/control instrument 2090 substantially mimics the shape and/or function of beads 2051*a*/2051*b* such that two lysing segments are defined on opposite ends between tip 2093 and bead 2051*a* on one side and between tip 2093 and bead 2051*b* on the other. In some embodiments, the portion of distal tip 2093 extending onto or beyond lysing plate 2060 may have an identical or at least similar distal shape and size to beads 2051*a*/2051*b*. For example, this portion of distal tip 2093 may have rounded/smooth surfaces that taper towards a rounded tip similar to beads. At the very least, it is preferred that distal tip 2093 be shaped and sized such that lysing plate 2060 can come in contact with or near contact with target tissues. Together, the beads 2051*a*/2051*b* and distal tip 2093 may function as blunt dissectors to separate tissues without cutting. While the device is energized with electrosurgical energy, beads 2051*a*/2051*b* and outer surface distal tip 2093 are preferably non-conductive in order to perform the blunt dissection function. The inside of jaws 2093*a* and/or its corresponding lower jaw 2093*b* define a receiving slot 2097 and one or both may be electrically conductive in order to permit electrosurgical energy to flow to the lysing plate 2060.

System 2000 is configured to prevent or limit lateral movement of outer beads 2051 by fixing bead holes 2053*a*/2053*b* in outer beads 2051*a*/2051*b* and corresponding lysing plate holes 2066*a*/2066*b* through which a resulting substantially solid object like a pin or glue may be inserted to effectively couple the beads 2051 to the lysing plate 2060. In alternative embodiments, lysing plate holes 2066*a*/2066*b* may be replaced with grooves that may receive the solid object(s) inserted through fixing bead holes 2053.

In alternative embodiments, the dimensions of plate 2060 may be reduced to approach the width and/or thickness of previously described lysing rods. In such embodiments, the corresponding tunnel in outer beads 2051*a*'/b' may be appropriately reduced to match corresponding dimensions and/or the corresponding grooves and in one or more of the jaws 2093*a*'/2093*b*' of the grasping instrument may similarly be modified to match that of at least a portion of rod 2060'. In alternative embodiments as shown in FIG. 200, upper jaw 2093*a*" may consist of a front portion that overhangs truncated lower jaw 2093*b*", thus reducing the possibility of tissue entry on forward motion. In other embodiments, the overhang may encompass a larger portion of the opposite jaw. In this depicted embodiment, jaws 2093*a*"/2093*b*" are configured such that despite the previously described overhang of upper jaw 2093*a*", when the jaws are in a closed configuration, the distal portion of the instrument 2090' substantially mimics the shape about the distal portions of the beads about the distal portion of the instrument 2090'.

In some embodiments, lysing member 2060' comprises a rigid and/or substantially rigid wire as shown in FIGS. 20*i*-20*o*. In such embodiments, one or both of jaws 2093*a*" and 2093*b*" may comprise a slot configured to receive the rigid wire/lysing rod 2060'. This slot 2097' may be configured so as to tightly receive lysing rod 2060' so as to prevent or at least inhibit rotation of lysing tip 2010'. Alternatively, slot 2097' may either be slightly larger than the diameter of lysing rod 2060' or may be configured to allow a user to adjust the size of slot 2097' by actuating one or both of jaws 2093*a*'/2093*b*' such that the user can provide for a desired amount of rotation corresponding with the force delivered to jaws 2093*a*'/2093*b*'. As previously mentioned, other features may be included to limit or selectively allow for rotation such as welds and/or spacers (for example, spacer 2062' extending from inside each outer bead or spacer 2062" coupled to lysing rod 2060' extending from side of outer bead to side of grasping jaw 2093*a*"/b"). For example, in some embodiments, spacers may be positioned adjacent to opposing outer beads 2051*a*'/b' such that jaw 2093*a*'/b' may grip lysing rod 2070' in between the two spacers. Such spacers may be used to either inhibit or selectively limit rotation by, for example, their shape, and/or proximity to jaws 2093*a*'/b'. In this embodiment, a surgeon may be able to dissect on one or more of the sides on the backstroke, possibly making surgery more efficient. In some preferred embodiments and implementations, allowing for reverse dissection, it may be preferable to either loosen the grip of the lysing rod or otherwise provide for a coupling between the jaws that is loose enough allow for rotation the lysing rod within the jaws. Alternatively, a rigid coupling between the lysing rod and the jaws may be provided and instead the beads may be configured to rotate about the lysing rod such that the distal ends of the beads become the proximal ends when the lysing tip is being reversed.

In alternative embodiments, lysing rod 2060' may not be end capped at the exact outermost portions of its tips. Instead any number of holes 2055' may be made at any number of angles to intersect the lysing rod 2060' and/or its tunnel 2054 or 2054' to deposit a material that restrains the lysing rod within the bead 2051*a*'/b' (for example, materials may include welds, glues, epoxies, plugs (2055*p*), and the like). In such embodiments, tunnel 2054' may be a blind tunnel not requiring full passage through bead 2051*a*'/b' as bead may be fixed/restrained internally. See for example FIGS. 20*j*/k showing side views of beads 2051*a*' and 2051*a*". FIG. 20*k* shows full passage of tunnel 2054 which intersects with hole 2055' (illustrated with dashed lines designating hole 2055' being internal to bead 2051*a*'). FIG. 20*j* illustrates tunnel 2054' (illustrated with dashed lines) which intersects with hole 2055' (illustrated with dashed lines designating hole 2055' being internal to bead 2051*a*") not extending to the outside of outer bead 2051*a*". This alternative embodiment may be applied to other embodiments herein. In alternative embodiments, beads 2051*a*'/b' may be replaced with beads of any shape, including but not limited to those depicted in FIGS. 12*aa* to 12*rr*. In some embodiments wherein a spacer is positioned between a lysing rod and grasper jaws, the tolerance between the lysing rod and a spacer may allow for rotation of the lysing rod within the spacer and thus allow for rotation of beads with respect to a spacer and/or grasper. The tolerance may be adjusted to allow for a predetermined amount of rotation.

In the embodiment illustrated in FIGS. 21*a*-*e*, the lysing tip 2110 comprises grasping plate 2161, lysing rod 2160, and beads 2151*a*/2151*b*. In this embodiment the inner surfaces of upper jaw 2193*a* and lower jaw 2193*b* (of grasping/control instrument 2190) are configured to match or substantially match the upper and lower surfaces of grasping plate 2161 in the closed configuration (thus creating receiving slot 2197). The lysing rod 2160 may be permanently or temporarily coupled to grasping plate 2161 for example by weld, and/or by snap-fit between the distal end of the grasping plate 2161 and the center/proximal portion of lysing rod 2160. In the depicted embodiment, the width of the grasping plate tapers from a widened portion of the proximal end to a narrowed portion of the distal end which tapering may mimic or substantially mimic similar tapering of the corresponding jaw 2193*a*/2193*b*. The length of grasping plate 2161 may be similar to or identical to the length of one or both jaws 2193*a*/2193*b*. In some embodiments, the outer surfaces of jaws 2193*a*/2193*b* may be surface-coated with a non-conductive dielectric coating.

Lysing tip 2110 may comprise a plurality of protrusions 2101 comprising distal portions of beads 2151 and recessions 2102 between each bead pair. The portions of lysing member 2160 extending between adjacent beads 2151*a*/2151*b* may be considered the lysing segment.

As previously mentioned, beads 2151 may be coupled with one another by way of a single lysing member 2160 extending through tunnels 2154 extending through each of the respective beads 2151. In the depicted embodiment, beads 2151 each comprise a non-symmetrical shape and/or may be eccentric relative to tunnels 2154. More particularly, tunnels 2154 are positioned distally of a central portion of beads 2151 such that there is more material proximally of tunnels 2154 than distally. Beads 2151*a* and 2151*b* have a similar distal or frontal shape (from the perspective of the treatment side of tip 2110) but have a flattened, thus shorter (from the elongated-axis perspective), rear end 2153*a*. In other embodiments, beads may have a greater elongated-axis dimension.

As previously mentioned, this may be preferable for some embodiments, particularly embodiments in which beads 2151 can at least partially rotate on the lysing rod or other lysing member 2160 to allow the lysing tip 2110 to be directed through tissue in a desired manner. In some contemplated embodiments, beads may be symmetrical.

Preferably, the entire surfaces of the beads 2151, or at least outer beads 2151a and 2151b, may be smooth or at least substantially smooth. Or, at least all surfaces that may be expected to contact tissue during a surgical procedure may be substantially smooth. For example, providing a smooth front end and a smooth trailing end may allow the lysing tip to be moved in a forward direction and then in a rearward direction back and forth without catching an undesirable amount of tissue on beads to inhibit such movement. As shown, in some embodiments, the trailing end of some beads, such as beads 2151a and 2151b, may comprise a flat surface such that each bead comprises a frusto shape or another similar shape. Preferably, at least the forward or distal surface of each bead is substantially smooth and defines an ellipsoidal shape or another shape having a substantially smooth forward surface. In the depicted embodiment, beads surfaces may have facets 2152.

In other contemplated embodiments, providing a rough trailing end may create frictional drag on that portion of the bead thus helping reorient the front end of the bead for further tissue passage. Thus, in some embodiments, the trailing end may have a rougher surface than the front end.

As previously mentioned, in some embodiments, it may be desirable to allow beads 2151 to rotate, at least partially, on lysing member 2160. Thus, beads 2151 may not be fixed three-dimensionally with respect to lysing member 2160 and/or one or more other elements of lysing tip 2110. In some such embodiments, beads 2151 may be at least partially rotatable with respect to the remainder of lysing tip 2110. In embodiments in which beads 2151 are rotatable in this manner, it may be desirable to use a lysing member having a circular cross section.

Preferably, lysing member 2160 terminates within outer beads 2151a and 2151b. Thus, it may be desirable to melt, tip, ball, crimp, fold, tie, or otherwise couple the ends of lysing member 2160 within outer beads 2151a and 2151b at opposing lysing member coupling tips 2163a and 2163b. Preferably, lysing tip 2110 is configured such that each of beads 2151 is rotatable independent of one another.

Coupling tip 2163a/b may be configured to engage a ledge positioned at a transition point between two concentric tunnels (2159a/2159b) (similar to that depicted in FIG. 17c at tunnels 1759a/1759b). More particularly, outer tunnel 2159b may comprise a larger diameter or other cross-sectional dimension than inner tunnel 2159a such that lysing member 2160 may extend through inner tunnel 2159a but coupling tip 2163a due to its larger size may be configured to extend through outer tunnel 2159b without passing through inner tunnel 2159a. In other embodiments, there may be a single tunnel that tapers (similar to tunnel 1759c in FIG. 17c) from a larger dimension on the outer side of bead 2151 to a smaller dimension toward the inside of the bead relative to the lysing tip 2110.

In some embodiments, at least a portion of grasping plate 2161 may comprise a conductive material and may be configured to receive electrosurgical energy, such as from a grasping/control instrument 2190 or another surgical tool or external wire, and deliver such energy to lysing member 2160. For example, in some such embodiments, electrosurgical energy may be delivered through grasping jaws 2193a/2193b, into grasping plate 2161 and into lysing member 2160. In other embodiments, grasping plate 2161 may be insulated and electrosurgical energy may instead be delivered to lysing tip 2110 in another manner. For example, upper jaw 2193a may be insulated but comprise one or more non-insulated projections 2196a and 2196b that may correspond to one or more non-insulated openings 2173a and 2173b respectively in grasping plate 2161 (that is otherwise substantially insulated). Although a single projection/opening may be used in some embodiments, it may be preferable to have two such projections/openings as depicted in FIGS. 21b and 21c. Providing two or more projections/openings may improve stability of the lysing tip during treatment. One or both of the projections/openings may be configured to deliver electrosurgical energy from instrument 2190 to lysing tip 2110. This configuration with multiple projection/opening pairs may be used in similar embodiments disclosed herein.

In embodiments comprising a free-floating lysing tip, including the embodiments of FIGS. 17-31 and 35-38, certain preferred embodiments may have a size/length TL (as illustrated in FIGS. 10d/10e) of about 15 mm from the end of one protrusion and/or bead to the opposite protrusion/bead on the opposite end; the height BH (as illustrated in FIGS. 10d/10e) of the largest outer beads may range from 2 mm to 10 mm. In some embodiments, this dimension may be defined by the distance from the upper end of one or more (in some embodiments, each) beads to the lower end of one or more beads. In some free-floating embodiments, the lysing tip may have a size/width TW (as illustrated in FIGS. 10d/10e) of about 4.5 mm from the distal end of the beads to the proximal end of the lysing tip. However, it should be understood that a wide variety of alternative shapes and/or sizes may be usable depending upon the particular surgical procedure involved.

FIGS. 22a-e illustrate system 2200 comprises lysing tip 2210 and grasping/delivery instrument 2290, this embodiment only differing from system 2100 in that beads 2251a/2251b are rounded on the outer proximal corners 2253a/2253b relative to the axis of the grasping/control instrument 2290. Rounding the outer proximal corners may further inhibit lysing tip 2210 from catching tissue rather than cutting or bluntly separating said tissue. Lysing tip 2210 comprises grasping plate 2261, lysing rod 2260, and 2 beads 2251a/2251b through which lysing rod 2260 extends (through tunnels in beads 2251 similar to tunnels through beads 2151a/2151b in FIG. 21a-21e). Each of beads 2251 may be coupled to lysing rod 2260 by coupling tips 2263a/2263b and as otherwise set forth herein. Upper and lower jaws 2293a/2293b (that, when closed, define receiving slot 2297) respectively may grasp grasping plate 2261. Lysing tip 2210 is configured to be completely separable from the grasping/control instrument 2290 of the system. Lysing tip 2210 may comprise a plurality of protrusions 2201 comprising beads 2251a/2251b and recessions 2202 between the bead pairs.

FIGS. 23a-d illustrate system 2300 comprising lysing tip 2310 and grasping/control instrument 2390, this embodiment only differing from systems 2100 and 2200 in that beads 2351 have an ellipsoidal shape along the entire length of the beads and comprise holes 2355 which may be configured for receipt of a cord that may be a suture, hook, or similar device that may grasp and hold lysing tip 2301. This may be used as a safety feature for ensuring that a surgeon has the ability to retrieve lysing tip 2301 in the event that it becomes uncoupled from instrument 2390. This additional length as compared to the shapes of the beads in embodiments in FIGS. 21a-e and 22a-e may assist in maintaining the optimal positioning for beads 2351 to migrate through and/or separate and/or cut tissue. Lysing tip 2310 comprises grasping plate 2361, lysing rod 2360, and 2 beads 2351 through which lysing rod 2360 extends (through tunnels in beads 2351 similar to tunnels through beads 2151a/2151b in FIG. 21a-21e). Each of beads 2351 may be coupled to lysing rod 2360 by coupling tips 2363 and as otherwise set forth herein. Upper and lower jaws 2393a/2393b respectively may grasp grasping plate 2361. Lysing tip 2310 is configured to be completely separable from the grasping/control instrument 2390 of the system. Lysing tip 2310 may comprise a plurality of protrusions 2301 comprising beads 2351 and recessions 2302 between the bead pair.

Given the extra length of the beads 2351 in this embodiment, material is available for holes 2355. Hole(s) 2355 may, together with a cord 2344, for example, comprise an example of means for detachably maintaining retrievability of a lysing tip. In preferred embodiments and/or implementations, suture 2344 or another loopable element may be looped through one or more such hole(s) and then may extend through one or more cannulas used to deliver lysing tip 2310 proximally back to a surgeon. In this manner, in the event of a failure to grasp or otherwise couple lysing tip 2310 to a grasping/control instrument, such as grasping/control instrument 2390, lysing tip 2310 may be retrieved from within a patient's body by pulling on suture 2344 to retract lysing tip 2310 though a cannula. In some embodiments, hole 2355 may also or alternatively be used to maintain position of lysing tip 2310 while awaiting delivery of a grasping/control instrument 2390 for performing surgical procedures. Upon properly coupling lysing tip 2310 with an appropriate tool for grasping and/or controlling lysing tip 2310, such as grasping/control instrument 2390, a surgeon may cut suture 2344, preferably near a knot or other feature used to form a loop around hole 2355. If a suture 2344 or other similar material/element is used that is sufficiently flexible and non-disruptive, this shorter loop may be configured to be present during a surgical procedure using lysing tip 2310 without unduly interfering with the procedure. In alternative embodiments, holes 2355 may be available as a platform/location to add other features/components such as providing a location for a placement of one or more sensors and/or RFID location component(s) and/or being used for placement of luminescent and/or light production element(s) for visualization, for example, tritium and the like.

In alternative embodiments, hole 2355 may be moved to fully or partially intersect tunnel 2354 thus allowing communication with lysing rod 2360; thus a weld, plug, glue, insert or other method of fixation may be inserted via hole 2355 to attach to lysing rod 2360 thus restricting lateral movement of a bead. To reduce escape of electrosurgical energy through hole 2355, an insulator comprised of epoxy, plastic, ceramic or the like may be placed in part or all of the remaining hole 2355. This alternative embodiment may be applied to other embodiments herein.

Another embodiment is depicted in FIGS. 24a and 24b. System 2400 comprises modular lysing tip 2410 comprising recessions 2402 created by adjacent protrusions 2401. Lysing tip 2410 further comprises a support member 2470 defining a bow shape 2470 that may be coupled physically and electrically to a shaft 2499a extending proximally from bow 2470. Shaft 2499a may be conductive and/or may reversibly couple with conductive slot 2479s formed in an electrosurgical instrument 2479 which may be an electrosurgical pencil (such as a 'Bovie' and/or other electrosurgical pencil and/or other electrosurgical adaptive device(s)) capable of receiving shaft 2499a, through which electrosurgical energy may be directed and controlled to lysing tip 2410. Lead 2479L may be coupled with an electrosurgical generator. Beads 2451a/2451b/2451c/2451d may comprise facets 2452 and may be coupled to support member 2470 by lysing rod (not shown in FIGS. 24a/24b) which is covered by spacers 2462a/2462b/2462c. Coupling tips 2463, as stated earlier herein, couple the lysing rod in place within outer beads 2451a/2451d. Insulation 2499b may cover or substantially cover shaft 2499a to facilitate handling by personnel and may be extended to cover all or portions of bow 2470 preventing electrosurgical energy from being distributed to tissue from the bow 2470. This embodiment may have uses in open surgeries and/or non-CDTD procedures.

An alternative embodiment is depicted in FIG. 24c. System 2400' comprises modular lysing tip 2410' (which is comprised of outer beads 2451a'/2451d', and lysing rod 2460'), shaft 2499a' and insulated covering 2499b' that terminates distally with bulbous projection/protrusion 2499t. One or more of the exposed segments of lysing rod 2460' may be covered by spacers 2462'. Lysing rod 2460' may be electrically coupled to a shaft 2499a' extending proximally from lysing rod 2460'. Shaft 2499a' may be conductive and/or may reversibly couple with an electrosurgical instrument 2479 which may be an electrosurgical pencil (such as a 'Bovie' and/or other electrosurgical pencil and/or other electrosurgical adaptive device(s)) capable of receiving shaft 2499a' within a conductive slot 2479s through which electrosurgical energy may be directed and controlled to lysing tip 2410'. Insulated covering 2499b' may cover or substantially cover shaft 2499a' to facilitate handling by personnel and may be extended distally in the shape of or to substantially mimic the shape of the distal portion of a bead 2451a'/2451d', thus serving as a $3^{rd}$ projection/bead. More particularly, this bulbous protrusion 2499t may extend distally as far as the tips of beads 2451a'/2451d'. This embodiment may have uses in open surgeries and/or non-CDTD procedures.

The CDTD and/or non-CDTD systems and/or apparatus (hereafter "TD") disclosed herein may be used to treat the following disclosed below.

In a general implementation of a method using one or more of the devices described herein, a tip deployment pocket may be created at or near the entrance incision, for example, in skin or muscle. Alternatively, some implementations may not require a tip deployment pocket. The lysing tip of the TD may be inserted through the entrance incision and in some implementations into the tip deployment pocket while in other implementations directly into a body cavity. The lysing tip may then be reconfigured from a delivery configuration to a treatment configuration such as by rotating the lysing tip and/or coupling the lysing tip to a grasping/control instrument. The lysing tip may then be activated. A dissection path may then be made to one or more target tissues. The lysing tip may then be used to dissect around or through target tissues and/or used to treat the target tissue. In some implementations, the one or more target tissues and/or surrounding tissues may then be treated to achieve hemostasis with the lysing tip or the tissue modification tip (TMT). The lysing tip may then be rotated back to a delivery configuration to allow the lysing tip to be withdrawn. In some implementations, the lysing tip may delivered and/or withdrawn using one or more cannulas. In other implementations, the lysing tip may delivered and/or withdrawn without a cannula.

In FIGS. 25a-e, system 2500 a tether 2544 extends through an opening 2593h formed in a jaw 2593 of the grasping/control instrument 2591. Tether 2544 may further be configured to be coupled with free-floating lysing tip 2510 that may be comprised of support member/bow 2570, grasping pad 2571 located on support member/bow 2570, beads 2551, spacers 2561, and rod (not shown). In the depicted embodiment, tether 2544 couples with grasping pad 2571. More particularly, grasping pad 2571 comprises an opening 2571h configured to receive the tether 2544 as shown in the cross-sectional view of FIG. 25d. In some embodiments, the opening 2571h may comprise a blind opening in which case tether 2544 may comprise a distal bulb 2544c and/or stop that prevents tether 2544 from pulling through the opening 2571h. Alternatively, opening 2571h may comprise a through-hole which may allow tether 2544 to extend all the way through opening 2571h on both ends of the opening.

In the depicted embodiment, by pulling on tether 2544 either manually or by way of a mechanism, tip 2510 may be configured to be directed into the jaws 2593/2594 of grasping/control instrument 2591. In still other embodiments, tether 2544 may be coupled with tip 2510 without also extending through one or both of jaws 2593/2594. In this manner the tip 2510 may be retrieved simply by pulling on the tether 2544. In other embodiments, a tether 2544 may extend through other portions of the grasping instrument, such as the bottom jaw 2594 and/or both jaws 2593/2594 and/or through the center of the grasping/control instrument 2591.

In some embodiments, one or more magnets may be used to guide lysing tip 2510 towards and/or lock lysing tip 2510 in a desired location such as within jaws 2593/2594 of the grasping control instrument 2591. For example, one or more magnets may be positioned along grasping pad 2571 (magnet 2592p) and/or within one or both of jaws 2593/2594 (magnet 2592j) of system 2500. If a magnet is positioned within one or both jaws 2593/2594, grasping pad 2571 may comprise a magnetic portion and/or element configured to engage such magnet(s). Similarly, if a magnet is positioned on grasping pad 2571, a magnetic portion and/or element may be positioned within one or both jaws. Alternatively, magnets may be positioned on both the grasping pad and one or both of the jaws.

The tether may be packaged with a tether already attached or medical personnel at the procedure may choose an appropriate tether to thread and catch in the lysing tip and thread through the jaw with the through-hole.

The surgeon may attach the cord/suture to hole 2571 leaving a tail of stitch that may be up to 50 cm long. The grasping instrument 2591 containing hole 2593h may be inserted into the body percutaneously and exit through an larger trocar for example located in the umbilicus. The tail of the suture/cord may then be pulled back out the original percutaneous incision and fed through hole 2593h. The grasping instrument containing hole 2593h may then be reinserted percutaneously and the lysing tip 2510 fed down the second (for example, umbilical trocar) percutaneous body cavity entry/wound. The cord/suture tail is then pulled by the surgeon to seat the frame within the grasper.

Yet another embodiment of a lysing tip 2610 comprising beads 2651a/2651b/2651c/2651d is depicted in FIGS. 26a and 26b. Lysing tip 2610 comprises a support member 2670 which may be in the approximate shape of a bow as previously discussed. However, the distal end of lysing tip 2610 is bowed in the opposite direction such that middle beads 2651b/2651c protrude distally to a greater degree than outer beads 2651a/2651d. In addition, lysing rod 2660 rather than being straight as in previous embodiments collectively curves and/or bows distally. In some embodiments, however, each of the various segments 2662a/2662b/2662c between adjacent beads may be straight or be substantially straight. As also previously discussed, support member 2670 may comprise an opening 2673 which may be configured to receive a tooth or other projection of a grasping/control instrument (not shown in this figure, but depicted in other embodiments). In FIG. 26a, support member 2670 may further comprise a tongue 2676 that protrudes distally to couple with the center segment of lysing rod 2660. More particularly, in the depicted embodiment, tongue 2676 comprises a groove defined on either side by edges 2676' configured to receive center segment of lysing rod 2660 so as to deliver electrosurgical energy from an instrument into lysing rod 2660. As previously discussed, each of the various segments of lysing rod 2660 is preferably electrically coupled through adjacent beads to its adjacent lysing member. As shown in FIG. 26a, spacers may be provided between outer beads and but not the adjacent middle beads. This may be because tongue 2676a/2676a' may serve as a suitable spacer. However, as shown in FIG. 26b, in some embodiments, center spacer 2662b may be provided on the center segment of lysing rod 2660 if needed or desired.

FIGS. 27-30 comprise various embodiments of free-floating lysing tips that may be used with the various surgical tools set forth, for example, in FIGS. 17a-m. However, alternative embodiments are contemplated in which these free-floating lysing tips may instead be modified so as to be coupleable with actuation rods and/or one or more cannulas as set forth herein such that the free-floating lysing tips become non-free-floating lysing tips. as shown, for example, in FIGS. 14a-n.

In FIGS. 27a-j, lysing tip 2710 is "free-floating" (can be uncoupled from any control instrument or cannula) and comprises a plurality of sleeves 2780/2781 positioned on lysing rod 2760 which may correspond in number to the number of beads 2751a/b/c/d. Beads 2751a/b/c/d may be molded onto or otherwise positioned onto one or more sleeve configurations, for example, outer bead sleeve configuration 2780a/2780b and middle bead sleeve configuration 2781a/2781b. Preferably sleeves 2780/2781 are made of a material configured to insulate the material making up the beads from the heat generated by the lysing rod 2760 during a surgical procedure. Sleeves 2780/2781 may also or alternatively serve as hubs permitting rotation of beads around the axis of lysing rod 2760. For example, the beads may rotate about the rod upon encountering tissue similar to that of a vegetable/fruit peeler.

Middle bead sleeve 2781 may comprise a raised band 2784 which is formed at a central or substantially central location around both middle-bead sleeves 2781a/2781b which may serve to prevent lateral movement of middle beads 2751b and/or 2751c off of middle-bead sleeves 2781a/2781b. Bead band channel 2753 may be configured to accept raised band 2784. Likewise, outer bead sleeves 2780a/2780b comprise an external ledge 2786a and internal ledge 2786b that transitions between a larger diameter portion 2782 and a smaller diameter portion 2783 of an inner tunnel of the outer bead sleeves. The larger diameter portion 2782 is alternatively referred to herein as a raised band. In some preferred embodiments comprising bead sleeves, the beads may comprise a molded or moldable material, such as a moldable, biocompatible plastic, gelatin (for example, protein, polysaccharides and/or derivatives thereof), or hydrogel, for example. In some such embodiments, the beads may be overmolded onto each of their respective sleeves.

External sleeve ledge 2786a may be configured to engage a corresponding internal bead ledge 2759 within outer beads 2750a/2750b. Similarly, outer bead sleeves 2780a/2780b may comprise two concentric holes with ledge 2786b approximately half-way between the opposite openings. Internal bead ledge 2786b may be configured to engage coupling tips 2763. This configuration creates a feature that may prevent lateral movement of outer beads 2751a/2751d off of outer bead sleeves 2781a/2781b. In other embodiments, coupling tip 2763 may engage a single tunnel that tapers (similar to tunnel 1759c in FIG. 17c) from a larger dimension on the outer side of bead to a smaller dimension toward the inside of the bead as depicted in FIG. 27j. In some embodiments, it may be desirable to provide features and/or elements that inhibit or limit the ability of the electrosurgical energy to discharge from the opposing ends of the lysing rod 2760 at coupling tips 2763. Thus, in some such embodiments, coupling tips 2763 may be coated or covered with a suitable insulating material such as an epoxy with non-conductive properties. Alternatively, outer bead hole 2754 at the end with the larger-opening may be capped or plugged with an element configured to be received or otherwise engage the larger opening of the bead. Preferably, this element will have non-conductive properties similar to the insulating material previously referenced.

As depicted in FIG. 27c, lysing tip 2710 may comprise protuberances 2765c/2765d positioned on/coupled to lysing rod 2760, one protuberance 2765c/d may be positioned on each side of each middle bead 2751c as shown in FIG. 27c. Protuberances 2765c/d may serve to prevent or limit lateral movement of middle beads 2751b/2751c on the lysing rod 2760 and/or may, depending upon a protuberance pair's distance from a bead, serve to limit or prevent rotation of beads around the axis of lysing rod 2760. In alternative embodiments, one or more spacers 2762 (and such as those in FIGS. 9a-9e, spacers 962) may be used in place of protuberances 2765c/d. In the depicted embodiment, spacer 2762 in FIG. 27c is pentagonal in cross-section; in other embodiments, alternative spacers with unique cross-sectional configurations, such as for example those set forth in FIGS. 12h-t, may be used. In alternative embodiments, lysing rod 2760 may be deformed prior to coupling with a middle bead sleeve such that the outer diameter of 2760 may couple via friction fit with the inner tunnel surface of middle bead sleeve 2781. FIGS. 27b and 27c purposefully have components removed to expose inner components and also illustrate different means to hold middle beads in an intended position via protuberances and/or spacers. Alternatively, middle bead sleeves 2781 may be more loosely coupled with lysing rod 2760 so as to allow for rotation of middle bead sleeve 2781 thereon, and thereby allow for at least some rotation of their corresponding beads on lysing rod 2760. In alternative embodiments, lysing tip 2710 may be configured without a solid lysing rod and/or without spacers and/or welds and the like. In such embodiments, internal bead tunnels 2754 and support member holes 2767a/2767b may be configured to accommodate a hollow lysing rod similar to that depicted in FIG. 17k. Between beads, the hollow lysing rod may be deformed in a manner to prevent lateral movement of beads and/or prevent rotation of beads. The hollow lysing rod may be deformed minimally or to a point that it is substantially flat. In such embodiments, it may be preferable for the front edge to point distally as the leading front edge. In such embodiments, screws may secure one or both ends of the hollow lysing rod within outer beads 2751a/2751d. The configurations of this alternative embodiment may be available for any other similar embodiment contemplated herein.

In this configuration, adjacent protrusions 2701 create recessions 2702 in which recessed lysing rod 2760 may deliver electrosurgical energy during a surgical procedure.

FIG. 27e illustrates a perspective view of outer bead 2751a coupled to outer bead sleeve 2780a with coupling tip 2763 being recessed within outer bead sleeve 2780a. Lysing rod 2760 is illustrated in FIG. 27d being received within outer bead sleeve 2780a. FIG. 27d illustrates how lysing rod, sleeve and bead may be assembled: Outer bead sleeve 2780a may be extended into outer bead 2751a stopping at the point that external sleeve ledge 2786a reaches the internal bead ledge 2759 which may be followed by extension of lysing rod 2760 through outer bead sleeve 2780a stopping at the point coupling tip 2763 reaches the internal sleeve ledge 2786b created by the larger-diameter bead sleeve hole 2786h and smaller-diameter sleeve hole 2787a. In alternative embodiments, as depicted in FIG. 27j, the sleeve 2780' may be configured to have a single cone-shaped tunnel 2786' that tapers (similar to tunnel 1759c in FIG. 17c) from a larger dimension on the outer side of bead to a smaller dimension toward the inside of the bead in order to engage coupling tip 2763.

Outer beads 2751a/d may comprise hole 2755 through which a cord may be hooked and/or tied in order to facilitate deployment or retrieval as earlier stated herein regarding hole 1755 in FIG. 17d.

Support member 2770 may be preferably insulated, except for regions on which it is desired to transfer electrosurgical energy such as (1) at one or more surfaces of grasping pad 2771, (2) within the 2 distal support member holes (as shown in FIG. 17e, 1767a/1767b), and/or (3) the opposing distal ends of support member 2770, in some cases distal of lysing rod 2760 in order to deliver electrosurgical energy not only through lysing rod 2760 but also through these distal ends of support member 2770.

Support member 2770 in the current embodiment comprises a bow shape comprising two opposing end tips comprising holes or other openings through which lysing rod 2760 extends. The two tips of support member 2770 may extend far enough distally to provide sufficient material to form the lysing rod through-holes. Alternatively, openings comprising slots or the like may be formed at one or both of the two opposing tips of support member 2770 if desired.

The two tips of support member 2770 preferably do not extend beyond the distal tip of any bead and preferably remain as proximal to lysing rod 2760 as possible. The ends/tips of support member 2770 may or may not be electrically insulated. If insulated, said tips will act more like beads 2751a/b/c/d to physically separate tissues or tissue planes; however, if not insulated, said tips may perform like lysing rod 2760 delivering electrosurgical energy to lyse tissue.

FIGS. 27h-i illustrates middle bead 2751b comprised of facets 2752 (2 of a total of 4 on this bead are identified in the illustration), coupled to middle bead sleeve 2781 through which lysing rod 2760 extends. Middle bead 2751b may differ from outer bead in that its length may be shorter and its rear wall 2758 may be flat or substantially flat. The length of middle bead 2751b may be such that the rear portion of middle bead 2751b/c may not contact support member 2770 in its relaxed state and/or when the bead's distal tip is pointing in the same direction as lysing tip 2710, however, middle bead 2751b may contact support member 2770 if lysing rod 2760 is pushed back or otherwise deformed during a surgical procedure and/or the middle bead 2751b/c is rotated about the lysing rod 2760 such that the top or bottom of the rear portion of the bead may contact support member 2770. For example, the spacing between middle beads 2751b/c and support member 2770 may be used to selectively limit the amount with which middle beads 2751b/c may rotate. Similarly, in some embodiments, this spacing may be configured to serve as a backstop to allow for a predetermined amount of proximal movement of middle beads 2751b/c during a procedure.

In FIGS. 28a-L, outer beads 2851a/2851d define an annular shape. to More particularly, outer beads 2851a/2851d comprise annular bead structure 2857. In addition, these beads may be elongated or oval in cross section. Middle beads 2851b/2851c on the other hand have similar defined protrusions on their distal ends, however, proximal ends of these beads terminate in opposing knobs 2855 rather than defining a full annular shape. In both middle and outer beads, a bead hub 2856 is positioned within annular bead structure 2857 to allow for coupling of beads 2851 with their corresponding sleeves. Bead hub 2856 is coupled to annular bead structure 2857 by way of one or more spokes 2858 and/or a bead hub frame 2856a. In the depicted embodiment, bead hub frame 2856a extends about a central portion of bead hub 2856 from bead hub 2856 to annular bead structure 2857. Bead hub frame 2856a is only coupled to a portion of annular bead structure, and a portion of bead hub 2856. However, alternative configurations are possible in which bead hub frame 2856a may be coupled to the entire annular bead structure 2857 and/or the full periphery of bead hub frame 2856a. A single spoke 2858 may extends from bead hub 2856 in a direction perpendicular to bead hub frame 2856a. As best depicted in FIG. 28k, spoke 2858 protrudes laterally (towards opposite lateral ends of the lysing tip) in both directions beyond a profile of the annular bead structure 2857. However, bead hub frame 2856a does not protrude laterally in this manner. Spoke 2858 also extends from bead hub frame 2856a. However, other embodiments are contemplated in which additional spokes may be used, in some such embodiments in place of a bead hub frame 2856a, as discussed below. Such annular shapes may be beneficial components may be less costly to produce, they may withstand heat generated from the interaction of electrosurgical energy with tissue, and they may provide more benefits for dissecting the more delicate tissues such as those found in the abdomen including tissues attached to bowel and mesentery.

In this configuration, adjacent protrusions 2801 create recessions 2802 in which recessed lysing rod 2860 may deliver electrosurgical energy during a surgical procedure.

FIG. 28d is a side view of lysing tip 2810 comprising support member 2870, coupling tip 2863, spokes 2858a/2858b/2858c coupling bead hub 2856 with bead annular structure 2857.

FIGS. 28e and 28f illustrate perspective and side views of outer beads 2851 coupled to outer bead sleeve 2880 through which lysing rod 2860 extends. Bead hub 2856 may be formed on outer bead sleeve 2880, said hub coupling to inner surface of annular structure 2857 via spokes 2858a/2858b/2858c.

Outer bead sleeves 2880a/2880b may comprise an internal and/or an external ledge that transition between a larger diameter portion and a smaller diameter portion of the outer bead sleeves. For example, outer bead sleeve may comprise an external sleeve ledge 2886a and internal sleeve ledge (as illustrated in FIGS. 27a-j, internal sleeve ledge 2786b). External sleeve ledge 2886a may be configured to engage a corresponding internal bead ledge (as illustrated in FIGS. 27a-j, internal bead ledge 2759). within outer beads 2850a/2850b. More particularly, outer bead sleeves 2880a/2880b may comprise two concentric holes with an internal bead ledge approximately half-way between the opposite openings. The internal bead ledge may be configured to engage coupling tips 2863. This configuration creates a feature that may prevent lateral movement of outer beads 2851a/2851d off of outer bead sleeves 2881a/2881b.

FIG. 28h illustrates how lysing rod, sleeve and bead may be assembled: Outer bead sleeve 2880a may be extended into outer bead 2851a stopping at the point that external sleeve ledge 2886a reaches the internal bead ledge which may be followed by extension of lysing rod 2860 through outer bead sleeve 2880a stopping at the point coupling tip 2863 reaches the internal sleeve ledge created by the larger-diameter inner sleeve hole and smaller-diameter sleeve hole (as illustrated in FIGS. 27a-j at internal sleeve hole 2786a and external sleeve hole 2786b).

As depicted in FIGS. 28a-L, lysing rod 2860 may be deformed prior to coupling with bead sleeves in the areas to be coupled with the sleeves such that the outer diameter of lysing rod 2860 may couple via friction fit with the inner tunnel surface of middle bead sleeve 2881. For example, these regions may be flattened slightly or otherwise made into a slightly elongated or oval shape so as to improve the ability of the sleeves to engage the lysing rod in these regions via friction fit. In alternative embodiments, lysing tip 2810 may comprise protuberances positioned on/coupled to lysing rod 2860, one protuberance, for example, may be positioned on each side of each middle bead 2851c. Protuberances may serve to prevent or limit lateral movement of middle beads 2851b/2851c on the lysing rod 2860 and/or may, depending upon a protuberance pair's distance from a bead, serve to limit or prevent rotation of beads around the axis of lysing rod 2860. In alternative embodiments, one or more spacers (and such as those in FIGS. 11a-f, spacers 1162a/b/c) may be used in place of protuberances 2865. Alternatively, middle bead sleeves 2881 may be more loosely coupled with lysing rod 2860 so as to allow for rotation of middle bead sleeve 2881 thereon, and thereby allow for at least some rotation of their corresponding beads on lysing rod 2860.

In alternative embodiments, the sleeve may be configured to have a single cone-shaped tunnel that tapers and may engage coupling tip (similar to tunnel 2786' in FIG. 27j) from a larger dimension on the outer side of bead to a smaller dimension toward the inside of the bead. In alternative embodiments, lysing tip 2810 may be configured without a solid lysing rod and/or without spacers and/or welds and the like similar to that depicted in FIG. 17k. Between beads, the hollow lysing rod may be deformed in a manner to prevent lateral movement of beads and/or prevent rotation of beads. The hollow lysing rod may be deformed minimally or to a point that it is substantially flat. In such embodiments, it may be preferable for the front edge to point distally as the leading front edge. In such embodiments, screws may secure one or both ends of the hollow lysing rod within outer beads 2851a/2851d. The configurations of this alternative embodiment may be available for any other similar embodiment contemplated herein.

FIGS. 28i-L illustrate middle bead 2851b/2851c coupled to middle bead sleeve 2881 through which lysing rod 2860 extends and from which middle band 2984 protrudes. Middle bead 2851b may differ from outer bead 2851a in that its length is truncated proximal to bead hub 2856 terminating in knobs 2855. Knobs 2855 may inhibit the lysing tip 2810 from catching tissue rather than cutting or separating it and/or may limit rotation of middle bead 2851 around lysing rod 2860. The length of middle bead 2851*b* may be such that knobs 2855 and proximal portions of bead hub 2856 may not contact support member 2870 in its relaxed state and/or when the bead's proximal tip is pointing in the same direction as lysing tip 2810. However, in this embodiment, middle bead knobs 2855 may contact support member 2870 if lysing rod 2860 is deformed during a surgical procedure and the middle bead 2851 is rotated about the lysing rod 2860 such that the top or bottom of the rear portion of the bead may contact support member 2870. The spacing between middle beads 2851 and support member 2870 may be used to selectively limit the amount with which middle beads 2851 may rotate. In this embodiment, support member 2870 may not serve as a backstop to permit a predetermined amount of proximal movement of middle beads 2851*a*/2851*b* during a procedure. Middle bead sleeve may comprise raised band 2884 to engage the bead to limit lateral movement.

FIGS. 29*a-f* differs from that of 28*a*-L in that middle beads 2951*b*/2951*c* instead of terminating at knobs (knobs 2855 in FIGS. 28*a*-L) define an annular shape having a flattened or slightly arced rear end 2955 and outer beads comprise less bead hub frame material by directly attaching the proximal portion of the distal tip to the bead hub 2256.

Adjacent protrusions 2901 create recessions 2902 in which recessed lysing rod 2960 may deliver electrosurgical energy during a surgical procedure.

FIG. 29*c* is a side view of lysing tip 2910 comprising support member 2970, coupling tip 2963, spoke 2958*a* with direct connection points 2958*g*/2958*h* coupling bead hub 2956 with outer bead 2951*a*/2951*d* annular structure 2957.

In both middle and outer beads, a bead hub 2956 couples with its corresponding sleeve. In middle beads, one or more spokes 2958*a*/2958*b*/2958*c* may extend from bead hub 2956 to the annular structure 2957 as support and bead hub frame 2956*a* by itself or in conjunction with spokes may couple the annular structure to bead hub 2956. As illustrated in FIG. 29*c*, outer beads 2951 comprise bead hub 2956 coupled to annular structure 2957 by spoke 2958*a* at the distal portion of the bead and direct coupling of bead hub 2956 to the material comprising internal portion of annular structure 2957 at direct connection points 2958*g* and 2958*h*.

FIGS. 29*e* and 29*f* illustrate perspective views of outer bead 2951 coupled to outer bead sleeve 2980 through which lysing rod 2960 extends. Bead hub 2956 may be formed on outer bead sleeve 2980.

Outer bead sleeves 2980 comprise a ledge 2986 that transitions between a larger diameter portion and a smaller diameter portion of the outer bead sleeves. Sleeve ledge 2986 may comprise an external sleeve ledge 2986*a* and an internal sleeve ledge (as illustrated in FIGS. 27*a-j*, internal sleeve ledge 2786*b*). External sleeve ledge 2986*a* may be configured to engage a corresponding internal bead ledge (as may be illustrated in FIGS. 27*a-j*, internal bead ledge 2159). within outer beads 2950*a*/2950*b*. Similarly, outer bead sleeves 2980 may comprise two concentric holes with internal bead ledge approximately half-way between the opposite openings. Internal bead ledge may be configured to engage coupling tips 2963. This configuration creates a feature that may prevent lateral movement of outer beads 2951*a*/2951*d* off of outer bead sleeves 2980.

In alternative embodiments, the sleeve may be configured to have a single cone-shaped tunnel that tapers and may engage coupling tip (similar to tunnel 2786' in FIG. 27*j*) from a larger dimension on the outer side of bead to a smaller dimension toward the inside of the bead.

As depicted in FIGS. 29*a-f*, lysing rod 2960 may be deformed prior to coupling with a middle bead sleeve such that the outer diameter of lysing rod 2960 may couple via friction fit with the inner tunnel surface of middle bead sleeve 2981. In alternative embodiments, lysing tip 2910 may comprise protuberances positioned on/coupled to lysing rod 2960, one protuberance, for example, may be positioned on each side of each middle bead 2951*c*. Protuberances may serve to prevent or limit lateral movement of middle beads 2951*b*/2951*c* on the lysing rod 2960 and/or may, depending upon a protuberance pair's distance from a bead, serve to limit or prevent rotation of beads around the axis of lysing rod 2960. In alternative embodiments, one or more spacers (and such as those in FIGS. 9*a*-9*e*, spacers 962) may be used in place of protuberances 2965 which may be positioned at any angle on the cross section of the lysing rod, in this depiction facing proximally 2965*c/d* and distally 2965*a/b*. Alternatively, middle bead sleeves 2981 may be more loosely coupled with lysing rod 2960 so as to allow for rotation of middle bead sleeve 2981 thereon, and thereby allow for at least some rotation of their corresponding beads on lysing rod 2960. In alternative embodiments, lysing tip 2910 may be configured without a solid lysing rod and/or without spacers and/or welds and the like similar to that depicted in FIG. 17*k*. Between beads, the hollow lysing rod may be deformed in a manner to prevent lateral movement of beads and/or prevent rotation of beads. The hollow lysing rod may be deformed minimally or to a point that it is substantially flat. In such embodiments, it may be preferable for the front edge to point distally as the leading front edge. In such embodiments, screws may secure one or both ends of the hollow lysing rod within outer beads 2951*a*/2951*d*. The configurations of this alternative embodiment may be available for any other similar embodiment contemplated herein.

FIG. 29*f* illustrates how lysing rod, sleeve and bead may be assembled: Outer bead sleeve 2980 may be extended into outer bead 2951*a* stopping at the point that external sleeve ledge 2986*a* reaches the internal bead ledge which may be followed by extension of lysing rod 2960 through outer bead sleeve 2980 stopping at the point coupling tip 2963 reaches the internal sleeve ledge 2986*b* created by the larger-diameter inner sleeve hole and smaller-diameter sleeve hole (as illustrated at internal sleeve hole 2787*a* and external sleeve hole 2786*h* in FIGS. 27*a-j*).

In FIGS. 30*a-k*, the beads again define an annular shape, however, these beads may be configured to be wider, unlike beads previously discussed which define in cross section an oval or circular shape, thus the beads in this embodiment may define a more cross-sectionally elongated shape and may be configured to have opposing upper and lower surfaces defining the annular structure that are parallel or at least substantially parallel in cross-section. These beads may be referred to as annular bands and may be flexible by way of material or a combination of material and/or thicknesses and/or configuration such that they can be compressed in some embodiments either from the top and bottom or from the opposing distal ends. In some embodiments, beads may be resiliently flexible such that they naturally return to their original state after being compressed. Various embodiments may enable greater compressibility, for example, by removing and/or angling a bead spoke between the bead hub and the annular structures 3057 of beads 3051*a/b/c/d*.

This ability to compress and be restored may be useful to allow the lysing tip 3010 to self-adjust during certain surgical procedures, in particular those involving the intermixing of delicate tissues with dense/fibrous tissues (such as pre-existing scar), for example, in the abdomen attached to the bowel and/or mesentery. To illustrate with more particularity, upon being compressed from the top or bottom, the distal tip may be deformed to form a more acute angle of attack facilitating tissue separation and the cross sectional profile along the height of the tip may be reduced. Similarly upon encountering more dense and/or more fibrous tissue at the distal tip, the tip may slow or cease movement, however, the force from the surgeon's motion will continue to push the lysing segment closer to the more dense and/or more fibrous target tissue effectively providing more enhanced power to lyse the tissue rather than requiring an increase of the power from the electrosurgical generator. In some embodiments, this may also reduce the need for increasing power from the electrosurgical generator in order to lyse and/or separate such tissues. This may also enhance safety because it may be safer for patient safety to operate electrosurgical generators at the minimum necessary power. FIGS. 30a and 30b illustrate perspective and upper views respectively of protrusions 3001, recessions 3002, beads 3051a/3051b/3051c/3051d, lysing rod 3060, and support member 3070 partially comprising grasping pad 3071. FIG. 30c is a side view of lysing tip 3010 illustrating the side and middle beads 3051a/b/c/d and support member 3070. FIG. 30d illustrates a middle bead 3051b or 3051c with bead hub 3056 and spokes 3058a/3058b; other than the shape of the bead, its structure in coupling to the lysing rod 3060 (middle and outer sleeves 3080 and 3081 respectively) is similar to outer beads 3051a/2451b and similar to the embodiments in FIGS. 27-29 via coupling tip 3063. FIGS. 30e-30k illustrate perspective, side elevation, and top plan views of an outer bead in relaxed and compressed states. FIGS. 30e/30h/30j illustrate bead 3051a/3051d in the relaxed and/or "as manufactured" state from perspective, side, and upper views. FIGS. 30f/30i/30k illustrate the same bead 3051a/3051d in a compressed state, thus, it is elongated along the beads BL axis as previously described in FIGS. 10d and 10e. FIG. 30g illustrates outer bead sleeve 3080 on which outer bead 3051a and/or 3051d may be coupled.

Outer beads 3051a/3051d and middle beads 3051b/3051c comprise bead hub 3056 and annular structure 3057 coupled via only 2 spokes 3058a/3058b terminating on annular structure 3057 proximally of bead hub 3056. This configuration may allow lysing rod 3060 to move closer to tissue located distally to deliver more concentrated electrosurgical energy when the most distal portion of outer bead annular structure 3057 is inhibited in its distal progress by dense/fibrous tissue. In some embodiments, spokes may comprise a different material from the bead hub. Such material may be more flexible to allow for greater movement of lysing rod 3060. Alternatively, spokes 3058a/3058b may comprise the same material and the flexibility may be provided by altering the thickness of the material.

As depicted in FIGS. 30a-k, in order to prevent lateral movement of middle beads, lysing rod 3060 may be deformed prior to coupling with a middle bead sleeve such that the outer diameter of lysing rod 3060 may couple via friction fit with the inner tunnel surface of middle bead sleeve 3081. In alternative embodiments, lysing tip 3010 may comprise protuberances positioned on/coupled to lysing rod 3060, one protuberance, for example, may be positioned on each side of each middle bead 3051c. In some embodiments, protuberance 3065 may be positioned to face in any direction, including distally and proximally. Protuberances may serve to prevent or limit lateral movement of middle beads 3051b/3051c on the lysing rod 3060 and/or may, depending upon a protuberance pair's distance from a bead, serve to limit or prevent rotation of beads around the axis of lysing rod 3060. In alternative embodiments, one or more spacers (and such as those in FIGS. 11a-11e, spacers 1162) may be used in place of protuberances 3065. Alternatively, middle bead sleeves 3081 may be more loosely coupled with lysing rod 3060 so as to allow for rotation of middle bead sleeve 3081 thereon, and thereby allow for at least some rotation of their corresponding beads on lysing rod 3060.

In FIG. 30b, the end tip of support member 3070 may be coated with a non-conductive coating, thus, the area of relative protrusion 3001 may be wider and may perform more blunt dissection than if the end tip were not so coated.

In alternative embodiments, the sleeve may be configured to have a single cone-shaped tunnel that tapers and may engage coupling tip (similar to tunnel 2786' in FIG. 27j) from a larger dimension on the outer side of bead to a smaller dimension toward the inside of the bead.

As depicted in FIGS. 31a-e, alternative embodiments are contemplated in which free-floating lysing tips may instead be modified so as to be coupleable with actuation rod pairs 3121/3123 and 3122/3124 and/or one or more cannulas 3131 and/or 3132 as set forth herein such that the free-floating lysing tips become non-free-floating lysing tips, as shown in FIGS. 31a-e. The figures only differ from one another as to the style of bead. In all configurations, bead length may be limited to ensure that lysing tip may rotate sufficiently into a delivery configuration that permits entry and egress of the lysing tip through an outer cannula and/or an entrance incision. FIGS. 31a and 31b depict beads 3151e-h which may be similar or identical to the middle beads of FIG. 28, namely 2851b/2851c. FIG. 31c depicts beads 3151i-L which may be similar or identical to the middle beads of FIGS. 27a-j, namely 2751b/2751c. FIG. 31d depicts beads 3151m-p which may be similar or identical to the middle beads of FIGS. 29a-f, namely 2951b/2951c. FIG. 31e depicts beads 3151q-t which may be similar or identical to the middle beads of FIGS. 30a-k, namely 3051b/3051c. Support member 3170 is coupled to the lysing rod supporting the beads.

Any of the configurations of FIGS. 31a-e may comprise canal(s) 3104 (shown in FIG. 31a only) which may be positioned to supply one or more fluids to the surgical site around or near lysing tip 3110 via a port located adjacent to the internal device cannula and/or lysing tip. Canal 3104 may be configured to be extended and withdrawn as needed. In alternative embodiments, other fluids that may pass down canal 3104 may include, but not be limited to, cold nitrogen gas, fluorocarbons, etc., which might cool and/or freeze tissue to alter it in a desired fashion.

FIGS. 32a/32b/32c illustrate a tissue modification tip (TMT) system 3200 comprising center-mounted actuation rod 3221, side actuation rod 3222 coupled to proximal actuation rod 3224, inner cannula 3231 and outer cannula 3232 and a TMT 3211 comprising energy window array 3213 and tip cover 3212. FIG. 32b illustrates the tip in the intermediate position between the delivery and treatment configurations. FIG. 32c illustrates the tip recessed within inner cannula 3231. In alternative embodiments, TMT 3211 may be configured such that it may not be able to recess within inner cannula 3231. Isolated energy window(s)/termini 3213' may be any shape or configuration of shapes so long as they are electrically isolated relative to the tissue being exposed.

In some embodiments, energy window array 3213 may comprise multiple isolated energy window termini 3213' through which energy is discharged to multiple locations on the exposed tissue at the same time. The tip of each isolated energy window termini 3213' may extend above the top surface of cover 3212 to attain a desired effect and/or be slightly recessed relative to cover 3212. The energy discharged may be electrosurgical energy of any type or, more specifically, may be 'coagulation' energy waveforms that are designed for an intended effect, for example, to incapacitate sweat glands and/or to tighten tissue, and the like. The energy delivered through energy window array 3213, which as in FIG. 32*a* may be electrode termini, may be pulsed in order to create, as the TMT is in motion, intermittent islands of undamaged tissue to feed and nourish the damaged tissue areas back to health. For example, the electrosurgical generator may be programmed to deliver 120 watts of 'coag' energy with a 40% duty cycle of 80 ms ON and 120 ms OFF. These settings might seem high if they were considered to be applied to a high density discharge device such as a bovie needle tip or a bovie paddle. However, 120 watts of 'coag' power pulsed at a 40% duty cycle applied over 6 termini may yield an energy distribution per electrode termini of under 8 watts.

In some embodiments, each of the energy window/termini 3213' may be coupled with one another and with a common energy source so as to each deliver the modality of energy. Alternatively, one or more of the energy windows/termini 3213' may be isolated both physically and electrically and/or otherwise energetically such that different modalities of energy may be created and/or delivered through each window/termini as desired.

In alternative embodiments, TMT 3211 may be configured to be free-floating and couple with a grasping/control instrument as disclosed in FIGS. 33*a-f*. Although, as discussed below, energy window 3312 does not comprise termini, this energy window may be replaced with energy window termini as shown in FIG. 32*a*. Similarly, the energy window termini shown in FIG. 32*a*, may be replaced with the bar energy window 3312 as depicted in FIG. 33*a-f*.

System 3200 may comprise canal(s) 3204 which may be positioned to supply one or more fluids to the surgical site around or near TMT 3211 via a port located adjacent to the internal device cannula and/or lysing tip (show in FIG. 32*a* only). Canal 3204 may be configured to be extended and withdrawn as needed. In alternative embodiments, other fluids that may pass down canal 3204 may include, but not be limited to, cold nitrogen gas, fluorocarbons, etc., which might cool and/or freeze tissue to alter it in a desired fashion.

FIG. 33 depicts a TMT system 3300 comprising a free-floating tissue modification tip (TMT) 3311 that may couple to grasping/control instrument 3391. In this embodiment, grasping tab 3318 may be coupled to one or more energy windows 3312 that may be positioned to face an upper and/or lower tissue plane that may have already been lysed/dissected. Cover 3313 may have one or more windows 3313' that may comprise one or more bars 3305 or other structural elements configured to separate an elongated energy window 3312 into a plurality of isolated energy windows. Although elongated energy window 3312 is in the shape of a bar, a wide variety of alternative shapes and sizes of energy windows and/or structures for defining emission regions of energy windows may be provided as desired. In some embodiments, cover 3313 may be formed with a plurality of circular openings such that elongated energy window 3312 may be functionally similar or equivalent to the energy windows depicted in FIG. 32. Cover 3313 may be over-molded onto baseplate 3315. In alternative embodiments, the region of energy window 3312 may comprise one or more (a plurality of) energy emitters positioned in a manner to optimize the intended tissue modification effect. Grasping tab 3318 may be coupled with a grasping/control instrument through which energy may flow through to energy window 3312. Grasping tab 3318 may be coupled at the receiving slot 3397 between upper and lower jaws 3393/3394 respectively.

For example as shown in FIG. 33*a*, energy conduit 3309 may be coupled with TMT 3311. Such an energy conduit may extend from energy window 3312 and through, for example, grasping tab 3318 or otherwise through base plate 3315 of TMT 3311. Energy conduit 3309 may in some embodiments extend through an opening and/or tunnel formed in grasping/control instrument 3391. Alternatively, energy conduit 3309 may extend from TMT 3311 up through a cannula (not shown) through which grasping control instrument 3391 may be delivered.

In alternative embodiments, the TMT system 3300 may be configured in any manner to accommodate the delivery or creation of any energy modality including, but not limited to, laser, intense pulse light, resistive heating, radiant heat, thermochromic, ultrasound, mechanical, and/or microwave. In some embodiments, the particular type of energy may be generated away from the TMT device and delivered to the TMT tip 3311 via one or more conduits 3309. Alternatively, the TMT or the assembly supporting the TMT may contain components for example, at or near energy window conduit 3315, that when activated with another energy, for example, AC and/or DC power and/or laser, may generate the desired energy type at the TMT energy window 3312. In some embodiments, these energy modalities may be delivered through or components that generate a particular energy type in TMT 3311 powered through grasping tab 3318, which energy may be delivered into/onto the one or more energy windows 3312. In some embodiments, such energy may be delivered by providing one or more energy delivery conduits such as 3309.

A tip energy window tongue 3319 may be formed in tip 3311. For example, tip energy window conduit(s) 3304*m* may terminate at a proximal end of a grasping pad 3318. Alternatively, a tongue or the like may be formed in a grasping/control instrument and configured to be received in a corresponding slot/conduit formed in tip 3311. A corresponding instrument 3391' energy window slot or conduit(s) 3304*f* may terminate within one or both jaws 3393/3394 or within instrument 3991' (lower jaw 3394 is not shown to facilitate viewing of other components). Thus, once jaws 3393/3394 have grasped or is about to grasp grasping pad 3318, the one or more energy-related conduits 3304/3304*a* may be aligned to allow for delivery of a desired form of energy therethrough. In some embodiments, a portion of one or both of the energy window conduits may protrude from either the tip or the instrument such that the protruding portion may be received in a corresponding female portion of the energy window conduit to form a secure connection. Thus, in the depicted embodiment, protruding tongue 3319 extends from the proximal portion of grasping pad 3318 and is configured to be received within a distal portion of instrument energy window conduit 3304*f* formed within a distal portion of instrument 3391' adjacent to jaws 3393/3394 and/or receiving slot 3397 of grasper 3391'.

In the depicted embodiment, 3347 represents an antenna configured to deliver a signal to a receiver unit. Antennae 3347 may be located within hole 3355*b*. In some embodiments, antenna 3347 may comprise radiofrequency identification (RFID) TAG. In some embodiments the RFID tag may comprise an RFID transponder. In other embodiments the RFID tag may comprise a passive tag. It should be understood that antenna 3347 is not depicted in every one of the other figures; any of the embodiments described herein may comprise one or more such elements. Other embodiments may comprise one or more antenna on any other suitable location on the embodiment, including but not limited to on the TMT or grasper tip or shaft. In embodiments in which antenna 3347 comprises an RFID transponder, the RFID transponder may comprise a microchip, such as a microchip having a rewritable memory. In some embodiments, the tag may measure less than a few millimeters. In some embodiments a reader may generate an alternating electromagnetic field which activates the RFID transponder and data may be sent via frequency modulation. In an embodiment, the position of the RFID tag or other antenna may be determined by an alternating electromagnetic field in the ultra-high frequency range. The position may be related to a 3 dimensional mapping of the subject. In an embodiment the reader may generate an alternating electromagnetic field. One or more receiver units may be set up to receive the signal from the tag. By evaluating, for example, the strength of the signal at various receiver units, the distances from the various receiver units may be determined. By so determining such distances, a precise location of the lysing tip relative to a patient and/or a particular organ or other surgical site on the patient may be determined. In some embodiments, a display screen with appropriate software may be coupled with the RFID or other localization technology to allow a surgeon to visualize at least an approximate location of the tag/antenna, and therefore the lysing tip, relative to the patient's body.

Some embodiments may be further configured such that data from the antenna(s) may be used in connection with sensor data from the device. For example, some embodiments comprising one or more sensors 3348 may be further coupled with one or more RFID tags. One or more sensors 3348 may be located within one or more holes 3355*a* or may be located on any other suitable location on the embodiment, including but not limited to on the TMT or grasper tip or shaft. As such, data from the one or more sensors may be paired or otherwise used in connection with data from the one or more RFID tags or other antennas. For example, some embodiments may be configured to provide information to a surgeon regarding one or more locations on the body from which one or more sensor readings were obtained. In some embodiments, temperature sensors may include thermistors and/or thermocouples. To further illustrate using another example, information regarding tissue temperature may be combined with a location from which such tissue temperature(s) were taken. In this manner, a surgeon may be provided with specific information regarding which locations within a patient's body have already been treated in an effective manner and thus which locations need not receive further treatment using the device.

In some such embodiments, a visual display may be provided comprising an image of the patient's body and/or one or more selected regions of a patient's body. Such a system may be configured so as to provide a visual indication for one or more regions within the image corresponding to regions of the patient's tissue that have been sufficiently treated. For example, a display of a patient's liver may change colors at locations on the display that correspond with regions of the liver that have experienced a sufficient degree of fibrosis or other treatment. Such regions may, in some embodiments, be configured such that pixels corresponding to particular regions only light up after the corresponding tissue in that region reaches a particular threshold temperature.

Such sensor 3348 may be coupled with an antenna, which may send and/or receive one or more signals to/from a processing unit. Alternatively, or additionally, data from such sensors resulting from tissue and/or fluid analysis using such sensors may be stored locally and transmitted later. As yet another alternative, such a signal may be transmitted following surgery. In such implementations, the signals need not necessarily be transmitted wirelessly. In fact, some embodiments may be configured to store data locally, after which a data module, such as a memory stick, may be removed from the device and uploaded to a separate computer for analysis.

In alternative embodiments which may be helpful for skin/cosmetic procedures, the TD tip and/or the anticipated and/or previous paths may be visualized using for example an internal camera such as an endoscopic or laparoscopic camera, and/or an external camera such as an infrared camera, (for example, a FLIR camera), an RFID tag or other antenna. In some implementations, such a device or devices may be positioned on the TD. In other implementations such a device or devices may be separate from the TD. A real time display may be created using the data of the cameras and/or antennae and/or tags, for example, showing the exact location of the tip and the during- and post-passage temperature effects. In alternative embodiments, the software presenting the visual information may hold (or slow the decay back to the body temperature) the color (designating temperature) at its maximum value during the remainder of the procedure so that the surgeon will know where the TD tip has been.

In some embodiments, the modular TMT 3311 may be used in a surgical procedure similar to that shown in FIGS. 35*a-f*. In such embodiments, it may be helpful to form a protrusion on the top and/or bottom of tab 3318. This may allow for rotation of TMT 3311 while it is in the jaws of a suitable instrument 3314*g*/3390 similar to engagement between protrusions 3570*t'* and 3570*b'* with jaws 3593 and 3594 respectively as depicted in FIG. 35*a*-35*f*.

FIGS. 34*a*-34*i* comprises dissector/tissue clamp system (D-TC) 3400 that is configured to be deployed through cannula 3432 in a deployment configuration in which two opposing portions 3405*a*/3406*a* of D-TC tip 3410 extend substantially parallel to the axis of cannula 3432. More particularly in the depicted embodiment D-TC tip 3410 comprises a first portion 3405*a* that nests with a second portion 3406*a* in the deployment configuration. First portion 3405*a* is configured to pivot with respect to second portion 3406*a* when D-TC tip 3410 is reconfigured from its deployment (also a treatment-clamping configuration) to one of its other treatment configurations. The deployment configuration is depicted in FIGS. 34*c*/34*d*. A first treatment configuration is shown in FIG. 34*a*; this treatment configuration may be referred to herein as treatment-dissecting configuration which may correspond with treatment configurations of other embodiments previously described. A second intermediate treatment configuration is shown in FIG. 34*b*; in this configuration, two tip portions 3405*a*/3406*a* are angled with respect to one another to prepare for capturing a vessel and/or duct 8. A third treatment configuration is shown in FIG. 34*c*; in this configuration, the duct and/or vessel 8 may be clamped in between the two tip portions (not shown). After performing this treatment, the D-TC tip 3410 may be withdrawn into cannula 3432 in this same configuration after the duct/vessel 8 has been severed. Thus, the configuration depicted in FIG. 34*c* may also be considered a deployment configuration once the duct/vessel 8 has been severed. FIG. 34*b* depicts D-TC tip 3410 as it is being reconfigured between deployment and treatment configurations or vice versa. As previously described, this intermediate configuration may also be considered a treatment configuration. For example, the configuration depicted in FIG. 34*b* may be used to treat tissue positioned adjacent to one or both of the tip portions 3405*a*/3406*a* without clamping/closing the jaws completely in some implementations. The pivoting of the tip portions 3405*a*/3406*a* may be done by using one or more control arms. In the depicted embodiment, the first control arm 3420 may be coupled at a pivot point 3420' between first portion 3405*a* and second portion 3406*a*. Thus, by advancing or retracting control arm 3420, first portion 3405*a* and second portion 3406*a* may be open and closed like jaws. Additional control arms may be used in some embodiments to passively control the positioning of the two tip portions. Thus, upper control arm 3421 may be pivotably coupled with first portion 3405*a* and lower control arm 3422 may be coupled with second portion 3406*a*. Upper and lower control arms 3421 and 3422 respectively may be pivotably coupled at their opposite ends at pivot base 3420' coupled to the inner sides of each first and second portion 3405*a*/3406*a*. The active control arm 3420 may extend through the inner/device cannula 3431 and may be manually controlled by a surgeon. In some embodiments, the active control arm 3420 may be operably coupled with an actuation component such as a control handpiece.

As depicted in FIG. 34*f*, first portion 3405*a* and second portion 3406*a* may comprise nonconductive covering 3405*b* and 3406*b* respectively which each are configured to receive electrode 3405*e* and 3406*e* respectively and their electrode segment(s). Pivot 7 and 7' in the electrodes of first portion 3405*a* and second portion 3406*a* may be coupled to control arm 3420. Additionally, pivots 3416 and 3416' positioned on electrodes 3405*e*/3406*e* may be coupled with upper control arm 3421 and lower control arm 3422 respectively. FIG. 34*g* depicts a rear view of all components coupled together.

In an example of a method for treating tissue using the system of FIGS. 34*a*-34*i*, the D-TC tip 3410 may first be delivered through cannula 3432 in its delivery configuration as shown in FIG. 34*d*. D-TC tip 3410 may then be advanced through the distal end of cannula 3432 as shown in FIG. 34*c*. The opposing portions or jaws of the D-TC tip 3405*a*/3406*a* may then be opened or at least partially opened as in FIG. 34*b*. If it is desired to use D-TC tip 3410 as a dissector/lysing tip, the opposing portions 3405*a*/3406*a* may be fully opened such that they are aligned perpendicular to or at least substantially perpendicular to the axis of the cannula as shown in FIG. 34*a*. D-TC tip 3410 may then be used in any of the procedures as previously described. If, on the other hand, it is desired to use D-TC tip 3410 in order to clamp/seal a blood vessel or duct 8, the open opposing jaws 3405*a*/3406*a* may be positioned about a blood vessel or duct 8 (as shown in FIG. 34*b*). In some such implementations, the opposing tip portions 3405*a*/3406*a* may not be fully opened as shown in FIG. 34*a*. The opposing jaws 3405*a*/3406*a* may then be at least partially closed onto the blood vessel or duct 8 in order to clamp the blood vessel and then electro-cut/electro-coagulate the blood vessel or duct 8 into opposing severed ends and/or a crushed/coagulated central portion of the blood vessel with opposing ends.

FIG. 34*h* depicts a bipolar embodiment of system 3400 that includes the D-TC tip 3410*b*. Upper portion 3405*a*' is configured to be electrically isolated from lower portion 3406*a*' including the control arm 3420*b* and middle hinge 3420*b*'. Upper portion 3405*a*' is coupled to energy conduit 3468*n* while lower portion 3406*a*' is coupled to energy conduit 3468*p*. Energy conduits 3468*n*/3468*p* may lead proximally and may enter and exit through holes 3431*h* in inner device cannula 3431. D-TC tip 3410*b* may be used in its open/treatment configuration as shown in FIG. 34*h* to dissect tissues and tissue planes. When upper and lower portions 3405*a*' and 3406*a*' are in the closed or substantially closed position as shown in FIGS. 34*b*/34*c*, system 3400 may be used to clamp/seal a blood vessel or duct.

FIG. 34*i* depicts an alternative embodiment that is similar to the embodiment depicted in FIG. 34*h*, however, it is configured such that every other lysing segment may be of a polarity opposite to the polarity of its adjacent lysing segment at any one time. In some embodiments, each of 5 lysing segments 3403*a*-3403*e* may be electrically isolated from one another. Energy conduit 3468*n*' may be electrically coupled to 2 lysing segments 3403*b*/3403*d* while energy conduit 3468*p*' may be electrically coupled to 3 lysing segments 3403*a*/3403*c*/3403*e*.

FIGS. 35*a*-35*f* depict yet another embodiment of a CDTD system 3500. However, as previously mentioned, other embodiments are contemplated in which system 3500 need not utilize a cannula and therefore may be considered a non-CDTD system. System 3500 comprises a lysing tip 3510 that is configured to be completely separable from any other element of the system and may therefore be referred to herein as a "free-floating" lysing tip. Lysing tip 3510 may comprise a plurality of beads 3551*a*-*d* and recessions 3502 between each bead pair. Lysing member 3560 (not visible, as covered by spacers 3561*a/b/c*), which in the depicted embodiment comprises a lysing rod 3560, is enclosed or may be partially enclosed by spacers 3561*a*/3561*b*/3561*c* positioned in recessions 3502, as previously described. Each of the portions of lysing member 3560 extending between adjacent beads 3551*a/b/c/d* defines a lysing segment.

As also previously mentioned, a grasping/control instrument 3590 may extend through a cannula 3532 to allow for grasping and/or control of lysing tip 3510 during an electrosurgical procedure. Grasping/control instrument 3590 may comprise one or more jaws configured to couple with support member 3570. As previously mentioned, in the depicted embodiment, support member 3570 comprises a bow shape extending between opposing ends of the support member 3570 and is coupled with lysing member/rod 3560 at or near such opposing ends.

In the depicted embodiment, grasping/control instrument 3590 comprises an upper jaw 3593 and a lower jaw 3594. One or both of these jaws may comprise a projection or opening configured to facilitate coupling with lysing tip 3510 by way of a mating opening/projection formed on the lysing tip 3510. Thus, support member 3570 comprises an upper projection 3570*t*' and a lower projection 3570*b*'. One or both of these projections may comprise a faceted and/or keyed shape to facilitate coupling of lysing tip 3510 with instrument 3590 in a particular rotational orientation. Preferably, this shape allows for repositioning of lysing tip 3510 at any of a plurality of preconfigured rotational positions. Thus, as shown in FIG. 35*d*, upper projection 3570*t*' comprises a plurality of flattened or faceted surfaces that may mate with a corresponding plurality of flattened or faceted surfaces formed within an opening 3593*h* formed in a lower surface of upper jaw 3593. A variety of alternative non-circular projection/opening pair shapes will be apparent to those of ordinary skill in the art after having received the benefit of this disclosure.

In some embodiments, one of the projection/opening pairs may be configured to lock the lysing tip in a particular rotational orientation and the other may be configured to allow the lysing tip to rotate while the projection is seated within the opening. For example, as also shown in FIG. 35d, lower projection 3570b' may comprise a rounded and/or smooth shape to allow for rotation when positioned within a corresponding opening (not shown in the figures) formed within an upper surface of lower jaw 3594. By providing one projection/opening pair that allows for rotation and another than locks the lysing tip in a particular rotational orientation, a surgeon may be able to release the locking projection/opening coupling while maintaining the rotating projection/opening pair coupling, rotate the lysing tip, and then re-lock the lysing tip in a different rotational orientation without completely releasing the lysing tip from the instrument.

However, a wide variety of alternative embodiments are contemplated. For example, although the protrusions are depicted in FIGS. 35a-35f as formed on the lysing tip 3510, in alternative embodiments they may instead be formed on the grasping/control instrument 3590 and the openings instead formed on the lysing tip 3510. In addition, a single projection/opening pair may be used instead of two separate pairs in some contemplated embodiments. In addition, in some embodiments, the lysing tip 3510 may be configured to rotate while fully grasped by instrument 3590. In other words, both protrusion/opening pairs may be spherical and/or rounded or only a single such protrusion/opening may be used.

In an alternative embodiment, protrusions 3570t' and 3570b' may be located toward the side of support member 3570' thus allowing a sharper angle between the axis of the lysing tip and the axis of the grasper/control instrument. Thus, the combined system may yield a smaller cross section during the deployment configuration through a cannula.

Yet another embodiment of a free-floating lysing tip 3610 is depicted in FIGS. 36a-36e. This embodiment again comprises a plurality of beads 3650 extending along a lysing member 3660 comprising a lysing rod. However, the beads 3651a and 3651b are positioned in between opposing, fixed protrusions 3676a and 3676b formed at opposite ends of lysing member 3660. As best seen in FIG. 36d, protrusions 3676a and 3676b are fixedly coupled with or, in some embodiments, an integral part of, support member 3670 at opposing ends of support member 3670. Thus, although inner beads 3651a and 3651b may be configured to rotate, at least partially, with respect to lysing member 3660 and/or lysing tip 3610, outer protrusions 3676a and 3676b may instead be fixed.

As previously described, a plurality of spacers 3661a, 3661b, and 3661c may be positioned in between each adjacent protrusion (such protrusion either being a bead or a fixed protrusion) along lysing tip 3610. In addition, opposing ends of lysing member 3660 may be formed with coupling tips 3664 to facilitate coupling of lysing member 3660 with outer protrusions 3676a and 3676b.

Coupling tips 3664 may have diameters larger than the inner diameter of their corresponding tunnels 3673 in outer protrusions 3676a/3676b respectively. The coupling tips 3664 may take various shapes, such as a ball, as depicted in FIG. 36b or, for example, a mushroom cap. In the depicted embodiment, both of outer protrusions 3676a/3676b comprises a recess 3670' that may have a larger diameter or other largest dimension than tunnels 3673 so as to accommodate/seat coupling tips 3664. Coupling tips 3664 may be made by, for example, liquefying the ends of lysing member 3660 by LASER and/or other heating methods. Alternatively, coupling tips 3664 may comprise separate structural elements, such as screw-on nuts or the like. In some embodiments, it may be desirable to provide features and/or elements that inhibit or limit the ability of the electrosurgical energy to discharge from the opposing ends of the lysing rod. Thus, in some such embodiments, coupling tips 3664 may be coated or covered with a suitable insulating material such as an epoxy with non-conductive properties.

Although in the depicted embodiment, outer protrusions 3676a/3676b are fixedly attached to support member 3670, it is contemplated that these protrusions may, in some alternative embodiments, be converted to beads by using bead structures that are loosely coupled with the ends of support member 3670 so as to provide for space in between these structures and support member 3670 so as to allow for a predetermined amount of rotation of these outer protrusions/beads, similar to inner beads 3651a/3651b.

Still another example of a free-floating lysing tip 3710 according to other embodiments is depicted in FIGS. 37a-37e. In this embodiment, both of outer beads 3751a/3751d comprise an inner recess 3758r to allow for respective opposing portions of support member 3770 to nest therein. This configuration may be useful to prevent the opposing tips of support member 3770 from discharging electrosurgical energy in an undesirable manner because these tips are nested within outer beads 3751a and 3751d. Although in the depicted embodiment opposing portions of support member 3770 are configured to be tightly or rigidly received within recesses 3758r, alternative embodiments are contemplated in which one or both of these recesses may be formed slightly larger than their respective support member 3770 arms to allow for a predetermined amount of rotation. For example, by adjusting the "height" of recesses 3758r (defined between upper and lower surfaces of lysing tip 3710 perpendicular to the length of outer beads 3751a and 3751d between their respective leading and trailing ends), rotation may be allowed along an axis defined by lysing member 3760. However, by adjusting the length and/or depth of recesses 3758r, possibly along with the dimensions of the tunnels 3758h formed therein, rotation along other axes may be permitted, such as rotation along an axis normal to the axis of the lysing member 3760 (resulting in swinging of the leading ends of the outer beads 3751a and 3751d to the left and right).

As previously described, a plurality of inner beads are also formed along lysing member 3760, namely, inner beads 3751b and 3751c. These inner beads 3751b and 3751c comprise a flattened trailing end positioned adjacent to a distal portion of support member 3770. As also previously described, in some embodiments, the distance between support member 3770 and inner beads 3751b and 3751c may be selected so as to allow a predetermined amount of flexing of lysing member 3760 during an electrosurgical procedure.

In addition, opposing ends of lysing member 3760 may be formed with coupling tips 3764 to facilitate coupling of lysing member 3760 with outer beads 3751a and 3751d. Lysing member 3760 may extend through tunnels 3758h extending through outer beads 3751a and 3751d. As shown in FIG. 37e, on the outer side of outer beads 3751a and 3751d, a secondary recess and/or ledge 3751L may be formed so as to allow coupling tips 3764 to be received within this recess and engage ledge 3751L without entering tunnel 3758h.

Finally, a plurality of spacers 3761a, 3761b, and 3761c may be positioned in between each adjacent bead along lysing tip 3710.

Another example of a free-floating lysing tip 3810 is shown in FIGS. 38a-38c. Lysing tip 3810 is depicted coupled with a grasping/control instrument 3890a/b in FIG.

38a. Lysing tip 3810 comprises a plurality of beads 3851 positioned along a lysing rod 3860. Although each of beads 3851 comprises a frusto-ellipsoidal shape having respective flattened trailing ends, any of the other bead shapes disclosed herein may be substituted for these beads as desired in alternative embodiments. Lysing tip 3810 differs from the previously-described embodiments in that lysing rod 3860 comprises opposing coupling tips 3869 configured to facilitate coupling of lysing tip 3810 with one or two grasping/control instruments and corresponding holes or recesses 3891h. For example, some embodiments may comprise a grasping/control instrument comprising opposing arms 3891L and 3891R comprised of receiving holes or recesses 3891h at the distal ends which are configured to receive and capture lysing rod coupling tips 3869. Opposing arms 3891L/3891R may in some embodiments comprise jaws that may be selectively moveable relative to one another. Thus, a surgeon may open these arms/jaws to position them at opposite ends of lysing tip 3810 adjacent to coupling tips 3869 and then close arms 3891L/3891R such that coupling tips 3869 may be trapped within a corresponding shaped hole and/or recess 3891h placed in the tips of the jaws of one or more grasping instruments on closure. Alternatively, arms 3891L/3891R may extend from distinct grasping control instruments that may use lysing tip 3810 to perform an electrosurgical procedure in unison.

FIG. 38b depicts a detailed view of the interface between modular grasping instrument 3814g, distal tip of shaft 3896 and pushrod 3897 of a surgical instrument, and tip 3814t together, the modular surgical tool 3814. As shown in this figure the distal end of pushrod 3897 may comprise a locking feature 3898. Locking lumen 3899' comprises a slot 3899s configured to receive locking feature 3898 at a predetermined rotational configuration. Upon aligning locking feature 3898 with slot 3899s, pushrod 3897 and shaft 3896 may be advanced into locking lumen 3899'. After advancing pushrod 3897 to terminal end of slot, pushrod 3897 and its accompanying pushrod locking feature 3899n may be rotated to lock pushrod locking feature 3899n in place within locking chamber 3899n'. In some embodiments, the extent of the rotation of locking feature 3898 within locking feature chamber 3898' and/or pushrod locking feature 3899n may be the same as the extent of rotation of locking feature 3898 which may in some embodiments be 90 degrees. In some embodiments, pushrod locking feature 3899n may comprise a plate or an elongated box or any other feature lacking rotational symmetry about the axis pushrod 3897. Locking chamber 3899n' may comprise for example a box or other similar feature given to engage pushrod locking feature 3899n upon rotation of pushrod 3897.

Locking chamber 3899n' is coupled with coupling rod 3892 via holes which in turn may be coupled with one or more locking teeth 3895 formed within one or both jaws 3893a/3893b. Thus, upon advancing or retracting pushrod 3897, coupling rod 3892 advances or retracts to advance or retract locking tooth/teeth 3895 so as to fix in place support member 3870 within slot 3893h of upper jaw 3893a. One or both of jaws 3893a/3893b may in some embodiments also be moveable with respect to the other jaw. In some such embodiments, the moveable jaw or jaws may be manually opened to allow for receipt of support member 3870 therein. The moveable jaw or jaws may then be closed and the locking tooth/teeth 3895 actuated to lock the support member at a desired rotational orientation such as a delivery configuration such as depicted in 38c. Then upon retracting the lysing tip into a patient's body, the locking tooth 3895 may be released to allow the lysing tip to be rotated to a treatment configuration. Such rotation may be accomplished by, for example, using an organ or another surgical instrument for leverage to reorient the lysing tip between delivery and treatment configurations.

As previously mentioned, in some embodiments, spacers 3861 may be positioned in between each two adjacent beads 3851 to restrict the beads 3851 to a confined region along lysing rod 3860 and/or limit or selectively facilitate rotation of the beads 3851 along lysing rod 3860. Although not depicted in the drawings, in some embodiments, outer spacers may be provided in between the two outer beads and their respective, adjacent coupling tip 3869. Alternatively, coupling tips 3869 may be positioned to contact the outer surface of both outer beads or the tunnels (not shown) extending through the outer beads and/or the diameter of the lysing rod 3860 may taper to provide for a suitable friction fit between the outer beads and the lysing rod 3860.

In some implementations of methods for manufacturing the lysing rod 3810 of FIGS. 38a and 38b/c, lysing rod 3860 may initially comprise a wire defining a cylindrical shape, or similar shape, along its entire length. Each of the various beads 3851 and, in some embodiments, spacers 3861 as needed, may then be strung along lysing rod 3860 and positioned as desired. Then, in order to form coupling tips 3869, opposing ends of lysing rod 3860 may be flattened and formed with a suitable hole and/or notch as desired. Lysing rod 3860 may be held in place on support member 3870 via loop 3877.

FIGS. 39a-39e depicts yet another example of a modular instrument/tip 3900 configured to be coupled with a surgical instrument. Modular instrument/tip 3900 comprises middle beads 3951i and outer beads 3951O coupled to lysing tip 3910 that may permanently couple with a modular instrument shaft 3991. As previously described in connection with FIGS. 17L and 17m, modular instrument shaft 3991 may be reversibly coupled with a surgical instrument at its distal end such as by using a pushrod and the locking elements previously described. Once this coupling has taken place, a handle or suitable actuator may be used to reposition a piston 3917p between a first configuration in which lysing tip is locked at a predetermined rotational configuration and a second configuration in which the lysing tip is allowed to be repositioned at any of a plurality of rotational orientations. More particularly, in the second configuration, the support member 3970 of the lysing tip is loosely received within a hole 3997 formed at the distal end of modular instrument shaft 3991. Thus, in this configuration, lysing tip can be rotated to a delivery configuration as shown in FIG. 39d. Then, upon advancing piston 3917p, the lysing tip may be locked in this position and delivered through an incision into a patient's body. After being delivered, piston 3917p may be retracted to allow the support member to slide within hole 3997 and rotate the lysing tip to the treatment configuration depicted in FIG. 39c after which the piston 3917p may be advanced to lock the lysing tip in this position for performing an electrosurgical procedure.

As also shown in FIGS. 39d and 39e, some embodiments may be configured to translate a proximal movement to a distal movement at or near the lysing tip. This may be useful for example to allow for a squeezing motion of an instrument handle to be used to force an actuation member such as piston 3917p' distally rather than proximally so as to allow a surgeon to lock lysing tip 3910 in place at a desired rotational orientation. For example in FIG. 39d, this may be accomplished with an lever mechanism which may comprise fulcrum 3918f on which pivots lever 3918w which is pivotably attached to rods 3918u and 3918L that each connect to distal piston 3917*p*' and proximal piston 3919*p*' respectively. As another example in FIG. 39*e*, this motion translation may be accomplished with a ratcheting mechanism which may comprise toothed cog 3917*c* positioned in between ratcheted rods 3917*u* and 3917L. Locking feature 3998 may reversibly couple with the distal tip of a control instrument.

FIG. 40 depicts a flow chart of an optional implementation for the other implementations disclosed herein of an energy emission-sensor feedback loop 4000 according to this disclosure: Step 4005 may comprise: setting one or more temperatures (a desired maximal temperature threshold, or a range). In other implementations one or more such temperatures may be preset by the manufacturer. Step 4010 may comprise setting one or more energy levels to lysing member(s) of a TD and/or energy window of a tissue modification tip (TMT) (a desired maximal energy threshold, or a range). In other implementations energy levels may be preset by the manufacturer.

Step 4013 comprises inserting the lysing tip through an entrance incision into the patient's body. In some implementations for example, step 4013 may comprise inserting the lysing tip via one or more cannulas. In some such implementations, the lysing tip may be delivered through the cannula or cannulas in a delivery configuration and be rotated/pivoted into a treatment configuration. Alternatively, the lysing tip may be inserted without using a cannula but instead a grasping/control instrument which may be a laparoscopic driver for example. In the implementations comprising 2 cannulas, the inner and outer cannulas may be inserted through the entrance wound either simultaneously or sequentially. In some implementations, the lysing tip may be free-floating such that it is inserted into the body and then coupled with grasping/control instrument after being positioned in the body. It should be understood that embodiments are contemplated wherein the dimensions of the tip relative to a cannula 1431 may vary as for example, as shown in FIGS. 14*k* and 14L. In other words, the lysing tip 1410 in the axial deployment configuration may be unable to be received within cannula 1431 such as shown in FIG. 16L or may be unable to be received within an inner cannula of two delivery cannulas as shown in FIG. 16*k*. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only need to correspond to the size of the entrance incision. With respect to such embodiments, the single cannula may primarily serve to protect and stabilize the control rods and provide rigidity to the assembly. Upon detecting that the tip has been rotated to its treatment configuration, actuating the temperature sensors and/or temperature feedback loop.

Step 4015 may comprise passing the TD or TMT through the target tissue area. In some implementations, the TD and/or TMT may comprise one or more sensors, such as temperature sensors. Alternatively or in addition, the sensor may be mounted in a position that always remains external to patient yet able to sense a residual energy release from the TD or TMT through tissue. Step 4020 may comprise applying electrosurgical energy. For example, in some implementations, electrosurgical energy may be applied to one or more lysing members. In other implementations, electrosurgical energy may be applied to one or more energy windows. In some implementations, such energy may be applied to both the lysing members and/or the energy window either simultaneously or sequentially. Step 4025 may comprise gathering sensor data, such as temperature data. Step 4030 may comprise comparing sensor data to one or more set temperature levels. Step 4035 may comprise, if the sensed temperature exceeds the threshold, reducing the amount of energy delivered through the lysing member and/or TMT.

FIG. 41 depicts a flow chart of an implementation of a method for separating and/or modifying tissue using a TD. In this particular implementation, the use of combined data from the TD generated from at least the temperature sensor and the antenna(s) may be used to provide suitable feedback to a user during treatment. In some implementations, the TD Wand may comprise a tip comprising a plurality of protrusions. One or more lysing member(s) may be positioned between at least two adjacent protrusions among the plurality of protrusions. A temperature sensor may be positioned on the TD. The temperature sensor may be configured to sense a temperature of at least one of tissue and fluid adjacent to the TD during an operation. The fluid of which a temperature reading is taken may comprise, for example, fluid from adjacent tissue(s) and/or fluid introduced during the procedure by way of the TD and/or another device or procedure. The TD may also comprise an antenna(s) such as an RFID tag positioned on the TD. In some implementations, the antenna(s) may be positioned on the tip and/or distal end of the shaft, such as on a bottom surface of the tip and/or distal end of the shaft. The antenna(s) may be configured to provide location data regarding a location of the TD, such as a particular portion or region of the TD for example, during an operation or procedure. Although method 4100 is shown in the figure beginning with step 4105, it should be understood that any of the preliminary steps described above in connection with other implementations may be performed in method 4100 as well. For example, one or more of steps (4005-4035) from method 4000 may be performed in method 4100 if desired. In some implementations, step 4105 may comprise: receiving data from the TD temperature sensor and/or a sensor not mounted on the TD but perhaps external to the patient. Step 4110 may comprise receiving data from the antenna(s) such as RFID tag data. Step 4115 may comprise combining the data generated from at least the temperature sensor and the antenna(s). In some implementations, the data from the temperature sensor and the antenna(s) may be combined before it is received. In other words, a step of "receiving combined data from the TD generated from at least the temperature sensor and the antenna(s)" may comprise receiving precombined data (data from the temperature sensor and the antenna(s) that was combined before it was received) or, alternatively, may comprise separately receiving temperature data and antenna(s) data that may be combined to allow for one or more particular features or functionalities. The combined data may be used to allow a surgeon or other user to determine one or more regions within a patient's body that have been adequately treated using the TD. For example, in some implementations, the combined data may allow a user to visualize one or more regions within a patient's body, such as one or more regions that have been sufficiently treated. This may be accomplished, for example, by creating an image corresponding with one or more regions of a patient's body. Such image or images may be highlighted, receive color changes, or otherwise modified on a display to indicate to the user which regions have been adequately treated. In some implementations, such regions may correspond with regions comprising tissue that has reached a predetermined threshold temperature.

One implementation of a method 4200 according to this disclosure for accessing an organ and/or target tissue with the assistance of a TD is shown in FIG. 42. In some implementations, surgeon(s) may need to access tissue and/or an organ to repair or treat it. In some implementations, the skin surrounding the anticipated entrance wound for the surgical area may be cleansed by, for example, with isopropyl alcohol (degreaser) followed by germicidal chlorhexidine scrub. Then, a local anesthetic may be applied (such as by injecting) 1% lidocaine+1:10,000 adrenaline to the skin. Although method 4200 is shown in the figure beginning with step 4205, it should be understood that any of the preliminary and later steps described above in connection with other implementations and/or methods 4000 and 4100 may be performed in method 4200 as well. For example, one or more other steps of any of the other implementations described herein such as for example, steps 4005-4035 of the method depicted in FIG. 40 and/or steps 4105-4140 of the method depicted in FIG. 41 may also be included in the method depicted in FIG. 42.

Step 4205 may comprise, for minimally invasive procedures or minimally invasive entrance wounds, performing a limited incision capable of accommodating the most minimal dimension of a tip that will pass and/or cannula that will pass into the entrance incision For example, as previously discussed, the incision may have a length that is the same or substantially the same or slightly larger than the width of the tip and/or the diameter of the cannula. Step 4205 may be performed with, for example, a #15 Bard-Parker™ Scalpel. This incision may be deepened by scalpel, scissors or other surgical instrument to enter the desired body structure or cavity. For larger approaches, such as open abdominal surgery or trauma surgery step 4205 may comprise the initial skin opening or body cavity opening steps of such a procedure. In some implementations, step 4205 may comprise making the skin incision using the lysing member comprising lysing member(s) of the TD. Step 4210 may comprise applying one or more fluids to the tissues. In some implementations, step 4210 may comprise applying fluids to the target tissue(s). In some implementations, embodiments with canals that may carry fluids may be used as described herein, for example, canal 304 of FIG. 3a, and/or canal 1404 of FIG. 14d. In alternative embodiments, other fluids that may pass down canal 304 may include, but not be limited to, cold nitrogen gas, fluorocarbons, etc., which might cool and/or freeze tissue to alter it in a desired fashion. In some implementations, step 4210 may comprise applying fluids to the tissues to be traversed en route to the target tissue, in addition to, or as an alternative to applying fluids directly to the target tissue(s). This step may be performed using for example canals 304 or 1404 depicted in FIGS. 3a and 14d respectively. In some implementations, the fluid(s) may comprise water. In some implementations, the fluid(s) may comprise an ionic fluid, such as a saline solution. The fluid(s) may be applied to the tissue via, for example, injection, or TD fluid port or via a separate cannula or catheter or via pouring or via spray. In some implementations, the fluid(s) may comprise an ionic fluid and an anesthetic, such as a tumescent anesthesia. Non-ionic fluids may be used in other implementations; such fluids may become more ionic by diffusion of some of the patients' ions present in the surgical field. In some implementations step 4210 may comprise applying one or more fluids that serve as an ionic fluid, and/or an anesthetic, and/or adrenaline. In some cutaneous implementations, the fluid(s) may comprise a Klein and or other tumescent formula. In some implementations, the Klein formula and amount used may be about 100 cc of Klein Formula with saline, 0.1% lidocaine, epinephrine 1:1,000,000, and $NaHCO_3$@5 meq/L. Those of ordinary skill in the art will appreciate that this step will most typically be followed in connection with procedures involving skin tissues. Other procedures may not require performing this step.

Step 4213 comprises inserting the lysing tip through an entrance incision into the patient's body. In some implementations for example, step 4213 may comprise inserting the lysing tip via one or more cannulas. In some such implementations, the lysing tip may be delivered through the cannula or cannulas in a delivery configuration and be rotated/pivoted into a treatment configuration. Alternatively, the lysing tip may be inserted without using a cannula but instead a grasping/control instrument which may be a laparoscopic driver for example. In the implementations comprising 2 cannulas, the inner and outer cannulas may be inserted through the entrance wound either simultaneously or sequentially. In some implementations, the lysing tip may be free-floating such that it is inserted into the body and then coupled with grasping/control instrument after being positioned in the body. It should be understood that embodiments are contemplated wherein the dimensions of the tip relative to a cannula may vary as for example, as shown in FIGS. 14k and 14L. In other words, the lysing tip 1410 in the axial deployment configuration may be unable to be received within cannula 1431 such as shown in FIG. 14L or may be unable to be received within an inner cannula 1431 of two delivery cannulas 1431 and 1432, as shown in FIG. 14k. In embodiments comprising two cannulas, this may be useful because if the lysing tip does not require substantial protection and can remain outside the inner cannula's lumen, then the critical dimensions of the lysing tip can correspond to the larger diameter outer cannula as opposed to being limited to the smaller dimensions of the inner/device cannula. In embodiments comprising a single cannula, this may be useful because if the lysing tip does not require substantial protection and can remain outside the inner cannula's lumen, then the critical dimensions of the lysing tip in its axial/delivery configuration only needs to correspond to the size of the entrance incision. With respect to such embodiments, the single cannula may primarily serve to protect and stabilize the control rods and provide rigidity to the assembly. Such embodiments may be useful for cosmetic procedures within the skin, for example, but not limited to, for face lifting and/or cellulite treatment.

Step 4215 may comprise a first sub-step that may be to activate the electrosurgical generator to cause cutting and/or a blend of cutting and coagulation energies to flow to the lysing member(s). The second sub-step may be passing the TD through the various layers of tissue to create a path to a target organ. In some implementations, creating a path to a target organ or other target tissue may comprise creating a path from the incision to the target organ or other target tissue and/or creating a path around the target organ or other target tissue to allow for access to other regions of the target organ or other target tissue. In some implementations, the lysing member(s) may be used to induce fibrosis along the path, including along a path that may traverse the perimeter of the target organ/tissue. In some implementations, the TD and/or the anticipated path may be visualized using for example an internal camera such as an endoscopic or laparoscopic camera. In some cutaneous and/or cosmetic implementations, an external camera such as a FLIR camera, an RFID tag or other antenna may be used. In some implementations, such a device or devices may be positioned on the TD. In other implementations such a device or devices may be separate from the TD. In some implementations, heat may be produced or energy may otherwise be released in the tissues through which the TD is passed. In some implementations, heating portions of the tissues the TD passes by may be undesirable. As such, in some implementations, undesirable heating of such tissues and/or adjacent tissues may be mitigated by applying a cooling step antecedent and or concurrent with energy delivery with the TD. Such steps may comprise use of one or more cooling fluids delivered via the TD or one or more separate catheters or cannulas or endoscopes. Other cooling mechanisms may comprise a dynamic cooling system wherein a cool liquid or gel is actively pumped into or through a contact cooling object. Step 4220 may comprise identifying critical tissue that is not to be treated, such as important blood vessels, nerves, ducts, organs or other anatomy along the path to the target organ/tissue and/or in the area surrounding the target organ/tissue. Step 4225 may comprise: adding additional fluids of the types previously described to the target and/or surrounding tissues via the TD port(s) or via one or more separate catheters or cannulas or endoscopes. Step 4230 may comprise: expanding one or more regions of the path to the target tissue. In some implementations, step 4230 may comprise expanding one or more path(s) from the incision to the target tissue. In some implementations, step 4230 may comprise expanding a region around the target tissue such as for example, via a fanning motion. In some implementations, one or more of the other steps described herein using the TD may also be performed with a fanning motion. In implementations using TDs with axially oriented protrusions, such a fanning motion may comprise a to and fro spokewheel pattern. In implementations using TDs with nonaxially oriented protrusions, such a fanning motion may comprise a side-to-side fanning motion; one example of a fanning motion using a TD having at least one nonaxially oriented protrusion may comprise a 'windshield wiper' motion. In some implementations step 4230 may further comprise activating the energy to the TD, for example, the energy to the lysing member(s). Alternatively, in some implementations, an additional step 4231 may be used comprising withdrawing the lysing tip and inserting and activating a TMT for a desired effect, for example, tissue modification/tightening. Step 4235 may comprise: observing for bleeding from larger vessels and achieving hemostasis as needed. In some implementations achieving hemostasis may be accomplished by cautery, electrifying, ligating, or chemical methods. In some implementations, the surgeon may activate the electrosurgical coagulation energy to the lysing member(s) to achieve the hemostasis. In some implementations, one or more other devices and/or suture may be used to achieve hemostasis for larger vessels.

Generally, step 4238 may comprise withdrawing the lysing tip. For example, step 4238 may comprise rotating the lysing tip such that it extends axially along the lumen of the one or more cannulas or at least substantially axial to such lumen(s). In some implementations the lysing tip may be rotated at an angle with respect to such lumen so long as the lysing tip can be withdrawn through this cannula in this configuration. After rotating the lysing tip sufficiently such that it can be received within the cannula or cannulas, the lysing tip may be withdrawn through the entrance incision.

In some implementations not utilizing a cannula, the lysing tip preferably is again rotated such that the elongated axis of the lysing tip is aligned or at least substantially aligned with the direction of withdrawal. After such rotation, the lysing tip may be withdrawn through the entrance incision. In some such implementations, a surgeon may rotate the lysing tip by palpation. Alternatively, an instrument may be used to perform the rotation and may be used to withdraw the lysing tip through the entrance incision. As previously mentioned, in some implementations, a first instrument may release its coupling with the lysing tip and then a second instrument may be used to rotate and/or withdraw the lysing tip. In alternative implementations, a cord, for example, a suture and/or thread, may have been previously tied to a hole in the lysing tip and may be used to pull the lysing tip through entrance incision.

Step 4240 may comprise: removing the TD with power off and suturing the wound in the standard fashion. In some implementations, the tissues traversed may require closure by suturing, stapling, gluing, and/or adhesive skin closure strips. In some implementations, organs and/or organ systems that the TD may be useful to access may include but not limited to skin, muscle, and/or parotid, and/or salivary gland, and/or thyroid, and/or lung, and/or heart, and/or gastrointestinal, and/or liver, and/or pancreas, and/or spleen, and/or gallbladder, and/or kidney, and/or adrenal, and/or prostate, and/or ovary, and/or uterus, and/or bladder, and/or vascular, and/or nervous, and/or lymph nodes and/or skeleton.

In some implementations, the TD may also aid in the treatment of trauma victims; for example, gunshot and/or blast injuries and/blunt force trauma. Such patients may be in shock and bleed to a greater degree than normal due to systemic changes, some changes of which may consume and/or alter platelets and/or clotting proteins in the blood. It may be beneficial for surgeons to reach a vigorously bleeding area more rapidly while achieving a degree of hemostasis by coagulating smaller vessels along the path to reaching said vigorously bleeding area (likely due to trauma to a larger blood vessel). The TD may have smaller vessel hemostatic capabilities when energy is applied to lysing member. Having a field of surgery with less bleeding may be beneficial to the surgeon who is working to find and repair a larger blood vessel (for example, a femoral or brachial artery). The size of the TD's lysing areas may be such that a larger vessel will not fit into the TD and thus not be affected by the TD; thus, the surgeon may feel more confident that the TD will not risk traumatizing a larger blood vessel further.

In some implementations such as method 4300, the TD may also aid in the treatment of hernias. Generally, herniated tissues are those that may have lost firmness and may have become lax allowing one or more organs to unwantedly protrude into adjacent spaces. To treat a hernia, surgeons may make paths to the site to be treated, may remove the lax hernia sac and/or other lax/herniated tissues by dissecting around said tissue(s), and may then connect/suture the edges of healthy tissue together to re-create the original healthy tissue wall, or, if insufficient healthy tissue is present, may use mesh to connect the healthy tissue to form the new tissue wall.

One implementation of a method 4300 according to this disclosure for repairing hernias with the assistance of a TD is shown in FIG. 43.

Step 4331 may comprise making a path to the site of the herniated tissue. Step 4331 may also comprise using additional instrumentation to put force upon and/or pull and/or stretch and/or make taught the herniated tissues and/or associated fibrous tissues and/or the surrounding tissue(s). Step 4331 may be performed using, for example, needles, sutures, hooks, clamps, retractors, probes, bars, endoscopes, rakes, tubes, and/or TD.

Step 4332 may comprise dissecting around the herniated tissue in order to remove it or free up adjacent structural tissue so that the TD or another instrument may cut/excise around the herniated tissues for removal. In some implementations step 4331 may be performed concurrently with step 4332. Step 4332 may further comprise passing the TD to at least substantially free or prepare for excision the herniated tissues and/or associated fibrous tissues from the surrounding tissues. In some implementations, step 4332 may further comprise applying energy to the lysing members during this TD passage.

Step 4333 may comprise excising and removing the herniated/lax tissues and/or hernia sac.

Step 4334 may comprise heating the tissue surrounding the herniated tissue and/or associated fibrous tissues and/or tissue(s) that a surgeon intends to incorporate into the region to secure and/or restrain the remaining tissue into its intended and/or original place. In some implementations, step 4334 may be performed using the TD, either with lysing segments of the TD or an energy window. Alternatively, the TD may be withdrawn and a TMT may be introduced having an energy window and used for this purpose.

Step 4335 may comprise (if further freeing/excision appears necessary) using additional instrumentation to put force upon and/or pull and/or stretch and/or make taught target tissue(s) while the TD may be passed to more uniformly apply energy to the target tissue via the lysing member(s) of the lysing tip and/or via the Tissue Modification Tip (TMT) or other applicable device that may induce hemostasis and/or induce postoperative fibrosis, and/or alter certain tissues.

Step 4336 may comprise sewing, stapling or binding the remaining tissues and/or herniated tissues into place. If insufficient healthy tissue is present to form a proper intended tissue wall, mesh may be used to bridge the space between the healthy tissues.

Step 4337 may comprise passing the TD adjacent to those tissues that have been sewn and/or otherwise bound. In some implementations, step 4337 may comprise activation of the lysing member or activation of a TMT to induce supportive fibrosis.

In some implementations, organs and/or organ systems that the TD may be useful to assist in remedying a herniated state may include but not limited to muscle, and/or parotid, and/or salivary gland, and/or gastrointestinal, and/or uterus, and/or bladder, and/or vascular, and/or genitourinary.

One implementation of a method 4400 according to this disclosure for accessing the central nervous system (CNS) with the assistance of a TD is shown in FIG. 44. Although method 4400 is shown in the figure beginning with step 4315, it should be understood that any of the preliminary and later steps described above in connection with other implementations and/or methods and/or methods 4000, 4100, and 4200 may be performed in method 4400 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 44.

After preparing the surgical field, making the entrance incision, and introducing the TD through the entrance incision, step 4415 may comprise making a path to the target tissue/organ. More particularly, in implementations accessing the brain, step 4415 may comprise moving the TD through the subgaleal layer; this may allow the scalp to be retracted for better access to open the skull via bone saw and/or other tools known in the art. In some implementations step 4415 may further comprise activating the lysing member to reduce bleeding from emissary blood vessels. In implementations accessing the spinal cord, step 4415 may comprise moving the TD through tissue surrounding the spine. In some implementations, such movement may comprise a fanning motion. Step 4420 may comprise dissecting the dura using the TD and/or identifying important blood vessels, and/or other anatomy in the area surrounding the target tissue. Step 4425 may comprise: adding additional fluids of the types previously described to the target and/or surrounding tissues via the TD port(s) or via one or more separate catheters or cannulas or endoscopes prior to and/or during the application of energy by TD. Step 4429 may comprise: activating the energy to the TD for example the energy to the lysing member(s). Step 4430 may further comprise passing the TD around and/or through the target tissue in the CNS such as for example, via a delicate fanning motion. In some implementations, the TD and/or the anticipated path may be visualized using for example an endoscope, a fiberoptic or camera, an RFID tag or other antenna. In some implementations, such a device or devices may be positioned on the TD. In other implementations such a device or devices may be separate from the TD. Step 4435 may comprise: observing for bleeding from larger vessels and achieving hemostasis as needed. In some implementations achieving hemostasis may be accomplished by cautery, electrifying, ligating, chemical methods, and/or use of a TMT. In some implementations, the lysing member(s) can be used to achieve the hemostasis. In some implementations, one or more other devices and/or suture may be used to achieve hemostasis for larger vessels. Step 4440 may comprise: removing the TD with power off and suturing the wound in the standard fashion.

One implementation of a method 4500 according to this disclosure for removing tissue from a peripheral nerve such as for example tumor and/or scar tissue and/or fibrosis with the assistance of a TD is shown in FIG. 40. Although method 4500 is shown in the figure beginning with step 4531, it should be understood that any of the preliminary and later steps described above in connection with other implementations and/or methods and/or methods 4000, 4100, and 4200 may be performed in method 4500 as well. For example, one or more of steps 4005-4035 in the method depicted in FIG. 40 may be performed in method 4500 if desired. Similarly, one or more other steps of any of the other implementations described herein such as for example, steps 4005-4045 of the method depicted in FIG. 40 may also be included in the method depicted in FIG. 45.

Step 4531 may comprise using additional instrumentation to put force upon and/or pull and/or stretch and/or make taught the nerve and/or tissue adjacent a peripheral nerve (such as for example tumor and/or scar tissue and/or fibrosis) and/or surrounding tissue(s). Step 4531 may be performed using, for example, needles, sutures, hooks, clamps, retractors, probes, bars, endoscopes, rakes, tubes, TD and/or by hand. In some implementations step 4531 may be performed concurrently with step 4532. Step 4532 may comprise passing the TD to at least substantially free the tumor(s) and/or scar tissue and/or fibrosis from the nerve and/or surrounding tissues. In some preferred implementations, step 4532 may comprise passing the TD to free, or at least substantially, free, the tumor(s) and/or scar tissue from the nerve and/or surrounding tissues without activating the lysing segments of the TD. In other words, because of the sensitive nature of nerve tissue, it may be preferred to use the TD as a blunt dissector without using electrosurgical energy. However, additional related steps may involve use of such energy. In addition, in alternative implementations, energy may be applied to the lysing members during this TD passage. Step 4533 may comprise identifying and/or testing the tissue (such as for example tumor and/or scar tissue and/or fibrosis) to determine if it has been sufficiently freed from the nerve and/or surrounding tissues for uncomplicated removal. In some implementations endoscopes and/or blunt probes and/or TD and/or surgeon's hands may be passed around the tumor and/or scar tissue and/or fibrosis to test the degree of freedom the tumor and/or scar tissue and/or fibrosis has from the nerve and/or surrounding tissues. Step 4534 may comprise (if further freeing appears necessary) using additional instrumentation to put force upon and/or pull and/or stretch and/or make taught the nerve and/or tumor and/or scar tissue and/or fibrosis. Step 4535 may comprise passing the TD to further free the nerve; energy may be applied to the lysing members during this TD passage (in order to attempt hemostasis and/or induce post-operative fibrosis). Step 4535 may be repeated as necessary until the tumor and/or scar tissue and/or fibrosis is sufficiently freed for removal. In an implementation the TD is passed longitudinally along the nerve in a 'stripping' fashion, such that a longitudinal axis of the TD is at least substantially parallel to a longitudinal axis of the nerve during step 4533. The shape of certain embodiments of lysing tips described herein may be particularly useful in allowing the tip to be moved along a nerve without causing undue damage to the nerve. More particularly, by providing smooth protrusions and recessing the sharpened or electro-cutting portions of the tip between the protrusions, the nerve may be protected from the cutting aspects of the device.

In an alternative implementation of method 4500, this method may be modified to allow for dissection of tissues to repair an aneurism. In such an implementation, each of the steps up to 4532 may be substantially identical to method 4500. Step 4532 may instead comprise dissecting vascular and connective tissues in and around the aneurism using the TD. This step may also include sealing small peripheral bleeders from and around the aorta. Step 4533 may comprise dissecting/cutting a section or sectioning the aorta with the TD.

In another alternative implementation of method 4500, this method may be modified to conduct a coronary artery bypass graft and/or other vascular graft. In such an implementation, each of the steps up to 4532 may be substantially identical to method 4500. Step 4532 may instead comprise dissecting out the saphenous vein from a leg or other suitable vessel (e.g., infra mammary). Step 4533 may comprise dissecting along the vessel to remove any adhesions and/or seal/disconnect small periphery blood vessels that may bleed and/or seal small peripheral vessels.

One implementation of a method 4600 according to this disclosure for creating a tissue flap and/or section with the assistance of a TD is shown in FIG. 46. (In this method 4600, the term 'flap' may include 'section'.) In some implementations, such a flap of tissue may be used for breast reconstruction. In some implementations, such a flap of tissue is a latissimus dorsi flap. In some implementations, such a flap of tissue is a TRAM (Transverse Rectus Abdominus Myocutaneous) flap. Although method 4600 is shown in the figure beginning with step 4631, it should be understood that any of the preliminary and later steps described above in connection with other implementations and/or methods and/or methods 4000, 4100, and 4200 may be performed in method 4600 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 46.

Step 4631 may comprise using additional instrumentation to put force upon and/or pull and/or stretch and/or make taught the target region of tissue to be used in creating a tissue flap and/or the surrounding tissue(s). Step 4631 may be performed using, for example, needles, sutures, hooks, clamps, retractors, probes, bars, endoscopes, rakes, tubes, TD and/or by hand. In some implementations step 4631 may be performed concurrently with step 4632. Step 4632 may comprise passing the TD to at least substantially separate a sufficient amount of tissue to create and/or free at least a portion of the tissue flap. In some implementations, step 4632 may further comprise applying energy to the lysing member(s) during this TD passage. Step 4633 may comprise testing the target tissue flap to determine if it has been sufficiently freed from the surrounding tissues for uncomplicated removal (excluding its pedicle). In some implementations endoscopes and/or blunt probes and/or TD and/or surgeon's hands may be passed around the target organ/tissue to determine the degree of freedom a target flap and/or tissue has from its surrounding tissues and/or organs. Step 4634 may comprise (if further freeing appears necessary) using additional instrumentation to put force upon and/or pull and/or stretch and/or make taught the target flap and/or tissue and/or other surrounding tissue while the TD may be passed to further free the target flap and/or tissue; energy may be applied to the lysing member(s) during this TD passage (in order to attempt hemostasis and/or induce post-operative fibrosis). Step 4635 may comprise passing the TD (after the target flap and/or tissue has been freed and/or moved) to the tissues that were adjacent and remaining in the body, which may aid the surgeon in examining for points of further bleeding and/or for further exploration; during such passage energy may be applied to the lysing members (in order to attempt hemostasis and/or induce postoperative fibrosis). In some implementations, traditional instruments may be used to achieve hemostasis. In some implementations, one or more of these steps using the TD may be performed with a fanning motion. In implementations using TD's with axially oriented protrusions, such a fanning motion may comprise a to and fro spokewheel pattern. In implementations using TD's with at least one nonaxially oriented protrusion, such a fanning motion may comprise a side-to-side fanning motion; one example of a fanning motion using a TD having at least one nonaxially oriented protrusion may comprise a 'windshield wiper' motion. In some implementations, the TD may be used to create flaps in and/or from tissues and/or organs including but not limited to muscle and/or fascia, and/or fibrous tissue and/or fat and/or vascular tissues. In some implementations, the TD may be used to create flaps and/or sections in and/or from tissues and/or organs including but not limited to, lung and/or liver and/or gastrointestinal and/or genital/urinary and/or uterus and/or bladder.

One implementation of a method 4700 according to this disclosure for creating a tissue graft with the assistance of a TD is shown in FIG. 47. In some implementations, such a graft of tissue may be used for reconstruction of traumatic wounds.

Although method 4700 is shown in the figure beginning with step 4731, it should be understood that any of the preliminary and later steps described above in connection with other implementations and/or methods and/or methods 4000, 4100, and 4200 may be performed in method 4700 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 47.

Step 4731 may comprise using additional instrumentation to put force upon and/or pull and/or stretch and/or make taught the target region of tissue to be used in creating a tissue graft and/or the surrounding tissue(s). Step 4731 may be performed using, for example, needles, sutures, hooks, clamps, retractors, probes, bars, endoscopes, rakes, tubes, TD and/or by hand. In some implementations step 4731 may be performed concurrently with step 4732. Step 4732 may comprise passing the TD to at least substantially separate a sufficient amount of tissue to create and/or free at least a portion of the tissue graft. In some implementations, step 4732 may further comprise applying energy to the lysing members during this TD passage. Step 4733 may comprise testing the target tissue graft to determine if it has been sufficiently freed from the surrounding tissues for uncomplicated removal. In some implementations endoscopes and/or blunt probes and/or TD and/or surgeon's hands may be passed around the target organ/tissue to determine the degree of freedom a target graft and/or tissue has from its surrounding tissues and/or organs. Step 4734 may comprise (if further freeing appears necessary) using additional instrumentation to put force upon and/or pull and/or stretch and/or make taught the target graft and/or tissue and/or other surrounding tissue while the TD may be passed to further free the target graft and/or tissue; energy may be applied to the lysing members during this TD passage (in order to attempt hemostasis and/or induce postoperative fibrosis). Step 4735 may comprise passing the TD (after the target graft and/or tissue has been freed and/or moved) to the tissues that were adjacent and remaining in the body, which may aid the surgeon in examining for points of further bleeding and/or for further exploration; during such passage energy may be applied to the lysing members (in order to attempt hemostasis and/or induce postoperative fibrosis). In some implementations, traditional instruments may be used to achieve hemostasis. In some implementations, one or more of these steps using the TD may be performed with a fanning motion. In implementations using TD's with axially oriented protrusions, such a fanning motion may comprise a to and fro spokewheel pattern. In implementations using TD's with at least one nonaxially oriented protrusion, such a fanning motion may comprise a side-to-side fanning motion; one example of a fanning motion using a TD having at least one nonaxially oriented protrusion may comprise a 'windshield wiper' motion. In some implementations, the TD may be used to create grafts in and/or from tissues and/or organs including but not limited to skin and/or mucosal and/or fascia, and/or connective/fibrous tissue (for example, tendon) and/or fat and/or vascular tissues. In some implementations, the TD may be used to create grafts in and/or from tissues and/or organs including but not limited to, lung and/or liver and/or gastrointestinal and/or genital/urinary and/or uterus and/or bladder. In some implementations, the TD may be used to harvest any or all of the aforementioned tissues for organ culture.

One implementation of a method 4800 according to this disclosure for removing tumor from an organ with the assistance of a TD is shown in FIG. 48. In some implementations, the tumor may be incompletely removed to 'debulk' it and/or to prevent disease spread within the body and/or pathologic analysis. In some implementations, the tumor may be completely removed to prevent disease spread within the body and/or pathologic analysis. Although method 4800 is shown in the figure beginning with step 4831, it should be understood that any of the preliminary and later steps described above in connection with other implementations and/or methods and/or methods 4000, 4100, and 4200 may be performed in method 4800 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 48.

Step 4831 may comprise using additional instrumentation to put force upon and/or pull and/or stretch and/or make taught the tumor and/or the surrounding tissue(s). Step 4831 may be performed using, for example, needles, sutures, hooks, clamps, retractors, probes, bars, endoscopes, rakes, tubes, TD and/or by hand. In some implementations, step 4831 may be performed concurrently with step 4832. Step 4832 may comprise passing the TD to at least substantially free the tumor(s) from the surrounding tissues. In some implementations, step 4832 may further comprise applying energy to the lysing segments and/or energy windows during this TD passage. Step 4833 may comprise identifying and/or testing the tumor to determine if it has been sufficiently freed from the surrounding tissues and/or organ for uncomplicated removal. In some implementations endoscopes and/or blunt probes and/or TD and/or surgeon's hands may be passed around the tumor to test the degree of freedom the tumor has from its surrounding tissues and/or organs. Step 4834 may comprise (if further freeing appears necessary) using additional instrumentation to put force upon and/or pull and/or stretch and/or make taught the tumor and/or the surrounding tissue and/or organ while the TD may be passed to further free the tumor; energy may be applied to the lysing segments and/or energy windows during this TD passage (in order to attempt hemostasis and/or induce postoperative fibrosis). In some implementations, traditional instruments may be used to achieve hemostasis. Step 4834 may be repeated as necessary until the tumor is sufficiently freed for removal. Step 4835 may comprise passing the TD (after the tumor has been removed) to the tissues that were adjacent to the tumor (and still remaining in the body), which may aid the surgeon in examining for points of further bleeding and/or for further exploration; during such TD passage, energy may be applied to the lysing segments and/or energy windows. Step 4836 may comprise using the TD to subdivide portions of the tumor which may aid in extracting the tumor in pieces if the surgery is done via a minimally invasive technique. In some implementations, if the surgical incision in the body is larger, the tumor tissue may pass more freely out of the body without piecemeal removal. In some implementations, the tumor is placed in the appropriate medium for a pathologist to examine or test. In some implementations, one or more of these steps using the TD may be performed with a fanning motion. In implementations using TD's with axially oriented protrusions, such a fanning motion may comprise a to and fro spokewheel pattern. In implementations using TD's with at least one nonaxially oriented protrusion, such a fanning motion may comprise a side-to-side fanning motion; one example of a fanning motion using a TD having at least one nonaxially oriented protrusion may comprise a 'windshield wiper' motion. In some implementations, organs and/or organ systems that the TD may be useful to remove tumors which may include but not limited to skin, and/or muscle, and/or fibrous tissues, and/or parotid, and/or salivary gland, and/or thyroid, and/or lung, and/or breast, and/or heart, and/or nervous system, and/or spleen, and/or gastrointestinal, and/or liver, and/or pancreas, and/or gallbladder, and/or genital/urinary, and/or kidney, and/or adrenal, and/or prostate, and/or ovary, and/or uterus, and/or bladder, and/or vascular, and/or lymph nodes and/or skeleton, and/or central nervous system, and/or peripheral nervous system and/or lung.

One implementation of a method 4900 according to this disclosure for removing an organ with the assistance of a TD is shown in FIG. 49. In some implementations, organ(s) may be removed from a donor to surgically implant into a recipient patient. In some implementations, organ(s) may be removed for disease and pathologic analysis. In some implementations, the donor may be the recipient patient (for example, a muscle graft). Although method 4900 is shown in the figure beginning with step 4931, it should be understood that any of the preliminary and later steps described above in connection with other implementations and/or methods and/or methods 4000, 4100, and 4200 may be performed in method 4900 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 49.

Step 4931 may comprise using additional instrumentation to put force upon and/or pull and/or stretch and/or make taught the target tissue and/or organ(s) and/or the surrounding tissue(s). Step 4931 may be performed using, for example, needles, sutures, hooks, clamps, retractors, probes, bars, endoscopes, rakes, tubes, TD and/or by hand. In some implementations, step 4931 may be performed concurrently with step 4932. Step 4932 may comprise passing the TD to at least substantially free the organ(s) from the surrounding tissues. In some implementations, step 4932 may further comprise applying energy to the tissues during this TD passage. Step 4933 may comprise testing the target tissue and/or organ to determine if it has been sufficiently freed from the surrounding tissues for uncomplicated removal. In some implementations endoscopes and/or blunt probes and/ or TD may be passed around the target organ/tissue to determine the degree of freedom a target tissue and/or organ has from its surrounding tissues and/or organs. Step 4934 may comprise (if further freeing appears necessary) using additional instrumentation to put force upon and/or pull and/or stretch and/or make taught the target tissue and/or organ and/or the surrounding tissue while the TD may be passed to further free the target tissue and/or organ; energy may be applied during this TD passage. Step 4935 may comprise passing the TD (after the target tissue and/or organ has been removed) to the tissues that were adjacent and remaining in the body, which may aid the surgeon in examining for points of further bleeding and/or for further exploration; during such passage energy may be applied to the lysing member(s) (in order to attempt hemostasis and/or induce postoperative fibrosis). In some implementations, traditional instruments may be used to achieve hemostasis. Step 4936 may comprise clamping and/or sealing critical ducts and/or blood vessels on the target tissue and/or organ so that the target tissue and/or organ may be properly transferred to and/or transported to and/or stored for the recipient patient if it is a donor organ. In some implementations, an organ may be cooled or refrigerated. In other implementations if the target tissue and/or organ is diseased, the tissue may be properly placed in the appropriate medium for a pathologist to examine or test. In some implementations, one or more of these steps using the TD may be performed with a fanning motion. In implementations using TD's with axially oriented protrusions, such a fanning motion may comprise a to and fro spokewheel pattern. In implementations using TD's with at least one nonaxially oriented protrusion, such a fanning motion may comprise a side-to-side fanning motion; one example of a fanning motion using a TD having at least one nonaxially oriented protrusion may comprise a 'windshield wiper' motion. In some implementations, organs and/or organ systems that the TD may be useful to remove may include but not limited to skin, and/or fibrous tissues, and/or muscle, and/or parotid, and/or salivary gland, and/or thyroid, and/or breast, and/or lung, and/or heart, and/or gastrointestinal, and/or liver, and/ or pancreas, and/or spleen, and/or gallbladder, and/or kidney, and/or adrenal, and/or prostate, and/or ovary, and/or uterus, and/or bladder, and/or vascular, and/or lymph nodes and/or skeleton, and/or central nervous system, and/or peripheral nervous system.

One implementation of a method 5000 according to this disclosure for removing and/or freeing target scar tissue and/or fibrosis (or another fibrous tissue) from an organ with the assistance of a TD is shown in FIG. 50. Although method 5000 is shown in the figure beginning with step 5031, it should be understood that any of the preliminary and later steps described above in connection with other implementations and/or methods and/or methods 4000, 4100, and 4200 may be performed in method 5000 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 50.

Step 5031 may comprise using additional instrumentation to put force upon and/or pull and/or stretch and/or make taught the scar tissue and/or fibrous tissue and/or the surrounding tissue(s). Step 5031 may be performed using, for example, needles, sutures, hooks, clamps, retractors, probes, bars, endoscopes, rakes, tubes, TD and/or by hand. In some implementations step 5031 may be performed concurrently with step 5032. Step 5032 may comprise passing the TD to at least substantially free the scar tissue and/or other fibrous tissue from the surrounding tissues. In some implementations, step 5032 may further comprise applying energy to the lysing member during this TD passage. Step 5033 may comprise identifying and/or testing the scar tissue and/or other fibrous tissue to determine if it has been sufficiently freed from the surrounding tissues and/or organ for uncomplicated removal. In some implementations endoscopes and/ or blunt probes and/or TD and/or surgeon's hands may be passed around the scar tissue and/or other fibrous tissue to test the degree of freedom the scar tissue and/or other fibrous tissue has from the surrounding tissues and/or organs (in order to attempt hemostasis and/or modulate postoperative fibrosis). Step 5034 may comprise (if further freeing appears necessary) using additional instrumentation to put force upon and/or pull and/or stretch and/or make taught the scar tissue and/or other fibrous tissue and/or the surrounding tissue and/or organ while the TD may be passed to further free the target scar tissue and/or other fibrous tissue; energy may be applied to the lysing member during this TD passage. Step 5034 may be repeated as necessary until the target scar tissue and/or other fibrous tissue is sufficiently freed and/or removed. Step 5035 may comprise passing the TD (after the target scar tissue and/or fibrosis has been removed) to the tissues that were adjacent to the removed tissues (and still remaining in the body), which may aid the surgeon in examining for points of further bleeding and/or for further exploration; during such TD passage, energy may be applied to the tissues via the lysing member(s) and/or the energy window(s). Step 5036 may comprise using the TD to subdivide portions of the scar tissue and/or other fibrous tissue which may aid in extracting the scar tissue and/or other fibrous tissue in pieces if the surgery is done via a minimally invasive technique. In some implementations, if the surgical incision in the body is larger, the scar tissue and/or other fibrous tissue may pass more freely out of the body without piecemeal removal. In some implementations, one or more of these steps using the TD may be performed with a fanning motion. In implementations using TD's with axially oriented protrusions, such a fanning motion may comprise a to and fro spokewheel pattern. In implementations using TD's with at least one nonaxially oriented protrusion, such a fanning motion may comprise a side-to-side fanning motion; one example of a fanning motion using a TD having at least one nonaxially oriented protrusion may comprise a 'windshield wiper' motion. In some implementations, organs and/or organ systems that the TD may be useful to free and/or remove scar tissue and/or other fibrous tissue from may include but not limited to muscle, and/or parotid, and/or salivary gland, and/or thyroid, and/or lung, and/or heart (pericardial adhesions), and/or gastrointestinal (strictures), and/or liver, and/or pancreas, and/or spleen, and/or gallbladder (adhesions), and/or kidney, and/or adrenal, and/or prostate, and/or ovary, and/or uterus, and/or bladder, and/or vascular, and/or lymph nodes and/or skeleton, and/or central nervous system, and/or peripheral nervous system and/or lung (pleural adhesions) and/or fat (fibrous bands of cellulite). In some implementations, scarred and/or other fibrous tissue may bleed more than normal tissues when acted upon by a standard scalpel and/or surgical scissors; the TD may aid in such scarred and/or fibrotic tissue removal as the TD may be able to coagulate synchronously with both blunt and sharp dissection capabilities. The TD lysing member(s) may be able to contact more small bleeding vessels (than a non-planar surgical device) due to TD's planar geometry and the chance that the geometry of the bleeding tissues may be substantially planar.

An implementation of a method 5100 for incapacitating apocrine glands is shown in FIG. 51. Although method 5100 is shown in the figure beginning with step 5105, it should be understood that any of the preliminary and later steps described above in connection with other implementations and/or methods and/or methods 4000, 4100, and 4200 may be performed in method 5100 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 51.

Step 5105 may comprise: having the surgical area cleaned by, for example, isopropyl alcohol (degreaser) followed by germicidal chlorhexidine scrub. Step 5110 may comprise: applying a local anesthetic (such as injecting), such as about 1 cc of a 1% lidocaine+1:10,000 adrenaline, to form about a wheal/hive on the periphery of the proposed dissection area on the axilla. Step 5115 may comprise, after allowing the local anesthetic to settle, making an entrance incision and creating a tip deployment pocket. The first sub-step of step 5115 may comprise, after allowing the local anesthetic to settle, performing a simple "stab" incision of the wheal, for example, a #15 Bard-Parker™ Scalpel into the subcutaneous fat. This incision may be about 3 mm in length or less. The second sub-step of step 5115 may comprise creating a tip deployment pocket that may receive the lysing tip; said pocket may be made using a scalpel, scissors and/or wide array of instruments known in the art to dissect tissue. The tip deployment pocket may be made by blunt dissection such as using a Metzenbaum scissors in a spreading fashion and/or by sharp dissection using scalpel blade and/or scissor and/or energized dissection (for example, by laser and/or electrosurgical needle and/or ultrasonic probe); bleeding points may be coagulated in the standard methods. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter. In alternative implementations, the surgeon may open an additional incision down the path closer to the treatment zone.

Step 5120 may comprise: applying one or more fluids to the tissue. In some implementations, the fluid(s) may comprise water. In some implementations, the fluid(s) may comprise an ionic fluid, such as a saline solution. The fluid(s) may be applied to the tissue by, for example, injection into the stab wound(s) and may comprise a fluid that is both ionic and an anesthetic, such as a tumescent anesthesia. Some implementations may comprise applying one or more fluids that serve as an ionic fluid, an anesthetic, and an adrenaline In some such implementations, the fluid(s) may comprise a Klein Formula, such as about 1 cc-3 cc of Klein Formula (such as a 0.1% lidocaine+epinephrine 1:1, 000,000+NaHCO$_3$@5 meq/L of saline) per square centimeter of anticipated dissection. This fluid(s) may be injected into the stab wounds via, for example, a 3 mm spatula cannula with syringe, and may be fanned out to match the area to be dissected/undermined. In some implementations, Tumescent Anesthesia (TA) may be allowed to settle for about 10-30 minutes.

One or more fluids may alternatively, or additionally, be applied to the tissue by using the TD. For example, the TD may comprise one or more canals for delivering fluids to the tissue (for example, canal 304 depicted in FIG. 3a). In some embodiments, the canal(s) may be configured to deliver the fluid(s) adjacent to the lysing tip such as via a port located adjacent to the internal device cannula and/or lysing tip. In some such embodiments, the canal(s) may be configured to deliver the fluid(s) to the area around the lysing tip.

In some implementations, heat may be produced or energy may otherwise be released in the dermis or subdermis as the TD is passed in a subdermal plane. Heat or energy from below may heat the dermis. In some implementations, heating portions of the dermis such as upper dermis or attached epidermis may be undesirable. As such, in some implementations, undesirable heating of such layers may be mitigated as described in the previous method 5100 for apocrine glands.

In some implementations, heat may be produced or energy may otherwise be released in the dermis or subdermis as the TD is passed in a subdermal plane. Heat or energy from below may heat the dermis. In some implementations, heating portions of the dermis such as upper dermis or attached epidermis may be undesirable. As such, in some implementations, undesirable heating of such layers may be mitigated by a applying a cooling step antecedent and or concurrent to energy delivery with the TD. Such steps may comprise use of a cooling mechanism such as a cooling mechanism comprising a contact cooling object such as a cooling pad or bag. Such cooling mechanism may comprise for example, a closed water bag at a temperature of less than 37° C. In some implementations, the fluid or gel may range in temperature of between 1° C. to 20° C. In some such implementations, the fluid or gel may be about 15° C. Other cooling mechanisms may comprise a dynamic cooling system wherein a cool liquid and/or gel and/or gas is actively pumped into or though the contact cooling object. In other implementations, a thermoelectric or Peltier cooling mechanism may be applied to externally cool the skin. One or more cooling fluids (which may include gasses and/or gels) may alternatively, or additionally, be applied to the tissue by using the TD. For example, the TD may comprise one or more canals for delivering fluids such as coolants to the tissue. In some embodiments, the canal(s) may be configured to deliver the fluid(s) adjacent to the lysing tip such as via a port located adjacent to the internal device cannula and/or lysing tip.

Step 5130 may comprise: inserting TD into the incision and fanning in strokes sufficient to cover a target area of for example, about 60 sqcm.

Step 5135 may comprise applying energy to one or more portions of the dissected area, for example, to heat the tissue to a desired temperature to cause a desired effect, for example, to alter sweat glands and/or nerves and/or the tissues surrounding said glands or nerves. In some implementations, such energy may be applied through the lysing tip by activating the electrosurgical generator's coagulation mode. In alternative embodiments, the lysing tip may be replaced with a tissue modifying tip (TMT) illustrated in FIGS. 32 and 33 which may be activated with coagulation energy. In alternative implementations, a surgeon may choose another method to apply energy to tissues. Applying cooling fluids and/or cooling methods during this step may be beneficial.

Step 5137 may comprise: milking the dissected area to determine if any significant bleeding or drainage is present.

Step 5140 may comprise closing the entrance wounds or surface incisions via glues, staples, adhesive skin closure strips, and/or sutures.

TD may be used in an implementation of a method 5200 for incapacitating eccrine glands as shown in FIG. 52. Although method 5200 is shown in the figure beginning with step 5205, it should be understood that any of the preliminary and later steps described above in connection with other implementations and/or methods and/or methods 4000, 4100, and 4200 may be performed in method 5200 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 52.

Step 5205 may comprise: having the surgical area cleaned by, for example, isopropyl alcohol (degreaser) followed by germicidal chlorhexidine scrub. Step 5210 may comprise: applying a local anesthetic (such as injecting), such as about 1 cc of a 1% lidocaine+1:10,000 adrenaline, to form a wheal/hive on the periphery of the proposed dissection area on the axilla. Step 5215 may comprise, after allowing the local anesthetic to settle, making an entrance incision and creating a tip deployment pocket. The first sub-step of step 5215 may comprise, after allowing the local anesthetic to settle, performing a simple "stab" incision of the wheal, for example, a #15 Bard-Parker™ Scalpel into the subcutaneous fat. This incision may be about 3 mm in length or less. The second sub-step of step 5215 may comprise creating a tip deployment pocket that may receive the lysing tip; said pocket may be made using a scalpel, scissors and/or wide array of instruments known in the art to dissect tissue. The tip deployment pocket may be made by blunt dissection such as using a Metzenbaum scissors in a spreading fashion and/or by sharp dissection using scalpel blade and/or scissor and/or energized dissection (for example, by laser and/or electrosurgical needle and/or ultrasonic probe); bleeding points may be coagulated in the standard methods. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter.

Step 5220 may comprise: applying one or more fluids to the tissue. In some implementations, the fluid(s) may comprise water. In some implementations, the fluid(s) may comprise an ionic fluid, such as a saline solution. The fluid(s) may be applied to the tissue by, for example, injection into the stab wound(s) and may comprise a fluid that is both ionic and an anesthetic, such as a tumescent anesthesia. Some implementations may comprise applying one or more fluids that serve as an ionic fluid, an anesthetic, and an adrenaline In some such implementations, the fluid(s) may comprise a Klein Formula, such as about 1 cc-3 cc of Klein Formula (such as a 0.1% lidocaine+epinephrine 1:1,000,000+NaHCO$_3$@5 meq/L of saline) per square centimeter of anticipated dissection. This fluid(s) may be injected into the stab wounds via, for example, a 3 mm spatula cannula with syringe, and may be fanned out to match the area to be dissected/undermined. In some implementations, Tumescent Anesthesia (TA) may be allowed to settle for about 10-30 minutes.

One or more fluids may alternatively, or additionally, be applied to the tissue by using syringes and/or other cannulas and/or tubing. Alternatively, the TD may comprise one or more canals for delivering fluids to the tissue. In some embodiments, the canal(s) may be configured to deliver the fluid(s) adjacent to the lysing tip such as via a port located adjacent to the internal device cannula and/or lysing tip. In some such embodiments, the canal(s) may be configured to deliver the fluid(s) to the area around the lysing tip.

In some implementations, heat may be produced or energy may otherwise be released in the dermis or subdermis as the TD is passed in a subdermal plane. Heat or energy from below may heat the dermis. In some implementations, heating portions of the dermis such as upper dermis or attached epidermis may be undesirable. As such, in some implementations, undesirable heating of such layers may be mitigated as described in the previous method 5000 for apocrine glands.

Step 5230 may comprise: inserting TD into the incision and fanning in strokes sufficient to cover a target area of for example, about 60 sqcm.

Step 5235 may comprise applying energy to one or more portions of the dissected area, for example, to heat the tissue to a desired temperature to cause a desired effect, for example, to alter sweat glands and/or nerves and/or the tissues surrounding said glands or nerves. In some implementations, such energy may be applied through the lysing tip by activating the electrosurgical generator's coagulation mode. In alternative embodiments, the lysing tip may be replaced with a tissue modifying tip (TMT) illustrated in FIGS. 32 and 33 which may be activated with coagulation energy. In alternative implementations, a surgeon may choose another method to apply energy to tissues. Applying cooling fluids and/or cooling methods during this step may be beneficial.

Step 5237 may comprise: milking the dissected area to determine if any significant bleeding or drainage is present.

Step 5240 may comprise closing the entrance wounds or surface incisions via glues, staples, adhesive skin closure strips, and/or sutures.

TD may be used in one implementation of a method 5300 for incapacitating hair follicles is shown in FIG. 53. Although method 5300 is shown in the figure beginning with step 5305, it should be understood that any of the preliminary and later steps described above in connection with other implementations and/or methods and/or methods 4000, 4100, and 4200 may be performed in method 5300 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 53.

Step 5305 may comprise: having the surgical area cleaned by, for example, isopropyl alcohol (degreaser) followed by germicidal chlorhexidine scrub. Step 5310 may comprise: applying a local anesthetic (such as injecting), such as about 1 cc of a 1% lidocaine+1:10,000 adrenaline, to form about a wheal/hive on the periphery of the proposed dissection area.

Step 5315 may comprise, after allowing the local anesthetic to settle, making an entrance incision and creating a tip deployment pocket. The first sub-step of step 5315 may comprise, after allowing the local anesthetic to settle, performing a simple "stab" incision of the wheal, for example, a #15 Bard-Parker™ Scalpel into the subcutaneous fat. This incision may be about 3 mm in length or less. The second sub-step of step 5315 may comprise creating a tip deployment pocket that may receive the lysing tip; said pocket may be made using a scalpel, scissors and/or wide array of instruments known in the art to dissect tissue. The tip deployment pocket may be made by blunt dissection such as using a Metzenbaum scissors in a spreading fashion and/or by sharp dissection using scalpel blade and/or scissor and/or energized dissection (for example, by laser and/or electrosurgical needle and/or ultrasonic probe); bleeding points may be coagulated in the standard methods. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter. In alternative implementations, the surgeon may open an additional incision down the path closer to the treatment zone.

Step 5320 may comprise: applying one or more fluids to the tissue. In some implementations, the fluid(s) may comprise water. In some implementations, the fluid(s) may comprise an ionic fluid, such as a saline solution. The fluid(s) may be applied to the tissue by, for example, injection into the stab wound(s) and may comprise a fluid that is both ionic and an anesthetic, such as a tumescent anesthesia. Some implementations may comprise applying one or more fluids that serve as an ionic fluid, an anesthetic, and an adrenaline In some such implementations, the fluid(s) may comprise a Klein Formula, such as about 1 cc-3 cc of Klein Formula (such as a 0.1% lidocaine+epinephrine 1:1,000,000+NaHCO$_3$@5 meq/L of saline) per square centimeter of anticipated dissection. This fluid(s) may be injected into the stab wounds via, for example, a 3 mm spatula cannula with syringe, and may be fanned out to match the area to be dissected/undermined. In some implementations, Tumescent Anesthesia (TA) may be allowed to settle for about 10-30 minutes.

One or more fluids may alternatively, or additionally, be applied to the tissue by using the TD. For example, the TD may comprise one or more canals for delivering fluids to the tissue. In some embodiments, the canal(s) may be configured to deliver the fluid(s) adjacent to the lysing tip such as via a port located adjacent to the internal device cannula and/or lysing tip. In some such embodiments, the canal(s) may be configured to deliver the fluid(s) to the area around the lysing tip. Alternatively, or additionally, the fluid(s) may be delivered elsewhere on the tip or elsewhere on the shaft of the TD.

In some implementations, heat may be produced or energy may otherwise be released in the dermis or subdermis as the TD is passed in a subdermal plane. Heat or energy from below may heat the dermis. In some implementations, heating portions of the dermis such as upper dermis or attached epidermis may be undesirable. As such, in some implementations, undesirable heating of such layers may be mitigated as described in the previous method 5000 for apocrine glands.

Step 5330 may comprise: inserting TD into the incision and fanning in strokes sufficient to cover an area of for example, about 60 sqcm.

Step 5335 may comprise applying energy to one or more portions of the dissected area, for example, to heat the tissue to a desired temperature to cause a desired effect, for example, to alter hair follicles and/or the tissues surrounding said follicles. In some implementations, such energy may be applied through the lysing tip by activating the electrosurgical generator's coagulation mode. In alternative embodiments, the lysing tip may be replaced with a tissue modifying tip (TMT) illustrated in FIGS. 32 and 33 which may be activated with coagulation energy. In alternative implementations, a surgeon may choose another method to apply energy to tissues. Applying cooling fluids and/or cooling methods during this step may be beneficial.

Step 5337 may comprise: milking the dissected area to determine if any significant bleeding or drainage is present.

Step 5340 may comprise closing the entrance wounds or surface incisions via glues, staples, adhesive skin closure strips, and/or sutures.

In one implementation, TD may be used for the treatment of cellulite, such as cellulite treatment zones 5401 and 5402 as shown in FIG. 54. Said implementation may comprise a method 5500 of steps listed in FIG. 55. A more particular example of such an implementation is further illustrated in FIG. 54. It should be understood that any of the steps described above in connection with other implementations and/or methods 4000, 4100, and 4200 may be performed in methods 5500 as well. For example, one or more other steps of any of the other implementations described herein such as for example, steps 4005-4035 of the method depicted in FIG. 40, steps 4105-4115 of the method depicted in FIG. 41, and steps 4205-4240 of the method depicted in FIG. 42 may also be included in the method depicted in FIG. 55.

Step 5505 comprises making an entrance incision. In some implementations step 5505 may comprises making a stab incision 5410 in a location that is not usually visible to the eye, for example, the bikini line. In some implementations the incision may be of sufficient length to receive the lysing tip and/or cannula in an axial/delivery configuration. Preferably, the length of the incision is no greater than as necessary to receive the lysing tip and/or cannula. Preferably, the length of the incision is smaller than the length of the lysing tip in its treatment configuration. In some implementations, the length of the incision may be between about 2 mm and 12 mm.

Step 5510 may comprise forming a tip deployment pocket 5411*a* for receipt and/or reconfiguring of the lysing tip from its delivery configuration to its treatment configuration. In some implementations, curved blunt scissors may be used to make this tip deployment pocket by for example inserting said scissors up to its pivot point and/or opening/closing the scissors. In some implementations, the tip deployment pocket may be approximately the size of half of a postage stamp. For example, the tip deployment pocket may have a width in the direction of the incision of about 1 cm. Similarly, the tip deployment pocket may have a length perpendicular to the width of between about 1 cm to 2 cm. The dissection plane of the pocket is preferably in the same plane of dissection of the path to the treatment zone and/or the treatment zone. However, it is contemplated that in an alternative implementation a surgeon may use the TD to move from the plane of the pocket into another tissue plane. Preferably, the width of the tip deployment pocket is larger than the length of the incision to, for example, minimize scarring but create an area large enough to accommodate the lysing tip being deployed to its treatment configuration. Preferably, the width of the tip deployment pocket is approximately equal to or slightly larger than the length of the lysing tip. In some implementations, the proximal edge of the tip deployment pocket defining the width of the pocket may be coincident with or positioned slightly distal of the incision line as shown in FIG. 54*a*. The tip deployment pocket may be made using a scalpel, scissors, and/or wide array of instruments known in the art to dissect tissue. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter. In alternative implementations, the surgeon may open an additional incision down the path closer to the treatment zone.

Step 5515 may comprise inserting the TD through the incision and deploying/securing the lysing tip. In some implementations, the TD may be deployed through a cannula and once within the tip deployment pocket may be reconfigured from its delivery configuration to its treatment configuration. In other implementations, the lysing tip and/or grasping/control means may be inserted through the incision to the tip deployment pocket in which the lysing tip and grasping/control means may be coupled together in the treatment configuration. For example, the lysing tip may be grasped in an axial configuration such as along one of the sides of the grasping pad 718 as shown in FIG. 7*e*. The lysing tip may then be released and rotated manually, such as by palpation, after which the lysing tip may be grasped in the treatment configuration with the elongated length of the lysing tip perpendicular or at least substantially perpendicular to the axis of the grasping/control. means.

In some implementations in which the lysing tip, either lysing tip 710 or any of the other free floating lysing tips disclosed herein, are manually inserted, a surgeon may insert the lysing tip through an entrance incision such that the longest axis of the lysing tip (typically the axis between the two outer protrusions and/or beads) is parallel or at least substantially parallel to the direction of insertion. Once the lysing tip has been inserted through the entrance incision, the lysing tip may be manually rotated such as by palpation, or by use of the control/grasping instrument, or an external device such as a hemostat or another suitable instrument. In some such implementations, a tip deployment pocket may be created before insertion of the lysing tip as discussed below. This tip deployment pocket may facilitate rotation of the lysing tip and/or may allow for coupling of the lysing tip with a suitable instrument for delivering electrosurgical energy and/or controlling the lysing tip during a surgical procedure.

Step 5516 may comprise having in place and utilizing an infrared and/or heat detecting camera 13 (e.g., FLIR®) connected by wire or wirelessly (for example via antennae 47*a*) to a central processing unit 14 and output video monitor 15; the camera data may be combined with data input that may be generated by signals originating from RFID chips and/or antennae 47 with further data that may originate from sensors 48 that may be located on or near lysing tips or TMTs (lysing tip and control grasping instrument system 16 are depicted in FIG. 54*a* with antennae 47 and sensor 48 mounted on grasping control instrument shaft). In some embodiments, sensor 48 may be a thermistor. Infrared camera images overlying sensor outputs and location outputs on the video screen may aid the surgeon in determining the proper speed of the tip and/or settings and/or dwelling time. One or more of these steps involving use of an infrared camera may be applied to other ski-related methods disclosed herein such as those related to treatment of apocrine and eccrine sweating, incapacitation of hair follicles, treatment of cellulite, wrinkles, lines, folds, and other defects, as well as rejuvenational treatments for the face, neck, and brow/scalp.

Step 5520 may comprise forming one or more paths 5412*a*/5412*b* to one or more treatment zones 5401 and/or 5402 respectively. In some implementations, a fifth step may comprise activating one or more lysing members and then advancing the lysing tip towards the treatment zone. This may be done for example in a series of substeps by advancing the lysing tip and pulling it back in a repeated fashion similar to a battering ram. The surgeon may create additional paths adjacent to the initial path, thus creating a triangular and/or cone shape between the incision and the treatment zone. In alternative implementations, wherein the surgeon may prefer to minimize the amount of energy deposited along the path to the target tissue/cellulite treatment zone, especially while using lysing tips of 3 protrusions or less, the lysing tip may be rotated with the lysing rod axis perpendicular to the plane of the skin to create the path. Rotating the lysing rod axis perpendicular may allow the tip to migrate in between the vertically oriented fibrous bands between the dermis and the lower/deeper tissues. As shown in FIG. 54*a*, if the treatment zone 5401 has a width wider than the width of the path, the surgeon may, either right before or simultaneously with movement of the tip into the treatment zone, manipulate the treatment zone, such as by traction (either manual or using instrumentation), into the path of the lysing tip. For example, as indicated by arrow 5415, initially a top portion of the treatment zone may be forced downward into the path of the lysing tip. The lysing tip may then be used to treat the top portion of the treatment zone. Subsequently, a bottom portion of the treatment zone may then be manipulated in the direction of arrow 5416 into the path of the lysing tip and the lysing tip may then be used to treat the bottom portion of the treatment zone. In some implementations, the lysing tip will extend beyond the boundaries of the treatment zone 5401; this "feathering" beyond the boundaries into more normal tissues may ensure full treatment of the condition. This step may be repeated to treat all of the various treatment zones such as 5402. Preferably, paths to each of the various treatment zones (for example, 5412b) may come from the same incision 5410 and tip deployment pocket 5411.

In an alternative implementation depicted in FIG. 54b, the tip deployment pocket 5411b may be more adjacent to the treatment zone 5401. In some such implementations the tip deployment pocket 5411b may be formed during the course of repositioning the lysing tip between its delivery and treatment configurations. For example, the proximal portion of the path 5413 may be formed by advancing the cannula and/or lysing tip from the incision in the delivery configuration after which the lysing members may be activated and the lysing tip rotated or otherwise repositioned from the delivery to the treatment configurations thereby forming a tip delivery pocket for delivery of the lysing tip to the treatment zone.

Step 5525 may comprise, after lysing the tissues in the treatment zone, applying energy to the treatment zone. In some implementations, energizing the lysing member(s) with a cut and/or coagulation and/or blend between cut and coagulation energy waveforms may accomplish a desired treatment, for example, heating/denaturing the subcutaneous adipose tissues which may result in their reduction and/or heating the subdermal tissue layers to cause a skin tightening effect. In other implementations, to apply energy to the treatment zone(s), the lysing tip may be withdrawn from the incision and another energy deposition device and/or a TMT (Tissue Modification Tip) may be energized to deposit energy in the treatment zone(s) for an intended effect. The TMT may be passed to or through the treatment zone with the energy window facing upwards towards the subdermal layers. Possible results of pointing upwards may include alteration of the collagen in that area yielding overlying skin tightening. In some implementations, the TMT may be turned upside down with the energy window directed at the subcutaneous adipose tissue layer and energized during at least part of the procedure. Possible results of this may include the alteration and/or damaging and/or death of some adipose cells that stimulate an inflammatory response in the subcutaneous adipose tissues that may transfer to the subdermal and/or dermal layers via cells and/or chemical/biological mediators thus possibly resulting in the alteration of tissue thickness and/or tissue tightening in tissues that had not been directly damaged/modified by the lysing tip and/or TMT.

In some implementations, a surgeon may reduce bleeding by use of such instruments as a bovie probe and/or grasper/clamp. In alternative implementations, the surgeon may use the lysing members of the lysing tip and/or the energy window of the TMT to modify tissues for various intended results, including but not limited to skin tightening and fat modification. In such implementations, the energy window of the TMT may be configured to deliver the following types of energy modalities including but not limited to laser, intense pulse light, resistive heating, radiant heat, thermochromic, ultrasound, and/or microwave.

Step 5530 may comprise rotating and/or reconfiguring the lysing tip back into the delivery configuration in either the treatment area and/or the tip deployment pocket and/or the path, if it is sufficiently wide, and withdrawing the lysing tip and/or cannula back through the incision.

An example of a method 5600 for face dissection and/or face lifting according to some implementations will now be described as illustrated in FIG. 56.

Step 5605 may comprise, after allowing the local anesthetic to settle, making and/or extending and/or using an existing entrance incision at the front/bottom/rear of the ear and creating a tip deployment pocket. However, incisions with endoscopic and/or laparoscopic instruments should not be limited to this area as cosmetic surgeons may prefer to place incisions at anatomical boundaries and/or natural crease areas. In further contemplated embodiments, intra-oral, intra-nasal, and routes of instrument passage through the inner eyelids may be used for device and/or tip delivery. For example, an incision may be made where the nose and lip meet the cheek. An incision may be made in the skin in such a selected area so as to introduce a laparoscopic/endoscopic instrument, scissors, and/or scalpel to create a tip deployment pocket adjacent the incision if desired. The first sub-step of step 5605 may comprise, after allowing the local anesthetic to settle, performing a simple "stab" incision of the wheal, for example, a #15 Bard-Parker™ Scalpel into the subcutaneous fat. This incision may be about 3 mm in length or less. The second sub-step of step 5605 may comprise creating a tip deployment pocket that may receive the lysing tip which may be positioned at the distal end of the device, which pocket may be made/enlarged with a scalpel, any laparoscopic instrument with or without electrosurgical current applied to it, an ultrasonic surgical device and/or microwave-powered instrument and/or laparoscopic scissors, and/or thermochromic media, electromagnetically energized instrument, and/or thermally energized instrument, and/or scissor tips, and/or knife tips. The tip deployment pocket may be made by blunt dissection such as using a Metzenbaum scissors in a spreading fashion and/or by sharp dissection using scalpel blade and/or scissor and/or energized dissection (for example, by laser and/or electrosurgical needle and/or ultrasonic probe); bleeding points may be coagulated in the standard methods. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter. The tip deployment pocket may or may not be the desired tissue layer of the dissection and/or the final dissection as various blends of dissection planes may be used by certain surgeons to achieve desired face lifting. However, a comfortable plane in which to create a tip deployment pocket would likely be the upper subcutaneous plane in the preauricular region. Tip deployment pockets may be created in other locations using endoscopic instruments farther along the planned path of dissection and/or via separate stab incision further along the path of dissection. The instrument that made the tip deployment pocket is then removed. Depending upon the quality of the tissue in the tip deployment pocket adjacent the entrance incision, the lysing tip of the TD may be used to form the tip deployment pocket by energizing the lysing members of the lysing tip while rotating the lysing tip from the delivery configuration to the treatment configuration.

Step 5610 may comprise inserting the TD through the incision into the tip deployment pocket for receipt and/or reconfiguring of the lysing tip from its delivery configuration to its treatment configuration.

In some implementations, the TD may be deployed through a cannula and once within the tip deployment pocket may be reconfigured from its delivery configuration to its treatment configuration. In other implementations, the lysing tip and/or grasping/control means may be inserted through the incision to the tip deployment pocket in which the lysing tip and grasping/control means may be coupled together in the treatment configuration. For example, the lysing tip may be grasped in an axial configuration such as along one of the sides of the grasping pad 718 as shown in FIG. 7e prior to inserting the TD in the incision. The lysing tip may then be inserted in the incision and released. Then the lysing tip may be rotated; if necessary, manual rotation may be implemented (for example, by palpation) after which the lysing tip may be grasped in the treatment configuration with the elongated length of the lysing tip perpendicular or at least substantially perpendicular to the axis of the grasping/control means.

Step 5615 may comprise making paths with the TD. In some implementations, after activating the TD, the surgeon may advance the tip a certain distance, for example, 2 cm. The tip may then be pulled back (with or without electrosurgical energy), in some cases to the tip deployment pocket, and dissection may then proceed along the same path or along an immediately adjacent path. It may be convenient for the surgeon to only partially overlap advancing strokes especially in more dense tissue. It may also be beneficial not to use energy on the withdrawal (non-forward) portion of the strokes. A possible example of only partially overlapping advancing strokes is, if the device is four bulbs wide (the initial path should be about four bulbs wide); a new adjacent path may be lysed with two bulbs in the new adjacent path and two bulbs in the previously dissected path. The device tip may then be pulled back, in some cases to the tip deployment pocket, and advanced on the other adjacent path immediately adjacent to the original dissection path with two bulbs in the new adjacent path and two bulbs in the original dissection path. If using the four bulb device example, the width of the original dissection would be four bulbs. Then the additional adjacent dissection paths would be two plus two bulbs in width resulting in an overall two plus two plus two equal six bulb width path after three forward strokes. The device path may be lengthened in segments in a similar fashion. The device path width may be increased in segments in a similar fashion.

The dissection may be increased segmentally until it occupies the entire area the surgeon desires to dissect at the appropriate depth or plane(s) of choice of the surgeon. Other endoscopic instruments may be used to observe and/or maintain the plane and/or address bleeding blood vessels and/or tissues. Upon completion of the desired dissection, within any point of the dissection with sufficient area, the lysing tip may be rotated from the treatment configuration to the delivery configuration and withdrawn through the entrance incision.

Step 5620 may comprise subjecting some or all exposed tissue(s) to additional energy via a lysing tip or a separate TMT. In some implementations, after dissection in segments and/or the total dissection, one or more additional types of energy may be applied to the inner and/or outer layers of the dissection plane. The lysing member of the TD and/or the energy window of the TMT may be directed at the subcutaneous adipose tissue layer and energized. Possible results of this may include the alteration and/or damaging and/or death of some adipose cells that stimulate an inflammatory response in the subcutaneous adipose tissues that may transfer to the subdermal and/or dermal layers via cells and/or chemical/biological mediators thus possibly resulting in the alternation of tissue thickness and/or tissue tightening in tissues that had not been directly damaged/modified by the lysing tip and/or TMT. In other implementations, energy applied to the inner layer of the dissection plane may alter and/or damage other tissues including fibrous tissues wherein the results of damaging said tissues may release mediators and/or products of damage such as charred debris which may also stimulate an inflammatory and/or immunologic response that may cause tissue contraction and/or fibrosis in that layer of the dissection plane and/or in an adjacent layer. In alternative implementations, the surgeon may use the lysing members of the lysing tip and/or the energy window of the TMT to modify tissues for various intended results, including but not limited to skin tightening and fat modification.

In some implementations, a surgeon may reduce bleeding by use of such instruments as a bovie probe and/or graspers or clamps and/or grasping and/or clamp-like instruments. In some implementations, a device utilizing ultrasonic vibration to cut and cauterize tissue such as a harmonic scalpel may be used to reduce bleeding. In alternative implementations, the surgeon may use the lysing members of the lysing tip and/or the energy window of the TMT to modify tissues for various intended results, including but not limited to skin tightening and/or fatty tissue modification. In such implementations, the energy window of the TMT may be configured to deliver the following types of energy: electrosurgical, ultrasound, intense pulse light, laser, radiant heat, thermochromic, and/or microwave. In such implementations, the energy window of the TMT may be configured to deliver the following types of energy modalities including, but not limited to, laser, intense pulse light, resistive heating, radiant heat, thermochromic, ultrasound, mechanical, and/or microwave.

Step 5623 may comprise: lightly milking the dissected area to determine if any significant bleeding or drainage is present.

Step 5624 may comprise closing the entrance wounds or surface incisions via glues, staples, adhesive skin closure strips, and/or sutures.

Step 5625 may comprise post-operative care. Some post-operative dressings may be appropriate to reduce the incidence of seromas and/or hematomas. Appropriate dressings may include some with pressure characteristics. Incisions may be dealt with by methods that may include suturing and/or stapling and/or tissue gluing and/or taping, for example, with Steri-Strips® and/or other methods that the surgeon may desire.

An example of a method 5700 for neck dissection and/or neck lifting according to some implementations will now be described as illustrated in FIG. 57. This method may be performed by itself or with other procedures including method 5600.

Step 5705 may comprise, after allowing the local anesthetic to settle, making and/or extending and/or using an existing entrance incision and creating a tip deployment pocket. In some implementations, the neck dissection may be carried out by extending the lower portion of the face lift dissection or separately as its own procedure. Therefore, neck dissection entrance wounds may be located in the submental crease area and/or around the chin. Other entrance areas may also include those around the ear.

However, incisions with endoscopic and/or laparoscopic instruments should not be limited to this area as cosmetic surgeons may prefer to place incisions at anatomical boundaries and/or natural crease areas. The first sub-step of step 5705 may comprise, after allowing the local anesthetic to settle, performing a simple "stab" incision of the wheal, for example, a #15 Bard-Parker™ Scalpel into the subcutaneous fat. This incision may be about 3 mm in length or less. The second sub-step of step 5705 may comprise creating a tip deployment pocket that may receive the lysing tip at the distal end of the device; the tip deployment pocket may be made using a scalpel, scissors, and/or wide array of instruments known in the art to dissect tissue. The tip deployment pocket may be made by blunt dissection such as using a Metzenbaum scissors in a spreading fashion and/or by sharp dissection using scalpel blade and/or scissor and/or energized dissection (for example, by laser and/or electrosurgical needle and/or ultrasonic probe); bleeding points may be coagulated in the standard methods. In certain implementations, a comfortable size of the tip deployment pocket may be about 150% of the length of the lysing tip with a comfortable range of 100% to 300% of length of the lysing tip. For example, a 13 mm lysing tip may deploy to the treatment configuration in a pocket of 2 cm squared or a circular pocket of 2 cm in diameter. The tip deployment pocket may or may not be the desired tissue layer of the dissection and/or the final dissection as various blends of dissection planes may be used by certain surgeons to achieve desired neck lifting. However, a comfortable plane in which to create a tip deployment pocket may be the upper subcutaneous plane in the preauricular region. Tip deployment pockets may be created in other locations using laparoscopic/endoscopic instruments farther along the planned path of dissection and/or via separate stab incision further along the path of dissection. The instrument that made the tip deployment pocket may then be removed. Depending upon the quality of the tissue in the tip deployment pocket adjacent the entrance incision, the lysing tip of the TD may be used to form the tip deployment pocket by energizing the lysing members of the lysing tip while rotating the lysing tip from the delivery configuration to the treatment configuration.

Step 5710 may comprise forming a tip deployment pocket for receipt and/or reconfiguring of the lysing tip from its delivery configuration to its treatment Step 5715 may comprise making paths with the TD. In some implementations, after activating the TD, the surgeon may advance the tip a certain distance, for example, 2 cm. The tip may then be pulled back (with or without electrosurgical energy), in some cases to the tip deployment pocket, and dissection may then proceed along the same path or along an immediately adjacent path. It may be beneficial to reduce the amount of potential tissue damaging energy to use energy on advancing strokes of the TD and not using energy on the withdrawal (non-forward) portion of the strokes. For example, if the device is four bulbs wide, that is the width of the initial path. The new adjacent path may be lysed with two bulbs in the new adjacent path and two bulbs in the previously dissected path. The device tip may then be pulled back, in some cases to the tip deployment pocket, and advanced on the other adjacent path immediately adjacent to the original dissection path with two bulbs in the new adjacent path and two bulbs in the original dissection path. If using the four bulb device example, the width of the original dissection would be four bulbs. Then the additional adjacent dissection paths would be two plus two bulbs in width resulting in an overall two plus two plus two equal six bulb width path after three forward strokes. The device path may be lengthened in segments in a similar fashion. The device path width may be increased in segments in a similar fashion.

The dissection may be increased segmentally until it occupies the entire area the surgeon desires to dissect at the appropriate depth or plane(s) of choice of the surgeon. Other endoscopic instruments may be used to observe and/or maintain the plane and/or address bleeding blood vessels and/or tissues. Upon completion of the desired dissection, within any point of the dissection with sufficient area, the lysing tip may be rotated from the treatment configuration to the delivery configuration and withdrawn through the entrance incision.

Step 5620 may comprise subjecting some or all exposed tissue(s) to additional energy via a lysing tip and/or a separate TMT. In some implementations, after dissection in segments and/or the total dissection, one or more additional types of energy may be applied to the inner and/or outer layers of the dissection plane. The lysing member of the TD and/or the energy window of the TMT may be directed at the subcutaneous adipose tissue layer and energized. Possible results of this may include the alteration and/or damaging and/or death of some adipose cells that stimulate an inflammatory response in the subcutaneous adipose tissues that may transfer to the subdermal and/or dermal layers via cells and/or chemical/biological mediators thus possibly resulting in the alternation of tissue thickness and/or tissue tightening in tissues that had not been directly damaged/modified by the lysing tip and/or TMT. In other implementations, energy applied to the inner layer of the dissection plane may alter and/or damage other tissues including fibrous tissues wherein the results of damaging said tissues may release mediators and/or products of damage such as charred debris which may also stimulate an inflammatory and/or immunologic response that may cause tissue contraction/tightening and/or fibrosis in that layer of the dissection plane and/or in an adjacent layer.

Step 5623 may comprise lightly milking the dissected area to determine if any significant bleeding or drainage is present.

Step 5624 may comprise closing the entrance wounds or surface incisions via glues, staples, adhesive skin closure strips, and/or sutures.

Step 5625 may comprise, after the neck has been dissected, addressing such other concerns as platysmal banding and/or prolapsed tissues such as salivary glands using sutures and/or meshes and/or other laparoscopic/endoscopic tools as known in the art. In some implementations, a surgeon may reduce bleeding by use of such instruments as a bovie probe and/or graspers or clamps and/or grasping and/or clamp-like instruments. In some implementations, a device utilizing ultrasonic vibration to cut and cauterize tissue such as a harmonic scalpel may be used to reduce bleeding. In alternative implementations, the surgeon may use the lysing members of the lysing tip and/or the energy window of the TMT to modify tissues for various intended results, including but not limited to skin tightening and/or fatty tissue modification. In such implementations, the energy window of the TMT may be configured to deliver the following types of energy: electrosurgical, ultrasound, intense pulse light, laser, radiant heat, thermochromic, and/or microwave.

Step 5630 may comprise post-operative care. Some post-operative dressings may be appropriate to reduce the incidence of seromas and/or hematomas. Appropriate dressings may include some with pressure characteristics. Incisions may be dealt with by methods that may include suturing and/or stapling and/or tissue gluing and/or taping, for example, with Steri-Strips® and/or other methods that the surgeon may desire.

The TD may be used to treat various skin wrinkles, lines, folds and other visible defects. In an implementation, dissecting with the TD through, or around the platysma muscle in the neck in areas of lines or wrinkles may alter the attachments of the platysma to overlying or adjacent skin and thus diminish the visible assessment of surface defects.

In an alternative implementation, dissecting and/or energizing with the TD through or around the muscles of facial expression located in the superior nose, glabellar region, and/or adjacent tissues, for example, the procerus muscle, depressor supercilii muscle, and corrugator supercilii muscle may damage, denature, fibrose, alter, denervate and/or disconnect the muscles and their action from the overlying or adjacent skin thus reducing the frown wrinkles or folds around the superior nose.

In some implementations, the surface skin effects of other muscles of facial expression may be altered by dissecting the tissues which may be attached between those muscles and the surface skin, no matter how loosely or indirect, using the TD. For example, some muscles of facial expression around the mouth contribute to the formation of the nasal labial fold which gives may give an aging appearance depending upon its depth, acuteness, and/or shadow effect. Disinserting the surface skin in the area from the underlying or adjacent tissues by dissecting with the TD may diminish the visibility of these folds. The entrance incision for the TD to approach or reach the nasal labial fold may be anywhere on the face or head as well as inside the mouth or nose.

In another implementation, dissection with the TD may be used to diminish forehead wrinkles wherein the dissection and/or energy may damage, denature, fibrose, alter, denervate and/or disconnect the muscles and their action from the overlying or adjacent skin thus reducing the brow and/or forehead wrinkling.

In another implementation, the wrinkles around the lower and outer eyelids may be altered by dissecting between the orbicularis oculi muscle and the skin wherein a sheet of fibrous tissue may be laid down following dissection and/or energy which may have a less foldable character than the previously soft and pliable tissues. The entrance incision for the TD to approach the eyelid may be inside the lower eyelid through the conjunctiva and/or in a wrinkle of the face or lower eyelid.

Steps: everything for creating a path except can enter from inside nose or mouth or eye for areas mentioned above. Likely 2 bulb unit used. Since wrinkle or fold, dissection will be along the length of or around the fold, not perpendicular to it. May be with or without energy. May use TMT after dissection is complete; may point up or down. May be used in conjunction with an implant, even an injectable, solid, semi-solid implant. Finally, withdraw and sew.

An example of a method 5800 for brow and/or scalp dissection and/or brow lifting according to some implementations will now be described as illustrated in FIG. 58. Step 5805 may comprise making a sufficient number of incisions at the back of neck near or at the hairline and/or forehead/frontal hairline that permits sufficient passage of TD for intended effect. In other implementations, incisions may be made anywhere within the scalp region. Step 5810 may comprise creating the tip deployment pocket as disclosed herein. Step 5810 may comprise forming a tip deployment pocket for receipt and/or reconfiguring of the lysing tip from its delivery configuration to its treatment. Step 5815 may comprise dissecting the subgaleal plane with TD and may comprise fanning in the subgaleal plane, for example, in a spokewheel pattern, to the extent desired by the surgeon. Step 5820 may comprise reconfiguring the TD from the treatment configuration to the delivery configuration and/or removal through the entrance incision. Step 5825 may comprise, after desired tissue plane separation, rotating the dissected scalp in to the desired position, for example, backward toward neck. Step 5830 may comprise applying a fixation mechanism, for example, screws.

An example of a method 5900 for creation of pockets for implants, including, but not limited to, cosmetic implants, medical device and identification implants is described. An implant may be defined herein as any material surgically deposited and left in a patient/recipient's body that was not manufactured by the recipient's body. The TD may be useful because it may expeditiously create said paths and said pockets with minimal bleeding. Examples of cosmetic implant procedures in which the TD may be used may include, but are not limited to, skin, breast, face (cheek, brow), muscle (biceps, triceps, calf), and buttocks implants, to name a few. Examples of medical device implants in which the TD may be used may include, but are not limited to, drug implant devices, for example, insulin infusion pumps, cardiac pacemakers, artificial joints, implantable neurologic devices, implantable tracking and/or identification (for example, RFID) chips, to name a few. The placement of many implants, to minimize visible scarring, may involve creating one or more paths to the implant zone. Method 5900 according to some implementations will now be described as illustrated in FIG. 59. The implementations and embodiments from FIGS. 54 and 55 involving the treatment of cellulite are incorporated herein and may be modified as follows.

Implementation 5900 to place a cosmetic implant may use same route(s) as for cellulite treatment, however, the tip may be deployed to its treatment configuration closer to implant zone. The width of the path and the entrance incision is preferably the minimum size needed for the implant to traverse the path from the opening incision to the implant pocket. In some implementations, the surgeon may have to open up an additional incision to place implant; this may depend upon whether the implant has a capsule or has gel that will be moved to through the path to the pocket. The surgeon may create a pocket appropriately sized for the implant to rest.

Step 5905 comprises making an entrance incision. In some implementations, step 5905 may comprises making a stab incision in a location that is not usually visible to the eye from a reasonable distance, for example, the umbilicus/bellybutton and/or under the axilla and/or around the nipple in the case of a breast implant. The width of the entrance incision is preferably the minimum size needed for the TD tip and shaft to traverse the entrance incision. Although the implant may be of a larger diameter, it may be preferable for optimizing traction keep the entrance incision its minimum size until the path to the implant zone and/or the implant pocket are created.

Step 5910 may comprise forming a tip deployment pocket similar to that depicted in 5411*a* at FIG. 54 for receipt and/or reconfiguring of the lysing tip from its delivery configuration to its treatment configuration. In some implementations, curved blunt scissors may be used to make this tip deployment pocket by for example inserting said scissors up to its pivot point and/or opening/closing the scissors. In some implementations, the tip deployment pocket may be approximately the size of half of a postage stamp. For example, the tip deployment pocket may have a width in the direction of the incision of about 1 cm. Similarly, the tip deployment pocket may have a length perpendicular to the width of between about 1 cm to 2 cm. In some implementations, the surgeon may desire to open an additional incision to place the implant; this may depend upon whether the implant has a capsule or has gel that will be moved to through the path to the pocket.

Step 5915 may comprise reconfiguring the lysing tip within the tip deployment pocket for receipt and/or reconfiguring of the lysing tip from its delivery configuration to its treatment In some implementations, a surgeon may make such a wide entrance incision that the lysing tip may even fit through the incision in the treatment configuration. In some implementations, the TD may be deployed through a cannula and once within the tip deployment pocket may be reconfigured from its delivery configuration to its treatment configuration. In other implementations, the lysing tip and/or grasping/control means may be inserted through the incision to the tip deployment pocket in which the lysing tip and grasping/control means may be coupled together in the treatment configuration.

Step 5920 may comprise forming one or more paths to one or more implant zones as depicted in FIG. 54a. In some implementations, this may comprise activating one or more lysing members and then advancing the lysing tip towards the implant zone. This may be done for example in a series of substeps by advancing the lysing tip and pulling it back in a repeated fashion. The surgeon may create additional paths adjacent to the initial path, thus creating a triangular and/or cone shape between the incision and the implant zone. As shown in FIG. 54a, if the treatment zone 5402 has a width wider than the width of the path, the surgeon may, either right before or simultaneously with movement of the tip into the treatment zone, manipulate the treatment zone, such as by traction (either manual or using instrumentation), into the path of the lysing tip. The width of the path may be the minimum dimensions needed for the implant to traverse the path.

Step 5921 may comprise the surgeon creating an implant pocket appropriately sized for the implant to rest.

Step 5922, perhaps after removal of the TD, may comprise expanding the entrance incision to the minimum dimensions required for the maximum dimension of the implant to traverse the entrance incision.

Step 5925 may comprise, after lysing the tissues, applying energy to the implant zone with the TD or a separate TMT. In some implementations, a surgeon may reduce bleeding by use of such instruments as a bovie probe and/or grasper/clamp. In alternative implementations, the surgeon may use the lysing members of the lysing tip and/or the energy window of the TMT to modify tissues for various intended results, including but not limited to skin tightening and fat modification. In such implementations, the energy window of the TMT may be configured to deliver the following types of energy modalities including but not limited to laser, intense pulse light, resistive heating, radiant heat, thermochromic, ultrasound, and/or microwave.

Step 5930 may comprise rotating and/or reconfiguring the lysing tip back into the delivery configuration in either the treatment area and/or the tip deployment pocket and/or the path, if it is sufficiently wide, and withdrawing the lysing tip and/or cannula back through the incision.

Step 5935 may comprise delivery and/or placement and/or securing of the implant according to manufacturers' recommendations and/or specifications and/or qualified surgeons' modifications. Securing of the implant may include, but not be limited to, placing sutures, staples, and/or retention devices either in the tissues around the implant and/or along the tissues along the path of the implant and/or the tissues along the entrance incision.

Step 5940 may comprise closing the entrance wounds or surface incisions via glues, staples, adhesive skin closure strips, and/or sutures.

An example of a method 6000 for a capsulotomy and/or a capsulectomy will now be described as illustrated in FIG. 60. As breast implants may be viewed by the human body as a foreign object, scar tissue may develop around a breast implant over a 3 to 4 year period. This capsule of scar/fibrous tissue may be of a spherical shape. Step 6005 may comprise making an entrance incision as previously described herein. Step 6010 may comprise creating a tip deployment pocket near to or away from the entrance incision as previously described herein. Step 6015 may comprise inserting the TD in its delivery configuration and re-configuring the TD to its treatment configuration as previously described herein. Step 6020 may comprise activating the TD and creating paths to the treatment zone, in this embodiment, around the capsule. Step 6025 may comprise activating the TD and lysing the adhesions attaching to the capsule to the implant and/or surrounding tissues by moving along the periphery of capsule. Step 6028 may comprise returning the lysing tip to a deployment configuration. Step 6030 may comprise removal of the TD as previously described herein. Step 6035 may comprise separation and/or removal of at least a portion of the capsule from the surrounding tissues and/or the implant. In some implementations, step 6035 may be performed before step 6030.

Step 6035 may comprise withdrawal of the lysing tip. Step 6040 may comprise closing the entrance wounds or surface incisions via glues, staples, adhesive skin closure strips, and/or sutures.

An example of a method 6100 for body lifting and skin excision will now be described as illustrated in FIG. 61. An example of a use of this method includes tightening of sagging tissue on arms. Generally, this procedure involves undermining skin, excising a portion of said skin, and pulling tight the remaining skin.

Step 6105 may comprise making the skin incision near the undermining zone as previously described herein which may be under the arm pit and hydrating/tumescent the area to be undermined as stated previously. The area to be undermined may be 10 to 20 cm beyond the location of the incision demarking the skin to be removed. Step 6110 may comprise widening the entrance incision and creating the tip deployment pocket as stated previously. Step 6115 may comprise inserting the lysing tip in its delivery configuration into the tip deployment pocket and deploying the lysing tip to the treatment configuration.

Step 6120 may comprise undermining/lysing skin in locations beneath the skin to be removed as well as locations adjacent thereto in order to have sufficient tissue to pull the edges of the remaining tissue together to be closed. In this step, fat may be heated/removed as well. Step 6125 may comprise withdrawal of the lysing tip.

Step 6130 may comprise making the incision, which may be in the form of an ellipse, demarking the edges of the tissue to be removed. Step 6135 may comprise removal of the tissue comprising the shape of the ellipse. Step 6140 may comprise sewing fascia together to take the stress off of the skin when the edges of the skin are sewn together. Step 6145 may comprise closing wounds or surface incisions via glues, staples, adhesive skin closure strips, and/or sutures.

Modification of localized cutaneous neurologic symptoms. E.g., localized itching or burning. E.g., Notalgia paresthetica is an intense localized itching area usually on the back. Dissecting the skin in the NP area as well as around it may denervate or alter the neurologic pattern in area thus may provide relief. Post zoster neuralgia is an often painful condition that may feel like it is coming from the skin in patients who have suffered from shingles. Dissecting the skin in the post zoster neuralgia area as well as around it may denervate or alter the neurologic pattern in area thus may provide relief. Other itching and painful conditions of the skin possibly related to neurologic alterations may be improved by dissection with TD.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Furthermore, the described features, components, structures, steps, or characteristics may be combined in any suitable manner in one or more alternative embodiments and/or implementations. In other words, any of the features, components, structures, steps, or characteristics disclosed in any one disclosed embodiment may be combined with features, components, structures, steps, or characteristics of other disclosed embodiments. The scope of the present invention should, therefore, be determined only by the following claims.

The invention claimed is:

1. An electrosurgical lysing device, comprising:
a lysing tip, comprising:
a plurality of beads, wherein each of the plurality of beads comprises an electrically non-conductive surface configured to prevent electrosurgical energy from being delivered from each of the plurality of beads;
at least one lysing member defining at least one lysing segment extending between each pair of adjacent beads, wherein at least a subset of the plurality of beads protrudes both distally and proximally relative to the at least one lysing member; and
a tunnel extending at least partially through each of the plurality of beads, wherein the at least one lysing member is positioned to extend at least partially through the tunnel to define the at least one lysing segment between each pair of adjacent beads.

2. A system comprising the electrosurgical lysing device of claim 1, and further comprising a surgical tool configured to selectively engage a conductive portion of the lysing tip and deliver electrosurgical energy to the lysing tip during a surgical procedure.

3. The system of claim 2, wherein the surgical tool comprises at least one jaw, and wherein the at least one jaw is configured to selectively engage the conductive portion of the lysing tip.

4. The system of claim 3, further comprising a slot formed in the at least one jaw, wherein the slot is configured to receive at least a portion of the conductive portion of the lysing tip therethrough.

5. The system of claim 3, wherein the at least one jaw comprises a non-conductive exterior surface, and wherein at least a portion of an interior surface of the at least one jaw is conductive to allow for delivery of electrosurgical energy through the at least one jaw to the lysing tip.

6. A system comprising the electrosurgical lysing device of claim 1, further comprising a surgical tool configured to selectively engage the lysing tip and deliver electrosurgical energy to the at least one lysing member during a surgical procedure, wherein the lysing tip is configured to be coupled with the surgical tool such that, while coupled with the lysing tip, a distal end of the surgical tool protruding distally beyond the at least one lysing member has a shape that at least substantially mimics the shapes of each of the plurality of beads.

7. The electrosurgical lysing device of claim 1, wherein the plurality of beads comprises a first outer bead and a second outer bead positioned opposite from the first outer bead, and wherein the lysing tip further comprises a grasping plate coupled with the at least one lysing member, wherein the grasping plate is configured to be selectively engaged by a surgical tool during a surgical procedure within a patient's body.

8. The electrosurgical lysing device of claim 1, wherein at least one of the plurality of beads comprises a hole extending to the at least one lysing member, and wherein the at least one lysing member is coupled to each of the plurality of beads within each hole.

9. The electrosurgical lysing device of claim 1, wherein the at least one lysing member comprises a lysing rod extending at least partially through each of the plurality of beads, and wherein the lysing tip further comprises at least one spacer positioned on the lysing rod so as to confine each of the plurality of beads to a predetermined location on the lysing rod.

10. The electrosurgical lysing device of claim 1, wherein each of at least a subset of the plurality of beads comprises a plurality of facets formed thereon.

11. The electrosurgical lysing device of claim 1, further comprising:
a conductive shaft configured to be electrically coupled with an electrosurgical device; and
an insulating cover extending over a portion of the conductive shaft, wherein the at least one lysing member extends through an opening formed in the conductive shaft such that a bulbous projection extends beyond the at least one lysing member, and wherein the plurality of beads comprises a first outer bead and a second outer bead positioned opposite from the first outer bead such that the bulbous projection is positioned between the first outer bead and the second outer bead and such that a first lysing segment is defined by the at least one lysing member in between the first outer bead and the bulbous projection and such that a second lysing segment is defined by the at least one lysing member in between the second outer bead and the bulbous projection.

12. The electrosurgical lysing device of claim 1, wherein each of the plurality of beads comprises a non-conductive coating.

13. The electrosurgical lysing device of claim 1, wherein each of the plurality of beads is wholly defined by a non-conductive material.

14. The electrosurgical lysing device of claim 1, wherein each of at least a subset of the plurality of beads comprises an at least substantially frusto-ellipsoidal shape.

15. The electrosurgical lysing device of claim 1, wherein each of at least a subset of the plurality of beads is configured to rotate in an upward direction relative to the lysing tip within a range of between about 2 degrees and about 110 degrees, and wherein each of the at least a subset of the plurality of beads is configured to rotate in a downward direction relative to the lysing tip within a range of between about 2 degrees and about 110 degrees.

16. The electrosurgical lysing device of claim 1, further comprising a support member configured to facilitate coupling of the lysing tip to a surgical tool used to control the lysing tip during a surgical procedure within a patient's body.

17. The electrosurgical lysing device of claim 1, wherein the at least one lysing member extends through at least a subset of the plurality of beads at a non-central location relative to a bead axis of each of the at least a subset of the plurality of beads.

18. The electrosurgical lysing device of claim 1, wherein each of at least a subset of the plurality of beads comprises an annular bead structure.

19. The electrosurgical lysing device of claim 18, wherein each of the at least a subset of the plurality of beads comprises a bead hub positioned within the annular bead structure, and wherein the annular bead structure comprises a resiliently flexible material such that the annular bead structure can deform during a surgical procedure and automatically return to a relaxed configuration.

20. The electrosurgical lysing device of claim 19, wherein each of the at least a subset of the plurality of beads further comprises at least two spokes extending between the bead hub and the annular bead structure, wherein the at least two spokes comprises only a first spoke extending between an upper portion of the annular bead structure and a second spoke extending between a lower portion of the annular bead structure, and wherein the first spoke and the second spoke are positioned and configured to allow the annular bead structure to compress during a surgical procedure.

21. The electrosurgical lysing device of claim 1, wherein each of the plurality of beads protrudes both distally and proximally relative to the at least one lysing member.

22. The electrosurgical lysing device of claim 1, wherein the lysing tip is configured for reverse dissection using the at least one lysing member.

23. A lysing tip, comprising:
a treatment side and an orientational-deployment side opposite from the treatment side;
a grasping pad on the orientational-deployment side, wherein the grasping pad is configured to receive and deliver electrosurgical energy;
a plurality of beads, wherein at least a subset of the plurality of beads is defined by a non-conductive material;
a conductive lysing rod defining a plurality of lysing segments, wherein each of the plurality of lysing segments extends between a pair of adjacent beads of the plurality of beads; and
a support member coupled to the lysing rod at opposite ends of the lysing rod, wherein the support member is configured to facilitate coupling of the lysing tip to a surgical tool used to control the lysing tip during a surgical procedure within a patient's body and deliver electrosurgical energy through the grasping pad and into the lysing rod.

24. An electrosurgical lysing device, comprising:
a lysing tip, comprising:
a plurality of beads, wherein each of the plurality of beads comprises a wholly non-conductive surface;
at least one lysing member defining at least one lysing segment extending between each pair of adjacent beads, wherein the at least one lysing segment comprises a conductive material configured to deliver electrosurgical energy therefrom, and wherein the lysing tip is configured for reverse dissection using the at least one lysing member; and
a tunnel extending at least partially through each of the plurality of beads, wherein the at least one lysing member is positioned to extend at least partially through the tunnel to define the at least one lysing segment between each pair of adjacent beads.

\* \* \* \* \*